United States Patent
Wakita et al.

(10) Patent No.: US 9,453,056 B2
(45) Date of Patent: Sep. 27, 2016

(54) NUCLEIC ACID CONSTRUCT COMPRISING NUCLEIC ACID DERIVED FROM GENOME OF HEPATITIS C VIRUS OF GENOTYPE 3A

(75) Inventors: Takaji Wakita, Tokyo (JP); Mohsan Saeed, Tokyo (JP); Patrick Maurel, Paris (FR); Claire Gondeau, Paris (FR); Hiroshi Yokokawa, Kanagawa (JP)

(73) Assignees: Japan as Represented by Director-General of National Institute of Infectious Diseases (JP); Inserm Institut National de la Sante et de la Recherche Medicale (FR); Toray Industries, Inc. (JP)

( * ) Notice: Subject to any disclaimer, the term of this patent is extended or adjusted under 35 U.S.C. 154(b) by 83 days.

(21) Appl. No.: 14/342,129

(22) PCT Filed: Aug. 31, 2012

(86) PCT No.: PCT/JP2012/072179
§ 371 (c)(1),
(2), (4) Date: Apr. 23, 2014

(87) PCT Pub. No.: WO2013/031956
PCT Pub. Date: Mar. 7, 2013

(65) Prior Publication Data
US 2014/0286995 A1 Sep. 25, 2014

(30) Foreign Application Priority Data
Aug. 31, 2011 (JP) .................................. 2011-189695

(51) Int. Cl.
| C07K 14/005 | (2006.01) |
| C07K 16/10 | (2006.01) |
| C12Q 1/18 | (2006.01) |
| G01N 33/576 | (2006.01) |
| C12N 7/00 | (2006.01) |
| G01N 33/50 | (2006.01) |

(52) U.S. Cl.
CPC ........... *C07K 14/005* (2013.01); *C07K 16/109* (2013.01); *C12N 7/00* (2013.01); *C12Q 1/18* (2013.01); *G01N 33/5008* (2013.01); *G01N 33/5767* (2013.01); *C12N 2770/24221* (2013.01); *C12N 2770/24222* (2013.01); *C12N 2770/24234* (2013.01); *G01N 2333/186* (2013.01)

(58) Field of Classification Search
None
See application file for complete search history.

(56) References Cited

FOREIGN PATENT DOCUMENTS

| CA | 2303526 A1 | 10/2000 |
| JP | 2001-017187 A | 1/2001 |
| JP | 2004-000179 A | 1/2004 |
| WO | 2004/104198 A1 | 12/2004 |
| WO | 2005/028652 A1 | 3/2005 |
| WO | 2005/080575 A1 | 9/2005 |
| WO | 2010/074249 A1 | 7/2010 |
| WO | 2013/006722 | 1/2013 |

OTHER PUBLICATIONS

Wakita et al. (GenBank Accession No. AB691595, Jan. 2012).*
Qui-Lim Choo et al., "Isolation of a cDNA Clone Derived from a Blood-Borne Non-A, Non-B Viral Hepatitis Genome," Science, vol. 244, Apr. 1989, pp. 359-362.
Hiroaki Okamoto et al., "Typing hepatitis C virus by polymerase chain reaction with type-specific primers: application to clinical surveys and tracing infectious sources," Journal of General Virology, vol. 73, 1992, pp. 673-679.
Shigehisa Mon et al., "A New Type of Hepatitis C Virus in Patients in Thailand," Biochemical and Biophysical Research Communications, vol. 183, No. 1, Feb. 28, 1992, pp. 334-342.
Kentaro Yoshioka et al., "Detection of Hepatitis C Virus by Polymerase Chain Reaction and Response to Interferon-α Therapy: Relationship to Genotypes of Hepatitis C Virus," Hepatology, vol. 16, 1992, pp. 293-299.
Peter Simmonds et al., "A Proposed System for the Nomenclature of Hepatitis C Viral Genotypes," Hepatology, vol. 19, No. 5, May 1994, pp. 1321-1324.
Takaji Wakita et al., "Specific Inhibition of Hepatitis C Virus Expression by Antisense Oligodeoxynucleotides," The Journal of Biological Chemistry, vol. 269, No. 19, May 13, 1994, pp. 14205-14210.
Hajime Tokita et al., "The entire nucleotide sequences of three hepatitis C virus isolates in genetic groups 7-9 and comparison with those in the other eight genetic groups," Journal of General Virology, vol. 79, 1998, pp. 1847-1857.
V. Lohmann et al., "Replication of Subgenomic Hepatitis C Virus RNAs in a Hepatome Cell Line," Science, vol. 285, Jul. 2, 1999, pp. 110-113.
Keril J. Blight et al., "Efficient Initiation of HCV RNA Replication in Cell Culture," Science, vol. 290, Dec. 8, 2000, pp. 1972-1974.

(Continued)

*Primary Examiner* — Agnieszka Boesen
(74) *Attorney, Agent, or Firm* — DLA Piper LLP (US)

(57) ABSTRACT

A nucleic acid includes, in the following order, a 5' untranslated region comprising a particular nucleotide sequence of the genome of hepatitis C virus genotype 3a; a nucleotide sequence encoding a particular amino acid sequence of an NS3 protein, a nucleotide sequence encoding a particular amino acid sequence of an NS4A protein, a nucleotide sequence encoding a particular amino acid sequence of an NS4B protein, a nucleotide sequence encoding a particular amino acid sequence of an NS5A protein, a nucleotide sequence encoding a particular amino acid sequence of an NS5B protein of the hepatitis C virus genotype 3a; and a 3' untranslated region comprising a particular nucleotide sequence of a genome of hepatitis C virus genotype 3a.

12 Claims, 16 Drawing Sheets

(56) References Cited

OTHER PUBLICATIONS

Takanobu Kato et al., "Sequence Analysis of Hepatitis C Virus Isolated From a Fulminant Hepatitis Patient," Journal of Medical Virology, vol. 64, 2001, pp. 334-339.
Volker Lohmann et al., "Mutations in Hepatitis C Virus RNAs Conferring Cell Culture Adaptation," Journal of Virology, vol. 75, No. 3, Feb. 2001 (Abstract only).
Peter Friebe et al., "Sequences in the 5' Nontranslated Region of Hepatitis C Virus Required for RNA Replication," Journal of Virology, vol. 75, No. 24, Dec. 2001, pp. 12047-12057.
Masanori Ikeda et al., "Selectable Subgenomic and Genome-Length Dicistronic RNAs Derived from an Infectious Molecular Clone of the HCV-N Strain of Hepatitis C Virus Replicate Efficiently in Cultured Huh7 Cells," Journal of Virology, vol. 76, No. 6, Mar. 2002, pp. 2997-3006.
Takanobu Kato et al., "Efficient Replication of the Genotype 2a Hepatitis C Virus Subgenomic Replicon," Gastroenterology, vol. 125, 2003, pp. 1808-1817.
Mohan Babu Appaiahgari et al., "Immunogenicity and protective efficacy in mice of a formaldehyde-inactivated Indian strain of Japanese encephalitis virus grown in Vero cells," Vaccine, vol. 22, Issues 27-28, Sep. 9, 2004, pp. 3369-3675 (Abstract only).
Takaji Wakita et al., "Production of infectious hepatitis C virus in tissue culture from a cloned viral genome," Nature Medicine, vol. 11, No. 7, Jul. 2005, pp. 791-796.
Brett D. Lindenbach et al., "Complete Replication of Hepatitis C Virus in Cell Culture," Science, vol. 309, No. 5734, Jul. 22, 2005, pp. 623-626 (Abstract only).
Robert E. Lanford et al., "Hepatitis C virus genotype 1b chimeric replicon containing genotype 3 NS5A domain," Virology, vol. 355, 2006, pp. 192-202.
Thomas Pietschmann et al., "Construction and characterization of infectious intragenotypic and intergenotypic hepatitis C virus chimeras," Proc. Natl. Acad. Sci., vol. 103, No. 19, May 9, 2006, pp. 7408-7413.
Juan Cristina et al., "Evidence of structural genomic region recombination in Hepatitis C virus," Virology Journal, vol. 3, No. 53, Jun. 30, 2006, pp. 1-8.
Judith M. Gottwein et al., "Robust Hepatitis C Genotype 3a Cell Culture Rele3asing Adapted Intergenotypic 3a/2a (S52/JFH1) Viruses," Gastroenterology, vol. 133, 2007, pp. 1614-1626.
Matthew J. Evans et al., "Claudin-1 is a hepatitis C virus co-receptor required for a late step in entry," Nature, vol. 446, Apr. 12, 2007, pp. 801-805 (Abstract only).
Daisuke Akazawa et al., "CD81 Expression Is Important for the Permissiveness of Huh7 Cell Clones for Heterogeneous Hepatitis C Virus Infection," Journal of Virology, vol. 81, No. 10, May 2007, pp. 5036-5045 (Abstract only).
Zhonghua Xiang et al., "Hepatitis C virus nonstructural protein-5A activates sterol regulatory element-binding protein-1c through transcription factor Sp1," Biochemical and Biophysical Research Communications, vol. 402, 2010, pp. 549-553.
Henk W. Reesink et al., "Rapid HCV-RNA Decline With Once Daily TMC435: A Phase 1 Study in Healthy Volunteers and Hepatitis C Patients," Gastroenterology, vol. 138, 2010, pp. 913-921.
Judith M. Gottwein et al., "Novel Infectious cDNA Clones of Hepatitis C Virus Genotype 3a (Strain S52) and 4a (Strain ED43): Genetic Analyses and In Vivo Pathogenesis Studies," Journal of Virology, vol. 84, No. 10, May 2010, pp. 5277-5293.
Sidra Rehman et al., "Antiviral drugs against heptitus C virus," Genetic Vaccines and Therapy, vol. 9, 2011, pp. 2-5.
Jin Hee Kim et al., "High Cleavage Efficiency of a 2A Peptide Derived from Porcine Teschovirus-1 in Human Cell Lines, Zebrafish and Mice," PLoS One, vol. 6(4), 2011, e18556.
Lauren Gravitz, "A smouldering public-health crisis," Nature, vol. 474, Jun. 9, 2011, pp. s2-s4.
Mohsan Saeed et al., "Efficient Replication of Genotype 3a and 4a Hepatitis C Virus Replicons in Human Hepatoma Cells," Antimicrobial Agents and Chemotherapy, vol. 56, No. 10, Oct. 2012, pp. 5365-5373 (Abstract only).
Extended European Search Report dated May 28, 2015 from corresponding European Patent Application No. 12 82 7627.
Humphreys, I. et al., "Full-Length Characterization of Hepatitis C Virus Subtype 3a Reveals Novel Hypervariable Regions under Positive Selection during Acute Infection," *Journal of Virology*, Nov. 2009, vol. 83, No. 22, pp. 11456-11466 (including 3 sheets of Sequence Listing.

* cited by examiner

```
                         SEQUENCE LISTING

<160> NUMBER OF SEQ ID NOS: 54

<210> SEQ ID NO 1
<211> LENGTH: 9655
<212> TYPE: DNA
<213> ORGANISM: Hepatitis c virus
<220> FEATURE:
<223> OTHER INFORMATION: cDNA sequence of full-length genome RNA of
      wild-type strain S310A
<220> FEATURE:
<221> NAME/KEY: misc_feature
<222> LOCATION: (1)..(340)
<223> OTHER INFORMATION: 5' UTR
<220> FEATURE:
<221> NAME/KEY: misc_feature
<222> LOCATION: (341)..(913)
<223> OTHER INFORMATION: Core
<220> FEATURE:
<221> NAME/KEY: misc_feature
<222> LOCATION: (914)..(1489)
<223> OTHER INFORMATION: E1
<220> FEATURE:
<221> NAME/KEY: misc_feature
<222> LOCATION: (1490)..(2596)
<223> OTHER INFORMATION: E2
<220> FEATURE:
<221> NAME/KEY: misc_feature
<222> LOCATION: (2597)..(2785)
<223> OTHER INFORMATION: p7
<220> FEATURE:
<221> NAME/KEY: misc_feature
<222> LOCATION: (2786)..(3436)
<223> OTHER INFORMATION: NS2
<220> FEATURE:
<221> NAME/KEY: misc_feature
<222> LOCATION: (3437)..(5329)
<223> OTHER INFORMATION: NS3
```

```
<220> FEATURE:
<221> NAME/KEY: misc_feature
<222> LOCATION: (5330)..(5491)
<223> OTHER INFORMATION: NS4A
<220> FEATURE:
<221> NAME/KEY: misc_feature
<222> LOCATION: (5492)..(6274)
<223> OTHER INFORMATION: NS4B
<220> FEATURE:
<221> NAME/KEY: misc_feature
<222> LOCATION: (6275)..(7630)
<223> OTHER INFORMATION: NS5A
<220> FEATURE:
<221> NAME/KEY: misc_feature
<222> LOCATION: (7631)..(9406)
<223> OTHER INFORMATION: NS5B
<220> FEATURE:
<221> NAME/KEY: misc_feature
<222> LOCATION: (9407)..(9655)
<223> OTHER INFORMATION: 3' UTR

<400> SEQUENCE: 1
```

| | | | | | |
|---|---|---|---|---|---|
| gacctgcctc | ttacgaggcg | acactccacc | atggatcact | cccctgtgag | gaacttctgt | 60 |
| cttcacgcgg | aaagcgccta | gccatggcgt | tagtacgagt | gtcgtgcagc | ctccaggacc | 120 |
| cccctcccg | ggagagccat | agtggtctgc | ggaaccggtg | agtacaccgg | aatcgctggg | 180 |
| gtgaccgggt | cctttcttgg | aacaacccgc | tcaataccca | gaaatttggg | cgtgccccg | 240 |
| cgagatcact | agccgagtag | tgttgggtcg | cgaaaggcct | tgtggtactg | cctgataggg | 300 |
| tgcttgcgag | tgccccggga | ggtctcgtag | accgtgcaac | atgagcacac | ttcctaaacc | 360 |
| ccaaagaaaa | accaaaagaa | acaccatccg | tcgcccacag | gacgtcaagt | tcccgggtgg | 420 |
| cggacagatc | gttggtggag | tatacgtgtt | gccgcgcagg | ggcccacggt | tgggtgtgcg | 480 |
| cgcggcgcgt | aaaacttctg | aacggtcaca | gcctcgtgga | cggcggcagc | ctatccccac | 540 |
| ggcgcgtcgg | agcgaaggcc | ggtcctgggc | tcagcccggg | tacccttggc | ccctctatgg | 600 |
| taatgagggc | tgcgggtggg | cagggtggct | cctgtcccg | cgcggctccc | gtccatcttg | 660 |
| gggcccgaac | gacccccggc | gaaggtcccg | caacttgggt | aaagtcatcg | ataccctcac | 720 |
| gtgcggggttc | gccgacctca | tggggtacat | cccgctcgtc | ggcgctcccg | taggggcgt | 780 |
| cgcaagagct | ctcgcgcatg | gcgtgagggc | ccttgaagac | gggataaatt | tcgcaacagg | 840 |
| gaacttgcct | ggttgctcct | tttctatctt | ccttcttgct | ctgctttctt | gcttagtcca | 900 |
| tcctgcagct | agtttagagt | ggcggaatgc | atctggcctc | tacatcctta | ccaacgactg | 960 |
| tcccaacagc | agtattgtgt | atgaggccga | tgatgttatt | ctgcacacac | ccggctgtat | 1020 |
| accttgtgtt | caggacggca | ataaatccac | gtgctggacc | tcagtgacac | ctacagtggc | 1080 |
| agtcaggtac | gtcggagcaa | ccaccgcttc | gatacgcagt | catgtggacc | tattagtggg | 1140 |
| cgcggccacg | atgtgctctg | cgctctacgt | gggtgatatg | tgtggggccg | tcttccttgt | 1200 |
| gggacaagcc | ttcacgttca | gacctcgtcg | ccatcaaacg | gtccagacct | gtaactgctc | 1260 |
| actgtacccg | ggccatctct | caggacaccg | aatggcttgg | gatatgatga | tgaactggtc | 1320 |
| ccccgctatg | ggtatggtgg | tagcgcacat | cctacgtctg | cctcagacct | tgtttgacat | 1380 |
| aatagccggg | gcccattggg | gcatcttggc | ggggctagcc | tattactcca | tgcagggcaa | 1440 |
| ctgggccaag | gtcgctatca | tcatggttat | gtttttcaggg | gtcgatgcca | ctacatatac | 1500 |
| caccggtggc | gcagtagctc | atggcgccaa | gggactaact | agtcttttta | gtctgggcgc | 1560 |
| ccaacagaaa | ctgcagttgg | tcaacaccaa | tggctcctgg | cacatcaaca | ggactgccct | 1620 |
| gaactgcaat | gagtccatac | acacgggggtt | cgtagctggg | ttgttttact | atcataagtt | 1680 |

```
caactctact ggatgccctc aaaggctcag cagctgcaag cccatcactt ccttcaagca      1740
ggggtggggc tccctgacag atgctaacat caccgggtct tctgaggaca aaccgtactg      1800
ctggcactac gcacccagac cttgcacaac tgttcaagca tcaagtgtct gcggccctgt      1860
gtactgcttc acaccatcgc cagtggttgt gggcactact gatgctgagg gcgtcccaac      1920
ctatacctgg ggtggaaata agacagacgt gttcctgctg aagtccttgc ggcctcccaa      1980
cggtcagtgt tttgggtgca cgtggatgaa ctccacgggg tttaccaaga cgtgcggggc      2040
tcccccttgt aacatctatg ggggtaaagg gagtcatcac aatgattcag acctcatctg      2100
ccctaccgac tgtttcagga aacatcccga ggccacatac agccggtgcg gtgcggggcc      2160
ctggttgaca cctcgatgca tggtcgacta tccataccgg ctttggcatt acccgtgcac      2220
agtcaatttt tcattgttca aggtgaggat gtttgtgggt gggtttgagc accggttcac      2280
cgccgcttgc aactggacca gggggagcg ctgcgatatc gaggatcgcg accgcagcga      2340
gcaacacccg ctgctgcatt caacgaccga gctcgctata ctgccttgct ccttcacgcc      2400
catgcctgcg ttgtcaacag gtttaataca cctccaccaa acatcgtgg atgtccagta      2460
cctttatggc gttggatctg gcatggtggg atgggcgctg aaatgggagt tcgtcgtcct      2520
cgttttcctc ctcctagcag acgcacgcgt gtgcgttgct cttcggctga tgctgatgat      2580
atcacaagca gaagcagcct tggagaacct tgtcacgctg aacgccatcg ctgctgccgg      2640
gacacatggt attggttggt actttgtagc cttttgcgcg catggtacg tgcggggtaa      2700
gcttgtcccg ctggtgacct acagcctgac gggtctctgg tctctggcgt tgctcgtcct      2760
cttgctcccc cagcgggcgt acgcctggtc aggtgaagac agcgctactc ttggcgctgg      2820
gatcttggtc ctctttggct tctttacctt gtcaccctgg tataagcatt ggatcggccg      2880
cctcatgtgg tggaaccagt acaccatatg tagatgcgag gccgccctcc aagtgtgggt      2940
ccccccctta ctcgcacgcg ggagtaggga cggtgttatc ctgctaacaa gtctgcttta      3000
tccatcttta attttgaca tcaccaagct actgatagca gtattgggcc cattatactt      3060
aatacaggct gccatcactg ccacccccta ctttgtgcgt gcacatgtat tggttcgcct      3120
ttgcatgctc gtgcgctctg taatgggggg aaaatacttc cagatgatca tactgagcat      3180
tggcagatgg tttaacacct atctgtacga ccacctagcg ccaatgcaat attgggctgc      3240
agctggcctc aaagacctag cagtggccac tgaacctgtg atatttagtc ccatggaaac      3300
caaggtcatc acctggggcg cggacacagc ggcttgcgga gatattcttt gcgggctgcc      3360
cgtctccgcg cgactaggcc gtgaggtgtt gttgggacct gctgatgatt accgggagat      3420
gggttggcgc ctgttggccc caatcacagc atacgcccag caaaccaggg gccttcttgg      3480
gactattgtg accagcttga ctggcaggga taagaatgtg gtgaccggcg aagtgcaggt      3540
gctttctacg gctacccaga ccttcctagg tacaacaata ggggggggtta tgtggactgt      3600
ttaccatggc gcaggctcaa ggacacttgc gggcgctaaa catcctgcgc tccaaatgta      3660
cacaaatgta gatcaggacc tcgttgggtg gccagcccct ccaggggcta agtctcttga      3720
accgtgcacc tgcgggtctg cagacttata cttggttacc cgcgatgctg acgtcatccc      3780
cgctcggcgc agggggggact ccacagcgag cttgctcagc cctaggcctc tcgcctgtct      3840
caagggctcc tctggaggtc ccgttatgtg cccttcgggg catgtcacgg ggatctttcg      3900
ggctgctgtg tgcaccagag gtgtagcaaa ccctacag ttcataccag tggaaaccct      3960
tagtacacag actaggtccc catccttctc tgacaattca actcctcccg ccgtcccaca      4020
gagctaccaa gtagggtatc ttcatgcccc gaccggtagt ggcaagagca caaaggtccc      4080
```

```
ggccgcttac gtagcacaag gataccatgt tctcgtgttg aatccatcag tggcggccac    4140
actaggcttc ggctcttaca tgtcgaaagc ctatgggatc gaccccaacg tccgcactgg    4200
gaaccgcact gtcacaactg gtgctaaact gacctattcc acctacggta agtttctcgc    4260 ggatggggt tgctctgggg gagcgtatga tgtgattatt tgtgatgaat gccatgccca    4320
agacgctact accatattgg gtattggcac ggtcttagat caggctgaga cggctggggt    4380
gaggctgacg gttctggcga cagcaactcc cccaggcagc atcactgtgc cacattctaa    4440
catcgaggag gtagccctgg gctctgaagg tgagatccct ttctacggta aggctatacc    4500
gatagcccga ctcaagggg ggaggcacct tatcttttgc cattccaaga aaaagtgtga    4560
tgagatagca tccaagctca gaggcatggg gctcaacgct gtagcattct ataggggtct    4620
tgatgtgtcc atcataccaa cagcaggaga cgtcgtggtt tgcgccactg acgccctcat    4680
gactgggtac accggagact ttgattctgt catagattgc aacgtgactg ttgaacagta    4740
cgttgacttc agcttggacc ccaccttttc cattgagact cacactgctc cccaagacgc    4800
ggtttcccgc agccaacgtc gtggccgtac gggccggggt agactcggca tataccgata    4860
tgtcaccccg ggtgaaagac cgtctggaat gtttgactcg gttgttctct gtgagtgcta    4920
tgatgcgggc tgctcgtggt acgatctgca gcccgctgag actacagtca gactgagagc    4980
ttacttgtcc acgccgggtt tacctgtctg tcaagaccat cttgactttt gggagagcgt    5040
ctttactgga ctaactcaca tagatgccca ctttctgtca cagactaagc agcagggact    5100 caactteccg tacctgactg cctaccaagc cactgtgtgc gcccgcgcgc aggctcctcc    5160
cccaagttgg gacgagacgt ggaaatgtct cgtacggctt aaaccaacac tacatggacc    5220
cacgccccct ctgtatcggt tgggccctat ccaaaatgaa acctgcttga cacaccccgt    5280
cacaaaatac atcatggcat gcatgtcagc tgatctggaa gtgaccacca gcgcctgggt    5340
gttgcttgga ggggtgctcg cggccctagc ggcttactgc ttgtcagtcg gctgcgttgt    5400
gatcgtgggt catattgagc tggggggcaa gccagcactc gttccagaca aagaggtgtt    5460
gtatcaacaa ttcgatgaga tggaggagtg ctcgcaagct gccccatata tcgaacaagc    5520
tcaggtaata gcccaccagt tcaaggagaa agtccttgga ttgctgcagc gagccaccca    5580
acaacaagct gtcattgagc ccatagtagc taccaactgg caaaagcttg aggcgttctg    5640
gcacaagcat atgtggaatt ttgtgagtgg gatccagtac ctagcaggcc tttccacttt    5700
gcctggcaac cccgctgtgg cgtctcttat ggcgttcacc gcttctgtca ccagtcccct    5760
gacgaccaac caaactatgt tcttcaacat actcggggg tgggttgcta cccatttggc    5820 agggcccag agctcttccg cattcgtggt aagcggcttg gccggcgctg ccataggggg    5880
tataggcctg gcagggtct tgattgacat cctggcagga tacggagctg tgtctcagg    5940 cgccttggtg gcttttaaga tcatgggagg agaactcccc actgctgagg acatggtcaa    6000
catgctgcct gccatactat ctccgggcgc cctcgttgtc ggtgtgatat gtgcagccat    6060
actgcgtcga cacgtaggac ctggggaggg ggcggtgcag tggatgaaca ggctcatcgc    6120
attcgcatcc cggggtaacc acgtctcacc gacgcactat gtccccgaga gcgatgctgc    6180
agcgaaggtt actgcattgc tgagttctct aactgtcaca agtctgctcc ggcgactgca    6240
ccagtggatc aatgaagact acccaagtcc ttgctgcggc gactggctgc gtaccatctg    6300
ggactgggtt tgcatggtgt tgtctgactt caagacatgg ctctccgcta agattatgcc    6360
agcgctccct gggctgcctt tcctttcctg tcagaaggga tacaagggcg tgtggcgggg    6420
```

```
agacggtgtg atgtcgacac gctgtccttg cggggcgaca ataaccggtc atgtgaagaa   6480
tgggtctatg cggcttgcag ggccacgcac atgtgctaac atgtggcacg gtactttccc   6540
catcaatgag tacaccaccg gacccggcac accttgccca gcacccaact acactcgcgc   6600
attattgcgc gtggctgcca acagctacgt tgaggtgcgc cgggtgggg acttccacta    6660 cattacgggg gctacagaag atgagctcaa gtgtccgtgc caagtgccgg ccgcagagtt   6720
ttttactgag gtggatgggg tgagactcca ccgttacgcc cctccatgca agccctgtt    6780 gagggatgaa atcactttca tggtagggtt gaactcctac gcaataggat ctcaactccc   6840
ctgtgagccc gaaccagatg tttctgtgct gacctcgatg ttgagagacc cttcccatat   6900
taccgctgag gcagcagcgc gccgccttgc gcgtgggtcc cctccatcag aggcaagctc   6960
atccgccagc caactgtcgg ctccgtcgtt gaaggccact tgtcagtcgt atgggcctca   7020
tctggacgct gagctagtgg atgccaacct gttatggcgg caggagatgg gcagcactat   7080
cacacgggta gagtctgaaa caaaggttgt gattcttgat tcattcgaac ctctgagagc   7140
cgaaactgat gacgccgagc tctcggtggc tgcagagtgt ttcaagaagc ctcccaagta   7200
tcctccagcc cttcctatct gggctaggcc agactacaac cctccattgt tagaccgctg   7260
gaaagcaccg gattatgttc caccaactgt tcatggatgc gccttaccac cacggggcgc   7320
tccaccggtg cctcccccte ggaggaagag aacaattcag ctggatggct ccaatgtgtc   7380
cgcggcgcta gctgcgctag cagaaaagtc attcccgtcc tcaaagccgc aggaagagaa   7440
tagctcatcc tcaggggtcg acacacagtc cagcactacc tctaaggtgc ccccccccc    7500 aggagggaa tccgactcag agtcgtgctc gtccatgcct cctctcgagg gagagccggg    7560
cgatccggat ttgagctgcg actcttggtc cactgtgagt gacaatgagg agcagaacgt   7620
agtctgctgc tccatgtcgt actcttggac cggcgccttg ataacaccat gtagtgctga   7680
ggaggagaaa ctacccatca gcccactcag caactccttg ttgagacacc ataatctggt   7740
ttattcaacg tcgtcaagaa gcgcttctca gcgtcagaag aaggttacct tcgacaggct   7800
gcaggtgctc gacgaccact acaaaactgc tttaaaggag gtaaaggagc gagcgtctgg   7860
ggtgaaggct cgcatgctca ccatcgagga agcgtgcaag cttgtccccc ccactctgc    7920 ccgttcgaag ttcgggtata gtgcgaagga cgctcgttcc ttgtccagca gggccgttaa   7980
ccagatccgc tccgtctggg aggacttgct ggaagacacc acaactccaa ttccaacaac   8040
catcatggcg aagaacgagg tgttttgtgt ggaccccgtt aagggggggcc gcaagcccgc   8100 tcgcctcatt gtgtaccctg acctgggggt gcgtgtctgt gagaaacgcg ccctatatga   8160
cgtgatacag aagttgtcaa tcgcgacgat gggtcctgct tatggattcc agtactcgcc   8220
tcagcagcgg gtcgaacgtc tgctgaagat gtggacctca aagagaaccc ccctgggggt   8280
ctcgtatgac acccgctgct tgactcgac tgtcactgaa caggatatca gggtggaaga    8340
ggagatatat caatgctgta accttgaacc ggaggccagg aaggtgatct cctccctcac   8400
ggagcggctt tactgcgggg gccccatgtt caacagcaag gggcccagt gcggttatcg     8460 ccgttgccgt gctagtggag ttctaccgac cagctttggc aacacaatca cttgttacat   8520
caaggccaca gcggctgcaa gggccgcggg tctccggaac ccggactttc ttgtctgcgg   8580
agatgatttg gtcgtggtgg ccgagagtga tggcgtcgac gaggatagg cagccctgag    8640 agccttcacg gaggctatga ccaggtactg tgctccaccc ggagatgctc cacagcctac   8700
ctacgacctt gagctcatca catcttgctc ctctaacgtc tccgtagcac atgacaacaa   8760
ggggaggagg tattactacc tcacccgtga tgccactact cccctggccc gtgcggcttg   8820
```

```
ggaaacagct cgtcacactc cagttaactc ctggttgggc aacatcatca tgtacgcgcc    8880
taccatctgg gtgcgcatgg tgatgatgac acactttttc tccatactcc aatcccagga    8940
gatacttgat cgcccccttg attttgaaat gtacggggcc acttactctg tcactccgct    9000
ggatttacca gcaatcattg aaagactcca tggtctaagc gcgttacaca tccacagtta    9060
ctctccagta gaactcaata gggtcgcggg gacactcagg aagcttgggt gccccccct     9120 acgagcttgg agacatcggg cacgagcagt gcgcgctaag cttattgccc agggaggtaa    9180
ggccaaaata tgtggccttt atctctttaa ctgggcagta cgcaccaaga ccaaactcac    9240
tccactgcca gccgctagcc agttggactt atccaattgg ttttcggttg gcgtcggcgg    9300
gaacgacatt tatcacagcg tgtcacatgc ccgaacccgc catttgctgc tttgcctact    9360
cctactaact gtaggggtag gcatctttct cctgccagca cgataagctg gtaggataac    9420
actccattcc ttttcccttg ttttatttt tttttttttt tttttttttt tttttttttt    9480 ttctttttt tttttttttt ttttttttttg ttttcctct ttccattctt ttctaacctt    9540 aaatttcct ttctttaggt ggctccatct tagccctagt cacggctagc tgtgaaggt     9600 ccgtgagccg catgactgca gagagtgccg taactggtct ctctgcagat catgt          9655
```

<210> SEQ ID NO 2
<211> LENGTH: 340
<212> TYPE: DNA
<213> ORGANISM: Hepatitis c virus
<220> FEATURE:
<223> OTHER INFORMATION: cDNA sequence of 5' UTR of genome RNA of wild-
      type strain S310A

<400> SEQUENCE: 2

```
gacctgcctc ttacgaggcg acactccacc atggatcact cccctgtgag gaacttctgt     60
cttcacgcgg aaagcgccta gccatggcgt tagtacgagt gtcgtgcagc ctccaggacc    120 cccctcccg ggagagccat agtggtctgc ggaaccggtg agtacaccgg aatcgctggg    180
gtgaccgggt cctttcttgg aacaacccgc tcaatacccca gaaatttggg cgtgcccccg    240
cgagatcact agccgagtag tgttgggtcg cgaaaggcct tgtggtactg cctgataggg    300
tgcttgcgag tgccccggga ggtctcgtag accgtgcaac                           340
```

<210> SEQ ID NO 3
<211> LENGTH: 573
<212> TYPE: DNA
<213> ORGANISM: Hepatitis c virus
<220> FEATURE:
<223> OTHER INFORMATION: cDNA sequence of Core-coding region of genome
      RNA of wild-type strain S310A

<400> SEQUENCE: 3

```
atgagcacac ttcctaaacc ccaaagaaaa accaaaagaa acaccatccg tcgcccacag     60
gacgtcaagt tcccgggtgg cggacagatc gttggtggag tatacgtgtt gccgcgcagg    120 ggccacggt tgggtgtgcg cgcggcgcgt aaaacttctg aacggtcaca gcctcgtgga    180
cggcggcagc ctatccccac ggcgcgtcgg agcgaaggcc ggtcctgggc tcagcccggg    240
tacccttggc ccctctatgg taatgagggc tgcgggtggg cagggtggct cctgtccccg    300
cgcggctccc gtccatcttg gggcccgaac gaccccggc gaaggtcccg caacttgggt    360
aaagtcatcg ataccctcac gtgcgggttc gccgacctca tggggtacat cccgctcgtc    420
ggcgctcccg tagggggcgt cgcaagagct ctcgcgcatg gcgtgagggc ccttgaagac    480
```

```
gggataaatt tcgcaacagg gaacttgcct ggttgctcct tttctatctt ccttcttgct    540
ctgctttctt gcttagtcca tcctgcagct agt                                 573
```

<210> SEQ ID NO 4
<211> LENGTH: 576
<212> TYPE: DNA
<213> ORGANISM: Hepatitis c virus
<220> FEATURE:
<223> OTHER INFORMATION: cDNA sequence of E1-coding region of genome RNA
      of wild-type S310A strain

<400> SEQUENCE: 4

```
ttagagtggc ggaatgcatc tggcctctac atccttacca acgactgtcc caacagcagt     60
attgtgtatg aggccgatga tgttattctg cacacacccg gctgtatacc ttgtgttcag    120
gacggcaata atccacgtg ctggacctca gtgacaccta cagtggcagt caggtacgtc    180
ggagcaacca ccgcttcgat acgcagtcat gtggacctat tagtgggcgc ggccacgatg    240
tgctctgcgc tctacgtggg tgatatgtgt ggggccgtct tccttgtggg acaagccttc    300
acgttcagac ctcgtcgcca tcaaacggtc cagacctgta actgctcact gtacccgggc    360
catctctcag acaccgaatg gcttgggat atgatgatga actggtcccc cgctatgggt    420
atggtggtag cgcacatcct acgtctgcct cagaccttgt ttgacataat agccggggcc    480
cattggggca tcttggcggg gctagcctat tactccatgc agggcaactg ggccaaggtc    540
gctatcatca tggttatgtt ttcaggggtc gatgcc                              576
```

<210> SEQ ID NO 5
<211> LENGTH: 1107
<212> TYPE: DNA
<213> ORGANISM: Hepatitis c virus
<220> FEATURE:
<223> OTHER INFORMATION: cDNA sequence of E1-coding region of genome RNA
      of wild-type S310A strain

<400> SEQUENCE: 5

```
actacatata ccaccggtgg cgcagtagct catggcgcca agggactaac tagtctttt     60 agtctgggcg cccaacagaa actgcagttg gtcaacacca atggctcctg gcacatcaac    120
aggactgccc tgaactgcaa tgagtccata cacacggggt tcgtagctgg gttgttttac    180
tatcataagt tcaactctac tggatgccct caaaggctca gcagctgcaa gcccatcact    240
tccttcaagc agggggtgggg ctccctgaca gatgctaaca tcaccgggtc ttctgaggac    300
aaaccgtact gctggcacta cgcacccaga ccttgcacaa ctgttcaagc atcaagtgtc    360
tgcggccctg tgtactgctt cacaccatcg ccagtggttg tgggcactac tgatgctgag    420
ggcgtcccaa cctatacctg gggtggaaat aagacagacg tgttcctgct gaagtccttg    480
cggcctccca acggtcagtg gtttgggtgc acgtggatga actccacggg gtttaccaag    540
acgtgcgggg ctccccttg taacatctat ggggtaaag ggagtcatca caatgattca    600
gacctcatct gccctaccga ctgtttcagg aaacatcccg aggccacata cagccggtgc    660
ggtgcggggc cctggttgac acctcgatgc atggtcgact atccataccg gctttggcat    720
tacccgtgca cagtcaattt ttcattgttc aaggtgagga tgtttgtggg tgggtttgag    780
caccggttca ccgccgcttg caactggacc agggggggagc gctgcgatat cgaggatcgc    840
gaccgcagcg agcaacaccc gctgctgcat tcaacgaccg agctcgctat actgccttgc    900
tccttcacgc ccatgcctgc gttgtcaaca ggtttaatac acctccacca aaacatcgtg    960
gatgtccagt acctttatgg cgttggatct ggcatggtgg atgggcgct gaaatgggag   1020
```

```
ttcgtcgtcc tcgttttcct cctcctagca gacgcacgcg tgtgcgttgc tctttggctg    1080
atgctgatga tatcacaagc agaagca                                       1107

<210> SEQ ID NO 6
<211> LENGTH: 189
<212> TYPE: DNA
<213> ORGANISM: Hepatitis c virus
<220> FEATURE:
<223> OTHER INFORMATION: cDNA sequence of p7-coding region of genome RNA
      of wild-type strain S310A

<400> SEQUENCE: 6
gccttggaga accttgtcac gctgaacgcc atcgctgctg ccgggacaca tggtattggt     60
tggtactttg tagccttttg cgcggcatgg tacgtgcggg gtaagcttgt cccgctggtg    120
acctacagcc tgacgggtct ctggtctctg gcgttgctcg tcctcttgct cccccagcgg    180
gcgtacgcc                                                            189

<210> SEQ ID NO 7
<211> LENGTH: 651
<212> TYPE: DNA
<213> ORGANISM: Hepatitis c virus
<220> FEATURE:
<223> OTHER INFORMATION: cDNA sequence of NS2-coding region of genome
      RNA of wild-type strain S310A

<400> SEQUENCE: 7
tggtcaggtg aagacagcgc tactcttggc gctgggatct tggtcctctt tggcttcttt     60
accttgtcac cctggtataa gcattggatc ggccgcctca tgtggtggaa ccagtacacc    120
atatgtagat gcgaggccgc cctccaagtg tgggtccccc ccttactcgc acgcggagt    180 agggacggtg ttatcctgct aacaagtctg ctttatccat ctttaatttt tgacatcacc    240
aagctactga tagcagtatt gggcccatta tacttaatac aggctgccat cactgccacc    300
ccctactttg tgcgtgcaca tgtattggtt cgcctttgca tgctcgtgcg ctctgtaatg    360
gggggaaaat acttccagat gatcatactg agcattggca gatggtttaa cacctatctg    420
tacgaccacc tagcgccaat gcaatattgg gctgcagctg gcctcaaaga cctagcagtg    480
gccactgaac ctgtgatatt tagtcccatg gaaaccaagg tcatcacctg ggcgcggac    540 acagcggctt cgcggagatat tctttgcggg ctgcccgtct ccgcgcgact aggccgtgag    600
gtgttgttgg gacctgctga tgattaccgg gagatgggtt ggcgcctgtt g             651

<210> SEQ ID NO 8
<211> LENGTH: 1893
<212> TYPE: DNA
<213> ORGANISM: Hepatitis c virus
<220> FEATURE:
<223> OTHER INFORMATION: cDNA sequence of NS3-coding region of genome
      RNA of wild-type strain S310A

<400> SEQUENCE: 8
gccccaatca cagcatacgc ccagcaaacc aggggccttc ttgggactat tgtgaccagc     60
ttgactggca gggataagaa tgtggtgacc ggcgaagtgc aggtgctttc tacggctacc    120
cagaccttcc taggtacaac aatagggggg gttatgtgga ctgtttacca tggcgcaggc    180
tcaaggacac ttgcgggcgc taaacatcct cgcgctccaa tgtacacaaa tgtagatcag    240
gacctcgttg ggtggccagc ccctccaggg gctaagtctc ttgaaccgtg cacctgcggg    300
tctgcagact atacttggt taccgcgat gctgacgtca tccccgctcg gcgcagggg      360
```

```
gactccacag cgagcttgct cagccctagg cctctcgcct gtctcaaggg ctcctctgga    420
ggtcccgtta tgtgcccttc ggggcatgtc acggggatct ttcgggctgc tgtgtgcacc    480
agaggtgtag caaagaccct acagttcata ccagtggaaa cccttagtac acagactagg    540
tccccatcct tctctgacaa ttcaactcct cccgccgtcc cacagagcta ccaagtaggg    600
tatcttcatg ccccgaccgg tagtggcaag agcacaaagg tcccggccgc ttacgtagca    660
caaggatacc atgttctcgt gttgaatcca tcagtggcgg ccacactagg cttcggctct    720
tacatgtcga aagcctatgg gatcgacccc aacgtccgca ctgggaaccg cactgtcaca    780
actggtgcta aactgaccta ttccacctac ggtaagtttc tcgcggatgg gggttgctct    840
gggggagcgt atgatgtgat tatttgtgat gaatgccatg cccaagacgc tactaccata    900
ttgggtattg gcacggtctt agatcaggct gagacggctg ggtgaggct gacggttctg    960
gcgacagcaa ctcccccagg cagcatcact gtgccacatt ctaacatcga ggaggtagcc   1020
ctgggctctg aaggtgagat ccctttctac ggtaaggcta taccgatagc ccagctcaag   1080
ggggggaggc accttatctt ttgccattcc aagaaaaagt gtgatgagat agcatccaag   1140
ctcagaggca tggggctcaa cgctgtagca ttctataggg gtcttgatgt gtccatcata   1200
ccaacagcag gagacgtcgt ggtttgcgcc actgacgccc tcatgactgg gtacaccgga   1260
gactttgatt ctgtcataga ttgcaacgtg actgttgaac agtacgttga cttcagcttg   1320
gaccccacct tttccattga gactcacact gctccccaag acgcggtttc ccgcagccaa   1380
cgtcgtggcc gtacgggccg gggtagactc ggcatatacc gatatgtcac cccgggtgaa   1440
agaccgtctg gaatgtttga ctcggttgtt ctctgtgagt gctatgatgc gggctgctcg   1500
tggtacgatc tgcagcccgc tgagactaca gtcagactga gagcttactt gtccacgccg   1560
ggtttacctg tctgtcaaga ccatcttgac ttttgggaga gcgtctttac tggactaact   1620
cacatagatg cccactttct gtcacagact aagcagcagg gactcaactt cccgtacctg   1680
actgcctacc aagccactgt gtgcgcccgc gcgcaggctc ctcccccaag ttgggacgag   1740
acgtggaaat gtctcgtacg gcttaaacca acactacatg gacccacgcc ccttctgtat   1800
cggttggggc ctatccaaaa tgaaacctgc ttgacacacc ccgtcacaaa atacatcatg   1860
gcatgcatgt cagctgatct ggaagtgacc acc                                 1893
```

<210> SEQ ID NO 9
<211> LENGTH: 162
<212> TYPE: DNA
<213> ORGANISM: Hepatitis c virus
<220> FEATURE:
<223> OTHER INFORMATION: cDNA sequence of NS4A-coding region of genome RNA of wild-type strain S310A

<400> SEQUENCE: 9

```
agcgcctggg tgttgcttgg aggggtgctc gcggccctag cggcttactg cttgtcagtc     60
ggctgcgttg tgatcgtggg tcatattgag ctggggggca agccagcact cgttccagac    120
aaagaggtgt tgtatcaaca attcgatgag atggaggagt gc                       162
```

<210> SEQ ID NO 10
<211> LENGTH: 783
<212> TYPE: DNA
<213> ORGANISM: Hepatitis c virus
<220> FEATURE:
<223> OTHER INFORMATION: cDNA sequence of NS4B-coding region of genome RNA of wild-type strain S310A

<400> SEQUENCE: 10

```
tcgcaagctg cccatatat cgaacaagct caggtaatag cccaccagtt caaggagaaa      60
gtccttggat tgctgcagcg agccacccaa caacaagctg tcattgagcc catagtagct     120
accaactggc aaaagcttga ggcgttctgg cacaagcata tgtggaattt tgtgagtggg     180
atccagtacc tagcaggcct ttccactttg cctggcaacc ccgctgtggc gtctcttatg     240
gcgttcaccg cttctgtcac cagtcccctg acgaccaacc aaactatgtt cttcaacata     300
ctcgggggt gggttgctac ccatttggca gggccccaga gctcttccgc attcgtggta      360
agcggcttgg ccggcgctgc catagggggt ataggcctgg gcagggtctt gattgacatc     420
ctggcaggat acgagctgg tgtctcaggc gccttggtgg cttttaagat catgggagga     480
gaactcccca ctgctgagga catggtcaac atgctgcctg ccatactatc tccgggcgcc     540
ctcgttgtcg gtgtgatatg tgcagccata ctgcgtcgac acgtaggacc tggggagggg     600
gcggtgcagt ggatgaacag gctcatcgca ttcgcatccc ggggtaacca cgtctcaccg     660
acgcactatg tccccgagag cgatgctgca gcgaaggtta ctgcattgct gagttctcta     720
actgtcacaa gtctgctccg gcgactgcac cagtggatca tgaagactac cccaagtcct     780
tgc                                                                   783
```

<210> SEQ ID NO 11
<211> LENGTH: 1356
<212> TYPE: DNA
<213> ORGANISM: Hepatitis c virus
<220> FEATURE:
<223> OTHER INFORMATION: cDNA sequence of NS5A-coding region of genome
RNA of wild-type strain S310A

<400> SEQUENCE: 11

```
tgcggcgact ggctgcgtac catctgggac tgggtttgca tggtgttgtc tgacttcaag      60
acatggctct ccgctaagat tatgccagcg ctccctgggc tgcctttcct ttcctgtcag     120
aagggataca agggcgtgtg cggggagac ggtgtgatgt cgacacgctg tccttgcggg      180
gcgacaataa ccggtcatgt gaagaatggg tctatgcggc ttgcagggcc acgcacatgt     240
gctaacatgt ggcacggtac tttccccatc aatgagtaca ccaccggacc cggcacacct     300
tgcccagcac ccaactacac tcgcgcatta ttgcgcgtgg ctgccaacag ctacgttgag     360
gtgcgccggg tggggactt ccactacatt acggggctca agaagatga gctcaagtgt      420
ccgtgccaag tgccggccgc agagttttt actgaggtgg atggggtgag actccaccgt     480
tacgccctc catgcaagcc cctgttgagg atgaaatca ctttcatggt agggttgaac       540
tcctacgcaa taggatctca actccctgt gagcccgaac cagatgtttc tgtgctgacc      600
tcgatgttga gaccccttc ccatattacc gctgaggcag cagcgcgccg ccttgcgcgt     660
gggtcccctc catcagaggc aagctcatcc gccagccaac tgtcggctcc gtcgttgaag     720
gccacttgtc agtcgtatgg gcctcatctg acgctgagc tagtgatgc caacctgtta      780
tggcggcagg agatgggcag cactatcaca cgggtagagt ctgaaacaaa ggttgtgatt     840
cttgattcat tcgaacctct gagagccgaa actgatgacg ccgagctctc ggtggctgca     900
gagtgtttca gaagcctcc caagtatcct ccagcccttc ctatctgggc taggccagac      960
tacaaccctc cattgttaga ccgctggaaa gcaccggatt atgttccacc aactgttcat    1020
ggatgcgcct accaccacg gggcgctcca ccggtgcctc cccctcggag gaagagaaca    1080
attcagctgg atggctccaa tgtgtccgcg gcgctagctg cgctagcaga aaagtcattc    1140
```

```
ccgtcctcaa agccgcagga agagaatagc tcatcctcag gggtcgacac acagtccagc   1200
actacctcta aggtgccccc cccccagga ggggaatccg actcagagtc gtgctcgtcc   1260
atgcctcctc tcgagggaga gccgggcgat ccggatttga gctgcgactc ttggtccact   1320
gtgagtgaca atgaggagca aacgtagtc tgctgc                              1356
```

<210> SEQ ID NO 12
<211> LENGTH: 1776
<212> TYPE: DNA
<213> ORGANISM: Hepatitis c virus
<220> FEATURE:
<223> OTHER INFORMATION: cDNA sequence of NS5B-coding region of genome
      RNA of wild-type strain S310A

<400> SEQUENCE: 12

```
tccatgtcgt actcttggac cggcgccttg ataacaccat gtagtgctga ggaggagaaa     60
ctacccatca gcccactcag caactccttg ttgagacacc ataatctggt ttattcaacg    120
tcgtcaagaa gcgcttctca gcgtcagaag aaggttacct tcgacaggct gcaggtgctc    180
gacgaccact acaaaactgc tttaaggag gtaaggagc gagcgtctgg ggtgaaggct     240
cgcatgctca ccatcgagga agcgtgcaag cttgtccccc cccactctgc ccgttcgaag    300
ttcgggtata gtgcgaagga cgctcgttcc ttgtccagca gggccgttaa ccagatccgc    360
tccgtctggg aggacttgct ggaagacacc acaactccaa ttccaacaac catcatggcg    420
aagaacgagg tgttttgtgt ggaccccgtt aagggggggcc gcaagcccgc tcgcctcatt    480
gtgtaccctg acctggggt gcgtgtctgt gagaaacgcg ccctatatga cgtgatacag    540
aagttgtcaa tcgcgacgat gggtcctgct tatggattcc agtactcgcc tcagcagcgg    600
gtcgaacgtc tgctgaagat gtggaccca aagagaaccc ccctgggtt ctcgtatgac    660 acccgctgct ttgactcgac tgtcactgaa caggatatca gggtggaaga ggagatatat    720
caatgctgta accttgaacc ggaggccagg aaggtgatct cctccctcac ggagcggctt    780
tactgcgggg gccccatgtt caacagcaag ggggcccagt gcggttatcg ccgttgccgt    840
gctagtggag ttctaccgac cagctttggc aacacaatca cttgttacat caaggccaca    900
gcggctgcaa gggccgcggg tctccggaac ccggactttc ttgtctgcgg agatgatttg    960
gtcgtggtgg ccgagagtga tggcgtcgac gaggataggg cagccctgag agccttcacg   1020
gaggctatga ccaggtactc tgctccaccc ggagatgctc cacagcctac ctacgacctt   1080
gagctcatca catcttgctc ctctaacgtc tccgtagcac atgacaacaa ggggaggagg   1140
tattactacc tcacccgtga tgccactact ccctggccc gtgcggcttg ggaaacagct   1200
cgtcacactc cagttaactc ctggttgggc aacatcatca tgtacgcgcc taccatctgg   1260
gtgcgcatgt tgatgatgac acactttttc tccatactcc aatcccagga gatacttgat   1320 cgccccttg atttgaaat gtacggggcc acttactctg tcactccgct ggatttacca   1380
gcaatcattg aaagactcca tggtctaagc gcgttcacac tccacagtta ctctccagta   1440
gaactcaata gggtcgcggg gacactcagg aagcttgggt gcccccccct acgagcttgg   1500
agacatcggg cacgagcagt gcgcgctaag cttattgccc agggaggtaa ggccaaaata   1560
tgtggccttt atctctttaa ctgggcagta cgcaccaaga ccaaactcac tccactgcca   1620
gccgctagcc agttggactt atccaattgg ttttcggttg gcgtcggcgg gaacgacatt   1680
tatcacagcg tgtcacatgc ccgaacccgc catttgctgc tttgcctact cctactaact   1740
gtaggggtag gcatctttct cctgccagca cgataa                             1776
```

```
<210> SEQ ID NO 13
<211> LENGTH: 249
<212> TYPE: DNA
<213> ORGANISM: Hepatitis c virus
<220> FEATURE:
<223> OTHER INFORMATION: cDNA sequence of 3' UTR of genome RNA of wild-
      type strain S310A

<400> SEQUENCE: 13
gctggtagga taacactcca ttccttttcc cttgttttta ttttttttt tttttttttt      60 tttttttttt tttttctttt tttttttttt tttttttttt tttgtttttc ctctttccat    120
tcttttctaa ccttaaattt tcctttcttt aggtggctcc atcttagccc tagtcacggc    180
tagctgtgaa aggtccgtga gccgcatgac tgcagagagt gccgtaactg gtctctctgc    240
agatcatgt                                                            249

<210> SEQ ID NO 14
<211> LENGTH: 3021
<212> TYPE: PRT
<213> ORGANISM: Hepatitis c virus
<220> FEATURE:
<223> OTHER INFORMATION: amino acid sequence of the precursor protein of
      wild-type strain S310A
<220> FEATURE:
<221> NAME/KEY: misc_feature
<222> LOCATION: (1)..(191)
<223> OTHER INFORMATION: Core
<220> FEATURE:
<221> NAME/KEY: misc_feature
<222> LOCATION: (192)..(383)
<223> OTHER INFORMATION: E1
<220> FEATURE:
<221> NAME/KEY: misc_feature
<222> LOCATION: (384)..(752)
<223> OTHER INFORMATION: E2
<220> FEATURE:
<221> NAME/KEY: misc_feature
<222> LOCATION: (753)..(815)
<223> OTHER INFORMATION: p7
<220> FEATURE:
<221> NAME/KEY: misc_feature
<222> LOCATION: (816)..(1032)
<223> OTHER INFORMATION: NS2
<220> FEATURE:
<221> NAME/KEY: misc_feature
<222> LOCATION: (1033)..(1663)
<223> OTHER INFORMATION: NS3
<220> FEATURE:
<221> NAME/KEY: misc_feature
<222> LOCATION: (1664)..(1717)
<223> OTHER INFORMATION: NS4A
<220> FEATURE:
<221> NAME/KEY: misc_feature
<222> LOCATION: (1718)..(1978)
<223> OTHER INFORMATION: NS4B
<220> FEATURE:
<221> NAME/KEY: misc_feature
<222> LOCATION: (1979)..(2430)
<223> OTHER INFORMATION: NS5A
<220> FEATURE:
<221> NAME/KEY: misc_feature
<222> LOCATION: (2431)..(3021)
<223> OTHER INFORMATION: NS5B

<400> SEQUENCE: 14
```

Met Ser Thr Leu Pro Lys Pro Gln Arg Lys Thr Lys Arg Asn Thr Ile
1               5                   10                  15

Arg Arg Pro Gln Asp Val Lys Phe Pro Gly Gly Gly Gln Ile Val Gly
            20                  25                  30

Gly Val Tyr Val Leu Pro Arg Arg Gly Pro Arg Leu Gly Val Arg Ala

-continued

```
                35                  40                  45
Ala Arg Lys Thr Ser Glu Arg Ser Gln Pro Arg Gly Arg Gln Pro
 50                  55                  60

Ile Pro Thr Ala Arg Arg Ser Glu Gly Arg Ser Trp Ala Gln Pro Gly
65                   70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
                100                 105                 110

Arg Arg Arg Ser Arg Asn Leu Gly Lys Val Ile Asp Thr Leu Thr Cys
            115                 120                 125

Gly Phe Ala Asp Leu Met Gly Tyr Ile Pro Leu Val Gly Ala Pro Val
            130                 135                 140

Gly Gly Val Ala Arg Ala Leu Ala His Gly Val Arg Ala Leu Glu Asp
145                 150                 155                 160

Gly Ile Asn Phe Ala Thr Gly Asn Leu Pro Gly Cys Ser Phe Ser Ile
                165                 170                 175

Phe Leu Leu Ala Leu Leu Ser Cys Leu Val His Pro Ala Ala Ser Leu
                180                 185                 190

Glu Trp Arg Asn Ala Ser Gly Leu Tyr Ile Leu Thr Asn Asp Cys Pro
            195                 200                 205

Asn Ser Ser Ile Val Tyr Glu Ala Asp Asp Val Ile Leu His Thr Pro
210                 215                 220

Gly Cys Ile Pro Cys Val Gln Asp Gly Asn Lys Ser Thr Cys Trp Thr
225                 230                 235                 240

Ser Val Thr Pro Thr Val Ala Val Arg Tyr Val Gly Ala Thr Thr Ala
                245                 250                 255

Ser Ile Arg Ser His Val Asp Leu Leu Val Gly Ala Ala Thr Met Cys
            260                 265                 270

Ser Ala Leu Tyr Val Gly Asp Met Cys Gly Ala Val Phe Leu Val Gly
            275                 280                 285

Gln Ala Phe Thr Phe Arg Pro Arg Arg His Gln Thr Val Gln Thr Cys
290                 295                 300

Asn Cys Ser Leu Tyr Pro Gly His Leu Ser Gly His Arg Met Ala Trp
305                 310                 315                 320

Asp Met Met Met Asn Trp Ser Pro Ala Met Gly Met Val Val Ala His
                325                 330                 335

Ile Leu Arg Leu Pro Gln Thr Leu Phe Asp Ile Ile Ala Gly Ala His
            340                 345                 350

Trp Gly Ile Leu Ala Gly Leu Ala Tyr Tyr Ser Met Gln Gly Asn Trp
            355                 360                 365

Ala Lys Val Ala Ile Ile Met Val Met Phe Ser Gly Val Asp Ala Thr
370                 375                 380

Thr Tyr Thr Thr Gly Gly Ala Val Ala His Gly Ala Lys Gly Leu Thr
385                 390                 395                 400

Ser Leu Phe Ser Leu Gly Ala Gln Gln Lys Leu Gln Leu Val Asn Thr
                405                 410                 415

Asn Gly Ser Trp His Ile Asn Arg Thr Ala Leu Asn Cys Asn Glu Ser
            420                 425                 430

Ile His Thr Gly Phe Val Ala Gly Leu Phe Tyr Tyr His Lys Phe Asn
            435                 440                 445

Ser Thr Gly Cys Pro Gln Arg Leu Ser Ser Cys Lys Pro Ile Thr Ser
450                 455                 460
```

-continued

```
Phe Lys Gln Gly Trp Gly Ser Leu Thr Asp Ala Asn Ile Thr Gly Ser
465                 470                 475                 480

Ser Glu Asp Lys Pro Tyr Cys Trp His Tyr Ala Pro Arg Pro Cys Thr
                485                 490                 495

Thr Val Gln Ala Ser Ser Val Cys Gly Pro Val Tyr Cys Phe Thr Pro
            500                 505                 510

Ser Pro Val Val Gly Thr Thr Asp Ala Glu Gly Val Pro Thr Tyr
        515                 520                 525

Thr Trp Gly Gly Asn Lys Thr Asp Val Phe Leu Leu Lys Ser Leu Arg
    530                 535                 540

Pro Pro Asn Gly Gln Trp Phe Gly Cys Thr Trp Met Asn Ser Thr Gly
545                 550                 555                 560

Phe Thr Lys Thr Cys Gly Ala Pro Pro Cys Asn Ile Tyr Gly Gly Lys
                565                 570                 575

Gly Ser His His Asn Asp Ser Asp Leu Ile Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
    610                 615                 620

Pro Cys Thr Val Asn Phe Ser Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asp Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Gly Met Val Gly Trp Ala Leu
705                 710                 715                 720

Lys Trp Glu Phe Val Val Leu Val Phe Leu Leu Leu Ala Asp Ala Arg
                725                 730                 735

Val Cys Val Ala Leu Trp Leu Met Leu Met Ile Ser Gln Ala Glu Ala
            740                 745                 750

Ala Leu Glu Asn Leu Val Thr Leu Asn Ala Ile Ala Ala Ala Gly Thr
        755                 760                 765

His Gly Ile Gly Trp Tyr Phe Val Ala Phe Cys Ala Ala Trp Tyr Val
    770                 775                 780

Arg Gly Lys Leu Val Pro Leu Val Thr Tyr Ser Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Ile Leu Val Leu Phe
            820                 825                 830

Gly Phe Phe Thr Leu Ser Pro Trp Tyr Lys His Trp Ile Gly Arg Leu
        835                 840                 845

Met Trp Trp Asn Gln Tyr Thr Ile Cys Arg Cys Glu Ala Ala Leu Gln
    850                 855                 860

Val Trp Val Pro Pro Leu Leu Ala Arg Gly Ser Arg Asp Gly Val Ile
865                 870                 875                 880
```

-continued

```
Leu Leu Thr Ser Leu Leu Tyr Pro Ser Leu Ile Phe Asp Ile Thr Lys
            885                 890                 895
Leu Leu Ile Ala Val Leu Gly Pro Leu Tyr Leu Ile Gln Ala Ala Ile
            900                 905                 910
Thr Ala Thr Pro Tyr Phe Val Arg Ala His Val Leu Val Arg Leu Cys
            915                 920                 925
Met Leu Val Arg Ser Val Met Gly Gly Lys Tyr Phe Gln Met Ile Ile
            930                 935                 940
Leu Ser Ile Gly Arg Trp Phe Asn Thr Tyr Leu Tyr Asp His Leu Ala
945                 950                 955                 960
Pro Met Gln Tyr Trp Ala Ala Ala Gly Leu Lys Asp Leu Ala Val Ala
            965                 970                 975
Thr Glu Pro Val Ile Phe Ser Pro Met Glu Thr Lys Val Ile Thr Trp
            980                 985                 990
Gly Ala Asp Thr Ala Ala Cys Gly Asp Ile Leu Cys Gly Leu Pro Val
            995                1000                1005
Ser Ala Arg Leu Gly Arg Glu Val Leu Leu Gly Pro Ala Asp Asp
            1010                1015                1020
Tyr Arg Glu Met Gly Trp Arg Leu Leu Ala Pro Ile Thr Ala Tyr
            1025                1030                1035
Ala Gln Gln Thr Arg Gly Leu Leu Gly Thr Ile Val Thr Ser Leu
            1040                1045                1050
Thr Gly Arg Asp Lys Asn Val Val Thr Gly Glu Val Gln Val Leu
            1055                1060                1065
Ser Thr Ala Thr Gln Thr Phe Leu Gly Thr Thr Ile Gly Gly Val
            1070                1075                1080
Met Trp Thr Val Tyr His Gly Ala Gly Ser Arg Thr Leu Ala Gly
            1085                1090                1095
Ala Lys His Pro Ala Leu Gln Met Tyr Thr Asn Val Asp Gln Asp
            1100                1105                1110
Leu Val Gly Trp Pro Ala Pro Pro Gly Ala Lys Ser Leu Glu Pro
            1115                1120                1125
Cys Thr Cys Gly Ser Ala Asp Leu Tyr Leu Val Thr Arg Asp Ala
            1130                1135                1140
Asp Val Ile Pro Ala Arg Arg Gly Asp Ser Thr Ala Ser Leu
            1145                1150                1155
Leu Ser Pro Arg Pro Leu Ala Cys Leu Lys Gly Ser Ser Gly Gly
            1160                1165                1170
Pro Val Met Cys Pro Ser Gly His Val Thr Gly Ile Phe Arg Ala
            1175                1180                1185
Ala Val Cys Thr Arg Gly Val Ala Lys Thr Leu Gln Phe Ile Pro
            1190                1195                1200
Val Glu Thr Leu Ser Thr Gln Thr Arg Ser Pro Ser Phe Ser Asp
            1205                1210                1215
Asn Ser Thr Pro Pro Ala Val Pro Gln Ser Tyr Gln Val Gly Tyr
            1220                1225                1230
Leu His Ala Pro Thr Gly Ser Gly Lys Ser Thr Lys Val Pro Ala
            1235                1240                1245
Ala Tyr Val Ala Gln Gly Tyr His Val Leu Val Leu Asn Pro Ser
            1250                1255                1260
Val Ala Ala Thr Leu Gly Phe Gly Ser Tyr Met Ser Lys Ala Tyr
            1265                1270                1275
Gly Ile Asp Pro Asn Val Arg Thr Gly Asn Arg Thr Val Thr Thr
```

```
              1280                1285                1290
Gly Ala Lys Leu Thr Tyr Ser Thr Tyr Gly Lys Phe Leu Ala Asp
         1295                1300                1305
Gly Gly Cys Ser Gly Gly Ala Tyr Asp Val Ile Ile Cys Asp Glu
         1310                1315                1320
Cys His Ala Gln Asp Ala Thr Thr Ile Leu Gly Ile Gly Thr Val
         1325                1330                1335
Leu Asp Gln Ala Glu Thr Ala Gly Val Arg Leu Thr Val Leu Ala
         1340                1345                1350
Thr Ala Thr Pro Pro Gly Ser Ile Thr Val Pro His Ser Asn Ile
         1355                1360                1365
Glu Glu Val Ala Leu Gly Ser Glu Gly Glu Ile Pro Phe Tyr Gly
         1370                1375                1380
Lys Ala Ile Pro Ile Ala Gln Leu Lys Gly Gly Arg His Leu Ile
         1385                1390                1395
Phe Cys His Ser Lys Lys Lys Cys Asp Glu Ile Ala Ser Lys Leu
         1400                1405                1410
Arg Gly Met Gly Leu Asn Ala Val Ala Phe Tyr Arg Gly Leu Asp
         1415                1420                1425
Val Ser Ile Ile Pro Thr Ala Gly Asp Val Val Val Cys Ala Thr
         1430                1435                1440
Asp Ala Leu Met Thr Gly Tyr Thr Gly Asp Phe Asp Ser Val Ile
         1445                1450                1455
Asp Cys Asn Val Thr Val Glu Gln Tyr Val Asp Phe Ser Leu Asp
         1460                1465                1470
Pro Thr Phe Ser Ile Glu Thr His Thr Ala Pro Gln Asp Ala Val
         1475                1480                1485
Ser Arg Ser Gln Arg Arg Gly Arg Thr Gly Arg Gly Arg Leu Gly
         1490                1495                1500
Ile Tyr Arg Tyr Val Thr Pro Gly Glu Arg Pro Ser Gly Met Phe
         1505                1510                1515
Asp Ser Val Val Leu Cys Glu Cys Tyr Asp Ala Gly Cys Ser Trp
         1520                1525                1530
Tyr Asp Leu Gln Pro Ala Glu Thr Thr Val Arg Leu Arg Ala Tyr
         1535                1540                1545
Leu Ser Thr Pro Gly Leu Pro Val Cys Gln Asp His Leu Asp Phe
         1550                1555                1560
Trp Glu Ser Val Phe Thr Gly Leu Thr His Ile Asp Ala His Phe
         1565                1570                1575
Leu Ser Gln Thr Lys Gln Gln Gly Leu Asn Phe Pro Tyr Leu Thr
         1580                1585                1590
Ala Tyr Gln Ala Thr Val Cys Ala Arg Ala Gln Ala Pro Pro Pro
         1595                1600                1605
Ser Trp Asp Glu Thr Trp Lys Cys Leu Val Arg Leu Lys Pro Thr
         1610                1615                1620
Leu His Gly Pro Thr Pro Leu Leu Tyr Arg Leu Gly Pro Ile Gln
         1625                1630                1635
Asn Glu Thr Cys Leu Thr His Pro Val Thr Lys Tyr Ile Met Ala
         1640                1645                1650
Cys Met Ser Ala Asp Leu Glu Val Thr Thr Ser Ala Trp Val Leu
         1655                1660                1665
Leu Gly Gly Val Leu Ala Ala Leu Ala Ala Tyr Cys Leu Ser Val
         1670                1675                1680
```

-continued

```
Gly Cys Val Val Ile Val Gly His Ile Glu Leu Gly Gly Lys Pro
1685                1690                1695

Ala Leu Val Pro Asp Lys Glu Val Leu Tyr Gln Gln Phe Asp Glu
1700                1705                1710

Met Glu Glu Cys Ser Gln Ala Ala Pro Tyr Ile Glu Gln Ala Gln
1715                1720                1725

Val Ile Ala His Gln Phe Lys Glu Lys Val Leu Gly Leu Leu Gln
1730                1735                1740

Arg Ala Thr Gln Gln Ala Val Ile Glu Pro Ile Val Ala Thr
1745                1750                1755

Asn Trp Gln Lys Leu Glu Ala Phe Trp His Lys His Met Trp Asn
1760                1765                1770

Phe Val Ser Gly Ile Gln Tyr Leu Ala Gly Leu Ser Thr Leu Pro
1775                1780                1785

Gly Asn Pro Ala Val Ala Ser Leu Met Ala Phe Thr Ala Ser Val
1790                1795                1800

Thr Ser Pro Leu Thr Thr Asn Gln Thr Met Phe Phe Asn Ile Leu
1805                1810                1815

Gly Gly Trp Val Ala Thr His Leu Ala Gly Pro Gln Ser Ser Ser
1820                1825                1830

Ala Phe Val Val Ser Gly Leu Ala Gly Ala Ala Ile Gly Gly Ile
1835                1840                1845

Gly Leu Gly Arg Val Leu Ile Asp Ile Leu Ala Gly Tyr Gly Ala
1850                1855                1860

Gly Val Ser Gly Ala Leu Val Ala Phe Lys Ile Met Gly Gly Glu
1865                1870                1875

Leu Pro Thr Ala Glu Asp Met Val Asn Met Leu Pro Ala Ile Leu
1880                1885                1890

Ser Pro Gly Ala Leu Val Val Gly Val Ile Cys Ala Ala Ile Leu
1895                1900                1905

Arg Arg His Val Gly Pro Gly Glu Gly Ala Val Gln Trp Met Asn
1910                1915                1920

Arg Leu Ile Ala Phe Ala Ser Arg Gly Asn His Val Ser Pro Thr
1925                1930                1935

His Tyr Val Pro Glu Ser Asp Ala Ala Ala Lys Val Thr Ala Leu
1940                1945                1950

Leu Ser Ser Leu Thr Val Thr Ser Leu Leu Arg Arg Leu His Gln
1955                1960                1965

Trp Ile Asn Glu Asp Tyr Pro Ser Pro Cys Cys Gly Asp Trp Leu
1970                1975                1980

Arg Thr Ile Trp Asp Trp Val Cys Met Val Leu Ser Asp Phe Lys
1985                1990                1995

Thr Trp Leu Ser Ala Lys Ile Met Pro Ala Leu Pro Gly Leu Pro
2000                2005                2010

Phe Leu Ser Cys Gln Lys Gly Tyr Lys Gly Val Trp Arg Gly Asp
2015                2020                2025

Gly Val Met Ser Thr Arg Cys Pro Cys Gly Ala Thr Ile Thr Gly
2030                2035                2040

His Val Lys Asn Gly Ser Met Arg Leu Ala Gly Pro Arg Thr Cys
2045                2050                2055

Ala Asn Met Trp His Gly Thr Phe Pro Ile Asn Glu Tyr Thr Thr
2060                2065                2070
```

```
Gly Pro Gly Thr Pro Cys Pro Ala Pro Asn Tyr Thr Arg Ala Leu
    2075            2080                2085

Leu Arg Val Ala Ala Asn Ser Tyr Val Glu Val Arg Arg Val Gly
    2090            2095                2100

Asp Phe His Tyr Ile Thr Gly Ala Thr Glu Asp Glu Leu Lys Cys
    2105            2110                2115

Pro Cys Gln Val Pro Ala Ala Glu Phe Phe Thr Glu Val Asp Gly
    2120            2125                2130

Val Arg Leu His Arg Tyr Ala Pro Pro Cys Lys Pro Leu Leu Arg
    2135            2140                2145

Asp Glu Ile Thr Phe Met Val Gly Leu Asn Ser Tyr Ala Ile Gly
    2150            2155                2160

Ser Gln Leu Pro Cys Glu Pro Glu Pro Asp Val Ser Val Leu Thr
    2165            2170                2175

Ser Met Leu Arg Asp Pro Ser His Ile Thr Ala Glu Ala Ala Ala
    2180            2185                2190

Arg Arg Leu Ala Arg Gly Ser Pro Pro Ser Glu Ala Ser Ser Ser
    2195            2200                2205

Ala Ser Gln Leu Ser Ala Pro Ser Leu Lys Ala Thr Cys Gln Ser
    2210            2215                2220

Tyr Gly Pro His Leu Asp Ala Glu Leu Val Asp Ala Asn Leu Leu
    2225            2230                2235

Trp Arg Gln Glu Met Gly Ser Thr Ile Thr Arg Val Glu Ser Glu
    2240            2245                2250

Thr Lys Val Val Ile Leu Asp Ser Phe Glu Pro Leu Arg Ala Glu
    2255            2260                2265

Thr Asp Asp Ala Glu Leu Ser Val Ala Ala Glu Cys Phe Lys Lys
    2270            2275                2280

Pro Pro Lys Tyr Pro Pro Ala Leu Pro Ile Trp Ala Arg Pro Asp
    2285            2290                2295

Tyr Asn Pro Pro Leu Leu Asp Arg Trp Lys Ala Pro Asp Tyr Val
    2300            2305                2310

Pro Pro Thr Val His Gly Cys Ala Leu Pro Pro Arg Gly Ala Pro
    2315            2320                2325

Pro Val Pro Pro Pro Arg Arg Lys Arg Thr Ile Gln Leu Asp Gly
    2330            2335                2340

Ser Asn Val Ser Ala Ala Leu Ala Ala Leu Ala Glu Lys Ser Phe
    2345            2350                2355

Pro Ser Ser Lys Pro Gln Glu Glu Asn Ser Ser Ser Ser Gly Val
    2360            2365                2370

Asp Thr Gln Ser Ser Thr Thr Ser Lys Val Pro Pro Pro Pro Gly
    2375            2380                2385

Gly Glu Ser Asp Ser Glu Ser Cys Ser Ser Met Pro Pro Leu Glu
    2390            2395                2400

Gly Glu Pro Gly Asp Pro Asp Leu Ser Cys Asp Ser Trp Ser Thr
    2405            2410                2415

Val Ser Asp Asn Glu Glu Gln Asn Val Val Cys Cys Ser Met Ser
    2420            2425                2430

Tyr Ser Trp Thr Gly Ala Leu Ile Thr Pro Cys Ser Ala Glu Glu
    2435            2440                2445

Glu Lys Leu Pro Ile Ser Pro Leu Ser Asn Ser Leu Leu Arg His
    2450            2455                2460

His Asn Leu Val Tyr Ser Thr Ser Ser Arg Ser Ala Ser Gln Arg
```

-continued

```
                2465                2470                2475
Gln Lys Lys Val Thr Phe Asp Arg Leu Gln Val Leu Asp Asp His
        2480                2485                2490
Tyr Lys Thr Ala Leu Lys Glu Val Lys Glu Arg Ala Ser Gly Val
        2495                2500                2505
Lys Ala Arg Met Leu Thr Ile Glu Glu Ala Cys Lys Leu Val Pro
        2510                2515                2520
Pro His Ser Ala Arg Ser Lys Phe Gly Tyr Ser Ala Lys Asp Ala
        2525                2530                2535
Arg Ser Leu Ser Ser Arg Ala Val Asn Gln Ile Arg Ser Val Trp
        2540                2545                2550
Glu Asp Leu Leu Glu Asp Thr Thr Pro Ile Pro Thr Thr Ile
        2555                2560                2565
Met Ala Lys Asn Glu Val Phe Cys Val Asp Pro Val Lys Gly Gly
        2570                2575                2580
Arg Lys Pro Ala Arg Leu Ile Val Tyr Pro Asp Leu Gly Val Arg
        2585                2590                2595
Val Cys Glu Lys Arg Ala Leu Tyr Asp Val Ile Gln Lys Leu Ser
        2600                2605                2610
Ile Ala Thr Met Gly Pro Ala Tyr Gly Phe Gln Tyr Ser Pro Gln
        2615                2620                2625
Gln Arg Val Glu Arg Leu Leu Lys Met Trp Thr Ser Lys Arg Thr
        2630                2635                2640
Pro Leu Gly Phe Ser Tyr Asp Thr Arg Cys Phe Asp Ser Thr Val
        2645                2650                2655
Thr Glu Gln Asp Ile Arg Val Glu Glu Ile Tyr Gln Cys Cys
        2660                2665                2670
Asn Leu Glu Pro Glu Ala Arg Lys Val Ile Ser Ser Leu Thr Glu
        2675                2680                2685
Arg Leu Tyr Cys Gly Gly Pro Met Phe Asn Ser Lys Gly Ala Gln
        2690                2695                2700
Cys Gly Tyr Arg Arg Cys Arg Ala Ser Gly Val Leu Pro Thr Ser
        2705                2710                2715
Phe Gly Asn Thr Ile Thr Cys Tyr Ile Lys Ala Thr Ala Ala Ala
        2720                2725                2730
Arg Ala Ala Gly Leu Arg Asn Pro Asp Phe Leu Val Cys Gly Asp
        2735                2740                2745
Asp Leu Val Val Val Ala Glu Ser Asp Gly Val Asp Glu Asp Arg
        2750                2755                2760
Ala Ala Leu Arg Ala Phe Thr Glu Ala Met Thr Arg Tyr Ser Ala
        2765                2770                2775
Pro Pro Gly Asp Ala Pro Gln Pro Thr Tyr Asp Leu Glu Leu Ile
        2780                2785                2790
Thr Ser Cys Ser Ser Asn Val Ser Val Ala His Asp Asn Lys Gly
        2795                2800                2805
Arg Arg Tyr Tyr Tyr Leu Thr Arg Asp Ala Thr Thr Pro Leu Ala
        2810                2815                2820
Arg Ala Ala Trp Glu Thr Ala Arg His Thr Pro Val Asn Ser Trp
        2825                2830                2835
Leu Gly Asn Ile Ile Met Tyr Ala Pro Thr Ile Trp Val Arg Met
        2840                2845                2850
Val Met Met Thr His Phe Phe Ser Ile Leu Gln Ser Gln Glu Ile
        2855                2860                2865
```

```
Leu Asp Arg Pro Leu Asp Phe Glu Met Tyr Gly Ala Thr Tyr Ser
    2870            2875                2880

Val Thr Pro Leu Asp Leu Pro Ala Ile Ile Glu Arg Leu His Gly
    2885            2890                2895

Leu Ser Ala Phe Thr Leu His Ser Tyr Ser Pro Val Glu Leu Asn
    2900            2905                2910

Arg Val Ala Gly Thr Leu Arg Lys Leu Gly Cys Pro Pro Leu Arg
    2915            2920                2925

Ala Trp Arg His Arg Ala Arg Ala Val Arg Ala Lys Leu Ile Ala
    2930            2935                2940

Gln Gly Gly Lys Ala Lys Ile Cys Gly Leu Tyr Leu Phe Asn Trp
    2945            2950                2955

Ala Val Arg Thr Lys Thr Lys Leu Thr Pro Leu Pro Ala Ala Ser
    2960            2965                2970

Gln Leu Asp Leu Ser Asn Trp Phe Ser Val Gly Val Gly Gly Asn
    2975            2980                2985

Asp Ile Tyr His Ser Val Ser His Ala Arg Thr Arg His Leu Leu
    2990            2995                3000

Leu Cys Leu Leu Leu Leu Thr Val Gly Val Gly Ile Phe Leu Leu
    3005            3010                3015

Pro Ala Arg
    3020

<210> SEQ ID NO 15
<211> LENGTH: 1989
<212> TYPE: PRT
<213> ORGANISM: Hepatitis c virus
<220> FEATURE:
<223> OTHER INFORMATION: amino acid sequence of the region from NS3
      protein to NS5B protein in the precursor protein of wild-type
      strain S310A

<400> SEQUENCE: 15

Ala Pro Ile Thr Ala Tyr Ala Gln Gln Thr Arg Gly Leu Leu Gly Thr
1               5                   10                  15

Ile Val Thr Ser Leu Thr Gly Arg Asp Lys Asn Val Val Thr Gly Glu
                20                  25                  30

Val Gln Val Leu Ser Thr Ala Thr Gln Thr Phe Leu Gly Thr Thr Ile
            35                  40                  45

Gly Gly Val Met Trp Thr Val Tyr His Gly Ala Gly Ser Arg Thr Leu
        50                  55                  60

Ala Gly Ala Lys His Pro Ala Leu Gln Met Tyr Thr Asn Val Asp Gln
65                  70                  75                  80

Asp Leu Val Gly Trp Pro Ala Pro Gly Ala Lys Ser Leu Glu Pro
                85                  90                  95

Cys Thr Cys Gly Ser Ala Asp Leu Tyr Leu Val Thr Arg Asp Ala Asp
            100                 105                 110

Val Ile Pro Ala Arg Arg Gly Asp Ser Thr Ala Ser Leu Leu Ser
            115                 120                 125

Pro Arg Pro Leu Ala Cys Leu Lys Gly Ser Ser Gly Gly Pro Val Met
    130                 135                 140

Cys Pro Ser Gly His Val Thr Gly Ile Phe Arg Ala Ala Val Cys Thr
145                 150                 155                 160

Arg Gly Val Ala Lys Thr Leu Gln Phe Ile Pro Val Glu Thr Leu Ser
                165                 170                 175
```

-continued

```
Thr Gln Thr Arg Ser Pro Ser Phe Ser Asp Asn Ser Thr Pro Pro Ala
            180                 185                 190

Val Pro Gln Ser Tyr Gln Val Gly Tyr Leu His Ala Pro Thr Gly Ser
        195                 200                 205

Gly Lys Ser Thr Lys Val Pro Ala Ala Tyr Val Ala Gln Gly Tyr His
    210                 215                 220

Val Leu Val Leu Asn Pro Ser Val Ala Ala Thr Leu Gly Phe Gly Ser
225                 230                 235                 240

Tyr Met Ser Lys Ala Tyr Gly Ile Asp Pro Asn Val Arg Thr Gly Asn
                245                 250                 255

Arg Thr Val Thr Thr Gly Ala Lys Leu Thr Tyr Ser Thr Tyr Gly Lys
            260                 265                 270

Phe Leu Ala Asp Gly Gly Cys Ser Gly Gly Ala Tyr Asp Val Ile Ile
        275                 280                 285

Cys Asp Glu Cys His Ala Gln Asp Ala Thr Thr Ile Leu Gly Ile Gly
    290                 295                 300

Thr Val Leu Asp Gln Ala Glu Thr Ala Gly Val Arg Leu Thr Val Leu
305                 310                 315                 320

Ala Thr Ala Thr Pro Pro Gly Ser Ile Thr Val Pro His Ser Asn Ile
                325                 330                 335

Glu Glu Val Ala Leu Gly Ser Glu Gly Glu Ile Pro Phe Tyr Gly Lys
            340                 345                 350

Ala Ile Pro Ile Ala Gln Leu Lys Gly Gly Arg His Leu Ile Phe Cys
        355                 360                 365

His Ser Lys Lys Lys Cys Asp Glu Ile Ala Ser Lys Leu Arg Gly Met
    370                 375                 380

Gly Leu Asn Ala Val Ala Phe Tyr Arg Gly Leu Asp Val Ser Ile Ile
385                 390                 395                 400

Pro Thr Ala Gly Asp Val Val Cys Ala Thr Asp Ala Leu Met Thr
                405                 410                 415

Gly Tyr Thr Gly Asp Phe Asp Ser Val Ile Asp Cys Asn Val Thr Val
            420                 425                 430

Glu Gln Tyr Val Asp Phe Ser Leu Asp Pro Thr Phe Ser Ile Glu Thr
        435                 440                 445

His Thr Ala Pro Gln Asp Ala Val Ser Arg Ser Gln Arg Arg Gly Arg
    450                 455                 460

Thr Gly Arg Gly Arg Leu Gly Ile Tyr Arg Tyr Val Thr Pro Gly Glu
465                 470                 475                 480

Arg Pro Ser Gly Met Phe Asp Ser Val Val Leu Cys Glu Cys Tyr Asp
                485                 490                 495

Ala Gly Cys Ser Trp Tyr Asp Leu Gln Pro Ala Glu Thr Thr Val Arg
            500                 505                 510

Leu Arg Ala Tyr Leu Ser Thr Pro Gly Leu Pro Val Cys Gln Asp His
        515                 520                 525

Leu Asp Phe Trp Glu Ser Val Phe Thr Gly Leu Thr His Ile Asp Ala
    530                 535                 540

His Phe Leu Ser Gln Thr Lys Gln Gly Leu Asn Phe Pro Tyr Leu
545                 550                 555                 560

Thr Ala Tyr Gln Ala Thr Val Cys Ala Arg Ala Gln Ala Pro Pro Pro
                565                 570                 575

Ser Trp Asp Glu Thr Trp Lys Cys Leu Val Arg Leu Lys Pro Thr Leu
            580                 585                 590

His Gly Pro Thr Pro Leu Leu Tyr Arg Leu Gly Pro Ile Gln Asn Glu
```

```
                595                 600                 605
Thr Cys Leu Thr His Pro Val Thr Lys Tyr Ile Met Ala Cys Met Ser
            610                 615                 620
Ala Asp Leu Glu Val Thr Thr Ser Ala Trp Val Leu Leu Gly Gly Val
625                 630                 635                 640
Leu Ala Ala Leu Ala Ala Tyr Cys Leu Ser Val Gly Cys Val Val Ile
                645                 650                 655
Val Gly His Ile Glu Leu Gly Gly Lys Pro Ala Leu Val Pro Asp Lys
            660                 665                 670
Glu Val Leu Tyr Gln Gln Phe Asp Glu Met Glu Glu Cys Ser Gln Ala
            675                 680                 685
Ala Pro Tyr Ile Glu Gln Ala Gln Val Ile Ala His Gln Phe Lys Glu
            690                 695                 700
Lys Val Leu Gly Leu Leu Gln Arg Ala Thr Gln Gln Gln Ala Val Ile
705                 710                 715                 720
Glu Pro Ile Val Ala Thr Asn Trp Gln Lys Leu Glu Ala Phe Trp His
                725                 730                 735
Lys His Met Trp Asn Phe Val Ser Gly Ile Gln Tyr Leu Ala Gly Leu
            740                 745                 750
Ser Thr Leu Pro Gly Asn Pro Ala Val Ala Ser Leu Met Ala Phe Thr
            755                 760                 765
Ala Ser Val Thr Ser Pro Leu Thr Thr Asn Gln Thr Met Phe Phe Asn
770                 775                 780
Ile Leu Gly Gly Trp Val Ala Thr His Leu Ala Gly Pro Gln Ser Ser
785                 790                 795                 800
Ser Ala Phe Val Val Ser Gly Leu Ala Gly Ala Ala Ile Gly Ile Gly
                805                 810                 815
Gly Leu Gly Arg Val Leu Ile Asp Ile Leu Ala Gly Tyr Gly Ala Gly
            820                 825                 830
Val Ser Gly Ala Leu Val Ala Phe Lys Ile Met Gly Gly Glu Leu Pro
            835                 840                 845
Thr Ala Glu Asp Met Val Asn Met Leu Pro Ala Ile Leu Ser Pro Gly
850                 855                 860
Ala Leu Val Val Gly Val Ile Cys Ala Ala Ile Leu Arg Arg His Val
865                 870                 875                 880
Gly Pro Gly Glu Gly Ala Val Gln Trp Met Asn Arg Leu Ile Ala Phe
            885                 890                 895
Ala Ser Arg Gly Asn His Val Ser Pro Thr His Tyr Val Pro Glu Ser
            900                 905                 910
Asp Ala Ala Ala Lys Val Thr Ala Leu Leu Ser Ser Leu Thr Val Thr
            915                 920                 925
Ser Leu Leu Arg Arg Leu His Gln Trp Ile Asn Glu Asp Tyr Pro Ser
            930                 935                 940
Pro Cys Cys Gly Asp Trp Leu Arg Thr Ile Trp Asp Trp Val Cys Met
945                 950                 955                 960
Val Leu Ser Asp Phe Lys Thr Trp Leu Ser Ala Lys Ile Met Pro Ala
                965                 970                 975
Leu Pro Gly Leu Pro Phe Leu Ser Cys Gln Lys Gly Tyr Lys Gly Val
            980                 985                 990
Trp Arg Gly Asp Gly Val Met Ser  Thr Arg Cys Pro Cys  Gly Ala Thr
            995                 1000                1005
Ile Thr  Gly His Val Lys Asn  Gly Ser Met Arg Leu  Ala Gly Pro
    1010                1015                1020
```

```
Arg Thr Cys Ala Asn Met Trp His Gly Thr Phe Pro Ile Asn Glu
    1025            1030            1035

Tyr Thr Thr Gly Pro Gly Thr Pro Cys Pro Ala Pro Asn Tyr Thr
    1040            1045            1050

Arg Ala Leu Leu Arg Val Ala Ala Asn Ser Tyr Val Glu Val Arg
    1055            1060            1065

Arg Val Gly Asp Phe His Tyr Ile Thr Gly Ala Thr Glu Asp Glu
    1070            1075            1080

Leu Lys Cys Pro Cys Gln Val Pro Ala Ala Glu Phe Phe Thr Glu
    1085            1090            1095

Val Asp Gly Val Arg Leu His Arg Tyr Ala Pro Pro Cys Lys Pro
    1100            1105            1110

Leu Leu Arg Asp Glu Ile Thr Phe Met Val Gly Leu Asn Ser Tyr
    1115            1120            1125

Ala Ile Gly Ser Gln Leu Pro Cys Glu Pro Glu Pro Asp Val Ser
    1130            1135            1140

Val Leu Thr Ser Met Leu Arg Asp Pro Ser His Ile Thr Ala Glu
    1145            1150            1155

Ala Ala Ala Arg Arg Leu Ala Arg Gly Ser Pro Pro Ser Glu Ala
    1160            1165            1170

Ser Ser Ser Ala Ser Gln Leu Ser Ala Pro Ser Leu Lys Ala Thr
    1175            1180            1185

Cys Gln Ser Tyr Gly Pro His Leu Asp Ala Glu Leu Val Asp Ala
    1190            1195            1200

Asn Leu Leu Trp Arg Gln Glu Met Gly Ser Thr Ile Thr Arg Val
    1205            1210            1215

Glu Ser Glu Thr Lys Val Val Ile Leu Asp Ser Phe Glu Pro Leu
    1220            1225            1230

Arg Ala Glu Thr Asp Asp Ala Glu Leu Ser Val Ala Ala Glu Cys
    1235            1240            1245

Phe Lys Lys Pro Pro Lys Tyr Pro Pro Ala Leu Pro Ile Trp Ala
    1250            1255            1260

Arg Pro Asp Tyr Asn Pro Pro Leu Leu Asp Arg Trp Lys Ala Pro
    1265            1270            1275

Asp Tyr Val Pro Pro Thr Val His Gly Cys Ala Leu Pro Pro Arg
    1280            1285            1290

Gly Ala Pro Pro Val Pro Pro Pro Arg Arg Lys Arg Thr Ile Gln
    1295            1300            1305

Leu Asp Gly Ser Asn Val Ser Ala Ala Leu Ala Ala Leu Ala Glu
    1310            1315            1320

Lys Ser Phe Pro Ser Ser Lys Pro Gln Glu Glu Asn Ser Ser Ser
    1325            1330            1335

Ser Gly Val Asp Thr Gln Ser Ser Thr Thr Ser Lys Val Pro Pro
    1340            1345            1350

Pro Pro Gly Gly Glu Ser Asp Ser Glu Ser Cys Ser Ser Met Pro
    1355            1360            1365

Pro Leu Glu Gly Glu Pro Gly Asp Pro Asp Leu Ser Cys Asp Ser
    1370            1375            1380

Trp Ser Thr Val Ser Asp Asn Glu Glu Gln Asn Val Val Cys Cys
    1385            1390            1395

Ser Met Ser Tyr Ser Trp Thr Gly Ala Leu Ile Thr Pro Cys Ser
    1400            1405            1410
```

```
Ala Glu Glu Glu Lys Leu Pro Ile Ser Pro Leu Ser Asn Ser Leu
    1415                1420                1425

Leu Arg His His Asn Leu Val Tyr Ser Thr Ser Ser Arg Ser Ala
    1430                1435                1440

Ser Gln Arg Gln Lys Lys Val Thr Phe Asp Arg Leu Gln Val Leu
    1445                1450                1455

Asp Asp His Tyr Lys Thr Ala Leu Lys Glu Val Lys Glu Arg Ala
    1460                1465                1470

Ser Gly Val Lys Ala Arg Met Leu Thr Ile Glu Glu Ala Cys Lys
    1475                1480                1485

Leu Val Pro Pro His Ser Ala Arg Ser Lys Phe Gly Tyr Ser Ala
    1490                1495                1500

Lys Asp Ala Arg Ser Leu Ser Ser Arg Ala Val Asn Gln Ile Arg
    1505                1510                1515

Ser Val Trp Glu Asp Leu Leu Glu Asp Thr Thr Thr Pro Ile Pro
    1520                1525                1530

Thr Thr Ile Met Ala Lys Asn Glu Val Phe Cys Val Asp Pro Val
    1535                1540                1545

Lys Gly Gly Arg Lys Pro Ala Arg Leu Ile Val Tyr Pro Asp Leu
    1550                1555                1560

Gly Val Arg Val Cys Glu Lys Arg Ala Leu Tyr Asp Val Ile Gln
    1565                1570                1575

Lys Leu Ser Ile Ala Thr Met Gly Pro Ala Tyr Gly Phe Gln Tyr
    1580                1585                1590

Ser Pro Gln Gln Arg Val Glu Arg Leu Leu Lys Met Trp Thr Ser
    1595                1600                1605

Lys Arg Thr Pro Leu Gly Phe Ser Tyr Asp Thr Arg Cys Phe Asp
    1610                1615                1620

Ser Thr Val Thr Glu Gln Asp Ile Arg Val Glu Glu Glu Ile Tyr
    1625                1630                1635

Gln Cys Cys Asn Leu Glu Pro Glu Ala Arg Lys Val Ile Ser Ser
    1640                1645                1650

Leu Thr Glu Arg Leu Tyr Cys Gly Gly Pro Met Phe Asn Ser Lys
    1655                1660                1665

Gly Ala Gln Cys Gly Tyr Arg Arg Cys Arg Ala Ser Gly Val Leu
    1670                1675                1680

Pro Thr Ser Phe Gly Asn Thr Ile Thr Cys Tyr Ile Lys Ala Thr
    1685                1690                1695

Ala Ala Ala Arg Ala Ala Gly Leu Arg Asn Pro Asp Phe Leu Val
    1700                1705                1710

Cys Gly Asp Asp Leu Val Val Val Ala Glu Ser Asp Gly Val Asp
    1715                1720                1725

Glu Asp Arg Ala Ala Leu Arg Ala Phe Thr Glu Ala Met Thr Arg
    1730                1735                1740

Tyr Ser Ala Pro Pro Gly Asp Ala Pro Gln Pro Thr Tyr Asp Leu
    1745                1750                1755

Glu Leu Ile Thr Ser Cys Ser Ser Asn Val Ser Val Ala His Asp
    1760                1765                1770

Asn Lys Gly Arg Arg Tyr Tyr Tyr Leu Thr Arg Asp Ala Thr Thr
    1775                1780                1785

Pro Leu Ala Arg Ala Ala Trp Glu Thr Ala Arg His Thr Pro Val
    1790                1795                1800

Asn Ser Trp Leu Gly Asn Ile Ile Met Tyr Ala Pro Thr Ile Trp
```

Val Arg Met Val Met Met Thr His Phe Phe Ser Ile Leu Gln Ser
1805                1810                1815

Gln Glu Ile Leu Asp Arg Pro Leu Asp Phe Glu Met Tyr Gly Ala
     1820                1825                1830

Thr Tyr Ser Val Thr Pro Leu Asp Leu Pro Ala Ile Ile Glu Arg
          1835                1840                1845

Leu His Gly Leu Ser Ala Phe Thr Leu His Ser Tyr Ser Pro Val
               1850                1855                1860

Glu Leu Asn Arg Val Ala Gly Thr Leu Arg Lys Leu Gly Cys Pro
                    1865                1870                1875

Pro Leu Arg Ala Trp Arg His Arg Ala Arg Ala Val Arg Ala Lys
                         1880                1885                1890

Leu Ile Ala Gln Gly Gly Lys Ala Lys Ile Cys Gly Leu Tyr Leu
1895                1900                1905

Phe Asn Trp Ala Val Arg Thr Lys Thr Lys Leu Thr Pro Leu Pro
     1910                1915                1920

Ala Ala Ser Gln Leu Asp Leu Ser Asn Trp Phe Ser Val Gly Val
          1925                1930                1935

Gly Gly Asn Asp Ile Tyr His Ser Val Ser His Ala Arg Thr Arg
               1940                1945                1950

His Leu Leu Leu Cys Leu Leu Leu Leu Thr Val Gly Val Gly Ile
                    1955                1960                1965

Phe Leu Leu Pro Ala Arg
                         1970

<210> SEQ ID NO 16
<211> LENGTH: 7995
<212> TYPE: DNA
<213> ORGANISM: Hepatitis c virus
<220> FEATURE:
<223> OTHER INFORMATION: cDNA sequence of HCV subgenomic replicon RNA of
      wild-type strain S310A

<400> SEQUENCE: 16
gacctgcctc ttacgaggcg acactccacc atggatcact cccctgtgag gaacttctgt    60
cttcacgcgg aaagcgccta gccatggcgt tagtacgagt gtcgtgcagc ctccaggacc   120 cccctcccg  ggagagccat agtggtctgc ggaaccggtg agtacaccgg aatcgctggg   180
gtgaccgggt cctttcttgg aacaacccgc tcaataccca gaaatttggg cgtgcccccg   240
cgagatcact agccgagtag tgttgggtcg cgaaaggcct gtggtactg  cctgataggg   300 tgcttgcgag tgccccggga ggtctcgtag accgtgcaac atgagcacac ttcctaaacc   360
ccaaagaaaa accaaaagaa acaccatccg tcgcccaatg attgaacaag atggattgca   420
cgcaggttct ccggccgctt gggtggagag ctattcggc  tatgactggg cacaacagac   480
aatcggctgc tctgatgccg ccgtgttccg gctgtcagcg caggggcgcc cggttctttt   540
tgtcaagacc gacctgtccg gtgccctgaa tgaactgcag gacgaggcag cgcggctatc   600
gtggctggcc acgacgggcg ttccttgcgc agctgtgctc gacgttgtca ctgaagcggg   660
aagggactgg ctgctattgg gcgaagtgcc ggggcaggat ctcctgtcat ctcaccttgc   720
tcctgccgag aaagtatcca tcatggctga tgcaatgcgg cggctgcata cgcttgatcc   780
ggctacctgc ccattcgacc accaagcgaa acatcgcatc gagcgagcac gtactcggat   840
ggaagccggt cttgtcgatc aggatgatct ggacgaagag catcagggc  tcgcgccagc   900

```
cgaactgttc gccaggctca aggcgcgcat gcccgacggc gaggatctcg tcgtgaccca    960
tggcgatgcc tgcttgccga atatcatggt ggaaaatggc cgcttttctg gattcatcga   1020
ctgtggccgg ctgggtgtgg cggaccgcta tcaggacata gcgttggcta cccgtgatat   1080
tgctgaagag cttggcggcg aatgggctga ccgcttcctc gtgctttacg gtatcgccgc   1140
tcccgattcg cagcgcatcg ccttctatcg ccttcttgac gagttcttct gagtttaaac   1200
cctctccctc ccccccccct aacgttactg gccgaagccg cttggaataa ggccggtgtg   1260
cgtttgtcta tatgttattt tccaccatat tgccgtcttt tggcaatgtg agggcccgga   1320
aacctggccc tgtcttcttg acgagcattc ctaggggtct ttcccctctc gccaaaggaa   1380
tgcaaggtct gttgaatgtc gtgaaggaag cagttcctct ggaagcttct tgaagacaaa   1440
caacgtctgt agcgaccctt tgcaggcagc ggaaccccccc acctggcgac aggtgcctct   1500
gcggccaaaa gccacgtgta aagatacac ctgcaaaggc ggcacaaccc cagtgccacg    1560
ttgtgagttg gatagttgtg gaaagagtca aatggctctc ctcaagcgta ttcaacaagg   1620
ggctgaagga tgcccagaag gtaccccatt gtatgggatc tgatctgggg cctcggtgca   1680
catgctttac atgtgtttag tcgaggttaa aaaaacgtct aggcccccccg aaccacgggg   1740
acgtggtttt cctttgaaaa acacgatgat accatggccc cgatcactgc ttacgcccag   1800
caaaccaggg gccttcttgg gactattgtg accagcttga ctggcaggga taagaatgtg   1860
gtgaccggcg aagtgcaggt gctttctacg gctacccaga ccttcctagg tacaacaata   1920
gggggggtta tgtggactgt ttaccatggc gcaggctcaa ggacacttgc gggcgctaaa   1980
catcctgcgc tccaaatgta cacaaatgta gatcaggacc tcgttgggtg gccagccccct  2040
ccaggggcta agtctcttga accgtgcacc tgcgggtctg cagacttata cttggttacc   2100
cgcgatgctg acgtcatccc cgctcggcgc aggggggact ccacagcgag cttgctcagc   2160
cctaggcctc tcgcctgtct caagggctcc tctggaggtc ccgttatgtg cccttcgggg   2220
catgtcacgg ggatctttcg ggctgctgtg tgcaccagag gtgtagcaaa gaccctacag   2280
ttcataccag tggaaaccct tagtacacag actaggtccc catccttctc tgacaattca   2340
actcctcccg ccgtcccaca gagctaccaa gtagggtatc ttcatgcccc gaccggtagt   2400
ggcaagagca caaaggtccc ggccgcttac gtagcacaag gataccatgt tctcgtgttg   2460
aatccatcag tggcggccac actaggcttc ggctcttaca tgtcgaaagc ctatgggatc   2520
gaccccaacg tccgcactgg gaaccgcact gtcacaactg gtgctaaact gacctattcc   2580
acctacggta gtttctcgc ggatgggggt tgctctgggg gagcgtatga tgtgattatt    2640
tgtgatgaat gccatgccca agacgctact accatattgg gtattggcac ggtcttagat   2700
caggctgaga cggctggggt gaggctgacg gttctggcga cagcaactcc cccaggcagc   2760
atcactgtgc cacattctaa catcgaggag gtagccctgg gctctgaagg tgagatccct   2820
ttctacggta aggctatacc gatagcccag ctcaagggg gaggcacct tatcttttgc     2880
cattccaaga aaagtgtga tgagatagca tccaagctca gaggcatggg gctcaacgct    2940
gtagcattct ataggggtct tgatgtgtcc atcataccaa cagcaggaga cgtcgtggtt   3000
tgcgccactg acgccctcat gactgggtac accggagact tgattctgt catagattgc    3060
aacgtgactg ttgaacagta cgttgacttc agcttggacc ccaccttttc cattgagact   3120
cacactgctc cccaagacgc ggtttcccgc agccaacgtc gtggccgtac gggccggggt   3180
agactcggca tataccgata tgtcaccccg ggtgaaagac cgtctggaat gtttgactcg   3240
gttgttctct gtgagtgcta tgatgcgggc tgctcgtggt acgatctgca gcccgctgag   3300
```

```
actacagtca gactgagagc ttacttgtcc acgccgggtt tacctgtctg tcaagaccat    3360
cttgactttt gggagagcgt ctttactgga ctaactcaca tagatgccca ctttctgtca    3420
cagactaagc agcagggact caacttcccg tacctgactg cctaccaagc cactgtgtgc    3480
gcccgcgcg aggctcctcc cccaagttgg gacgagacgt ggaaatgtct cgtacggctt     3540
aaaccaacac tacatggacc cacgcccctt ctgtatcggt tggggcctat ccaaaatgaa    3600
acctgcttga cacaccccgt cacaaaatac atcatggcat gcatgtcagc tgatctggaa    3660
gtgaccacca gcgcctgggt gttgcttgga ggggtgctcg cggccctagc ggcttactgc    3720
ttgtcagtcg gctgcgttgt gatcgtgggt catattgagc tggggggcaa gccagcactc    3780
gttccagaca aagaggtgtt gtatcaacaa ttcgatgaga tggaggagtg ctcgcaagct    3840
gccccatata tcgaacaagc tcaggtaata gcccaccagt tcaaggagaa agtccttgga    3900
ttgctgcagc gagccaccca acaacaagct gtcattgagc ccatagtagc taccaactgg    3960
caaaagcttg aggcgttctg gcacaagcat atgtggaatt ttgtgagtgg gatccagtac    4020
ctagcaggcc tttccacttt gcctggcaac cccgctgtgg cgtctcttat ggcgttcacc    4080
gcttctgtca ccagtcccct gacgaccaac caaactatgt tcttcaacat actcgggggg    4140
tgggttgcta cccatttggc agggccccag agctcttccg cattcgtggt aagcggcttg    4200
gccggcgctg ccataggggg tataggcctg gcagggtct tgattgacat cctggcagga    4260
tacgagctg gtgtctcagg cgccttggtg gcttttaaga tcatgggagg agaactcccc    4320
actgctgagg acatggtcaa catgctgcct gccatactat ctccgggcgc cctcgttgtc    4380
ggtgtgatat gtgcagccat actgcgtcga cacgtaggac ctggggaggg ggcggtgcag    4440
tggatgaaca ggctcatcgc attcgcatcc cggggtaacc acgtctcacc gacgcactat    4500
gtccccgaga gcgatgctgc agcgaaggtt actgcattgc tgagttctct aactgtcaca    4560
agtctgctcc ggcgactgca ccagtggatc aatgaagact acccaagtcc ttgctgcggc    4620
gactggctgc gtaccatctg ggactgggtt tgcatggtgt tgtctgactt caagacatgg    4680
ctctccgcta agattatgcc agcgctccct gggctgcctt tccttttcctg tcagaaggga    4740
tacaagggcg tgtggcgggg agacggtgtg atgtcgacac gctgtccttg cggggcgaca    4800
ataaccggtc atgtgaagaa tgggtctatg cggcttgcag ggccacgcac atgtgctaac    4860
atgtggcacg gtactttccc catcaatgag tacaccaccg gacccggcac accttgccca    4920
gcacccaact acactcgcgc attattgcgc gtggctgcca acagctacgt tgaggtgcgc    4980
cgggtggggg acttccacta cattacgggg gctacagaag atgagctcaa gtgtccgtgc    5040
caagtgccgg ccgcagagtt ttttactgag gtggatgggg tgagactcca ccgttacgcc    5100
cctccatgca gcccctgtt gagggatgaa atcactttca tggtagggtt gaactcctac    5160
gcaataggat ctcaactccc ctgtgagccc gaaccagatg tttctgtgct gacctcgatg    5220
ttgagagacc cttcccatat taccgctgag gcagcagcgc gccgccttgc gcgtgggtcc    5280
cctccatcag aggcaagctc atccgccagc caactgtcgg ctccgtcgtt gaaggccact    5340
tgtcagtcgt atgggcctca tctggacgct gagctagtgg atgccaacct gttatggcgg    5400
caggagatgg gcagcactat cacacgggta gagtctgaaa caaggttgt gattcttgat    5460
tcattcgaac tctgagagc cgaaactgat gacgccgagc tctcggtggc tgcagagtgt    5520
ttcaagaagc ctcccaagta tcctccagcc cttcctatct gggctaggcc agactacaac    5580
cctccattgt tagaccgctg gaaagcaccg gattatgttc caccaactgt tcatggatgc    5640
```

```
gccttaccac cacggggcgc tccaccggtg cctcccccte ggaggaagag aacaattcag   5700
ctggatggct ccaatgtgtc cgcggcgcta gctgcgctag cagaaaagtc attcccgtcc   5760
tcaaagccgc aggaagagaa tagctcatcc tcaggggtcg acacacagtc cagcactacc   5820
tctaaggtgc cccccccccc aggagggaa tccgactcag agtcgtgctc gtccatgcct    5880
cctctcgagg gagagccggg cgatccggat ttgagctgcg actcttggtc cactgtgagt   5940
gacaatgagg agcagaacgt agtctgctgc tccatgtcgt actcttggac cggcgccttg   6000
ataacaccat gtagtgctga ggaggagaaa ctacccatca gcccactcag caactccttg   6060
ttgagacacc ataatctggt ttattcaacg tcgtcaagaa gcgcttctca gcgtcagaag   6120
aaggttacct tcgacaggct gcaggtgctc gacgaccact acaaaactgc tttaaaggag   6180
gtaaaggagc gagcgtctgg ggtgaaggct cgcatgctca ccatcgagga agcgtgcaag   6240
cttgtccccc cccactctgc ccgttcgaag ttcgggtata gtgcgaagga cgctcgttcc   6300
ttgtccagca gggccgttaa ccagatccgc tccgtctggg aggacttgct ggaagacacc   6360
acaactccaa ttccaacaac catcatggcg aagaacgagg tgttttgtgt ggaccccgtt   6420
aagggggggcc gcaagcccgc tcgcctcatt gtgtaccctg acctgggggt gcgtgtctgt   6480
gagaaacgcg cccctatatga cgtgatacag aagttgtcaa tcgcgacgat gggtcctgct   6540
tatggattcc agtactcgcc tcagcagcgg gtcgaacgtc tgctgaagat gtggacctca   6600
aagagaaccc ccctgggggtt ctcgtatgac acccgctgct ttgactcgac tgtcactgaa   6660
caggatatca gggtggaaga ggagatatat caatgctgta accttgaacc ggaggccagg   6720
aaggtgatct cctcccctcac ggagcggctt tactgcgggg gccccatgtt caacagcaag   6780
ggggcccagt gcggttatcg ccgttgccgt gctagtggag ttctaccgac cagctttggc   6840
aacacaatca cttgttacat caaggccaca gcggctgcaa gggccgcggg tctccggaac   6900
ccggactttc ttgtctgcgg agatgatttg gtcgtggtgg ccgagagtga tggcgtcgac   6960
gaggataggg cagccctgag agccttcacg gaggctatga ccaggtactc tgctccaccc   7020
ggagatgctc cacagcctac ctacgacctt gagctcatca catcttgctc ctctaacgtc   7080
tccgtagcac atgacaacaa ggggaggagg tattactacc tcacccgtga tgccactact   7140
cccctggccc gtgcggcttg ggaaacagct cgtcacactc cagttaactc ctggttgggc   7200
aacatcatca tgtacgcgcc taccatctgg gtgcgcatgg tgatgatgac acactttttc   7260
tccatactcc aatcccagga gatacttgat cgcccccttg attttgaaat gtacggggcc   7320
acttactctg tcactccgct ggatttacca gcaatcattg aaagactcca tggtctaagc   7380
gcgttcacac tccacagtta ctctccagta gaactcaata gggtcgcggg gacactcagg   7440
aagcttgggt gccccccccct acgagcttgg agacatcggg cacgagcagt gcgcgctaag   7500
cttattgccc agggaggtaa ggccaaaata tgtggccttt atctctttaa ctgggcagta   7560
cgcaccaaga ccaaactcac tccactgcca gccgctagcc agttggactt atccaattgg   7620
ttttcggttg gcgtcggcgg gaacgacatt tatcacagcg tgtcacatgc ccgaacccgc   7680
catttgctgc tttgcctact cctactaact gtaggggtag gcatctttct cctgccagca   7740
cgataagctg gtaggataac actccattcc ttttcccttg tttttatttt tttttttttt   7800
tttttttttt tttttttttt ttctttttt tttttttttt tttttttttg tttttcctct   7860
ttccattctt ttctaacctt aaattttcct ttctttaggt ggctccatct tagccctagt   7920
cacggctagc tgtgaaaggt ccgtgagccg catgactgca gagagtgccg taactggtct   7980
ctctgcagat catgt                                                    7995
```

<210> SEQ ID NO 17
<211> LENGTH: 7995
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA sequence of mutant S310A T1286I HCV subgenomic replicon RNA

<400> SEQUENCE: 17
gacctgcctc ttacgaggcg acactccacc atggatcact cccctgtgag gaacttctgt 60
cttcacgcgg aaagcgccta gccatggcgt tagtacgagt gtcgtgcagc ctccaggacc 120
ccccctcccg ggagagccat agtggtctgc ggaaccggtg agtacaccgg aatcgctggg 180
gtgaccgggt cctttcttgg aacaacccgc tcaataccca gaaatttggg cgtgcccccg 240
cgagatcact agccgagtag tgttgggtcg cgaaaggcct tgtggtactg cctgataggg 300
tgcttgcgag tgccccggga ggtctcgtag accgtgcaac atgagcacac ttcctaaacc 360
ccaaagaaaa accaaaagaa acaccatccg tcgcccaatg attgaacaag atggattgca 420
cgcaggttct ccggccgctt gggtggagag gctattcggc tatgactggg cacaacagac 480
aatcggctgc tctgatgccg ccgtgttccg gctgtcagcg caggggcgcc cggttctttt 540
tgtcaagacc gacctgtccg gtgccctgaa tgaactgcag gacgaggcag cgcggctatc 600
gtggctggcc acgacgggcg ttccttgcgc agctgtgctc gacgttgtca ctgaagcggg 660
aagggactgg ctgctattgg gcgaagtgcc ggggcaggat ctcctgtcat ctcaccttgc 720
tcctgccgag aaagtatcca tcatggctga tgcaatgcgg cggctgcata cgcttgatcc 780
ggctacctgc ccattcgacc accaagcgaa acatcgcatc gagcgagcac gtactcggat 840
ggaagccggt cttgtcgatc aggatgatct ggacgaagag catcaggggc tcgcgccagc 900
cgaactgttc gccaggctca aggcgcgcat gcccgacggc gaggatctcg tcgtgaccca 960
tggcgatgcc tgcttgccga atatcatggt ggaaaatggc cgcttttctg gattcatcga 1020
ctgtggccgg ctgggtgtgg cggaccgcta tcaggacata gcgttggcta cccgtgatat 1080
tgctgaagag cttggcggcg aatgggctga ccgcttcctc gtgctttacg gtatcgccgc 1140
tcccgattcg cagcgcatcg ccttctatcg ccttcttgac gagttcttct gagtttaaac 1200
cctctccctc cccccccct aacgttactg gccgaagccg cttggaataa ggccggtgtg 1260
cgtttgtcta tatgttattt tccaccatat tgccgtcttt tggcaatgtg agggcccgga 1320
aacctggccc tgtcttcttg acgagcattc ctaggggtct ttcccctctc gccaaaggaa 1380
tgcaaggtct gttgaatgtc gtgaaggaag cagttcctct ggaagcttct tgaagacaaa 1440
caacgtctgt agcgaccctt tgcaggcagc ggaacccccc acctggcgac aggtgcctct 1500
gcggccaaaa gccacgtgta taagatacac ctgcaaaggc ggcacaaccc cagtgccacg 1560
ttgtgagttg gatagttgtg gaaagagtca aatggctctc ctcaagcgta ttcaacaagg 1620
ggctgaagga tgcccagaag gtaccccatt gtatgggatc tgatctgggg cctcggtgca 1680
catgctttac atgtgtttag tcgaggttaa aaaaacgtct aggccccccg aaccacgggg 1740
acgtggtttt cctttgaaaa acacgatgat accatggccc cgatcactgc ttacgcccag 1800
caaaccaggg gccttcttgg gactattgtg accagcttga ctggcaggga taagaatgtg 1860
gtgaccggcg aagtgcaggt gctttctacg gctacccaga ccttcctagg tacaacaata 1920

```
ggggggggtta tgtggactgt ttaccatggc gcaggctcaa ggacacttgc gggcgctaaa    1980
catcctgcgc tccaaatgta cacaaatgta gatcaggacc tcgttgggtg gccagcccct    2040
ccagggccta agtctcttga accgtgcacc tgcgggtctg cagacttata cttggttacc    2100
cgcgatgctg acgtcatccc cgctcggcgc agggggggact ccacagcgag cttgctcagc    2160
cctaggcctc tcgcctgtct caagggctcc tctggaggtc ccgttatgtg cccttcgggg    2220
catgtcacgg ggatctttcg ggctgctgtg tgcaccagag gtgtagcaaa gaccctacag    2280
ttcataccag tggaaaccct tagtacacag actaggtccc catccttctc tgacaattca    2340
actcctcccg ccgtcccaca gagctaccaa gtagggtatc ttcatgcccc gaccggtagt    2400
ggcaagagca caaaggtccc ggccgcttac gtagcacaag gataccatgt tctcgtgttg    2460
aatccatcag tggcggccac actaggcttc ggctcttaca tgtcgaaagc ctatgggatc    2520
gaccccaacg tccgcattgg gaaccgcact gtcacaactg gtgctaaact gacctattcc    2580
acctacggta agtttctcgc ggatgggggt tgctctgggg gagcgtatga tgtgattatt    2640
tgtgatgaat gccatgccca agacgctact accatattgg gtattggcac ggtcttagat    2700
caggctgaga cggctggggt gaggctgacg gttctggcga cagcaactcc cccaggcagc    2760
atcactgtgc cacattctaa catcgaggag gtagccctgg gctctgaagg tgagatccct    2820
ttctacggta aggctatacc gatagcccag ctcaagggg ggaggcacct tatcttttgc    2880
cattccaaga aaagtgtga tgagatagca tccaagctca gaggcatggg gctcaacgct    2940
gtagcattct atagggtct tgatgtgtcc atcataccaa cagcaggaga cgtcgtggtt    3000
tgcgccactg acgccctcat gactgggtac accggagact tgattctgt catagattgc    3060
aacgtgactg ttgaacagta cgttgacttc agcttggacc ccaccttttc cattgagact    3120
cacactgctc cccaagacgc ggtttcccgc agccaacgtc gtggccgtac gggccggggt    3180
agactcggca tataccgata tgtcaccccg ggtgaaagac cgtctggaat gtttgactcg    3240
gttgttctct gtgagtgcta tgatgcgggc tgctcgtggt acgatctgca gcccgctgag    3300
actacagtca gactgagagc ttacttgtcc acgccgggtt tacctgtctg tcaagaccat    3360
cttgactttt gggagagcgt ctttactgga ctaactcaca tagatgccca cttctctgtca   3420
cagactaagc agcagggact caacttcccg tacctgactg cctaccaagc cactgtgtgc    3480
gcccgcgcgc aggctcctcc cccaagttgg gacgagacgt ggaaatgtct cgtacggctt    3540
aaaccaacac tacatggacc cacgccccttc tgtatcggt tggggcctat ccaaaatgaa    3600
acctgcttga cacaccccgt cacaaaatac atcatggcat gcatgtcagc tgatctggaa    3660
gtgaccacca gcgcctgggt gttgcttgga ggggtgctcg cggccctagc ggcttactgc    3720
ttgtcagtcg gctgcgttgt gatcgtgggt catattgagc tgggggggcaa gccagcactc    3780
gttccagaca aagaggtgtt gtatcaacaa ttcgatgaga tggaggagtg ctcgcaagct    3840
gccccatata tcgaacaagc tcaggtaata gcccaccagt tcaaggagaa agtccttgga    3900
ttgctgcagc gagccaccca acaacaagct gtcattgagc ccatagtagc taccaactgg    3960
caaaagcttg aggcgttctg gcacaagcat atgtggaatt ttgtgagtgg gatccagtac    4020
ctagcaggcc tttccacttt gcctggcaac cccgctgtgg cgtctcttat ggcgttcacc    4080
gcttctgtca ccagtccct gacgaccaac caaactatgt tcttcaacat actcggggg    4140
tgggttgcta cccatttggc agggcccag agctcttccg cattcgtggt aagcggcttg    4200
gccgcgctc ccataggggg tataggcctg ggcagggtct tgattgacat cctggcagga    4260
tacggagctg gtgtctcagg cgccttggtg gcttttaaga tcatgggagg agaactcccc    4320
```

```
actgctgagg acatggtcaa catgctgcct gccatactat ctccgggcgc cctcgttgtc    4380
ggtgtgatat gtgcagccat actgcgtcga cacgtaggac ctggggaggg ggcggtgcag    4440
tggatgaaca ggctcatcgc attcgcatcc cggggtaacc acgtctcacc gacgcactat    4500
gtccccgaga gcgatgctgc agcgaaggtt actgcattgc tgagttctct aactgtcaca    4560
agtctgctcc ggcgactgca ccagtggatc aatgaagact acccaagtcc ttgctgcggc    4620
gactggctgc gtaccatctg ggactgggtt tgcatggtgt tgtctgactt caagacatgg    4680
ctctccgcta agattatgcc agcgctccct gggctgcctt tcctttcctg tcagaaggga    4740
tacaagggcg tgtggcgggg agacggtgtg atgtcgacac gctgtccttg cggggcgaca    4800
ataaccggtc atgtgaagaa tgggtctatg cggcttgcag ggccacgcac atgtgctaac    4860
atgtggcacg gtactttccc catcaatgag tacaccaccg gacccggcac accttgccca    4920
gcacccaact acactcgcgc attattgcgc gtggctgcca acagctacgt tgaggtgcgc    4980
cgggtgggga acttccacta cattacgggg gctacagaag atgagctcaa gtgtccgtgc    5040
caagtgccgg ccgcagagtt ttttactgag gtggatgggg tgagactcca ccgttacgcc    5100
cctccatgca agccnctgtt gagggatgaa atcacttttca tggtagggtt gaactcctac    5160
gcaataggat ctcaactccc ctgtgagccc gaaccagatg tttctgtgct gacctcgatg    5220
ttgagagacc cttcccatat taccgctgag gcagcagcgc gccgccttgc gcgtgggtcc    5280
cctccatcag aggcaagctc atccgccagc caactgtcgg ctccgtcgtt gaaggccact    5340
tgtcagtcgt atgggcctca tctggacgct gagctagtgg atgccaacct gttatggcgg    5400
caggagatgg gcagcactat cacacgggta gagtctgaaa caaaggttgt gattcttgat    5460
tcattcgaac ctctgagagc cgaaactgat gacgccgagc tctcggtggc tgcagagtgt    5520
ttcaagaagc ctcccaagta tcctccagcc cttcctatct gggctaggcc agactacaac    5580
cctccattgt tagaccgctg gaaagcaccg gattatgttc caccaactgt tcatggatgc    5640
gccttaccac cacgggcgc tccaccggtg cctcccctc ggaggaagag aacaattcag    5700
ctggatggct ccaatgtgtc cgcggcgcta gctgcgctag cagaaaagtc attcccgtcc    5760
tcaaagccgc aggaagagaa tagctcatcc tcagggtcg acacacagtc cagcactacc    5820
tctaaggtgc ccccccccccc aggaggggaa tccgactcag agtcgtgctc gtccatgcct    5880
cctctcgagg gagagccggg cgatccggat ttgagctgcg actcttggtc cactgtgagt    5940
gacaatgagg agcagaacgt agtctgctgc tccatgtcgt actcttggac cggcgccttg    6000
ataacaccat gtagtgctga ggaggagaaa ctacccatca gcccactcag caactccttg    6060
ttgagacacc ataatctggt ttattcaacg tcgtcaagaa gcgcttctca gcgtcagaag    6120
aaggttacct tcgacaggct gcaggtgctc gacgaccact acaaaactgc tttaaaggag    6180
gtaaaggagc gagcgtctgg ggtgaaggct cgcatgctca ccatcgagga agcgtgcaag    6240
cttgtccccc cccactctgc ccgttcgaag ttcgggtata tgcgaagga cgctcgttcc    6300 ttgtccagca gggccgttaa ccagatccgc tccgtctggg aggacttgct ggaagacacc    6360
acaactccaa ttccaacaac catcatggcg aagaacgagg tgttttgtgt ggaccccgtt    6420 aagggggggcc gcaagcccgc tcgcctcatt gtgtaccctg acctggggt gcgtgtctgt    6480 gagaaacgcg ccctatatga cgtgatacag aagttgtcaa tcgcgacgat gggtcctgct    6540
tatggattcc agtactcgcc tcagcagcgg gtcgaacgtc tgctgaagat gtggaccaca    6600
aagagaaccc ccctgggggtt ctcgtatgac acccgctgct tgactcgac tgtcactgaa    6660
```

| caggatatca | gggtggaaga | ggagatatat | caatgctgta | accttgaacc | ggaggccagg | 6720 |
| aaggtgatct | cctccctcac | ggagcggctt | tactgcgggg | gccccatgtt | caacagcaag | 6780 |
| ggggcccagt | gcggttatcg | ccgttgccgt | gctagtggag | ttctaccgac | cagctttggc | 6840 |
| aacacaatca | cttgttacat | caaggccaca | gcggctgcaa | gggccgcggg | tctccggaac | 6900 |
| ccggactttc | ttgtctgcgg | agatgatttg | gtcgtggtgg | ccgagagtga | tggcgtcgac | 6960 |
| gaggataggg | cagccctgag | agccttcacg | gaggctatga | ccaggtactc | tgctccaccc | 7020 |
| ggagatgctc | cacagcctac | ctacgacctt | gagctcatca | catcttgctc | ctctaacgtc | 7080 |
| tccgtagcac | atgacaacaa | ggggaggagg | tattactacc | tcacccgtga | tgccactact | 7140 |
| cccctggccc | gtgcggcttg | ggaaacagct | cgtcacactc | cagttaactc | ctggttgggc | 7200 |
| aacatcatca | tgtacgcgcc | taccatctgg | gtgcgcatgg | tgatgatgac | acacttttc | 7260 |
| tccatactcc | aatcccagga | gatacttgat | cgccccttg | attttgaaat | gtacggggcc | 7320 |
| acttactctg | tcactccgct | ggatttacca | gcaatcattg | aaagactcca | tggtctaagc | 7380 |
| gcgttcacac | tccacagtta | ctctccagta | gaactcaata | gggtcgcggg | gacactcagg | 7440 |
| aagcttgggt | gcccccccct | acgagcttgg | agacatcggg | cacgagcagt | gcgcgctaag | 7500 |
| cttattgccc | agggaggtaa | ggccaaaata | tgtggccttt | atctctttaa | ctgggcagta | 7560 |
| cgcaccaaga | ccaaactcac | tccactgcca | gccgctagcc | agttggactt | atccaattgg | 7620 |
| ttttcggttg | gcgtcggcgg | gaacgacatt | tatcacagcg | tgtcacatgc | ccgaacccgc | 7680 |
| catttgctgc | tttgcctact | cctactaact | gtaggggtag | gcatctttct | cctgccagca | 7740 |
| cgataagctg | gtaggataac | actccattcc | tttccttg | ttttatttt | ttttttttt | 7800 |
| ttttttttt | ttttttttt | ttcttttttt | ttttttttt | tttttttg | ttttcctct | 7860 |
| ttccattctt | ttctaacctt | aaatttcct | ttctttaggt | ggctccatct | tagccctagt | 7920 |
| cacggctagc | tgtgaaaggt | ccgtgagccg | catgactgca | gagagtgccg | taactggtct | 7980 |
| ctctgcagat | catgt | | | | | 7995 |

<210> SEQ ID NO 18
<211> LENGTH: 7995
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA sequence of mutant S310A R2198H HCV
      subgenomic replicon RNA

<400> SEQUENCE: 18

| gacctgcctc | ttacgaggcg | acactccacc | atggatcact | cccctgtgag | gaacttctgt | 60 |
| cttcacgcgg | aaagcgccta | gccatggcgt | tagtacgagt | gtcgtgcagc | ctccaggacc | 120 |
| cccctcccg | ggagagccat | agtggtctgc | ggaaccggtg | agtacaccgg | aatcgctggg | 180 |
| gtgaccgggt | cctttcttgg | aacaacccgc | tcaataccca | gaaatttggg | cgtgccccg | 240 |
| cgagatcact | agccgagtag | tgttgggtcg | cgaaaggcct | tgtggtactg | cctgataggg | 300 |
| tgcttgcgag | tgccccggga | ggtctcgtag | accgtgcaac | atgagcacac | ttcctaaacc | 360 |
| ccaaagaaaa | accaaaagaa | acaccatccg | tcgcccaatg | attgaacaag | atggattgca | 420 |
| cgcaggttct | ccggccgctt | gggtggagag | gctattcggc | tatgactggg | cacaacagac | 480 |
| aatcggctgc | tctgatgccg | ccgtgttccg | gctgtcagcg | caggggcgcc | cggttctttt | 540 |
| tgtcaagacc | gacctgtccg | gtgccctgaa | tgaactgcag | gacgaggcag | cgcggctatc | 600 |

```
gtggctggcc acgacgggcg ttccttgcgc agctgtgctc gacgttgtca ctgaagcggg    660
aagggactgg ctgctattgg gcgaagtgcc ggggcaggat ctcctgtcat ctcaccttgc    720
tcctgccgag aaagtatcca tcatggctga tgcaatgcgg cggctgcata cgcttgatcc    780
ggctacctgc ccattcgacc accaagcgaa acatcgcatc gagcgagcac gtactcggat    840
ggaagccggt cttgtcgatc aggatgatct ggacgaagag catcaggggc tcgcgccagc    900
cgaactgttc gccaggctca aggcgcgcat gcccgacggc gaggatctcg tcgtgaccca    960
tggcgatgcc tgcttgccga atatcatggt ggaaaatggc cgcttttctg gattcatcga   1020
ctgtggccgg ctgggtgtgg cggaccgcta tcaggacata gcgttggcta cccgtgatat   1080
tgctgaagag cttggcggcg aatgggctga ccgcttcctc gtgctttacg gtatcgccgc   1140
tcccgattcg cagcgcatcg ccttctatcg ccttcttgac gagttcttct gagtttaaac   1200
cctctccctc cccccccct aacgttactg gccgaagccg cttggaataa ggccggtgtg    1260
cgtttgtcta tatgttattt tccaccatat tgccgtcttt tggcaatgtg agggcccgga   1320
aacctggccc tgtcttcttg acgagcattc ctaggggtct ttcccctctc gccaaggaa    1380 tgcaaggtct gttgaatgtc gtgaaggaag cagttcctct ggaagcttct tgaagacaaa   1440
caacgtctgt agcgaccctt tgcaggcagc ggaaccccc acctggcgac aggtgcctct    1500
gcggccaaaa gccacgtgta taagatacac ctgcaaaggc ggcacaaccc cagtgccacg   1560
ttgtgagttg atagttgtg gaaagagtca aatggctctc ctcaagcgta ttcaacaagg   1620
ggctgaagga tgcccagaag gtaccccatt gtatgggatc tgatctgggg cctcggtgca   1680
catgctttac atgtgtttag tcgaggttaa aaaaacgtct aggcccccg aaccacgggg    1740 acgtggtttt cctttgaaaa acacgatgat accatggccc cgatcactgc ttacgcccag   1800
caaaccaggg gccttcttgg gactattgtg accagcttga ctggcaggga taagaatgtg   1860
gtgaccggcg aagtgcaggt gctttctacg gctacccaga ccttcctagg tacaacaata   1920
gggggggtta tgtggactgt ttaccatggc gcaggctcaa ggacacttgc gggcgctaaa   1980
catcctgcgc tccaaatgta cacaaatgta gatcaggacc tcgttgggtg gccagcccct   2040 ccagggcta agtctcttga accgtgcacc tgcgggtctg cagacttata cttggttacc    2100
cgcgatgctg acgtcatccc cgctcggcgc aggggggact ccacagcgag cttgctcagc   2160
cctaggcctc tcgcctgtct caagggctcc tctggaggtc ccgttatgtg cccttcgggg   2220
catgtcacgg ggatctttcg ggctgctgtg tgcaccagag gtgtagcaaa gaccctacag   2280
ttcataccag tggaaaccct tagtacacag actaggtccc catccttctc tgacaattca   2340
actcctcccg ccgtcccaca gagctaccaa gtagggtatc ttcatgcccc gaccggtagt   2400
ggcaagagca caaggtccc ggccgcttac gtagcacaag gataccatgt tctcgtgttg    2460
aatccatcag tggcggccac actaggcttc ggctcttaca tgtcgaaagc ctatgggatc   2520
gaccccaacg tccgcactgg gaaccgcact gtcacaactg tgctaaaact gacctattcc   2580
acctacggta agtttctcgc ggatgggggt tgctctgggg gagcgtatga tgtgattatt   2640
tgtgatgaat gccatgccca agacgctact accatattgg gtattggcac ggtcttagat   2700
caggctgaga cggctggggt gaggctgacg gttctggcga cagcaactcc cccaggcagc   2760
atcactgtgc cacattctaa catcgaggag gtagccctgg gctctgaagg tgagatccct   2820
ttctacggta aggctatacc gatagcccag ctcaagggg ggaggcacct tatcttttgc    2880
cattccaaga aaaagtgtga tgagatagca tccaagctca gaggcatggg gctcaacgct   2940
```

```
gtagcattct ataggggtct tgatgtgtcc atcataccaa cagcaggaga cgtcgtggtt      3000
tgcgccactg acgccctcat gactgggtac accggagact ttgattctgt catagattgc      3060
aacgtgactg ttgaacagta cgttgacttc agcttggacc ccacctttc cattgagact       3120 cacactgctc cccaagacgc ggtttcccgc agccaacgtc gtggccgtac gggccggggt      3180
agactcggca tataccgata tgtcaccccg ggtgaaagac cgtctggaat gtttgactcg      3240
gttgttctct gtgagtgcta tgatgcgggc tgctcgtggt acgatctgca gcccgctgag      3300
actacagtca gactgagagc ttacttgtcc acgccgggtt tacctgtctg tcaagaccat      3360
cttgactttt gggagagcgt ctttactgga ctaactcaca tagatgccca ctttctgtca      3420
cagactaagc agcagggact caacttcccg tacctgactg cctaccaagc cactgtgtgc      3480
gcccgcgcgc aggctcctcc cccaagttgg gacgagacgt ggaaatgtct cgtacggctt      3540
aaaccaacac tacatggacc cacgccccct ctgtatcggt tggggcctat ccaaaatgaa      3600
acctgcttga cacaccccgt cacaaaatac atcatggcat gcatgtcagc tgatctggaa      3660
gtgaccacca gcgcctgggt gttgcttgga ggggtgctcg cggccctagc ggcttactgc      3720
ttgtcagtcg gctgcgttgt gatcgtgggt catattgagc tgggggggcaa gccagcactc      3780 gttccagaca aagaggtgtt gtatcaacaa ttcgatgaga tggaggagtg ctcgcaagct      3840
gccccatata tcgaacaagc tcaggtaata gcccaccagt tcaaggagaa agtccttgga      3900
ttgctgcagc gagccaccca acaacaagct gtcattgagc ccatagtagc taccaactgg      3960
caaaagcttg aggcgttctg gcacaagcat atgtggaatt ttgtgagtgg gatccagtac      4020
ctagcaggcc tttccacttt gcctggcaac cccgctgtgg cgtctcttat ggcgttcacc      4080
gcttctgtca ccagtcccct gacgaccaac caaactatgt tcttcaacat actcggggg      4140 tgggttgcta cccatttggc agggcccag agctcttccg cattcgtggt aagcggcttg       4200
gccggcgctg ccatagggg tataggcctg gcagggtct tgattgacat cctggcagga       4260 tacgagctg tgtctcagg cgccttggtg gcttttaaga tcatgggagg agaactcccc        4320
actgctgagg acatggtcaa catgctgcct gccatactat ctccgggcgc cctcgttgtc      4380
ggtgtgatat gtgcagccat actgcgtcga cacgtaggac ctggggaggg ggcggtgcag      4440
tggatgaaca ggctcatcgc attcgcatcc cggggtaacc acgtctcacc gacgcactat      4500
gtccccgaga gcgatgctgc agcgaaggtt actgcattgc tgagttctct aactgtcaca      4560
agtctgctcc ggcgactgca ccagtggatc aatgaagact acccaagtcc ttgctgcggc      4620
gactggctgc gtaccatctg ggactgggtt tgcatggtgt tgtctgactt caagacatgg      4680
ctctccgcta agattatgcc agcgctccct gggctgcctt cctttcctg tcagaaggga       4740 tacaagggcg tgtggcgggg agacggtgtg atgtcgacac gctgtccttg cggggcgaca      4800
ataaccggtc atgtgaagaa tgggtctatg cggcttgcag ggccacgcac atgtgctaac      4860
atgtggcacg gtactttccc catcaatgag tacaccaccg acccggcac accttgccca       4920 gcacccaact acactcgcgc attattgcgc gtggctgcca acagctacgt tgaggtcgcg      4980
cgggtggggg acttccacta cattacgggg gctacagaag atgagctcaa gtgtccgtgc      5040
caagtgccgg ccgcagagtt ttttactgag gtggatgggg tgagactcca ccgttacgcc      5100
cctccatgca agcccctgtt gagggatgaa atcacttca tggtagggtt gaactcctac        5160
gcaataggat ctcaactccc ctgtgagccc gaaccagatg tttctgtgct gacctcgatg      5220
ttgagagacc cttcccatat taccgctgag gcagcagcgc gccgccttgc gcatgggtcc      5280
cctccatcag aggcaagctc atccgccagc caactgtcgg ctccgtcgtt gaaggccact      5340
```

-continued

| | |
|---|---|
| tgtcagtcgt atgggcctca tctggacgct gagctagtgg atgccaacct gttatggcgg | 5400 |
| caggagatgg gcagcactat cacacgggta gagtctgaaa caaaggttgt gattcttgat | 5460 |
| tcattcgaac ctctgagagc cgaaactgat gacgccgagc tctcggtggc tgcagagtgt | 5520 |
| ttcaagaagc ctcccaagta tcctccagcc cttcctatct gggctaggcc agactacaac | 5580 |
| cctccattgt tagaccgctg gaaagcaccg gattatgttc caccaactgt tcatggatgc | 5640 |
| gccttaccac cacggggcgc tccaccggtg cctccccctc ggaggaagag aacaattcag | 5700 |
| ctggatggct ccaatgtgtc cgcggcgcta gctgcgctag cagaaaagtc attcccgtcc | 5760 |
| tcaaagccgc aggaagagaa tagctcatcc tcaggggtcg acacacagtc cagcactacc | 5820 |
| tctaaggtgc cccccccccc aggagggaa tccgactcag agtcgtgctc gtccatgcct | 5880 |
| cctctcgagg gagagccggg cgatccggat ttgagctgcg actcttggtc cactgtgagt | 5940 |
| gacaatgagg agcagaacgt agtctgctgc tccatgtcgt actcttggac cggcgccttg | 6000 |
| ataacaccat gtagtgctga ggaggagaaa ctacccatca gcccactcag caactccttg | 6060 |
| ttgagacacc ataatctggt ttattcaacg tcgtcaagaa gcgcttctca gcgtcagaag | 6120 |
| aaggttacct tcgacaggct gcaggtgctc gacgaccact acaaaactgc tttaaaggag | 6180 |
| gtaaaggagc gagcgtctgg ggtgaaggct cgcatgctca ccatcgagga agcgtgcaag | 6240 |
| cttgtccccc cccactctgc ccgttcgaag ttcgggtata gtgcgaagga cgctcgttcc | 6300 |
| ttgtccagca gggccgttaa ccagatccgc tccgtctggg aggacttgct ggaagacacc | 6360 |
| acaactccaa ttccaacaac catcatggcg aagaacgagg tgttttgtgt ggaccccgtt | 6420 |
| aaggggggcc gcaagcccgc tcgcctcatt gtgtaccctg acctggggt gcgtgtctgt | 6480 |
| gagaaacgcg ccctatatga cgtgatacag aagttgtcaa tcgcgacgat gggtcctgct | 6540 |
| tatggattcc agtactcgcc tcagcagcgg gtcgaacgtc tgctgaagat gtggacctca | 6600 |
| aagagaaccc ccctgggtt ctcgtatgac acccgctgct ttgactcgac tgtcactgaa | 6660 |
| caggatatca gggtggaaga ggagatatat caatgctgta accttgaacc ggaggccagg | 6720 |
| aaggtgatct cctccctcac ggagcggctt tactgcgggg gccccatgtt caacagcaag | 6780 |
| ggggcccagt gcggttatcg ccgttgccgt gctagtggag ttctaccgac cagctttggc | 6840 |
| aacacaatca cttgttacat caaggccaca gcggctgcaa gggccgcggg tctccggaac | 6900 |
| ccggactttc ttgtctgcgg agatgatttg gtcgtggtgg ccgagagtga tggcgtcgac | 6960 |
| gaggatagg cagccctgag agccttcacg gaggctatga ccaggtactc tgctccaccc | 7020 |
| ggagatgctc cacagcctac ctacgacctt gagctcatca catcttgctc ctctaacgtc | 7080 |
| tccgtagcac atgacaacaa ggggaggagg tattactacc tcacccgtga tgccactact | 7140 |
| cccctggccc gtgcggcttg ggaaacagct cgtcacactc cagttaactc ctggttgggc | 7200 |
| aacatcatca tgtacgcgcc taccatctgg gtgcgcatgg tgatgatgac acacttttc | 7260 |
| tccatactcc aatcccagga gatacttgat cgcccccttg attttgaaat gtacggggcc | 7320 |
| acttactctg tcactccgct ggatttacca gcaatcattg aaagactcca tggtctaagc | 7380 |
| gcgttcacac tccacagtta ctctccagta gaactcaata gggtcgcggg gacactcagg | 7440 |
| aagcttgggt gcccccccct acgagcttgg agacatcggg cacgagcagt gcgcgctaag | 7500 |
| cttattgccc agggaggtaa ggccaaaata tgtggccttt atctctttaa ctgggcagta | 7560 |
| cgcaccaaga ccaaactcac tccactgcca gccgctagcc agttggactt atccaattgg | 7620 |
| ttttcggttg gcgtcggcgg gaacgacatt tatcacagcg tgtcacatgc ccgaacccgc | 7680 |

| catttgctgc | tttgcctact | cctactaact | gtaggggtag | gcatctttct | cctgccagca | 7740 |
| cgataagctg | gtaggataac | actccattcc | ttttcccttg | tttttatttt | tttttttttt | 7800 |
| tttttttttt | tttttttttt | ttctttttt | tttttttttt | tttttttttg | ttttcctct | 7860 |
| ttccattctt | ttctaacctt | aaattttcct | ttctttaggt | ggctccatct | tagccctagt | 7920 |
| cacggctagc | tgtgaaaggt | ccgtgagccg | catgactgca | gagagtgccg | taactggtct | 7980 |
| ctctgcagat | catgt | | | | | 7995 |

<210> SEQ ID NO 19
<211> LENGTH: 7995
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA sequence of mutant S310A R2895K HCV subgenomic replicon RNA

<400> SEQUENCE: 19

| gacctgcctc | ttacgaggcg | acactccacc | atggatcact | ccctgtgag | gaacttctgt | 60 |
| cttcacgcgg | aaagcgccta | gccatggcgt | tagtacgagt | gtcgtgcagc | ctccaggacc | 120 |
| ccccctcccg | ggagagccat | agtggtctgc | ggaaccggtg | agtacaccgg | aatcgctggg | 180 |
| gtgaccgggt | cctttcttgg | aacaacccgc | tcaatacca | gaaatttggg | cgtgccccg | 240 |
| cgagatcact | agccgagtag | tgttgggtcg | cgaaaggcct | tgtggtactg | cctgataggg | 300 |
| tgcttgcgag | tgccccggga | ggtctcgtag | accgtgcaac | atgagcacac | ttcctaaacc | 360 |
| ccaaagaaaa | accaaaagaa | acaccatccg | tcgcccaatg | attgaacaag | atggattgca | 420 |
| cgcaggttct | ccggccgctt | gggtggagag | gctattcggc | tatgactggg | cacaacagac | 480 |
| aatcggctgc | tctgatgccg | ccgtgttccg | gctgtcagcg | caggggcgcc | cggttctttt | 540 |
| tgtcaagacc | gacctgtccg | gtgccctgaa | tgaactgcag | gacgaggcag | cgcggctatc | 600 |
| gtggctggcc | acgacgggcg | ttccttgcgc | agctgtgctc | gacgttgtca | ctgaagcggg | 660 |
| aagggactgg | ctgctattgg | gcgaagtgcc | ggggcaggat | ctcctgtcat | ctcaccttgc | 720 |
| tcctgccgag | aaagtatcca | tcatggctga | tgcaatgcgg | cggctgcata | cgcttgatcc | 780 |
| ggctacctgc | ccattcgacc | accaagcgaa | acatcgcatc | gagcgagcac | gtactcggat | 840 |
| ggaagccggt | cttgtcgatc | aggatgatct | ggacgaagag | catcaggggc | tcgcgccagc | 900 |
| cgaactgttc | gccaggctca | aggcgcgcat | gcccgacggc | gaggatctcg | tcgtgaccca | 960 |
| tggcgatgcc | tgcttgccga | atatcatggt | ggaaaatggc | cgcttttctg | gattcatcga | 1020 |
| ctgtggccgg | ctgggtgtgg | cggaccgcta | tcaggacata | gcgttggcta | cccgtgatat | 1080 |
| tgctgaagag | cttggcggcg | aatgggctga | ccgcttcctc | gtgctttacg | gtatcgccgc | 1140 |
| tcccgattcg | cagcgcatcg | ccttctatcg | ccttcttgac | gagttcttct | gagtttaaac | 1200 |
| cctctccctc | ccccccccct | aacgttactg | gccgaagccg | cttggaataa | ggccggtgtg | 1260 |
| cgtttgtcta | tatgttattt | tccaccatat | tgccgtcttt | tggcaatgtg | agggcccgga | 1320 |
| aacctggccc | tgtcttcttg | acgagcattc | ctagggtct | ttcccctctc | gccaaaggaa | 1380 |
| tgcaaggtct | gttgaatgtc | gtgaaggaag | cagttcctct | ggaagcttct | tgaagacaaa | 1440 |
| caacgtctgt | agcgaccctt | tgcaggcagc | ggaaccccc | acctggcgac | aggtgcctct | 1500 |
| gcggccaaaa | gccacgtgta | taagatacac | ctgcaaaggc | ggcacaaccc | cagtgccacg | 1560 |
| ttgtgagttg | gatagttgtg | gaaagagtca | aatggctctc | ctcaagcgta | ttcaacaagg | 1620 |

```
ggctgaagga tgcccagaag gtaccccatt gtatgggatc tgatctgggg cctcggtgca    1680
catgctttac atgtgtttag tcgaggttaa aaaaacgtct aggccccccg aaccacgggg    1740
acgtggtttt cctttgaaaa acacgatgat accatggccc cgatcactgc ttacgcccag    1800
caaaccaggg gccttcttgg gactattgtg accagcttga ctggcaggga taagaatgtg    1860
gtgaccggcg aagtgcaggt gctttctacg gctacccaga ccttcctagg tacaacaata    1920 ggggggggtta tgtggactgt ttaccatggc gcaggctcaa ggacacttgc gggcgctaaa    1980
catcctgcgc tccaaatgta cacaaatgta gatcaggacc tcgttgggtg gccagcccct    2040
ccaggggcta agtctcttga accgtgcacc tgcgggtctg cagacttata cttggttacc    2100
cgcgatgctg acgtcatccc cgctcggcgc aggggggact ccacagcgag cttgctcagc    2160
cctaggcctc tcgcctgtct caagggctcc tctggaggtc ccgttatgtg cccttcgggg    2220
catgtcacgg ggatctttcg ggctgctgtg tgcaccagag gtgtagcaaa gaccctacag    2280
ttcataccag tggaaaccct tagtacacag actaggtccc catccttctc tgacaattca    2340
actcctcccg ccgtcccaca gagctaccaa gtagggtatc ttcatgcccc gaccggtagt    2400
ggcaagagca caaggtccc ggccgcttac gtagcacaag gataccatgt tctcgtgttg    2460
aatccatcag tggcggccac actaggcttc ggctcttaca tgtcgaaagc ctatgggatc    2520
gaccccaacg tccgcactgg gaaccgcact gtcacaactg gtgctaaaact gacctattcc    2580 acctacggta agtttctcgc ggatgggggt tgctctgggg gagcgtatga tgtgattatt    2640
tgtgatgaat gccatgccca agacgctact accatattgg gtattggcac ggtcttagat    2700
caggctgaga cggctggggt gaggctgacg gttctggcga cagcaactcc cccaggcagc    2760
atcactgtgc cacattctaa catcgaggag gtagccctgg gctctgaagg tgagatccct    2820
ttctacggta aggctatacc gatagcccag ctcaagggg ggaggcacct tatcttttgc    2880
cattccaaga aaaagtgtga tgagatagca tccaagctca gaggcatggg gctcaacgct    2940
gtagcattct atagggggtct tgatgtgtcc atcataccaa cagcaggaga cgtcgtggtt    3000
tgcgccactg acgccctcat gactgggtac accggagact ttgattctgt catagattgc    3060
aacgtgactg ttgaacagta cgttgacttc agcttggacc ccaccttttc cattgagact    3120
cacactgctc cccaagacgc ggtttcccgc agccaacgtc gtggccgtac gggccggggt    3180
agactcggca tataccgata tgtcaccccg ggtgaaagac cgtctggaat gtttgactcg    3240
gttgttctct gtgagtgcta tgatgcgggc tgctcgtggt acgatctgca gcccgctgag    3300
actacagtca gactgagagc ttacttgtcc acgccgggtt tacctgtctg tcaagaccat    3360
cttgactttt gggagagcgt ctttactgga ctaactcaca tagatgccca ctttctgtca    3420
cagactaagc agcagggact caacttcccg tacctgactg cctaccaagc cactgtgtgc    3480
gcccgcgcgc aggctcctcc cccaagttgg gacgagacgt ggaaatgtct cgtacggctt    3540
aaaccaacac tacatggacc cacgcccctt ctgtatcggt tggggcctat ccaaaatgaa    3600
acctgcttga cacaccccgt cacaaaatac atcatggcat gcatgtcagc tgatctggaa    3660
gtgaccacca gcgcctgggt gttgcttgga ggggtgctcg cggccctagc ggcttactgc    3720
ttgtcagtcg gctgcgttgt gatcgtgggt catattgagc tggggggcaa gccagcactc    3780
gttccagaca aagaggtgtt gtatcaacaa ttcgatgaga tggaggagtg ctcgcaagct    3840
gccccatata tcgaacaagc tcaggtaata gcccaccagt tcaaggagaa agtccttgga    3900
ttgctgcagc gagccaccca acaacaagct gtcattgagc ccatagtagc taccaactgg    3960
```

```
caaaagcttg aggcgttctg gcacaagcat atgtggaatt ttgtgagtgg gatccagtac   4020
ctagcaggcc tttccacttt gcctggcaac cccgctgtgg cgtctcttat ggcgttcacc   4080
gcttctgtca ccagtcccct gacgaccaac caaactatgt tcttcaacat actcgggggg   4140
tgggttgcta cccatttggc agggcccag agctcttccg cattcgtggt aagcggcttg    4200
gccggcgctg ccatagggggg tataggcctg gcagggtct tgattgacat cctggcagga   4260
tacggagctg tgtctcagg cgccttggtg gcttttaaga tcatgggagg agaactcccc   4320
actgctgagg acatggtcaa catgctgcct gccatactat ctccgggcgc cctcgttgtc   4380
ggtgtgatat gtgcagccat actgcgtcga cacgtaggac ctggggaggg ggcggtgcag   4440
tggatgaaca ggctcatcgc attcgcatcc cggggtaacc acgtctcacc gacgcactat   4500
gtccccgaga gcgatgctgc agcgaaggtt actgcattgc tgagttctct aactgtcaca   4560
agtctgctcc ggcgactgca ccagtggatc aatgaagact acccaagtcc ttgctgcggc   4620
gactggctgc gtaccatctg ggactgggtt tgcatggtgt tgtctgactt caagacatgg   4680
ctctccgcta agattatgcc agcgctccct gggctgcctt tcctttcctg tcagaaggga   4740
tacaagggcg tgtggcgggg agacggtgtg atgtcgacac gctgtccttg cggggcgaca   4800 ataccggtc atgtgaagaa tgggtctatg cggcttgcag ggccacgcac atgtgctaac   4860
atgtggcacg gtactttccc catcaatgag tacaccaccg gacccggcac accttgccca   4920
gcacccaact acactcgcgc attattgcgc gtggctgcca acagctacgt tgaggtgcgc   4980
cgggtggggg acttccacta cattacgggg gctacagaag atgagctcaa gtgtccgtgc   5040
caagtgccgg ccgcagagtt ttttactgag gtggatgggg tgagactcca ccgttacgcc   5100
cctccatgca agcccctgtt gagggatgaa atcactttca tggtagggtt gaactcctac   5160
gcaataggat ctcaactccc ctgtgagccc gaaccagatg tttctgtgct gacctcgatg   5220
ttgagagacc cttcccatat taccgctgag gcagcagcgc gccgccttgc gcgtgggtcc   5280
cctccatcag aggcaagctc atccgccagc caactgtcgg ctccgtcgtt gaaggccact   5340
tgtcagtcgt atgggcctca tctggacgct gagctagtgg atgccaacct gttatggcgg   5400
caggagatgg gcagcactat cacacgggta gagtctgaaa caaaggttgt gattcttgat   5460
tcattcgaac ctctgagagc cgaaactgat gacgccgagc tctcggtggc tgcagagtgt   5520
ttcaagaagc ctcccaagta tcctccagcc cttcctatct gggctaggcc agactacaac   5580
cctccattgt tagaccgctg gaaagcaccg gattatgttc caccaactgt tcatggatgc   5640
gccttaccac cacggggcgc tccaccggtg cctcccccctc ggaggaagag aacaattcag   5700
ctggatggct ccaatgtgtc cgcggcgcta gctgcgctag cagaaaagtc attcccgtcc   5760
tcaaagccgc aggaagagaa tagctcatcc tcagggtcg acacacagtc cagcactacc   5820
tctaaggtgc ccccccccc aggaggggaa tccgactcag agtcgtgctc gtccatgcct   5880
cctctcgagg gagagccggg cgatccggat ttgagctgcg actcttggtc cactgtgagt   5940
gacaatgagg agcagaacgt agtctgctgc tccatgtcgt actcttggac cggcgccttg   6000
ataacaccat gtagtgctga ggaggagaaa ctacccatca gcccactcag caactccttg   6060
ttgagacacc ataatctggt ttattcaacg tcgtcaagaa gcgcttctca gcgtcagaag   6120
aaggttacct tcgacaggct gcaggtgctc gacgaccact acaaaactgc tttaaaggag   6180
gtaaaggagc gagcgtctgg ggtgaaggct cgcatgctca ccatcgagga agcgtgcaag   6240
cttgtccccc cccactctgc ccgttcgaag ttcgggtata gtgcgaagga cgctcgttcc   6300
ttgtccagca gggccgttaa ccagatccgc tccgtctggg aggacttgct ggaagacacc   6360
```

-continued

```
acaactccaa ttccaacaac catcatggcg aagaacgagg tgttttgtgt ggaccccgtt      6420
aaggggggcc gcaagcccgc tcgcctcatt gtgtaccctg acctgggggt gcgtgtctgt      6480
gagaaacgcg ccctatatga cgtgatacag aagttgtcaa tcgcgacgat gggtcctgct      6540
tatggattcc agtactcgcc tcagcagcgg gtcgaacgtc tgctgaagat gtggacctca      6600
aagagaaccc ccctggggtt ctcgtatgac acccgctgct ttgactcgac tgtcactgaa      6660
caggatatca gggtggaaga ggagatatat caatgctgta accttgaacc ggaggccagg      6720
aaggtgatct cctccctcac ggagcggctt tactgcgggg ccccatgtt caacagcaag       6780
ggggcccagt gcggttatcg ccgttgccgt gctagtggag ttctaccgac cagctttggc      6840
aacacaatca cttgttacat caaggccaca gcggctgcaa gggccgcggg tctccggaac      6900
ccggactttc ttgtctgcgg agatgatttg gtcgtggtgg ccgagagtga tggcgtcgac      6960
gaggataggg cagccctgag agccttcacg gaggctatga ccaggtactc tgctccaccc      7020
ggagatgctc cacagcctac ctacgacctt gagctcatca catcttgctc ctctaacgtc      7080
tccgtagcac atgacaacaa ggggaggagg tattactacc tcacccgtga tgccactact      7140
cccctggccc gtgcggcttg ggaaacagct cgtcacactc cagttaactc ctggttgggc      7200
aacatcatca tgtacgcgcc taccatctgg gtgcgcatgg tgatgatgac acactttttc      7260
tccatactcc aatcccagga gatacttgat cgccccttg attttgaaat gtacggggcc       7320
acttactctg tcactccgct ggatttacca gcaatcattg aaaaactcca tggtctaagc      7380
gcgttcacac tccacagtta ctctccagta gaactcaata gggtcgcggg gacactcagg      7440
aagcttgggt gcccccccct acgagcttgg agacatcggg cacgagcagt gcgcgctaag      7500
cttattgccc aggaggtaa ggccaaaata tgtggccttt atctctttaa ctgggcagta       7560
cgcaccaaga ccaaactcac tccactgcca gccgctagcc agttggactt atccaattgg      7620
ttttcggttg gcgtcggcgg gaacgacatt tatcacagcg tgtcacatgc ccgaacccgc      7680
catttgctgc tttgcctact cctactaact gtaggggtag gcatctttct cctgccagca      7740
cgataagctg gtaggataac actccattcc tttttccctg tttttatttt tttttttttt      7800
tttttttttt tttttttttt ttctttttttt tttttttttt tttttttttg tttttcctct     7860
ttccattctt ttctaacctt aaattttcct ttctttaggt ggctccatct tagccctagt      7920
cacggctagc tgtgaaaggt ccgtgagccg catgactgca gagagtgccg taactggtct      7980
ctctgcagat catgt                                                      7995
```

<210> SEQ ID NO 20
<211> LENGTH: 7995
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA sequence of mutant S310A T2496I/R2895K HCV subgenomic replicon RNA

<400> SEQUENCE: 20

```
gacctgcctc ttacgaggcg acactccacc atgatcact cccctgtgag gaacttctgt        60
cttcacgcgg aaagcgccta gccatggcgt tagtacgagt gtcgtgcagc ctccaggacc       120
ccccctcccg ggagagccat agtggtctgc ggaaccggtg agtacaccgg aatcgctggg       180
gtgaccgggt cctttcttgg aacaacccgc tcaatacccca gaaatttggg cgtgccccg       240
```

```
cgagatcact agccgagtag tgttgggtcg cgaaaggcct tgtggtactg cctgataggg      300
tgcttgcgag tgccccggga ggtctcgtag accgtgcaac atgagcacac ttcctaaacc      360
ccaaagaaaa accaaaagaa acaccatccg tcgcccaatg attgaacaag atggattgca      420
cgcaggttct ccggccgctt gggtggagag gctattcggc tatgactggg cacaacagac      480
aatcggctgc tctgatgccg ccgtgttccg gctgtcagcg caggggcgcc cggttctttt      540
tgtcaagacc gacctgtccg gtgccctgaa tgaactgcag gacgaggcag cgcggctatc      600
gtggctggcc acgacgggcg ttccttgcgc agctgtgctc gacgttgtca ctgaagcggg      660
aagggactgg ctgctattgg gcgaagtgcc ggggcaggat ctcctgtcat ctcaccttgc      720
tcctgccgag aaagtatcca tcatggctga tgcaatgcgg cggctgcata cgcttgatcc      780
ggctacctgc ccattcgacc accaagcgaa acatcgcatc gagcgagcac gtactcggat      840
ggaagccggt cttgtcgatc aggatgatct ggacgaagag catcaggggc tcgcgccagc      900
cgaactgttc gccaggctca aggcgcgcat gcccgacggc gaggatctcg tcgtgaccca      960
tggcgatgcc tgcttgccga atatcatggt ggaaaatggc cgcttttctg gattcatcga     1020
ctgtggccgg ctgggtgtgg cggaccgcta tcaggacata gcgttggcta cccgtgatat     1080
tgctgaagag cttggcggcg aatgggctga ccgcttcctc gtgctttacg gtatcgccgc     1140
tcccgattcg cagcgcatcg ccttctatcg ccttcttgac gagttcttct gagtttaaac     1200
cctctccctc ccccccccct aacgttactg gccgaagccg cttggaataa ggccggtgtg     1260
cgtttgtcta tatgttattt tccaccatat tgccgtcttt tggcaatgtg agggcccgga     1320
aacctggccc tgtcttcttg acgagcattc ctaggggtct ttcccctctc gccaaaggaa     1380
tgcaaggtct gttgaatgtc gtgaaggaag cagttcctct ggaagcttct tgaagacaaa     1440
caacgtctgt agcgaccctt tgcaggcagc ggaaccccc acctggcgac aggtgcctct     1500
gcggccaaaa gccacgtgta taagatacac ctgcaaaggc ggcacaaccc cagtgccacg     1560
ttgtgagttg gatagttgtg gaaagagtca aatggctctc ctcaagcgta ttcaacaagg     1620
ggctgaagga tgcccagaag gtaccccatt gtatgggatc tgatctgggg cctcggtgca     1680
catgctttac atgtgtttag tcgaggttaa aaaaacgtct aggccccccg aaccacgggg     1740
acgtggtttt cctttgaaaa acacgatgat accatggccc cgatcactgc ttacgcccag     1800
caaaccaggg gccttcttgg gactattgtg accagcttga ctggcaggga taagaatgtg     1860
gtgaccggcg aagtgcaggt gctttctacg gctacccaga ccttcctagg tacaacaata     1920
gggggggtta tgtggactgt ttaccatggc gcaggctcaa ggacacttgc gggcgctaaa     1980
catcctgcgc tccaaatgta cacaaatgta gatcaggacc tcgttgggtg gccagcccct     2040 ccagggggcta agtctcttga accgtgcacc tgcgggtctg cagacttata cttggttacc     2100
cgcgatgctg acgtcatccc cgctcggcgc agggggggact ccacagcgag cttgctcagc     2160
cctaggcctc tcgcctgtct caagggctcc tctggaggtc ccgttatgtg cccttcgggg     2220
catgtcacgg ggatctttcg ggctgctgtg tgcaccagag tgtagcaaa gaccctacag     2280 ttcataccag tggaaaccct tagtacacag actaggtccc catccttctc tgacaattca     2340
actcctcccg ccgtcccaca gagctaccaa gtagggtatc ttcatgcccc gaccggtagt     2400
ggcaagagca caaaggtccc ggccgcttac gtagcacaag gataccatgt tctcgtgttg     2460
aatccatcag tggcggccac actaggcttc ggctcttaca tgtcgaaagc ctatgggatc     2520
gaccccaacg tccgcactgg gaaccgcact gtcacaactg gtgctaaact gacctattcc     2580
acctacggta agtttctcgc ggatgggggt tgctctgggg gagcgtatga tgtgattatt     2640
```

```
tgtgatgaat gccatgccca agacgctact accatattgg gtattggcac ggtcttagat    2700
caggctgaga cggctggggt gaggctgacg gttctggcga cagcaactcc cccaggcagc    2760
atcactgtgc cacattctaa catcgaggag gtagccctgg gctctgaagg tgagatccct    2820
ttctacggta aggctatacc gatagcccag ctcaagggg ggaggcacct tatcttttgc    2880
cattccaaga aaaagtgtga tgagatagca tccaagctca gaggcatggg gctcaacgct    2940
gtagcattct atagggggtct tgatgtgtcc atcataccaa cagcaggaga cgtcgtggtt    3000
tgcgccactg acgccctcat gactgggtac accggagact ttgattctgt catagattgc    3060
aacgtgactg ttgaacagta cgttgacttc agcttggacc ccaccttttc cattgagact    3120
cacactgctc cccaagacgc ggtttcccgc agccaacgtc gtggccgtac gggccggggt    3180
agactcggca tataccgata tgtcaccccg ggtgaaagac cgtctggaat gtttgactcg    3240
gttgttctct gtgagtgcta tgatgcgggc tgctcgtggt acgatctgca gcccgctgag    3300
actacagtca gactgagagc ttacttgtcc acgccgggtt tacctgtctg tcaagaccat    3360
cttgactttt gggagagcgt ctttactgga ctaactcaca tagatgccca ctttctgtca    3420
cagactaagc agcagggact caacttcccg tacctgactg cctaccaagc cactgtgtgc    3480
gcccgcgcgc aggctcctcc cccaagttgg gacgagacgt ggaaatgtct cgtacggctt    3540
aaaccaacac tacatggacc cacgccccctt ctgtatcggt tggggcctat ccaaaatgaa    3600
acctgcttga cacaccccgt cacaaaatac atcatggcat gcatgtcagc tgatctggaa    3660
gtgaccacca gcgcctgggt gttgcttgga ggggtgctcg cggccctagc ggcttactgc    3720
ttgtcagtcg gctgcgttgt gatcgtgggt catattgagc tgggggcaa gccagcactc    3780 gttccagaca aagaggtgtt gtatcaacaa ttcgatgaga tggaggagtg ctcgcaagct    3840
gccccatata tcgaacaagc tcaggtaata gcccaccagt tcaaggagaa agtccttgga    3900
ttgctgcagc gagccaccca acaacaagct gtcattgagc ccatagtagc taccaactgg    3960
caaaagcttg aggcgttctg gcacaagcat atgtggaatt ttgtgagtgg gatccagtac    4020
ctagcaggcc ttttccacttt gcctggcaac cccgctgtgg cgtctcttat ggcgttcacc    4080
gcttctgtca ccagtcccct gacgaccaac caaactatgt tcttcaacat actcgggggg    4140
tgggttgcta cccatttggc agggcccccag agctcttccg cattcgtggt aagcggcttg    4200
gccggcgctc catagggggg tataggcctg gcagggtct tgattgacat cctggcagga    4260
tacggagctg gtgtctcagg cgccttggtg gcttttaaga tcatgggagg agaactcccc    4320
actgctgagg acatggtcaa catgctgcct gccatactat ctccgggcgc cctcgttgtc    4380
ggtgtgatat gtgcagccat actgcgtcga cacgtaggac ctgggggagg gcggtgcag    4440 tggatgaaca ggctcatcgc attcgcatcc cggggtaacc acgtctcacc gacgcactat    4500
gtccccgaga gcgatgctgc agcgaaggtt actgcattgc tgagttctct aactgtcaca    4560
agtctgctcc ggcgactgca ccagtggatc aatgaagact acccaagtcc ttgctgcggc    4620
gactggctgc gtaccatctg ggactgggtt tgcatggtgt tgtctgactt caagacatgg    4680
ctctccgcta agattatgcc agcgctccct gggctgcctt ccttttcctg tcagaaggga    4740
tacaagggcg tgtggcgggg agacggtgtg atgtcgacac gctgtccttg cggggcgaca    4800
ataaccggtc atgtgaagaa tgggtctatg cggcttgcag ggccacgcac atgtgctaac    4860
atgtggcacg gtacttccc catcaatgag tacaccaccg gacccggcac accttgccca    4920
gcacccaact acactcgcgc attattgcgc gtggctgcca acagctacgt tgaggtgcgc    4980
```

```
cgggtggggg acttccacta cattacgggg gctacagaag atgagctcaa gtgtccgtgc    5040
caagtgccgg ccgcagagtt ttttactgag gtggatgggg tgagactcca ccgttacgcc    5100
cctccatgca agccctgtt gagggatgaa atcactttca tggtagggtt gaactcctac     5160
gcaataggat ctcaactccc ctgtgagccc gaaccagatg tttctgtgct gacctcgatg    5220
ttgagagacc cttcccatat taccgctgag gcagcagcgc gccgccttgc gcgtgggtcc    5280
cctccatcag aggcaagctc atccgccagc caactgtcgg ctccgtcgtt gaaggccact    5340
tgtcagtcgt atgggcctca tctggacgct gagctagtgg atgccaacct gttatggcgg    5400
caggagatgg gcagcactat cacacgggta gagtctgaaa caaaggttgt gattcttgat    5460
tcattcgaac tctgagagc cgaaactgat gacgccgagc tctcggtggc tgcagagtgt     5520
ttcaagaagc ctcccaagta tcctccagcc cttcctatct gggctaggcc agactacaac    5580
cctccattgt tagaccgctg gaaagcaccg gattatgttc caccaactgt tcatggatgc    5640
gccttaccac cacggggcgc tccaccggtg cctcccccctc ggaggaagag aacaattcag   5700
ctggatggct ccaatgtgtc cgcggcgcta gctgcgctag cagaaaagtc attcccgtcc    5760
tcaaagccgc aggaagagaa tagctcatcc tcaggggtcg acacacagtc cagcactacc    5820
tctaaggtgc ccccccccc aggaggggaa tccgactcag agtcgtgctc gtccatgcct    5880
cctctcgagg gagagccggg cgatccggat ttgagctgcg actcttggtc cactgtgagt    5940
gacaatgagg agcagaacgt agtctgctgc tccatgtcgt actcttggac cggcgccttg    6000
ataacaccat gtagtgctga ggaggagaaa ctacccatca gcccactcag caactccttg    6060
ttgagacacc ataatctggt ttattcaacg tcgtcaagaa gcgcttctca gcgtcagaag    6120
aaggttacct tcgacaggct gcaggtgctc gacgaccact acaaaattgc tttaaaggag    6180
gtaaaggagc gagcgtctgg ggtgaaggct cgcatgctca ccatcgagga agcgtgcaag    6240
cttgtccccc cccactctgc ccgttcgaag ttcgggtata gtgcgaagga cgctcgttcc    6300
ttgtccagca gggccgttaa ccagatccgc tccgtctggg aggacttgct ggaagacacc    6360
acaactccaa ttccaacaac catcatggcg aagaacgagg tgttttgtgt ggaccccgtt    6420
aaggggggcc gcaagcccgc tcgcctcatt gtgtaccctg acctgggggt gcgtgtctgt    6480
gagaaacgcg ccctatatga cgtgatacag aagttgtcaa tcgcgacgat gggtcctgct    6540
tatggattcc agtactcgcc tcagcagcgg gtcgaacgtc tgctgaagat gtggacctca    6600
aagagaaccc ccctggggtt ctcgtatgac acccgctgct tgactcgac tgtcactgaa     6660
caggatatca gggtggaaga ggagatatat caatgctgta accttgaacc ggaggccagg    6720
aaggtgatct cctccctcac ggagcggctt tactgcgggg gccccatgtt caacagcaag    6780
ggggcccagt gcggttatcg ccgttgccgt gctagtggag ttctaccgac cagctttggc    6840
aacacaatca cttgttacat caaggccaca gcggctgcaa gggccgcggg tctccggaac    6900
ccggactttc ttgtctgcgg agatgatttg gtcgtggtgg ccgagagtga tggcgtcgac    6960
gaggataggg cagccctgag agccttcacg gaggctatga ccaggtactc tgctccaccc    7020
ggagatgctc cacagcctac ctacgacctt gagctcatca catcttgctc ctctaacgtc    7080
tccgtagcac atgacaacaa ggggaggagg tattactacc tcacccgtga tgccactact    7140
cccctggccc gtgcggcttg ggaaacagct cgtcacactc cagttaactc ctggttgggc    7200
aacatcatca tgtacgcgcc taccatctgg gtgcgcatgg tgatgatgac acacttttc    7260
tccatactcc aatcccagga gatacttgat cgccccttg attttgaaat gtacggggcc    7320
acttactctg tcactccgct ggatttacca gcaatcattg aaaaactcca tggtctaagc    7380
```

```
gcgttcacac tccacagtta ctctccagta gaactcaata gggtcgcggg gacactcagg    7440
aagcttgggt gccccccct acgagcttgg agacatcggg cacgagcagt gcgcgctaag     7500
cttattgccc agggaggtaa ggccaaaata tgtggccttt atctctttaa ctgggcagta    7560
cgcaccaaga ccaaactcac tccactgcca gccgctagcc agttggactt atccaattgg   7620
ttttcggttg gcgtcggcgg gaacgacatt tatcacagcg tgtcacatgc ccgaacccgc    7680
catttgctgc tttgcctact cctactaact gtaggggtag gcatctttct cctgccagca   7740
cgataagctg gtaggataac actccattcc ttttcccttg ttttattttt tttttttttt   7800
tttttttttt tttttttttt ttctttttttt tttttttttt tttttttttg ttttcctct   7860 ttccattctt ttctaacctt aaattttcct ttctttaggt ggctccatct tagccctagt   7920
cacggctagc tgtgaaaggt ccgtgagccg catgactgca gagagtgccg taactggtct   7980
ctctgcagat catgt                                                     7995
```

<210> SEQ ID NO 21
<211> LENGTH: 7995
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA sequence of mutant S310A T2188A HCV
      subgenomic replicon RNA

<400> SEQUENCE: 21

```
gacctgcctc ttacgaggcg acactccacc atggatcact cccctgtgag gaacttctgt    60
cttcacgcgg aaagcgccta gccatggcgt tagtacgagt gtcgtgcagc ctccaggacc   120 cccctcccg ggagagccat agtggtctgc ggaaccggtg agtacaccgg aatcgctggg    180
gtgaccgggt cctttcttgg aacaacccgc tcaataccca gaaatttggg cgtgcccccg    240
cgagatcact agccgagtag tgttgggtcg cgaaaggcct tgtggtactg cctgataggg    300
tgcttgcgag tgccccggga ggtctcgtag accgtgcaac atgagcacac ttcctaaacc    360
ccaaagaaaa accaaaagaa acaccatccg tcgcccaatg attgaacaag atggattgca    420
cgcaggttct ccggccgctt gggtggagag gctattcggc tatgactggg cacaacagac    480
aatcggctgc tctgatgccg ccgtgttccg gctgtcagcg caggggcgcc cggttctttt    540
tgtcaagacc gacctgtccg gtgccctgaa tgaactgcag gacgaggcag cgcggctatc    600
gtggctggcc acgacgggcg ttccttgcgc agctgtgctc gacgttgtca ctgaagcggg    660
aagggactgg ctgctattgg gcgaagtgcc ggggcaggat ctcctgtcat ctcaccttgc    720
tcctgccgag aaagtatcca tcatggctga tgcaatgcgg cggctgcata cgcttgatcc    780
ggctacctgc ccattcgacc accaagcgaa acatcgcatc gagcgagcac gtactcggat    840
ggaagccggt cttgtcgatc aggatgatct ggacgaagag catcagggc tcgcgccagc    900 cgaactgttc gccaggctca aggcgcgcat gcccgacggc gaggatctcg tcgtgaccca    960
tggcgatgcc tgcttgccga atatcatggt ggaaaatggc cgcttttctg gattcatcga   1020
ctgtggccgc tgggtgtgg cggaccgcta tcaggacata gcgttggcta cccgtgatat   1080
tgctgaagag cttggcggcg aatgggctga ccgcttcctc gtgctttacg gtatcgccgc   1140
tcccgattcg cagcgcatcg ccttctatcg ccttcttgac gagttcttct gagtttaaac   1200
cctctccctc ccccccccct aacgttactg gccgaagccg cttggaataa ggccggtgtg    1260
```

```
cgtttgtcta tatgttattt tccaccatat tgccgtcttt tggcaatgtg agggcccgga   1320
aacctggccc tgtcttcttg acgagcattc ctagggtct  ttcccctctc gccaaaggaa   1380
tgcaaggtct gttgaatgtc gtgaaggaag cagttcctct ggaagcttct tgaagacaaa   1440
caacgtctgt agcgacccct tgcaggcagc ggaaccccc  acctggcgac aggtgcctct   1500
gcggccaaaa gccacgtgta taagatacac ctgcaaaggc ggcacaaccc cagtgccacg   1560
ttgtgagttg gatagttgtg gaaagagtca aatggctctc ctcaagcgta ttcaacaagg   1620
ggctgaagga tgcccagaag gtaccccatt gtatgggatc tgatctgggg cctcggtgca   1680
catgctttac atgtgtttag tcgaggttaa aaaaacgtct aggcccccg  aaccacgggg   1740 acgtggtttt cctttgaaaa acacgatgat accatggccc cgatcactgc ttacgcccag   1800
caaaccaggg gccttcttgg gactattgtg accagcttga ctggcaggga taagaatgtg   1860
gtgaccggcg aagtgcaggt gctttctacg gctacccaga ccttcctagg tacaacaata   1920 ggggggggtta tgtggactgt ttaccatggc gcaggctcaa ggacacttgc gggcgctaaa   1980
catcctgcgc tccaaatgta cacaaatgta gatcaggacc tcgttgggtg gccagcccct   2040
ccaggggcta agtctcttga accgtgcacc tgcgggtctg cagacttata cttggttacc   2100
cgcgatgctg acgtcatccc cgctcggcgc aggggggact ccacagcgag cttgctcagc   2160
cctaggcctc tcgcctgtct caagggctcc tctggaggtc ccgttatgtg cccttcgggg   2220
catgtcacgg ggatctttcg ggctgctgtg tgcaccagag gtgtagcaaa gaccctacag   2280
ttcataccag tggaaaccct tagtacacag actaggtccc catccttctc tgacaattca   2340
actcctcccg ccgtcccaca gagctaccaa gtagggtatc ttcatgcccc gaccggtagt   2400
ggcaagagca caaggtcccc ggccgcttac gtagcacaag gataccatgt tctcgtgttg   2460
aatccatcag tggcggccac actaggcttc ggctcttaca tgtcgaaagc ctatgggatc   2520
gaccccaacg tccgcactgg gaaccgcact gtcacaactg gtgctaaact gacctattcc   2580
acctacggta agtttctcgc ggatgggggt tgctctgggg gagcgtatga tgtgattatt   2640
tgtgatgaat gccatgccca agacgctact accatattgg gtattggcac ggtcttagat   2700
caggctgaga cggctgggt  gaggctgacg gttctggcga cagcaactcc cccaggcagc   2760
atcactgtgc cacattctaa catcgaggag gtagccctgg gctctgaagg tgagatccct   2820
ttctacggta aggctatacc gatagcccag ctcaagggg  ggaggcacct tatcttttgc   2880
cattccaaga aaagtgtga  tgagatagca tccaagctca gaggcatggg gctcaacgct   2940
gtagcattct atagggtct  tgatgtgtcc atcataccaa cagcaggaga cgtcgtggtt   3000
tgcgccactg acgccctcat gactgggtac accggagact ttgattctgt catagattgc   3060
aacgtgactt ttgaacagta cgttgacttc agcttggacc ccaccttttc cattgagact   3120
cacactgctc cccaagacgc ggtttcccgc agccaacgtc gtggccgtac gggccggggt   3180
agactcggca tataccgata tgtcaccccg ggtgaaagac cgtctggaat gtttgactcg   3240
gttgttctct gtgagtgcta tgatgcgggc tgctcgtggt acgatctgca gcccgctgag   3300
actacagtca gactgagagc ttacttgtcc acgccgggtt tacctgtctg tcaagaccat   3360
cttgactttt gggagagcgt ctttactgga ctaactcaca tagatgccca ctttctgtca   3420
cagactaagc agcagggact caacttcccg tacctgactg cctaccaagc cactgtgtgc   3480
gcccgcgcgc aggctcctcc cccaagttgg gacgagacgt ggaaatgtct cgtacggctt   3540
aaaccaacac tacatggacc cacgccccct ctgtatcggt tggggcctat ccaaaatgaa   3600
acctgcttga cacacccccgt cacaaaatac atcatggcat gcatgtcagc tgatctggaa   3660
```

```
gtgaccacca gcgcctgggt gttgcttgga ggggtgctcg cggccctagc ggcttactgc   3720
ttgtcagtcg gctgcgttgt gatcgtgggt catattgagc tgggggggcaa gccagcactc   3780 gttccagaca aagaggtgtt gtatcaacaa ttcgatgaga tggaggagtg ctcgcaagct   3840
gccccatata tcgaacaagc tcaggtaata gcccaccagt tcaaggagaa agtccttgga   3900
ttgctgcagc gagccaccca acaacaagct gtcattgagc ccatagtagc taccaactgg   3960
caaaagcttg aggcgttctg gcacaagcat atgtggaatt ttgtgagtgg gatccagtac   4020
ctagcaggcc tttccactttt gcctggcaac ccgctgtgg cgtctcttat ggcgttcacc   4080
gcttctgtca ccagtcccct gacgaccaac caaactatgt tcttcaacat actcgggggg   4140
tgggttgcta cccatttggc agggcccag agctcttccg cattcgtggt aagcggcttg   4200
gccggcgctg ccatagggggg tataggcctg gcagggtct tgattgacat cctggcagga   4260
tacggagctg gtgtctcagg cgccttggtg gcttttaaga tcatgggagg agaactcccc   4320
actgctgagg acatggtcaa catgctgcct gccatactat ctccgggcgc cctcgttgtc   4380
ggtgtgatat gtgcagccat actgcgtcga cacgtaggac ctggggaggg ggcggtgcag   4440
tggatgaaca ggctcatcgc attcgcatcc cggggtaacc acgtctcacc gacgcactat   4500
gtccccgaga gcgatgctgc agcgaaggtt actgcattgc tgagttctct aactgtcaca   4560
agtctgctcc ggcgactgca ccagtggatc aatgaagact acccaagtcc ttgctgcggc   4620
gactggctgc gtaccatctg ggactgggtt tgcatggtgt tgtctgactt caagacatgg   4680
ctctccgcta agattatgcc agcgctccct gggctgcctt tcctttcctg tcagaaggga   4740
tacaagggcg tgtggcgggg agacggtgtg atgtcgacac gctgtccttg cggggcgaca   4800
ataaccggtc atgtgaagaa tgggtctatg cggcttgcag ggccacgcac atgtgctaac   4860
atgtggcacg gtactttccc catcaatgag tacaccaccg acccggcac accttgccca   4920 gcacccaact acactcgcgc attattgcgc gtggctgcca acagctacgt tgaggtgcgc   4980
cgggtggggg acttccacta cattacgggg gctacagaag atgagctcaa gtgtccgtgc   5040
caagtgccgg ccgcagagtt ttttactgag gtggatgggg tgagactcca ccgttacgcc   5100
cctccatgca agcccctgtt gagggatgaa atcactttca tggtagggtt gaactcctac   5160
gcaataggat ctcaactccc ctgtgagccc gaaccagatg tttctgtgct gacctcgatg   5220
ttgagagacc cttcccatat tgccgctgag gcagcagcgc gccgcttgc gcgtgggtcc   5280 cctccatcag aggcaagctc atccgccagc caactgtcgg ctccgtcgtt gaaggccact   5340
tgtcagtcgt atgggcctca tctggacgct gagctagtgg atgccaacct gttatgcgg   5400 caggagatgg gcagcactat cacacgggta gagtctgaaa caaaggttgt gattcttgat   5460
tcattcgaac ctcgagagc cgaaactgat gacgccgagc tctcggtggc tgcagagtgt   5520
ttcaagaagc ctcccaagta tcctccagcc cttcctatct gggctaggcc agactacaac   5580
cctccattgt tagaccgctg gaaagcaccg gattatgttc caccaactgt tcatggatgc   5640
gccttaccac cacggggcgc tccaccggtg cctcccctc ggaggaagag aacaattcag   5700
ctggatggct ccaatgtgtc cgcggcgcta gctgcgctag cagaaaagtc attcccgtcc   5760
tcaaagccgc aggaagagaa tagctcatcc tcaggggtcg acacacagtc cagcactacc   5820
tctaaggtgc ccccccccc aggagggaa tccgactcag agtcgtgctc gtccatgcct   5880
cctctcgagg gagagccggg cgatccggat ttgagctgcg actcttggtc cactgtgagt   5940
gacaatgagg agcagaacgt agtctgctgc tccatgtcgt actcttggac cggcgccttg   6000
```

```
ataacaccat gtagtgctga ggaggagaaa ctacccatca gcccactcag caactccttg     6060
ttgagacacc ataatctggt ttattcaacg tcgtcaagaa gcgcttctca gcgtcagaag     6120
aaggttacct tcgacaggct gcaggtgctc gacgaccact acaaaactgc tttaaaggag     6180
gtaaaggagc gagcgtctgg ggtgaaggct cgcatgctca ccatcgagga agcgtgcaag     6240
cttgtccccc cccactctgc ccgttcgaag ttcgggtata gtgcgaagga cgctcgttcc     6300
ttgtccagca gggccgttaa ccagatccgc tccgtctggg aggacttgct ggaagacacc     6360
acaactccaa ttccaacaac catcatggcg aagaacgagg tgttttgtgt ggaccccgtt     6420 aagggggggcc gcaagcccgc tcgcctcatt gtgtaccctg acctgggggt gcgtgtctgt     6480
gagaaacgcg ccctatatga cgtgatacag aagttgtcaa tcgcgacgat gggtcctgct     6540
tatggattcc agtactcgcc tcagcagcgg gtcgaacgtc tgctgaagat gtggaccctca     6600 aagagaaccc ccctggggtt ctcgtatgac acccgctgct ttgactcgac tgtcactgaa     6660
caggatatca gggtggaaga ggagatatat caatgctgta accttgaacc ggaggccagg     6720
aaggtgatct cctccctcac ggagcggctt tactgcgggg cccccatgtt caacagcaag     6780
ggggcccagt gcggttatcg ccgttgccgt gctagtggag ttctaccgac cagctttggc     6840
aacacaatca cttgttacat caaggccaca gcggctgcaa gggccgcggg tctccggaac     6900
ccggactttc ttgtctgcgg agatgatttg gtcgtggtgg ccgagagtga tggcgtcgac     6960
gaggataggg cagccctgag agccttcacg gaggctatga ccaggtactc tgctccaccc     7020
ggagatgctc cacagcctac ctacgacctt gagctcatca catcttgctc ctctaacgtc     7080
tccgtagcac atgacaacaa ggggaggagg tattactacc tcacccgtga tgccactact     7140
cccctggccc gtgcggcttg ggaaacagct cgtcacactc cagttaactc ctggttgggc     7200
aacatcatca tgtacgcgcc taccatctgg gtgcgcatgg tgatgatgac acactttttc     7260
tccatactcc aatcccagga gatacttgat cgcccccttg attttgaaat gtacggggcc     7320
acttactctg tcactccgct ggatttacca gcaatcattg aaagactcca tggtctaagc     7380
gcgttcacac tccacagtta ctctccagta gaactcaata gggtcgcggg gacactcagg     7440
aagcttgggt gccccccccct acgagcttgg agacatcggg cacgagcagt gcgcgctaag     7500
cttattgccc agggaggtaa ggccaaaata tgtggccttt atctctttaa ctgggcagta     7560
cgcaccaaga ccaaactcac tccactgcca gccgctagcc agttggactt atccaattgg     7620
ttttcggttg gcgtcggcgg gaacgacatt tatcacagcg tgtcacatgc ccgaacccgc     7680
catttgctgc tttgcctact cctactaact gtaggggtag gcatctttct cctgccagca     7740
cgataagctg gtaggataac actccattcc tttttccttg ttttatttt ttttttttt     7800 ttttttttt tttttttttt ttcttttttt tttttttttt tttttttttg ttttcctct     7860 ttccattctt ttctaacctt aaattttcct ttctttaggt ggctccatct tagccctagt     7920
cacggctagc tgtgaaaggt ccgtgagccg catgactgca gagagtgccg taactggtct     7980
ctctgcagat catgt                                                     7995
```

<210> SEQ ID NO 22
<211> LENGTH: 7995
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA sequence of mutant S310A T2496I HCV subgenomic replicon RNA

<400> SEQUENCE: 22

```
gacctgcctc ttacgaggcg acactccacc atggatcact cccctgtgag gaacttctgt      60
cttcacgcgg aaagcgccta gccatggcgt tagtacgagt gtcgtgcagc ctccaggacc     120
cccctcccg ggagagccat agtggtctgc ggaaccggtg agtacaccgg aatcgctggg     180
gtgaccgggt cctttcttgg aacaacccgc tcaataccca gaaatttggg cgtgcccccg     240
cgagatcact agccgagtag tgttgggtcg cgaaaggcct tgtggtactg cctgataggg     300
tgcttgcgag tgccccggga ggtctcgtag accgtgcaac atgagcacac ttcctaaacc     360
ccaaagaaaa accaaaagaa acaccatccg tcgcccaatg attgaacaag atggattgca     420
cgcaggttct ccggccgctt gggtggagag gctattcggc tatgactggg cacaacagac     480
aatcggctgc tctgatgccg ccgtgttccg gctgtcagcg caggggcgcc cggttctttt     540
tgtcaagacc gacctgtccg gtgccctgaa tgaactgcag gacgaggcag cgcggctatc     600
gtggctggcc acgacgggcg ttccttgcgc agctgtgctc gacgttgtca ctgaagcggg     660
aagggactgg ctgctattgg gcgaagtgcc ggggcaggat ctcctgtcat ctcaccttgc     720
tcctgccgag aaagtatcca tcatggctga tgcaatgcgg cggctgcata cgcttgatcc     780
ggctacctgc ccattcgacc accaagcgaa acatcgcatc gagcgagcac gtactcggat     840
ggaagccggt cttgtcgatc aggatgatct ggacgaagag catcagggc tcgcgccagc     900
cgaactgttc gccaggctca aggcgcgcat gcccgacggc gaggatctcg tcgtgaccca     960
tggcgatgcc tgcttgccga atatcatggt ggaaaatggc cgcttttctg gattcatcga    1020
ctgtggccgg ctgggtgtgg cggaccgcta tcaggacata gcgttggcta cccgtgatat    1080
tgctgaagag cttggcggcg aatgggctga ccgcttcctc gtgctttacg gtatcgccgc    1140
tcccgattcg cagcgcatcg ccttctatcg ccttcttgac gagttcttct gagtttaaac    1200
cctctccctc ccccccccct aacgttactg gccgaagccg cttggaataa ggccggtgtg    1260
cgtttgtcta tatgttattt tccaccatat tgccgtcttt tggcaatgtg agggcccgga    1320
aacctggccc tgtcttcttg acgagcattc ctagggtct ttcccctctc gccaaaggaa    1380
tgcaaggtct gttgaatgtc gtgaaggaag cagttcctct ggaagcttct tgaagacaaa    1440
caacgtctgt agcgacccct tgcaggcagc ggaacccccc acctggcgac aggtgcctct    1500
gcggccaaaa gccacgtgta taagatacac ctgcaaaggc ggcacaaccc cagtgccacg    1560
ttgtgagttg gatagttgtg gaaagagtca aatggctctc ctcaagcgta ttcaacaagg    1620
ggctgaagga tgcccagaag gtaccccatt gtatgggatc tgatctgggg cctcggtgca    1680
catgctttac atgtgtttag tcgaggttaa aaaacgtct aggccccccg aaccacgggg    1740
acgtggtttt cctttgaaaa acacgatgat accatggccc cgatcactgc ttacgcccag    1800
caaaccaggg gccttcttgg gactattgtg accagcttga ctggcaggga taagaatgtg    1860
gtgaccggca aagtgcaggt gctttctacg gctacccaga ccttcctagg tacaacaata    1920
gggggggtta tgtggactgt ttaccatggc gcaggctcaa ggacacttgc gggcgctaaa    1980
catcctgcgc tccaaatgta cacaaatgta gatcaggacc tcgttgggtg ccagcccct    2040
ccaggggcta agtctcttga accgtgcacc tgcgggtctg cagacttata cttggttacc    2100
cgcgatgctg acgtcatccc cgctcggcgc aggggggact ccacagcgag cttgctcagc    2160
cctaggcctc tcgcctgtct caagggctcc tctggaggtc ccgttatgtg cccttcgggg    2220
catgtcacgg ggatctttcg ggctgctgtg tgcaccagag gtgtagcaaa gaccctacag    2280
```

```
ttcataccag tggaaaccct tagtacacag actaggtccc catccttctc tgacaattca   2340
actcctcccg ccgtcccaca gagctaccaa gtagggtatc ttcatgcccc gaccggtagt   2400
ggcaagagca caaaggtccc ggccgcttac gtagcacaag gataccatgt tctcgtgttg   2460
aatccatcag tggcggccac actaggcttc ggctcttaca tgtcgaaagc ctatgggatc   2520
gaccccaacg tccgcactgg gaaccgcact gtcacaactg gtgctaaact gacctattcc   2580
acctacggta agtttctcgc ggatgggggt tgctctgggg gagcgtatga tgtgattatt   2640
tgtgatgaat gccatgccca agacgctact accatattgg gtattggcac ggtcttagat   2700
caggctgaga cggctggggt gaggctgacg gttctggcga cagcaactcc cccaggcagc   2760
atcactgtgc cacattctaa catcgaggag gtagccctgg gctctgaagg tgagatccct   2820
ttctacggta aggctatacc gatagcccag ctcaaggggg ggaggcacct tatcttttgc   2880
cattccaaga aaaagtgtga tgagatagca tccaagctca gaggcatggg gctcaacgct   2940
gtagcattct atagggggtct tgatgtgtcc atcataccaa cagcaggaga cgtcgtggtt   3000
tgcgccactg acgccctcat gactgggtac accggagact ttgattctgt catagattgc   3060
aacgtgactg ttgaacagta cgttgacttc agcttggacc ccaccttttc cattgagact   3120
cacactgctc cccaagacgc ggtttcccgc agccaacgtc gtggccgtac gggccggggt   3180
agactcggca tataccgata tgtcaccccg ggtgaaagac cgtctggaat gtttgactcg   3240
gttgttctct gtgagtgcta tgatgcgggc tgctcgtggt acgatctgca gcccgctgag   3300
actacagtca gactgagagc ttacttgtcc acgccgggtt tacctgtctg tcaagaccat   3360
cttgactttt gggagagcgt ctttactgga ctaactcaca tagatgccca ctttctgtca   3420
cagactaagc agcagggact caacttcccg tacctgactg cctaccaagc cactgtgtgc   3480
gcccgcgcgc aggctcctcc cccaagttgg gacgagacgt ggaaatgtct cgtacggctt   3540
aaaccaacac tacatggacc cacgccccct ctgtatcggt tggggcctat ccaaaatgaa   3600
acctgcttga cacaccccgt cacaaaatac atcatggcat gcatgtcagc tgatctggaa   3660
gtgaccacca gcgcctgggt gttgcttgga ggggtgctcg cggccctagc ggcttactgc   3720
ttgtcagtcg gctgcgttgt gatcgtgggt catattgagc tggggggcaa gccagcactc   3780
gttccagaca agaggtgtt gtatcaacaa ttcgatgaga tggaggagtg ctcgcaagct   3840
gccccatata tcgaacaagc tcaggtaata gccaccagt tcaaggagaa agtccttgga   3900
ttgctgcagc gagccaccca caacaagct gtcattgagc ccatagtagc taccaactgg   3960
caaaagcttg aggcgttctg gcacaagcat atgtggaatt ttgtgagtgg gatccagtac   4020
ctagcaggcc tttccacttt gcctggcaac cccgctgtgg cgtctcttat ggcgttcacc   4080
gcttctgtca ccagtcccct gacgaccaac caaactatgt tcttcaacat actcgggggg   4140
tgggttgcta cccatttggc agggccccag agctcttccg cattcgtggt aagcggcttg   4200
gccggcgctg ccatagggg tataggcctg gcagggtct tgattgacat cctggcagga   4260 tacgagctg gtgtctcagg cgccttggtg gcttttaaga tcatgggagg agaactcccc   4320
actgctgagg acatggtcaa catgctgcct gccatactat ctccgggcgc cctcgttgtc   4380
ggtgtgatat gtgcagccat actgcgtcga cacgtaggac ctgggagg gcgggtgcag   4440 tggatgaaca ggctcatcgc attcgcatcc cggggtaacc acgtctcacc gacgcactat   4500
gtccccgaga gcgatgctgc agcgaaggtt actgcattgc tgagttctct aactgtcaca   4560
agtctgctcc ggcgactgca ccagtggatc aatgaagact acccaagtcc ttgctgcggc   4620
gactggctgc gtaccatctg ggactgggtt tgcatggtgt tgtctgactt caagacatgg   4680
```

-continued

```
ctctccgcta agattatgcc agcgctccct gggctgcctt tcctttcctg tcagaaggga   4740
tacaagggcg tgtggcgggg agacggtgtg atgtcgacac gctgtccttg cggggcgaca   4800
ataaccggtc atgtgaagaa tgggtctatg cggcttgcag ggccacgcac atgtgctaac   4860
atgtggcacg gtactttccc catcaatgag tacaccaccg gacccggcac accttgccca   4920
gcacccaact acactcgcgc attattgcgc gtggctgcca acagctacgt tgaggtgcgc   4980
cgggtggggg acttccacta cattacgggg gctacagaag atgagctcaa gtgtccgtgc   5040
caagtgccgg ccgcagagtt ttttactgag gtggatgggg tgagactcca ccgttacgcc   5100
cctccatgca agccctgtt gagggatgaa atcactttca tggtagggtt gaactcctac    5160
gcaataggat ctcaactccc ctgtgagccc gaaccagatg tttctgtgct gacctcgatg   5220
ttgagagacc cttcccatat taccgctgag gcagcagcgc gccgccttgc gcgtgggtcc   5280
cctccatcag aggcaagctc atccgccagc caactgtcgg ctccgtcgtt gaaggccact   5340
tgtcagtcgt atgggcctca tctggacgct gagctagtgg atgccaacct gttatggcgg   5400
caggagatgg gcagcactat cacacgggta gagtctgaaa caaaggttgt gattcttgat   5460
tcattcgaac ctctgagagc cgaaactgat gacgccgagc tctcggtggc tgcagagtgt   5520
ttcaagaagc ctcccaagta tcctccagcc cttcctatct gggctaggcc agactacaac   5580
cctccattgt tagaccgctg gaaagcaccg gattatgttc caccaactgt tcatggatgc   5640
gccttaccac cacggggcgc tccaccggtg cctccccctc ggaggaagag aacaattcag   5700
ctggatggct ccaatgtgtc cgcggcgcta gctgcgctag cagaaaagtc attcccgtcc   5760
tcaaagccgc aggaagagaa tagctcatcc tcaggggtcg acacacagtc cagcactacc   5820
tctaaggtgc ccccccccc aggaggggaa tccgactcag agtcgtgctc gtccatgcct    5880
cctctcgagg gagagccggg cgatccggat ttgagctgcg actcttggtc cactgtgagt   5940
gacaatgagg agcagaacgt agtctgctgc tccatgtcgt actcttggac cggcgccttg   6000
ataacaccat gtagtgctga ggaggagaaa ctacccatca gcccactcag caactccttg   6060
ttgagacacc ataatctggt ttattcaacg tcgtcaagaa gcgcttctca gcgtcagaag   6120
aaggttacct tcgacaggct gcaggtgctc gacgaccact acaaaattgc tttaaaggag   6180
gtaaaggagc gagcgtctgg ggtgaaggct cgcatgctca ccatcgagga agcgtgcaag   6240
cttgtccccc cccactctgc ccgttcgaag ttcgggtata tgcgaaggac gctccgttcc   6300
ttgtccagca gggccgttaa ccagatccgc tccgtctggg aggacttgct ggaagacacc   6360
acaactccaa ttccaacaac catcatggcg aagaacgagg tgttttgtgt ggaccccgtt   6420
aagggggggcc gcaagcccgc tcgcctcatt gtgtaccctg acctgggggt gcgtgtctgt   6480
gagaaacgcg ccctatatga cgtgatacag aagttgtcaa tcgcgacgat gggtcctgct   6540
tatggattcc agtactcgcc tcagcagcgg gtcgaacgtc tgctgaagat gtggacctca   6600
aagagaaccc ccctgggggtt ctcgtatgac acccgctgct ttgactcgac tgtcactgaa   6660
caggatatca gggtggaaga ggagatatat caatgctgta accttgaacc ggaggccagg   6720
aaggtgatct cctccctcac ggagcggctt tactgcgggg gccccatgtt caacagcaag   6780
ggggcccagt gcggttatcg ccgttgccgt gctagtggaa ttctaccgac cagctttggc   6840
aacacaatca cttgttacat caaggccaca gcggctgcaa gggccgcggg tctccggaac   6900
ccggactttc ttgtctgcgg agatgatttg gtcgtggtgg ccgagagtga tggcgtcgac   6960
gaggataggg cagccctgag agccttcacg gaggctatga ccaggtactc tgctccaccc   7020
```

```
ggagatgctc cacagcctac ctacgacctt gagctcatca catcttgctc ctctaacgtc    7080
tccgtagcac atgacaacaa ggggaggagg tattactacc tcacccgtga tgccactact    7140
cccctggccc gtgcggcttg ggaaacagct cgtcacactc cagttaactc ctggttgggc    7200
aacatcatca tgtacgcgcc taccatctgg gtgcgcatgg tgatgatgac acactttttc    7260
tccatactcc aatcccagga gatacttgat cgccccttg attttgaaat gtacggggcc     7320
acttactctg tcactccgct ggatttacca gcaatcattg aaagactcca tggtctaagc    7380
gcgttcacac tccacagtta ctctccagta gaactcaata gggtcgcggg gacactcagg    7440
aagcttgggt gcccccccct acgagcttgg agacatcggg cacgagcagt gcgcgctaag    7500
cttattgccc agggaggtaa ggccaaaata tgtggccttt atctctttaa ctgggcagta    7560
cgcaccaaga ccaaactcac tccactgcca gccgctagcc agttggactt atccaattgg    7620
ttttcggttg gcgtcggcgg gaacgacatt tatcacagcg tgtcacatgc ccgaacccgc    7680
catttgctgc tttgcctact cctactaact gtaggggtag gcatcttct cctgccagca     7740 cgataagctg gtaggataac actccattcc ttttcccttg tttttatttt tttttttttt    7800
tttttttttt ttttttttt ttctttttt ttttttttt ttttttttg ttttcctct         7860 ttccattctt ttctaacctt aaattttcct ttctttaggt ggctccatct tagccctagt    7920
cacggctagc tgtgaaaggt ccgtgagccg catgactgca gagagtgccg taactggtct    7980
ctctgcagat catgt                                                     7995

<210> SEQ ID NO 23
<211> LENGTH: 7995
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA sequence of mutant S310A R2895G HCV
      subgenomic replicon RNA

<400> SEQUENCE: 23
gacctgcctc ttacgaggcg acactccacc atggatcact cccctgtgag gaacttctgt     60
cttcacgcgg aaagcgccta gccatggcgt tagtacgagt gtcgtgcagc ctccaggacc    120 cccctcccg ggagagccat agtggtctgc ggaaccggtg agtacaccgg aatcgctggg     180
gtgaccgggt cctttcttgg aacaacccgc tcaataccca gaaatttggg cgtgccccccg   240 cgagatcact agccgagtag tgttgggtcg cgaaaggcct tgtggtactg cctgataggg    300
tgcttgcgag tgccccggga ggtctcgtag accgtgcaac atgagcacac ttcctaaacc    360
ccaaagaaaa accaaaagaa acaccatccg tcgcccaatg attgaacaag atggattgca    420
cgcaggttct ccggccgctt gggtggagag gctattcggc tatgactggg cacaacagac    480
aatcggctgc tctgatgccg ccgtgttccg gctgtcagcg caggggcgcc cggttctttt    540
tgtcaagacc gacctgtccg gtgccctgaa tgaactgcag gacgaggcag cgcggctatc    600
gtggctggcc acgacgggcg ttccttgcgc agctgtgctc gacgttgtca ctgaagcggg    660
aagggactgg ctgctattgg gcgaagtgcc ggggcaggat ctcctgtcat ctcaccttgc    720
tcctgccgag aaagtatcca tcatggctga tgcaatgcgg cggctgcata cgcttgatcc    780
ggctacctgc ccattcgacc accaagcgaa acatcgcatc gagcgagcac gtactcggat    840
ggaagccggt cttgtcgatc aggatgatct ggacgaagag catcagggc tcgcgccagc     900 cgaactgttc gccaggctca aggcgcgcat gcccgacggc gaggatctcg tcgtgaccca    960
```

```
tggcgatgcc tgcttgccga atatcatggt ggaaaatggc cgcttttctg gattcatcga    1020
ctgtggccgg ctgggtgtgg cggaccgcta tcaggacata gcgttggcta cccgtgatat    1080
tgctgaagag cttggcggcg aatgggctga ccgcttcctc gtgctttacg gtatcgccgc    1140
tcccgattcg cagcgcatcg ccttctatcg ccttcttgac gagttcttct gagtttaaac    1200
cctctccctc ccccccccct aacgttactg gccgaagccg cttggaataa ggccggtgtg    1260
cgtttgtcta tatgttattt tccaccatat tgccgtcttt tggcaatgtg agggcccgga    1320
aacctggccc tgtcttcttg acgagcattc ctaggggtct ttccctctc gccaaggaa      1380 tgcaaggtct gttgaatgtc gtgaaggaag cagttcctct ggaagcttct tgaagacaaa    1440
caacgtctgt agcgacccct tgcaggcagc ggaaccccc  acctggcgac aggtgcctct    1500
gcggccaaaa gccacgtgta taagatacac ctgcaaaggc ggcacaaccc cagtgccacg    1560
ttgtgagttg atagttgtg  gaaagagtca atggctctc  ctcaagcgta ttcaacaagg    1620
ggctgaagga tgcccagaag gtaccccatt gtatgggatc tgatctgggg cctcggtgca    1680
catgctttac atgtgtttag tcgaggttaa aaaaacgtct aggccccccg aaccacgggg    1740
acgtggtttt cctttgaaaa acacgatgat accatggccc cgatcactgc ttacgcccag    1800
caaaccaggg gccttcttgg gactattgtg accagcttga ctggcaggga taagaatgtg    1860
gtgaccggcg aagtgcaggt gctttctacg gctacccaga ccttcctagg tacaacaata    1920 ggggggggtta tgtggactgt ttaccatggc gcaggctcaa ggacacttgc gggcgctaaa    1980
catcctgcgc tccaaatgta cacaaatgta gatcaggacc tcgttgggtg gccagcccct    2040 ccagggcta  agtctcttga accgtgcacc tgcgggtctg cagacttata cttggttacc    2100
cgcgatgctg acgtcatccc cgctcggcgc agggggact  ccacagcgag cttgctcagc    2160
cctaggcctc tcgcctgtct caagggctcc tctggaggtc ccgttatgtg cccttcgggg    2220
catgtcacgg ggatctttcg ggctgctgtg tgcaccagag gtgtagcaaa gaccctacag    2280
ttcataccag tggaaaccct tagtacacag actaggtccc catccttctc tgacaattca    2340
actcctcccg ccgtcccaca gagctaccaa gtagggtatc ttcatgcccc gaccggtagt    2400
ggcaagagca caaaggtccc ggccgcttac gtagcacaag gataccatgt tctcgtgttg    2460
aatccatcag tggcggccac actaggcttc ggctcttaca tgtcgaaagc ctatgggatc    2520
gaccccaacg tccgcactgg gaaccgcact gtcacaactg gtgctaaact gacctattcc    2580
acctacggta agtttctcgc ggatgggggt tgctctgggg gagcgtatga tgtgattatt    2640
tgtgatgaat gccatgccca agacgctact accatattgg gtattggcac ggtcttagat    2700
caggctgaga cggctggggt gaggctgacg gttctggcga cagcaactcc cccaggcagc    2760
atcactgtgc cacattctaa catcgaggag gtagccctgg gctctgaagg tgagatccct    2820
ttctacggta aggctatacc gatagcccag ctcaagggg ggaggcacct tatcttttgc      2880
cattccaaga aaaagtgtga tgagatagca tccaagctca gaggcatggg gctcaacgct    2940
gtagcattct atagggtct  tgatgtgtcc atcataccaa cagcaggaga cgtcgtggtt    3000
tgcgccactg acgccctcat gactgggtac accggagact tgattctgt  catagattgc    3060 aacgtgactg ttgaacagta cgttgacttc agccttggacc ccacctttt  cattgagact    3120 cacactgctc cccaagacgc ggtttcccgc agccaacgtc gtggccgtac gggccggggt    3180
agactcggca tataccgata tgtcaccccg ggtgaaagac cgtctggaat gtttgactcg    3240
gttgttctct gtgagtgcta tgatgcgggc tgctcgtggt acgatctgca gcccgctgag    3300
```

```
actacagtca gactgagagc ttacttgtcc acgccgggtt tacctgtctg tcaagaccat    3360
cttgactttt gggagagcgt ctttactgga ctaactcaca tagatgccca ctttctgtca    3420
cagactaagc agcagggact caacttcccg tacctgactg cctaccaagc cactgtgtgc    3480
gcccgcgcgc aggctcctcc cccaagttgg gacgagacgt ggaaatgtct cgtacggctt    3540
aaaccaacac tacatggacc cacgcccctt ctgtatcggt tggggcctat ccaaaatgaa    3600
acctgcttga cacaccccgt cacaaaatac atcatggcat gcatgtcagc tgatctggaa    3660
gtgaccacca gcgcctgggt gttgcttgga ggggtgctcg cggccctagc ggcttactgc    3720
ttgtcagtcg gctgcgttgt gatcgtgggt catattgagc tggggggcaa gccagcactc    3780
gttccagaca aagaggtgtt gtatcaacaa ttcgatgaga tggaggagtg ctcgcaagct    3840
gccccatata tcgaacaagc tcaggtaata gcccaccagt tcaaggagaa agtccttgga    3900
ttgctgcagc gagccaccca acaacaagct gtcattgagc ccatagtagc taccaactgg    3960
caaaagcttg aggcgttctg gcacaagcat atgtggaatt ttgtgagtgg gatccagtac    4020
ctagcaggcc tttccacttt gcctggcaac cccgctgtgg cgtctcttat ggcgttcacc    4080
gcttctgtca ccagtcccct gacgaccaac caaactatgt tcttcaacat actcggggg    4140 tgggttgcta cccatttggc agggcccag agctcttccg cattcgtggt aagcggcttg    4200
gccggcgctg cctaggggg tataggcctg gcagggtct tgattgacat cctggcagga    4260 tacgagctg gtgtctcagg cgccttggtg gcttttaaga tcatgggagg agaactcccc    4320
actgctgagg acatggtcaa catgctgcct gccatactat ctccgggcgc cctcgttgtc    4380
ggtgtgatat gtgcagccat actgcgtcga cacgtaggac ctggggaggg ggcggtgcag    4440
tggatgaaca ggctcatcgc attcgcatcc cggggtaacc acgtctcacc gacgcactat    4500
gtccccgaga gcgatgctgc agcgaaggtt actgcattgc tgagttctct aactgtcaca    4560
agtctgctcc ggcgactgca ccagtggatc aatgaagact acccaagtcc ttgctgcggc    4620
gactggctgc gtaccatctg ggactgggtt tgcatggtgt tgtctgactt caagacatgg    4680
ctctccgcta agattatgcc agcgctccct gggctgcctt tcctttcctg tcagaaggga    4740
tacaagggcg tgtggcgggg agacggtgtg atgtcgacac gctgtccttg cggggcgaca    4800
ataaccggtc atgtgaagaa tgggtctatg cggcttgcag ggccacgcac atgtgctaac    4860
atgtggcacg gtactttccc catcaatgag tacaccaccg gacccggcac accttgccca    4920
gcacccaact acactcgcgc attattgcgc gtggctgcca acagctacgt tgaggtgcgc    4980
cgggtggggg acttccacta cattacgggg gctacagaag atgagctcaa gtgtccgtgc    5040
caagtgccgg ccgcagagtt ttttactgag gtggatgggg tgagactcca ccgttacgcc    5100
cctccatgca agcccctgtt gagggatgaa atcacttttca tggtagggtt gaactcctac    5160
gcaataggat ctcaactccc ctgtgagccc gaaccagatg tttctgtgct gacctcgatg    5220
ttgagagacc cttcccatat taccgctgag gcagcagcgc gccgccttgc gcgtgggtcc    5280
cctccatcag aggcaagctc atccgccagc caactgtcgg ctccgtcgtt gaaggccact    5340
tgtcagtcgt atgggcctca tctggacgct gagctagtgg atgccaacct gttatggcgg    5400
caggagatgg gcagcactat cacacgggta gagtctgaaa caaaggttgt gattcttgat    5460
tcattcgaac tctgagagc cgaaactgat gacgccgagc tctcggtggc tgcagagtgt    5520
ttcaagaagc ctcccaagta tcctccagca cttcctatct gggctaggcc agactacaac    5580
cctccattgt tagaccgctg gaaagcaccg gattatgttc caccaactgt tcatggatgc    5640
gccttaccac cacggggcgc tccaccggtg cctcccccctc ggaggaagag aacaattcag    5700
```

```
ctggatggct ccaatgtgtc cgcggcgcta gctgcgctag cagaaaagtc attcccgtcc    5760
tcaaagccgc aggaagagaa tagctcatcc tcaggggtcg acacacagtc cagcactacc    5820
tctaaggtgc cccccccccc aggaggggaa tccgactcag agtcgtgctc gtccatgcct    5880
cctctcgagg gagagccggg cgatccggat ttgagctgcg actcttggtc cactgtgagt    5940
gacaatgagg agcagaacgt agtctgctgc tccatgtcgt actcttggac cggcgccttg    6000
ataacaccat gtagtgctga ggaggagaaa ctacccatca gcccactcag caactccttg    6060
ttgagacacc ataatctggt ttattcaacg tcgtcaagaa gcgcttctca gcgtcagaag    6120
aaggttacct tcgacaggct gcaggtgctc gacgaccact acaaaactgc tttaaaggag    6180
gtaaaggagc gagcgtctgg ggtgaaggct cgcatgctca ccatcgagga agcgtgcaag    6240
cttgtccccc cccactctgc ccgttcgaag ttcgggtata gtgcgaagga cgctcgttcc    6300
ttgtccagca gggccgttaa ccagatccgc tccgtctggg aggacttgct ggaagacacc    6360
acaactccaa ttccaacaac catcatggcg aagaacgagg tgttttgtgt ggaccccgtt    6420
aaggggggcc gcaagcccgc tcgcctcatt gtgtaccctg acctgggggt gcgtgtctgt    6480
gagaaacgcg ccctatatga cgtgatacag aagttgtcaa tcgcgacgat gggtcctgct    6540
tatggattcc agtactcgcc tcagcagcgg gtcgaacgtc tgctgaagat gtggacctca    6600
aagagaaccc ccctggggtt ctcgtatgac acccgctgct ttgactcgac tgtcactgaa    6660
caggatatca gggtggaaga ggagatatat caatgctgta accttgaacc ggaggccagg    6720
aaggtgatct cctccctcac ggagcggctt tactgcgggg gccccatgtt caacagcaag    6780
ggggcccagt gcggttatcg ccgttgccgt gctagtggag ttctaccgac cagctttggc    6840
aacacaatca cttgttacat caaggccaca gcggctgcaa gggccgcggg tctccggaac    6900
ccggactttc ttgtctgcgg agatgatttg gtcgtggtgg ccgagagtga tggcgtcgac    6960
gaggataggg cagccctgag agccttcacg gaggctatga ccaggtactc tgctccaccc    7020
ggagatgctc cacagcctac ctacgacctt gagctcatca catcttgctc ctctaacgtc    7080
tccgtagcac atgacaacaa ggggaggagg tattactacc tcacccgtga tgccactact    7140
cccctggccc gtgcggcttg ggaaacagct cgtcacactc cagttaactc ctggttgggc    7200
aacatcatca tgtacgcgcc taccatctgg gtgcgcatgg tgatgatgac acactttttc    7260
tccatactcc aatcccagga gatacttgat cgccccttg attttgaaat gtacggggcc    7320
acttactctg tcactccgct ggatttacca gcaatcattg aaggactcca tggtctaagc    7380
gcgttcacac tccacagtta ctctccagta gaactcaata gggtcgcggg gacactcagg    7440
aagcttgggt gccccccccct acgagcttgg agacatcggg cacgagcagt gcgcgctaag    7500
cttattgccc agggaggtaa ggccaaaata tgtggccttt atctctttaa ctgggcagta    7560
cgcaccaaga ccaaactcac tccactgcca gccgctagcc agttggactt atccaattgg    7620
ttttcggttg gcgtcggcgg gaacgacatt tatcacagcg tgtcacatgc ccgaacccgc    7680
catttgctgc tttgcctact cctactaact gtaggggtag gcatctttct cctgccagca    7740
cgataagctg gtaggataac actccattcc ttttcccttg tttttatttt tttttttttt    7800
tttttttttt tttttttttt ttctttttttt tttttttttt tttttttttg tttttcctct    7860
ttccattctt ttctaacctt aaatttttcct ttctttaggt ggctccatct tagccctagt    7920
cacggctagc tgtgaaaggt ccgtgagccg catgactgca gagagtgccg taactggtct    7980
ctctgcagat catgt                                                     7995
```

```
<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      TaqMan probing primer

<400> SEQUENCE: 24
cgggagagcc atagtgg                                                    17

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      TaqMan probing primer

<400> SEQUENCE: 25
agtaccacaa ggcctttcg                                                  19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      TaqMan probing probe

<400> SEQUENCE: 26
ctgcggaacc ggtgagtaca c                                               21

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
taatacgact cactatag                                                   18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcggctcacg gacctttcac                                                 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer Neo-S4

<400> SEQUENCE: 29
tcctcgtgct ttacggtatc                                                 20
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer 1286R

<400> SEQUENCE: 30
gttcccaatg cggacgttgg                                           20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer 1286F

<400> SEQUENCE: 31
ccaacgtccg cattgggaac                                           20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic primer 5546R

<400> SEQUENCE: 32
tccttgaact ggtgggctat t                                         21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer 5240F

<400> SEQUENCE: 33
tggggcctgt ccaaaatgaa                                           20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic primer 2188R

<400> SEQUENCE: 34
gcctcagcgg caatatggga a                                         21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic primer 2188F

<400> SEQUENCE: 35
ttcccatatt gccgctgagg c                                         21

<210> SEQ ID NO 36

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer 7601R

<400> SEQUENCE: 36
actaacggtg gaccaagagt                                                   20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 2198R

<400> SEQUENCE: 37
gaggggaccc atgcgcaagg c                                                 21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 2198F

<400> SEQUENCE: 38
gccttgcgca tgggtcccct c                                                 21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 7276F

<400> SEQUENCE: 39
gtaccaccaa ctgtccatgg a                                                 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 2496R

<400> SEQUENCE: 40
ttaaagcaat tttgtagtgg t                                                 21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 2496F

<400> SEQUENCE: 41
accactacaa aattgcttta a                                                 21

<210> SEQ ID NO 42
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer 8579R

<400> SEQUENCE: 42
ccgcagacaa gaaagtccgg gt                                              22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 7988F

<400> SEQUENCE: 43
gctccgtctg ggaggacttg c                                               21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer R2895G-R

<400> SEQUENCE: 44
atggagtcct tcaatgattg c                                               21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer R2895G-F

<400> SEQUENCE: 45
gcaatcattg aaggactcca t                                               21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer 3X-54R-2a

<400> SEQUENCE: 46
gcggctcacg gacctttcac                                                 20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer R2895K-R

<400> SEQUENCE: 47
atggagtttt tcaatgattg c                                               21

<210> SEQ ID NO 48
<211> LENGTH: 21
<212> TYPE: DNA
```

<213> ORGANISM: Artificial Sequence
<220> FEATURE:
<223> OTHER INFORMATION: Description of Artificial Sequence: Synthetic
    primer R2895K-F

<400> SEQUENCE: 48
gcaatcattg aaaaactcca t                                              21

<210> SEQ ID NO 49
<211> LENGTH: 9655
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: cDNA sequence of mutant S310A S2210I HCV full
    genomic replicon RNA

<400> SEQUENCE: 49

| | | | | | |
|---|---|---|---|---|---|
| gacctgcctc | ttacgaggcg | acactccacc | atggatcact | cccctgtgag | gaacttctgt | 60 |
| cttcacgcgg | aaagcgccta | gccatggcgt | tagtacgagt | gtcgtgcagc | ctccaggacc | 120 |
| ccccctcccg | ggagagccat | agtggtctgc | ggaaccggtg | agtacaccgg | aatcgctggg | 180 |
| gtgaccgggt | cctttcttgg | aacaacccgc | tcaataccca | gaaatttggg | cgtgccccg | 240 |
| cgagatcact | agccgagtag | tgttgggtcg | cgaaaggcct | tgtggtactg | cctgataggg | 300 |
| tgcttgcgag | tgccccggga | ggtctcgtag | accgtgcaac | atgagcacac | ttcctaaacc | 360 |
| ccaaagaaaa | accaaaagaa | acaccatccg | tcgcccacag | gacgtcaagt | tcccgggtgg | 420 |
| cggacagatc | gttggtggag | tatacgtgtt | gccgcgcagg | ggcccacggt | tgggtgtgcg | 480 |
| cgcggcgcgt | aaaacttctg | aacggtcaca | gcctcgtgga | cggcggcagc | ctatccccac | 540 |
| ggcgcgtcgg | agcgaaggcc | ggtcctgggc | tcagcccggg | tacccttggc | ccctctatgg | 600 |
| taatgagggc | tgcgggtggg | cagggtggct | cctgtcccg | cgcggctccc | gtccatcttg | 660 |
| gggcccgaac | gacccccggc | gaaggtcccg | caacttgggt | aaagtcatcg | ataccctcac | 720 |
| gtgcgggttc | gccgacctca | tggggtacat | cccgctcgtc | ggcgctcccg | taggggcgt | 780 |
| cgcaagagct | ctcgcgcatg | gcgtgagggc | ccttgaagac | gggataaatt | cgcaacagg | 840 |
| gaacttgcct | ggttgctcct | tttctatctt | ccttcttgct | ctgctttctt | gcttagtcca | 900 |
| tcctgcagct | agtttagagt | ggcggaatgc | atctggcctc | tacatcctta | ccaacgactg | 960 |
| tcccaacagc | agtattgtgt | atgaggccga | tgatgttatt | ctgcacacac | ccggctgtat | 1020 |
| accttgtgtt | caggacggca | ataaatccac | gtgctggacc | tcagtgacac | ctacagtggc | 1080 |
| agtcaggtac | gtcggagcaa | ccaccgcttc | gatacgcagt | catgtggacc | tattagtggg | 1140 |
| cgcggccacg | atgtgtctg | cgctctacgt | gggtgatatg | tgtggggccg | tcttccttgt | 1200 |
| gggacaagcc | ttcacgttca | gacctcgtcg | ccatcaaacg | gtccagacct | gtaactgctc | 1260 |
| actgtacccg | ggccatctct | caggacaccg | aatggcttgg | gatatgatga | tgaactggtc | 1320 |
| ccccgctatg | ggtatggtgg | tagcgcacat | cctacgtctg | cctcagacct | tgtttgacat | 1380 |
| aatagccggg | gcccattggg | gcatcttggc | ggggctagcc | tattactcca | tgcagggcaa | 1440 |
| ctgggccaag | gtcgctatca | tcatggttat | gttttcaggg | gtcgatgcca | ctacatatac | 1500 |
| caccggtggc | gcagtagctc | atggcgccaa | gggactaact | agtctttta | gtctgggcgc | 1560 |
| ccaacagaaa | ctgcagttgg | tcaacaccaa | tggctcctgg | cacatcaaca | ggactgccct | 1620 |
| gaactgcaat | gagtccatac | acacgggggtt | cgtagctggg | ttgttttact | atcataagtt | 1680 |

```
caactctact ggatgccctc aaaggctcag cagctgcaag cccatcactt ccttcaagca    1740
ggggtggggc tccctgacag atgctaacat caccgggtct tctgaggaca aaccgtactg    1800
ctggcactac gcacccagac cttgcacaac tgttcaagca tcaagtgtct gcggccctgt    1860
gtactgcttc acaccatcgc cagtggttgt gggcactact gatgctgagg gcgtcccaac    1920
ctatacctgg ggtggaaata agacagacgt gttcctgctg aagtccttgc ggcctcccaa    1980
cggtcagtgt tttgggtgca cgtggatgaa ctccacgggg tttaccaaga cgtgcggggc    2040
tcccccttgt aacatctatg ggggtaaagg gagtcatcac aatgattcag acctcatctg    2100
ccctaccgac tgtttcagga aacatcccga ggccacatac agccggtgcg gtgcggggcc    2160
ctggttgaca cctcgatgca tggtcgacta tccataccgg ctttggcatt acccgtgcac    2220
agtcaatttt tcattgttca aggtgaggat gtttgtgggt gggtttgagc accggttcac    2280
cgccgcttgc aactggacca gggggagcg ctgcgatatc gaggatcgcg accgcagcga    2340
gcaacacccg ctgctgcatt caacgaccga gctcgctata ctgccttgct ccttcacgcc    2400
catgcctgcg ttgtcaacag gtttaataca cctccaccaa acatcgtgg atgtccagta    2460
cctttatggc gttggatctg gcatggtggg atgggcgctg aaatgggagt tcgtcgtcct    2520
cgttttcctc ctcctagcag acgcacgcgt gtgcgttgct ctttggctga tgctgatgat    2580
atcacaagca gaagcagcct tggagaacct tgtcacgctg aacgccatcg ctgctgccgg    2640
gacacatggt attggttggt actttgtagc cttttgcgcg gcatggtacg tgcggggtaa    2700
gcttgtcccg ctggtgacct acagcctgac gggtctctgg tctctggcgt tgctcgtcct    2760
cttgctcccc cagcgggcgt acgcctggtc aggtgaagac agcgctactc ttggcgctgg    2820
gatcttggtc ctctttggct tctttacctt gtcaccctgg tataagcatt ggatcggccg    2880
cctcatgtgt tggaaccagt acaccatatg tagatgcgag gccgccctcc aagtgtgggt    2940
ccccccctta ctcgcacgcg ggagtaggga cggtgttatc ctgctaacaa gtctgcttta    3000
tccatcttta attttgaca tcaccaagct actgatagca gtattgggcc cattatactt    3060
aatacaggct gccatcactg ccaccccta ctttgtgcgt gcacatgtat tggttcgcct    3120
ttgcatgctc gtgcgctctg taatgggggg aaaatacttc cagatgatca tactgagcat    3180
tggcagatgg tttaacacct atctgtacga ccacctagcg ccaatgcaat attgggctgc    3240
agctggcctc aaagacctag cagtggccac tgaacctgtg atatttagtc ccatggaaac    3300
caaggtcatc acctggggcg cggacacagc ggcttgcgga gatattcttt gcgggctgcc    3360
cgtctccgcg cgactaggcc gtgaggtgtt gttgggacct gctgatgatt accgggagat    3420
gggttggcgc ctgttggccc caatcacagc atacgcccag caaccaggg gccttcttgg    3480
gactattgtg accagcttga ctggcaggga taagaatgtg gtgaccggcg aagtgcaggt    3540
gctttctacg gctacccaga ccttcctagg tacaacaata gggggggtta tgtggactgt    3600
ttaccatggc gcaggctcaa ggacacttgc gggcgctaaa catcctgcgc tccaaatgta    3660
cacaaatgta gatcaggacc tcgttgggtg gccagcccct ccaggggcta agtctcttga    3720
accgtgcacc tgcgggtctg cagacttata cttggttacc cgcgatgctg acgtcatccc    3780
cgctcggcgc agggggggact ccacagcgag cttgctcagc cctaggcctc tcgcctgtct    3840
caagggctcc tctggaggtc ccgttatgtg cccttcgggg catgtcacgg ggatctttcg    3900
ggctgctgtg tgcaccagag gtgtagcaaa accctacagt tcataccagt ggaaaccct    3960
tagtacacag actaggtccc catccttctc tgacaattca actcctcccg ccgtcccaca    4020
gagctaccaa gtagggtatc ttcatgcccc gaccggtagt ggcaagagca caaaggtccc    4080
```

```
ggccgcttac gtagcacaag gataccatgt tctcgtgttg aatccatcag tggcggccac   4140
actaggcttc ggctcttaca tgtcgaaagc ctatgggatc gaccccaacg tccgcactgg   4200
gaaccgcact gtcacaactg gtgctaaact gacctattcc acctacggta agtttctcgc   4260 ggatggggt tgctctgggg gagcgtatga tgtgattatt tgtgatgaat gccatgccca   4320
agacgctact accatattgg gtattggcac ggtcttagat caggctgaga cggctggggt   4380
gaggctgacg gttctggcga cagcaactcc cccaggcagc atcactgtgc cacattctaa   4440
catcgaggag gtagccctgg gctctgaagg tgagatccct ttctacggta aggctatacc   4500
gatagcccga ctcaaggggg ggaggcacct tatcttttgc cattccaaga aaaagtgtga   4560
tgagatagca tccaagctca gaggcatggg gctcaacgct gtagcattct ataggggtct   4620
tgatgtgtcc atcataccaa cagcaggaga cgtcgtggtt tgcgccactg acgccctcat   4680
gactgggtac accggagact ttgattctgt catagattgc aacgtgactg ttgaacagta   4740
cgttgacttc agcttggacc ccacctttc cattgagact cacactgctc ccaagacgc   4800 ggtttcccgc agccaacgtc gtggccgtac gggccggggt agactcggca tataccgata   4860
tgtcaccccg ggtgaaagac cgtctggaat gtttgactcg gttgttctct gtgagtgcta   4920
tgatgcgggc tgctcgtggt acgatctgca gcccgctgag actacagtca gactgagagc   4980
ttacttgtcc acgccgggtt tacctgtctg tcaagaccat cttgactttt gggagagcgt   5040
ctttactgga ctaactcaca tagatgccca cttctgtca cagactaagc agcagggact   5100
caacttcccg tacctgactg cctaccaagc cactgtgtgc gcccgcgcgc aggctcctcc   5160
cccaagttgg gacgagacgt ggaaatgtct cgtacggctt aaaccaacac tacatggacc   5220
cacgcccctt ctgtatcggt tggggcctat ccaaaatgaa acctgcttga cacacccgt   5280 cacaaaatac atcatggcat gcatgtcagc tgatctggaa gtgaccacca gcgcctgggt   5340
gttgcttgga ggggtgctcg cggccctagc ggcttactgc ttgtcagtcg gctgcgttgt   5400
gatcgtgggt catattgagc tggggggcaa gccagcactc gttccagaca agaggtgtt   5460 gtatcaacaa ttcgatgaga tggaggagtg ctcgcaagct gccccatata tcgaacaagc   5520
tcaggtaata gcccaccagt tcaaggagaa agtccttgga ttgctgcagc gagccaccca   5580
acaacaagct gtcattgagc ccatagtagc taccaactgg caaaagcttg aggcgttctg   5640
gcacaagcat atgtggaatt ttgtgagtgg gatccagtac ctagcaggcc tttccacttt   5700
gcctggcaac cccgctgtgg cgtctcttat ggcgttcacc gcttctgtca ccagtcccct   5760
gacgaccaac caaactatgt tcttcaacat actcggggg tgggttgcta cccatttggc   5820
agggccccag agctcttccg cattcgtggt aagcggcttg gccggcgctg ccataggggg   5880
tataggcctg gcagggtct tgattgacat cctggcagga tacggagctg tgtctcagg   5940 cgccttggtg gcttttaaga tcatgggagg agaactcccc actgctgagg acatggtcaa   6000
catgctgcct gccatactat ctccgggcgc cctcgttgtc ggtgtgatat gtgcagccat   6060
actgcgtcga cacgtaggac ctggggaggg ggcggtgcag tggatgaaca ggctcatcgc   6120
attcgcatcc cggggtaacc acgtctcacc gacgcactat gtccccgaga gcgatgctgc   6180
agcgaaggtt actgcattgc tgagttctct aactgtcaca agtctgctcc ggcgactgca   6240
ccagtggatc aatgaagact acccaagtcc ttgctgcggc gactggctgc gtaccatctg   6300 ggactgggt tgcatggtgt tgtctgactt caagacatgg ctctccgcta agattatgcc   6360
agcgctccct gggctgcctt tcctttcctg tcagaaggga tacaagggcg tgtggcgggg   6420
```

```
agacggtgtg atgtcgacac gctgtccttg cggggcgaca ataaccggtc atgtgaagaa    6480
tgggtctatg cggcttgcag ggccacgcac atgtgctaac atgtggcacg gtactttccc    6540
catcaatgag tacaccaccg gacccggcac accttgccca gcacccaact acactcgcgc    6600
attattgcgc gtggctgcca acagctacgt tgaggtgcgc cgggtggggg acttccacta    6660
cattacgggg gctacagaag atgagctcaa gtgtccgtgc caagtgccgg ccgcagagtt    6720
ttttactgag gtggatgggg tgagactcca ccgttacgcc cctccatgca agccctgtt     6780
gagggatgaa atcactttca tggtagggtt gaactcctac gcataggat ctcaactccc     6840
ctgtgagccc gaaccagatg tttctgtgct gacctcgatg ttgagagacc cttcccatat    6900
taccgctgag gcagcagcgc gccgccttgc gcgtgggtcc cctccatcag aggcaagctc    6960
atccgccatc caactgtcgg ctccgtcgtt gaaggccact tgtcagtcgt atgggcctca    7020
tctggacgct gagctagtgg atgccaacct gttatggcgg caggagatgg gcagcactat    7080
cacacgggta gagtctgaaa caaaggttgt gattcttgat tcattcgaac ctctgagagc    7140
cgaaactgat gacgccgagc tctcggtggc tgcagagtgt ttcaagaagc ctcccaagta    7200
tcctccagcc cttcctatct gggctaggcc agactacaac cctccattgt tagaccgctg    7260
gaaagcaccg gattatgttc caccaactgt tcatggatgc gccttaccac cacggggcgc    7320
tccaccggtg cctcccccctc ggaggaagag aacaattcag ctggatggct ccaatgtgtc    7380
cgcggcgcta gctgcgctag cagaaaagtc attcccgtcc tcaaagccgc aggaagagaa    7440
tagctcatcc tcaggggtcg acacacagtc cagcactacc tctaaggtgc ccccccccc    7500
aggaggggaa tccgactcag agtcgtgctc gtccatgcct cctctcgagg gagagccggg    7560
cgatccggat ttgagctgcg actcttggtc cactgtgagt gacaatgagg agcagaacgt    7620
agtctgctgc tccatgtcgt actcttggac cggcgccttg ataacaccat gtagtgctga    7680
ggaggagaaa ctacccatca gcccactcag caactccttg ttgagacacc ataatctggt    7740
ttattcaacg tcgtcaagaa gcgcttctca gcgtcagaag aaggttacct tcgacaggct    7800
gcaggtgctc gacgaccact acaaaactgc tttaaaggag gtaaaggagc gagcgtctgg    7860
ggtgaaggct cgcatgctca ccatcgagga agcgtgcaag cttgtccccc ccactctgc    7920
ccgttcgaag ttcgggtata gtgcgaagga cgctcgttcc ttgtccagca gggccgttaa    7980
ccagatccgc tccgtctggg aggacttgct ggaagacacc acaactccaa ttccaacaac    8040
catcatggcg aagaacgagg tgttttgtgt ggaccccgtt aagggggggcc gcaagcccgc    8100
tcgcctcatt gtgtaccctg acctgggggt gcgtgtctgt gagaaacgcg ccctatatga    8160
cgtgatacag aagttgtcaa tcgcgacgat gggtcctgct tatggattcc agtactcgcc    8220
tcagcagcgg gtcgaacgtc tgctgaagat gtggaccctca aagagaaccc ccctgggggtt   8280
ctcgtatgac acccgctgct ttgactcgac tgtcactgaa caggatatca gggtggaaga    8340
ggagatatat caatgctgta accttgaacc ggaggccagg aaggtgatct cctccctcac    8400
ggagcggctt tactgcgggg gccccatgtt caacagcaag ggggcccagt gcggttatcg    8460
ccgttgccgt gctagtggag ttctaccgac cagctttggc aacacaatca cttgttacat    8520
caaggccaca gcggctgcaa gggccgcggg tctccggaac ccggactttc ttgtctgcgg    8580
agatgatttg gtcgtggtgg ccgagagtga tggcgtcgac gaggatagggg cagccctgag    8640
agccttcacg gaggctatga ccaggtactg tgctccaccc ggagatgctc cacagcctac    8700
ctacgacctt gagctcatca catcttgctc ctctaacgtc tccgtagcac atgacaacaa    8760
ggggaggagg tattactacc tcacccgtga tgccactact ccctggcc gtgcggcttg     8820
```

```
ggaaacagct cgtcacactc cagttaactc ctggttgggc aacatcatca tgtacgcgcc   8880
taccatctgg gtgcgcatgg tgatgatgac acacttttc tccatactcc aatcccagga   8940
gatacttgat cgccccttg attttgaaat gtacggggcc acttactctg tcactccgct   9000
ggatttacca gcaatcattg aaagactcca tggtctaagc gcgttcacac tccacagtta   9060
ctctccagta gaactcaata gggtcgcggg gacactcagg aagcttgggt gcccccccct   9120
acgagcttgg agacatcggg cacgagcagt gcgcgctaag cttattgccc agggaggtaa   9180
ggccaaaata tgtggccttt atctctttaa ctgggcagta cgcaccaaga ccaaactcac   9240
tccactgcca gccgctagcc agttggactt atccaattgg ttttcggttg cgtcggcgg   9300 gaacgacatt tatcacagcg tgtcacatgc ccgaacccgc catttgctgc tttgcctact   9360
cctactaact gtaggggtag gcatctttct cctgccagca cgataagctg gtaggataac   9420
actccattcc ttttcccttg tttttatttt tttttttttt tttttttttt tttttttttt   9480 ttctttttt tttttttttt tttttttttg ttttcctct ttccattctt ttctaacctt     9540
aaattttcct ttctttaggt ggctccatct tagccctagt cacggctagc tgtgaaaggt   9600
ccgtgagccg catgactgca gagagtgccg taactggtct ctctgcagat catgt         9655
```

<210> SEQ ID NO 50
<211> LENGTH: 9655
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA sequence of mutant S310A R2198H HCV full genomic replicon RNA

<400> SEQUENCE: 50

```
gacctgcctc ttacgaggcg acactccacc atggatcact cccctgtgag gaacttctgt     60
cttcacgcgg aaagcgccta gccatggcgt tagtacgagt gtcgtgcagc ctccaggacc    120
ccccctcccg ggagagccat agtggtctgc ggaaccggtg agtacaccgg aatcgctggg    180
gtgaccgggt cctttcttgg aacaacccgc tcaataccca gaaatttggg cgtgcccccg    240
cgagatcact agccgagtag tgttgggtcg cgaaaggcct tgtggtactg cctgataggg    300
tgcttgcgag tgccccggga ggtctcgtag accgtgcaac atgagcacac ttcctaaacc    360
ccaaagaaaa accaaaagaa acaccatccg tcgcccacag gacgtcaagt tcccgggtgg    420
cggacagatc gttggtggag tatacgtgtt gccgcgcagg ggcccacggt tgggtgtgcg    480
cgcggcgcgt aaaacttctg aacggtcaca gcctcgtgga cggcggcagc ctatccccac    540
ggcgcgtcgg agcgaaggcc ggtcctgggc tcagcccggg tacccttggc ccctctatgg    600
taatgagggc tgcgggtggg cagggtggct cctgtccccg cgcggctccc gtccatcttg    660
gggcccgaac gacccccggc gaaggtcccg caacttgggt aaagtcatcg ataccctcac    720
gtgcgggttc gccgacctca tggggtacat cccgctcgtc ggcgctcccg taggggggcgt   780
cgcaagagct ctcgcgcatg gcgtgagggc ccttgaagac gggataaatt tcgcaacagg    840
gaacttgcct ggttgctcct ttctatcttt ccttcttgct ctgctttctt gcttagtcca    900
tcctgcagct agtttagagt ggcggaatgc atctggcctc tacatcctta ccaacgactg    960
tcccaacagc agtattgtgt atgaggccga tgatgttatt ctgcacacac ccggctgtat   1020
accttgtgtt caggacggca ataaatccac gtgctggacc tcagtgacac ctacagtggc   1080
```

```
agtcaggtac gtcggagcaa ccaccgcttc gatacgcagt catgtggacc tattagtggg    1140
cgcggccacg atgtgctctg cgctctacgt gggtgatatg tgtggggccg tcttccttgt    1200
gggacaagcc ttcacgttca gacctcgtcg ccatcaaacg gtccagacct gtaactgctc    1260
actgtacccg ggccatctct caggacaccg aatggcttgg gatatgatga tgaactggtc    1320
ccccgctatg ggtatggtgg tagcgcacat cctacgtctg cctcagacct tgtttgacat    1380
aatagccggg gcccattggg gcatcttggc ggggctagcc tattactcca tgcagggcaa    1440
ctgggccaag gtcgctatca tcatggttat gttttcaggg gtcgatgcca ctacatatac    1500
caccggtggc gcagtagctc atggcgccaa gggactaact agtcttttta gtctgggcgc    1560
ccaacagaaa ctgcagttgg tcaacaccaa tggctcctgg cacatcaaca ggactgccct    1620
gaactgcaat gagtccatac acacggggtt cgtagctggg ttgtttttact atcataagtt    1680
caactctact ggatgccctc aaaggctcag cagctgcaag cccatcactt ccttcaagca    1740
ggggtggggc tccctgacag atgctaacat caccgggtct tctgaggaca aaccgtactg    1800
ctggcactac gcacccagac cttgcacaac tgttcaagca tcaagtgtct gcggccctgt    1860
gtactgcttc acaccatcgc cagtggttgt gggcactact gatgctgagg gcgtcccaac    1920
ctatacctgg ggtggaaata agacagacgt gttcctgctg aagtccttgc ggcctcccaa    1980
cggtcagtgg tttgggtgca cgtggatgaa ctccacgggg tttaccaaga cgtgcggggc    2040
tccccccttgt aacatctatg ggggtaaagg gagtcatcac aatgattcag acctcatctg    2100
ccctaccgac tgtttcagga acatcccga ggccacatac agccggtgcg gtgcggggcc    2160
ctggttgaca cctcgatgca tggtcgacta tccataccgg cttttggcatt acccgtgcac    2220
agtcaatttt tcattgttca aggtgaggat gtttgtgggt gggtttgagc accggttcac    2280
cgccgcttgc aactggacca gggggggagcg ctgcgatatc gaggatcgcg accgcagcga    2340
gcaacacccg ctgctgcatt caacgaccga gctcgctata ctgccttgct ccttcacgcc    2400
catgcctgcg ttgtcaacag gtttaataca cctccaccaa aacatcgtgg atgtccagta    2460
cctttatggc gttggatctg gcatggtggg atgggcgctg aaatgggagt tcgtcgtcct    2520
cgttttcctc ctcctagcag acgcacgcgt gtgcgttgct cttttggctga tgctgatgat    2580
atcacaagca gaagcagcct tggagaacct tgtcacgctg aacgccatcg ctgctgccgg    2640
gacacatggt attggttggt actttgtagc cttttgcgcg gcatggtacg tgcggggtaa    2700
gcttgtcccg ctggtgacct acagcctgac gggtctctgg tctctggcgt tgctcgtcct    2760
cttgctcccc cagcgggcgt acgcctggtc aggtgaagac agcgctactc ttggcgctgg    2820
gatcttggtc ctctttggct tctttacctt gtcaccctgg tataagcatt ggatcggccg    2880
cctcatgtgg tggaaccagt acaccatatg tagatgcgag gccgcccctcc aagtgtgggt    2940
ccccccctta ctcgcacgcg ggagtaggga cggtgttatc ctgctaacaa gtctgcttta    3000
tccatcttta attttttgaca tcaccaagct actgatagca gtattgggcc cattatactt    3060
aatacaggct gccatcactg ccacccccta ctttgtgcgt gcacatgtat tggttcgcct    3120
ttgcatgctc gtgcgctctg taatgggggg aaaatacttc cagatgatca tactgagcat    3180
tgcagatgg tttaacacct atctgtacga ccacctagcg ccaatgcaat attgggctgc    3240
agctggcctc aaagacctag cagtggccac tgaacctgtg atatttagtc ccatggaaac    3300
caaggtcatc acctggggcg cggacacagc ggcttgcgga gatattcttt gcgggctgcc    3360
cgtctccgcg cgactaggcc gtgaggtgtt gttgggacct gctgatgatt accgggagat    3420
gggttggcgc ctgttggccc caatcacagc atacgcccag caaaccaggg gccttcttgg    3480
```

```
gactattgtg accagcttga ctggcaggga taagaatgtg gtgaccggcg aagtgcaggt    3540
gctttctacg gctacccaga ccttcctagg tacaacaata gggggggtta tgtggactgt    3600
ttaccatggc gcaggctcaa ggacacttgc gggcgctaaa catcctgcgc tccaaatgta    3660
cacaaatgta gatcaggacc tcgttgggtg gccagcccct ccaggggcta agtctcttga    3720
accgtgcacc tgcgggtctg cagacttata cttggttacc cgcgatgctg acgtcatccc    3780
cgctcggcgc aggggggact ccacagcgag cttgctcagc cctaggcctc tcgcctgtct    3840
caagggctcc tctggaggtc ccgttatgtg cccttcgggg catgtcacgg ggatctttcg    3900
ggctgctgtg tgcaccagag gtgtagcaaa gaccctacag ttcataccag tggaaaccct    3960
tagtacacag actaggtccc catccttctc tgacaattca actcctcccg ccgtcccaca    4020
gagctaccaa gtagggtatc ttcatgcccc gaccggtagt ggcaagagca caaaggtccc    4080
ggccgcttac gtagcacaag gataccatgt tctcgtgttg aatccatcag tggcggccac    4140
actaggcttc ggctcttaca tgtcgaaagc ctatgggatc gaccccaacg tccgcactgg    4200
gaaccgcact gtcacaactg gtgctaaact gacctattcc acctacggta agtttctcgc    4260
ggatgggggt tgctctgggg gagcgtatga tgtgattatt tgtgatgaat gccatgccca    4320
agacgctact accatattgg gtattggcac ggtcttagat caggctgaga cggctgggt    4380 gaggctgacg gttctggcga cagcaactcc cccaggcagc atcactgtgc acattctaa    4440 catcgaggag gtagccctgg gctctgaagg tgagatccct ttctacggta aggctatacc    4500
gatagcccag ctcaaggggg ggaggcacct tatcttttgc cattccaaga aaaagtgtga    4560
tgagatagca tccaagctca gaggcatggg gctcaacgct gtagcattct atagggtct    4620 tgatgtgtcc atcataccaa cagcaggaga cgtcgtggtt tgcgccactg acgccctcat    4680
gactgggtac accggagact tgattctgt catagattgc aacgtgactg ttgaacagta    4740
cgttgacttc agcttggacc ccaccttttc cattgagact cacactgctc ccaagacgc    4800 ggtttcccgc agccaacgtc gtggccgtac gggccggggt agactcggca tataccgata    4860
tgtcaccccg ggtgaaagac cgtctggaat gtttgactcg gttgttctct gtgagtgcta    4920
tgatgcgggc tgctcgtggt acgatctgca gcccgctgag actacagtca gactgagagc    4980
ttacttgtcc acgccgggtt tacctgtctg tcaagaccat cttgactttt gggagagcgt    5040
ctttactgga ctaactcaca tagatgccca ctttctgtca cagactaagc agcagggact    5100
caacttcccg tacctgactg cctaccaagc cactgtgtgc gcccgcgcgc aggctcctcc    5160
cccaagttgg gacgagacgt ggaaatgtct cgtacggctt aaaccaacac tacatggacc    5220
cacgcccctt ctgtatcggt tgggcctat ccaaaatgaa acctgcttga cacacccgt    5280 cacaaaatac atcatggcat gcatgtcagc tgatctggaa gtgaccacca gcgcctgggt    5340
gttgcttgga ggggtgctcg cggccctagc ggcttactgc ttgtcagtcg gctgcgttgt    5400
gatcgtgggc catattgagc tggggggcaa gccagcactc gttccagaca agaggtgtt    5460 gtatcaacaa ttcgatgaga tggaggagtg ctcgcaagct gccccatata tcgaacaagc    5520
tcaggtaata gcccaccagt tcaaggagaa agtccttgga ttgctgcagc gagccaccca    5580
acaacaagct gtcattgagc ccatagtagc taccaactgg caaaagcttg aggcgttctg    5640
gcacaagcat atgtggaatt ttgtgagtgg gatccagtac ctagcaggcc tttccacttt    5700
gcctggcaac cccgctgtgg cgtctcttat ggcgttcacc gcttctgtca ccagtccct    5760 gacgaccaac caaactatgt tcttcaacat actcggggg tgggttgcta cccatttggc    5820
```

```
agggccccag agctcttccg cattcgtggt aagcggcttg gccggcgctg ccataggggg   5880
tataggcctg ggcagggtct tgattgacat cctggcagga tacggagctg gtgtctcagg   5940
cgccttggtg gcttttaaga tcatgggagg agaactcccc actgctgagg acatggtcaa   6000
catgctgcct gccatactat ctccgggcgc cctcgttgtc ggtgtgatat gtgcagccat   6060
actgcgtcga cacgtaggac ctggggaggg ggcggtgcag tggatgaaca ggctcatcgc   6120
attcgcatcc cggggtaacc acgtctcacc gacgcactat gtccccgaga gcgatgctgc   6180
agcgaaggtt actgcattgc tgagttctct aactgtcaca agtctgctcc ggcgactgca   6240
ccagtggatc aatgaagact acccaagtcc ttgctgcggc gactggctgc gtaccatctg   6300
ggactgggtt tgcatggtgt tgtctgactt caagacatgg ctctccgcta agattatgcc   6360
agcgctccct gggctgcctt tcctttcctg tcagaaggga tacaagggcg tgtggcgggg   6420
agacggtgtg atgtcgacac gctgtccttg cggggcgaca ataaccggtc atgtgaagaa   6480
tgggtctatg cggcttgcag ggccacgcac atgtgctaac atgtggcacg gtactttccc   6540
catcaatgag tacaccaccg gacccggcac accttgccca gcacccaact acactcgcgc   6600
attattgcgc gtggctgcca acagctacgt tgaggtgcgc cgggtggggg acttccacta   6660
cattacgggg gctacagaag atgagctcaa gtgtccgtgc caagtgccgg ccgcagagtt   6720
ttttactgag gtggatgggg tgagactcca ccgttacgcc cctccatgca agccctgtt    6780
gagggatgaa atcactttca tggtagggtt gaactcctac gcaataggat ctcaactccc   6840
ctgtgagccc gaaccagatg tttctgtgct gacctcgatg ttgagagacc cttcccatat   6900
taccgctgag gcagcagcgc gccgccttgc gcatgggtcc cctccatcag aggcaagctc   6960
atccgccagc caactgtcgg ctccgtcgtt gaaggccact tgtcagtcgt atgggcctca   7020
tctggacgct gagctagtgg atgccaacct gttatggcgg caggagatgg gcagcactat   7080
cacacgggta gagtctgaaa caaaggttgt gattcttgat tcattcgaac tctgagagc    7140
cgaaactgat gacgccgagc tctcggtggc tgcagagtgt ttcaagaagc tcccaagta    7200
tcctccagcc cttcctatct gggctaggcc agactacaac cctccattgt tagaccgctg   7260
gaaagcaccg gattatgttc caccaactgt tcatggatgc gccttaccac cacgggggcgc  7320
tccaccggtg cctcccccctc ggaggaagag aacaattcag ctggatggct ccaatgtgtc   7380
cgcggcgcta gctgcgctag cagaaaaagtc attcccgtcc tcaaagccgc aggaagagaa   7440
tagctcatcc tcagggggtcg acacacagtc cagcactacc tctaaggtgc cccccccccc   7500
aggaggggaa tccgactcag agtcgtgctc gtccatgcct cctctcgagg gagagccggg   7560
cgatccggat ttgagctgcg actcttggtc cactgtgagt gacaatgagg agcagaacgt   7620
agtctgctgc tccatgtcgt actcttggac cggcgccttg ataacaccat gtagtgctga   7680
ggaggagaaa ctacccatca gcccactcag caactccttg ttgagacacc ataatctggt   7740
ttattcaacg tcgtcaagaa gcgcttctca gcgtcagaag aaggttacct tcgacaggct   7800
gcaggtgctc gacgaccact acaaaactgc tttaaaggag gtaaaggagc gagcgtctgg   7860
ggtgaaggct cgcatgctca ccatcgagga agcgtgcaag cttgtccccc cccactctgc   7920
ccgttcgaag ttcgggtata gtgcgaagga cgctcgttcc ttgtccagca gggccgttaa   7980
ccagatccgc tccgtctggg aggacttgct ggaagacacc acaactccaa ttccaacaac   8040
catcatggcg aagaacgagg tgtttttgtgt ggaccccgtt aagggggggcc gcaagcccgc   8100
tcgcctcatt gtgtaccctg acctgggggt gcgtgtctgt gagaaacgcg ccctatatga   8160
cgtgatacag aagttgtcaa tcgcgacgat gggtcctgct tatggattcc agtactccgc   8220
```

```
tcagcagcgg gtcgaacgtc tgctgaagat gtggacctca aagagaaccc ccctgggggtt    8280 ctcgtatgac acccgctgct tgactcgac tgtcactgaa caggatatca gggtggaaga    8340
ggagatatat caatgctgta accttgaacc ggaggccagg aaggtgatct cctccctcac    8400
ggagcggctt tactgcgggg gccccatgtt caacagcaag ggggcccagt gcggttatcg    8460
ccgttgccgt gctagtggag ttctaccgac cagctttggc aacacaatca cttgttacat    8520
caaggccaca gcggctgcaa gggccgcggg tctccggaac ccggactttc ttgtctgcgg    8580
agatgatttg gtcgtggtgg ccgagagtga tggcgtcgac gaggataggg cagccctgag    8640
agccttcacg gaggctatga ccaggtactc tgctccaccc ggagatgctc acagcctac    8700 ctacgacctt gagctcatca catcttgctc ctctaacgtc tccgtagcac atgacaacaa    8760
ggggaggagg tattactacc tcacccgtga tgccactact cccctggccc gtgcggcttg    8820
ggaaacagct cgtcacactc cagttaactc ctggttgggc aacatcatca tgtacgcgcc    8880
taccatctgg gtgcgcatgg tgatgatgac acacttttc tccatactcc aatcccagga    8940
gatacttgat cgccccctgg attttgaaat gtacgggggcc acttactctg tcactccgct    9000
ggatttacca gcaatcattg aaagactcca tggtctaagc gcgttcacac tccacagtta    9060
ctctccagta gaactcaata gggtcgcggg gacactcagg aagcttgggt gcccccccct    9120
acgagcttgg agacatcggg cacgagcagt gcgcgctaag cttattgccc agggaggtaa    9180
ggccaaaata tgtggccttt atctctttaa ctgggcagta cgcaccaaga ccaaactcac    9240
tccactgcca gccgctagcc agttggactt atccaattgg ttttcggttg gcgtcggcgg    9300
gaacgacatt tatcacagcg tgtcacatgc ccgaacccgc catttgctgc tttgcctact    9360
cctactaact gtaggggtag gcatctttct cctgccagca cgataagctg gtaggataac    9420
actccattcc ttttcccttg ttttatttt ttttttttt ttttttttt tttttttt    9480 ttcttttttt tttttttttt ttttttttg ttttcctct ttccattctt ttctaacctt    9540
aaattttcct ttctttaggt ggctccatct tagcccctagt cacggctagc tgtgaaaggt    9600
ccgtgagccg catgactgca gagagtgccg taactggtct ctctgcagat catgt    9655
```

<210> SEQ ID NO 51
<211> LENGTH: 9655
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: cDNA sequence of mutant S310A R2895K HCV full genomic replicon RNA

<400> SEQUENCE: 51

```
gacctgcctc ttacgaggcg acactccacc atggatcact cccctgtgag gaacttctgt      60
cttcacgcgg aaagcgccta gccatggcgt tagtacgagt gtcgtgcagc ctccaggacc     120 cccctcccg ggagagccat agtggtctgc ggaaccggtg agtacaccgg aatcgctggg     180
gtgaccgggt cctttcttgg aacaacccgc tcaatacca gaaatttggg cgtgccccg     240 cgagatcact agccgagtag tgttgggtcg cgaaaggcct tgtggtactg cctgataggg     300
tgcttgcgag tgccccggga ggtctcgtag accgtgcaac atgagcacac ttcctaaacc     360
ccaaagaaaa accaaaagaa acaccatccg tcgcccacag gacgtcaagt tcccgggtgg     420
cggacagatc gttggtggag tatacgtgtt gccgcgcagg ggcccacggt tgggtgtgcg     480
```

```
cgcggcgcgt aaaacttctg aacggtcaca gcctcgtgga cggcggcagc ctatccccac    540
ggcgcgtcgg agcgaaggcc ggtcctgggc tcagcccggg tacccttggc ccctctatgg    600
taatgagggc tgcgggtggg cagggtggct cctgtccccg cgcggctccc gtccatcttg    660
gggcccgaac gaccccggc gaaggtcccg caacttgggt aaagtcatcg atacccctcac   720
gtgcgggttc gccgacctca tggggtacat cccgctcgtc ggcgctcccg taggggggcgt   780
cgcaagagct ctcgcgcatg gcgtgagggc ccttgaagac gggataaatt tcgcaacagg   840
gaacttgcct ggttgctcct tttctatctt ccttcttgct ctgctttctt gcttagtcca    900
tcctgcagct agtttagagt ggcggaatgc atctggcctc tacatcctta ccaacgactg    960
tcccaacagc agtattgtgt atgaggccga tgatgttatt ctgcacacac ccggctgtat   1020
accttgtgtt caggacggca ataaatccac gtgctggacc tcagtgacac ctacagtggc   1080
agtcaggtac gtcggagcaa ccaccgcttc gatacgcagt catgtggacc tattagtggg   1140
cgcggccacg atgtgctctg cgctctacgt gggtgatatg tgtggggccg tcttccttgt   1200
gggacaagcc ttcacgttca gacctcgtcg ccatcaaacg gtccagacct gtaactgctc   1260
actgtacccg ggccatctct caggacaccg aatggcttgg gatatgatga tgaactggtc   1320
ccccgctatg ggtatggtgg tagcgcacat cctacgtctg cctcagacct tgtttgacat   1380
aatagccggg gcccattggg gcatcttggc ggggctagcc tattactcca tgcagggcaa   1440
ctgggccaag gtcgctatca tcatggttat gttttcaggg gtcgatgcca ctacatatac   1500
caccggtggc gcagtagctc atggcgccaa gggactaact agtcttttta gtctgggcgc   1560
ccaacagaaa ctgcagttgg tcaacaccaa tggctcctgg cacatcaaca ggactgccct   1620
gaactgcaat gagtccatac acacgggggtt cgtagctggg ttgtttttact atcataagtt   1680
caactctact ggatgccctc aaaggctcag cagctgcaag cccatcactt ccttcaagca   1740
ggggtggggc tccctgacag atgctaacat caccgggtct tctgaggaca aaccgtactg   1800
ctggcactac gcacccagac cttgcacaac tgttcaagca tcaagtgtct gcggccctgt   1860
gtactgcttc acaccatcgc cagtggttgt gggcactact gatgctgagg gcgtcccaac   1920
ctatacctgg ggtggaaata agacagacgt gttcctgctg aagtccttgc ggcctcccaa   1980
cggtcagtgg tttgggtgca cgtggatgaa ctccacgggg tttaccaaga cgtgcggggc   2040
tcccccttgt aacatctatg ggggtaaagg gagtcatcac aatgattcag acctcatctg   2100
ccctaccgac tgtttcagga acatcccga ggccacatac agccggtgcg gtgcggggcc    2160
ctggttgaca cctcgatgca tggtcgacta tccataccgg cttttggcatt acccgtgcac   2220
agtcaatttt tcattgttca aggtgaggat gtttgtgggt gggtttgagc accggttcac   2280
cgccgcttgc aactgaccca ggggggagcg ctgcgatatc gaggatcgcg accgcagcga   2340
gcaacacccg ctgctgcatt caacgaccga gctcgctata ctgccttgct ccttcacgcc   2400
catgcctgcg ttgtcaacag gtttaataca cctccaccaa acatcgtggg atgtccagta   2460
cctttatggc gttggatctg gcatggtggg atgggcgctg aaatgggagt tcgtcgtcct   2520
cgttttcctc ctcctagcag acgcacgcgt gtgcgttgct cttttggctga tgctgatgat   2580
atcacaagca gaagcagcct ggagaacct tgtcacgctg aacgccatcg ctgctgccgg   2640
gacacatggt attggttggt actttgtagc cttttgcgcg gcatggtacg tgcggggtaa    2700
gcttgtcccg ctggtgacct acagcctgac gggtctctgg tctctggcgt tgctcgtcct    2760
cttgctcccc cagcgggcgt acgcctggtc aggtgaagac agcgctactc ttggcgctgg   2820
gatcttggtc ctctttggct tctttacctt gtcaccctgg tataagcatt ggatcggccg   2880
```

```
cctcatgtgg tggaaccagt acaccatatg tagatgcgag gccgccctcc aagtgtgggt    2940
ccccccctta ctcgcacgcg ggagtaggga cggtgttatc ctgctaacaa gtctgcttta    3000
tccatcttta atttttgaca tcaccaagct actgatagca gtattgggcc cattatactt    3060
aatacaggct gccatcactg ccaccccta ctttgtgcgt gcacatgtat tggttcgcct     3120
ttgcatgctc gtgcgctctg taatgggggg aaaatacttc cagatgatca tactgagcat    3180
tggcagatgg tttaacacct atctgtacga ccacctagcg ccaatgcaat attgggctgc    3240
agctggcctc aaagacctag cagtggccac tgaacctgtg atatttagtc ccatggaaac    3300
caaggtcatc acctggggcg cggacacagc ggcttgcgga gatattcttt gcgggctgcc    3360
cgtctccgcg cgactaggcc gtgaggtgtt gttgggacct gctgatgatt accgggagat    3420
gggttggcgc ctgttggccc caatcacagc atacgcccag caaaccaggg gccttcttgg    3480
gactattgtg accagcttga ctggcaggga taagaatgtg gtgaccggcg aagtgcaggt    3540
gctttctacg gctacccaga ccttcctagg tacaacaata gggggggtta tgtggactgt    3600
ttaccatggc gcaggctcaa ggacacttgc gggcgctaaa catcctgcgc tccaaatgta    3660
cacaaatgta gatcaggacc tcgttgggtg gccagcccct ccaggggcta agtctcttga    3720
accgtgcacc tgcgggtctg cagacttata cttggttacc cgcgatgctg acgtcatccc    3780
cgctcggcgc agggggact ccacagcgag cttgctcagc cctaggcctc tcgcctgtct     3840
caagggctcc tctggaggtc ccgttatgtg cccttcgggg catgtcacgg ggatctttcg    3900
ggctgctgtg tgcaccagag gtgtagcaaa gaccctacag ttcataccag tggaaaccct    3960
tagtacacag actaggtccc catccttctc tgacaattca actcctcccg ccgtcccaca    4020
gagctaccaa gtagggtatc ttcatgcccc gaccggtagt ggcaagagca caaaggtccc    4080
ggccgcttac gtagcacaag gataccatgt tctcgtgttg aatccatcag tggcggccac    4140
actaggcttc ggctcttaca tgtcgaaagc ctatggatc gacccaacg tccgcactgg      4200
gaaccgcact gtcacaactg gtgctaaact gacctattcc acctacggta gtttctcgc     4260
ggatgggggt tgctctgggg gagcgtatga tgtgattatt tgtgatgaat gccatgccca    4320
agacgctact accatattgg gtattggcac ggtcttagat caggctgaga cggctggggt    4380
gaggctgacg gttctggcga cagcaactcc cccaggcagc atcactgtgc cacattctaa    4440
catcgaggag gtagccctgg gctctgaagg tgagatccct ttctacggta aggctatacc    4500
gatagcccag ctcaaggggg ggaggcacct tatcttttgc cattccaaga aaagtgtga    4560
tgagatagca tccaagctca gaggcatggg gctcaacgct gtagcattct ataggggtct    4620
tgatgtgtcc atcataccaa cagcaggaga cgtcgtggtt tgcgccactg acgccctcat    4680
gactgggtac accggagact ttgattctgt catagattgc aacgtgactg ttgaacagta    4740
cgttgacttc agcttggacc ccacctttc cattgagact cacactgctc cccaagacgc     4800
ggtttcccgc agccaacgtc gtggccgtac gggccgggt agactcggca tataccgata    4860
tgtcaccccg ggtgaaagac cgtctggaat gtttgactcg gttgttctct gtgagtgcta    4920
tgatgcgggc tgctcgtggt acgatctgca gcccgctgag actacagtca gactgagagc    4980
ttacttgtcc acgccgggtt tacctgtctg tcaagaccat cttgactttt gggagagcgt    5040
ctttactgga ctaactcaca tagatgccca cttttctgtca cagactaagc agcagggact    5100
caacttcccg tacctgactg cctaccaagc cactgtgtgc gcccgcgcgc aggctcctcc    5160
cccaagttgg gacgagacgt ggaaatgtct cgtacggctt aaaccaacac tacatggacc    5220
```

```
cacgccccct ctgtatcggt tggggcctat ccaaaatgaa acctgcttga cacaccccgt    5280
cacaaaatac atcatggcat gcatgtcagc tgatctggaa gtgaccacca gcgcctgggt    5340
gttgcttgga ggggtgctcg cggccctagc ggcttactgc ttgtcagtcg gctgcgttgt    5400
gatcgtgggt catattgagc tgggggggcaa gccagcactc gttccagaca aagaggtgtt    5460
gtatcaacaa ttcgatgaga tggaggagtg ctcgcaagct gccccatata tcgaacaagc    5520
tcaggtaata gcccaccagt tcaaggagaa agtccttgga ttgctgcagc gagccaccca    5580
acaacaagct gtcattgagc ccatagtagc taccaactgg caaaagcttg aggcgttctg    5640
gcacaagcat atgtggaatt ttgtgagtgg gatccagtac ctagcaggcc ttttccacttt    5700 gcctggcaac cccgctgtgg cgtctcttat ggcgttcacc gcttctgtca ccagtcccct    5760
gacgaccaac caaactatgt tcttcaacat actcgggggg tgggttgcta cccatttggc    5820
agggccccag agctcttccg cattcgtggt aagcggcttg gccggcgctg ccataggggg    5880
tataggcctg gcagggtct tgattgacat cctggcagga tacggagctg gtgtctcagg    5940
cgccttggtg gcttttaaga tcatgggagg agaactcccc actgctgagg acatggtcaa    6000
catgctgcct gccatactat ctccgggcgc cctcgttgtc ggtgtgatat gtgcagccat    6060
actgcgtcga cacgtaggac ctggggaggg ggcggtgcag tggatgaaca ggctcatcgc    6120
attcgcatcc cggggtaacc acgtctcacc gacgcactat gtccccgaga gcgatgctgc    6180
agcgaaggtt actgcattgc tgagttctct aactgtcaca agtctgctcc ggcgactgca    6240
ccagtggatc aatgaagact acccaagtcc ttgctgcggc gactggctgc gtaccatctg    6300
ggactgggtt tgcatggtgt tgtctgactt caagacatgg ctctccgcta agattatgcc    6360
agcgctccct gggctgcctt tccttcctg tcagaaggga tacaagggcg tgtggcgggg    6420
agacggtgtg atgtcgacac gctgtccttg cggggcgaca ataaccggtc atgtgaagaa    6480
tgggtctatg cggcttgcag ggccacgcac atgtgctaac atgtggcacg gtactttccc    6540
catcaatgag tacaccaccg gacccggcac accttgccca gcacccaact acactcgcgc    6600
attattgcgc gtggctgcca acagctacgt tgaggtgcgc cgggtggggg acttccacta    6660
cattacgggg gctacagaag atgagctcaa gtgtccgtgc caagtgccgg ccgcagagtt    6720
ttttactgag gtggatgggg tgagactcca ccgttacgcc cctccatgca gcccctgtt    6780 gagggatgaa atcactttca tggtagggtt gaactcctac gcaataggat ctcaactccc    6840
ctgtgagccc gaaccagatg tttctgtgct gacctcgatg ttgagagacc cttcccatat    6900
taccgctgag gcagcagcgc gccgccttgc gcgtgggtcc cctccatcag aggcaagctc    6960
atccgccagc caactgtcgg ctccgtcgtt gaaggccact tgtcagtcgt atgggcctca    7020
tctggacgct gagctagtgg atgccaacct gttatggcgg caggagatgg gcagcactat    7080
cacacgggta gagtctgaaa caaaggttgt gattcttgat tcattcgaac ctctgagagc    7140
cgaaactgat gacgccgagc tctccggtgg tgcagagtgt ttcaagaagc tcccaagta    7200 tcctccagcc cttcctatct gggctaggcc agactacaac cctccattgt tagaccgctg    7260
gaaagcaccg gattatgttc caccaactgt tcatggatgc gccttaccac cacggggcgc    7320
tccaccggtg cctccccctc ggaggaagag aacaattcag ctggatggct caatgtgtc    7380 cgcggcgcta gctgcgctag cagaaaagtc attcccgtcc tcaaagccgc aggaagagaa    7440
tagctcatcc tcaggggtcg acacacagtc cagcactacc tctaaggtgc cccccccccc    7500
aggaggggaa tccgactcag agtcgtgctc gtccatgcct cctctcgagg gagagccggg    7560
cgatccggat ttgagctgcg actcttggtc cactgtgagt gacaatgagg agcagaacgt    7620
```

-continued

```
agtctgctgc tccatgtcgt actcttggac cggcgccttg ataacaccat gtagtgctga    7680
ggaggagaaa ctaccatca gcccactcag caactccttg ttgagacacc ataatctggt     7740
ttattcaacg tcgtcaagaa gcgcttctca gcgtcagaag aaggttacct tcgacaggct    7800
gcaggtgctc gacgaccact acaaaactgc tttaaaggag gtaaaggagc gagcgtctgg    7860
ggtgaaggct cgcatgctca ccatcgagga agcgtgcaag cttgtccccc cccactctgc    7920
ccgttcgaag ttcgggtata gtgcgaagga cgctcgttcc ttgtccagca gggccgttaa    7980
ccagatccgc tccgtctggg aggacttgct ggaagacacc acaactccaa ttccaacaac    8040
catcatggcg aagaacgagg tgttttgtgt ggacccgtt aaggggggcc gcaagcccgc     8100
tcgcctcatt gtgtaccctg acctgggggt gcgtgtctgt gagaaacgcg ccctatatga    8160
cgtgatacag aagttgtcaa tcgcgacgat gggtcctgct tatggattcc agtactcgcc    8220
tcagcagcgg gtcgaacgtc tgctgaagat gtggacctca aagagaaccc ccctggggtt    8280
ctcgtatgac acccgctgct ttgactcgac tgtcactgaa caggatatca gggtggaaga    8340
ggagatatat caatgctgta accttgaacc ggaggccagg aaggtgatct cctccctcac    8400
ggagcggctt tactgcgggg gccccatgtt caacagcaag ggggcccagt gcggttatcg    8460
ccgttgccgt gctagtggag ttctaccgac cagctttggc aacacaatca cttgttacat    8520
caaggccaca gcggctgcaa gggccgcggg tctccggaac ccggactttc ttgtctgcgg    8580
agatgatttg gtcgtggtgg ccgagagtga tggcgtcgac gaggataggg cagccctgag    8640
agccttcacg gaggctatga ccaggtactc tgctccaccc ggagatgctc cacagcctac    8700
ctacgacctt gagctcatca catcttgctc ctctaacgtc tccgtagcac atgacaacaa    8760 gggagaggg tattactacc tcacccgtga tgccactact cccctggccc gtgcggcttg    8820
ggaaacagct cgtcacactc cagttaactc ctggttgggc aacatcatca tgtacgcgcc    8880
taccatctgg gtgcgcatgg tgatgatgac acacttttc tccatactcc aatcccagga    8940
gatacttgat cgcccccttg attttgaaat gtacggggcc acttactctg tcactccgct    9000
ggatttacca gcaatcattg aaaaactcca tggtctaagc gcgttcacac tccacagtta    9060
ctctccagta gaactcaata gggtcgcggg gacactcagg aagcttgggt gcccccccct    9120
acgagcttgg agacatcggg cacgagcagt gcgcgctaag cttattgccc agggaggtaa    9180
ggccaaaata tgtggccttt atctctttaa ctgggcagta cgcaccaaga ccaaactcac    9240
tccactgcca gccgctagcc agttggactt atccaattgg ttttcggttg gcgtcggcgg    9300
gaacgacatt tatcacagcg tgtcacatgc ccgaacccgc catttgctgc tttgcctact    9360
cctactaact gtaggggtag gcatctttct cctgccagca cgataagctg gtaggataac    9420
actccattcc ttttcccttg ttttattttt tttttttttt tttttttttt tttttttttt    9480
ttcttttttt tttttttttt tttttttttg ttttcctct ttccattctt ttctaacctt     9540
aaattttcct ttcttaggt ggctccatct tagcccctagt cacggctagc tgtgaaaggt    9600
ccgtgagccg catgactgca gagagtgccg taactggtct ctctgcagat catgt         9655
```

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
    primer 2210R

<400> SEQUENCE: 52

-continued cgacagttgg atggcggatg a                                        21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer 2210F

<400> SEQUENCE: 53
tcatccgcca tccaactgtc g                                        21

<210> SEQ ID NO 54
<211> LENGTH: 7995
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cDNA sequence of mutant S310A S2210I HCV
      subgenomic replicon RNA

<400> SEQUENCE: 54
gacctgcctc ttacgaggcg acactccacc atggatcact ccctgtgag gaacttctgt      60 cttcacgcgg aaagcgccta gccatggcgt tagtacgagt gtcgtgcagc ctccaggacc    120 cccctcccg ggagagccat agtggtctgc ggaaccggtg agtacaccgg aatcgctggg    180
gtgaccgggt cctttcttgg aacaacccgc tcaataccca gaaatttggg cgtgccccg    240 cgagatcact agccgagtag tgttgggtcg cgaaaggcct tgtggtactg cctgatagg    300 tgcttgcgag tgccccggga ggtctcgtag accgtgcaac atgagcacac ttcctaaacc    360
ccaaagaaaa accaaaagaa acaccatccg tcgcccaatg attgaacaag atggattgca    420
cgcaggttct ccggccgctt gggtggagag gctattcggc tatgactggg cacaacagac    480
aatcggctgc tctgatgccg ccgtgttccg gctgtcagcg caggggcgcc cggttctttt    540
tgtcaagacc gacctgtccg gtgccctgaa tgaactgcag gacgaggcag cgcggctatc    600
gtggctggcc acgacgggcg ttccttgcgc agctgtgctc gacgttgtca ctgaagcggg    660
aagggactgg ctgctattgg gcgaagtgcc ggggcaggat ctcctgtcat ctcaccttgc    720
tcctgccgag aaagtatcca tcatggctga tgcaatgcgg cggctgcata cgcttgatcc    780
ggctacctgc ccattcgacc accaagcgaa acatcgcatc gagcgagcac gtactcggat    840
ggaagccggt cttgtcgatc aggatgatct ggacgaagag catcaggggc tcgcgccagc    900
cgaactgttc gccaggctca aggcgcgcat gcccgacggc gaggatctcg tcgtgaccca    960
tggcgatgcc tgcttgccga atatcatggt ggaaaatggc cgcttttctg gattcatcga   1020
ctgtggccgg ctgggtgtgg cggaccgcta tcaggacata gcgttggcta cccgtgatat   1080
tgctgaagag cttggcggcg aatgggctga ccgcttcctc gtgctttacg gtatcgccgc   1140
tcccgattcg cagcgcatcg ccttctatcg ccttcttgac gagttcttct gagtttaaac   1200
cctctccctc ccccccccct aacgttactg gccgaagccg cttggaataa ggccggtgtg   1260
cgtttgtcta tatgttattt tccaccatat tgccgtcttt tggcaatgtg agggcccgga   1320
aacctggccc tgtcttcttg acgagcattc ctagggtct ttcccctctc gccaaggaa   1380 tgcaaggtct gttgaatgtc gtgaaggaag cagttcctct ggaagcttct tgaagacaaa   1440
caacgtctgt agcgaccctt tgcaggcagc ggaacccccc acctggcgac aggtgcctct   1500

```
gcggccaaaa gccacgtgta taagatacac ctgcaaaggc ggcacaaccc cagtgccacg   1560
ttgtgagttg gatagttgtg gaaagagtca aatggctctc ctcaagcgta ttcaacaagg   1620
ggctgaagga tgcccagaag gtaccccatt gtatgggatc tgatctgggg cctcggtgca   1680
catgctttac atgtgtttag tcgaggttaa aaaaacgtct aggcccccg aaccacgggg    1740 acgtggtttt cctttgaaaa acacgatgat accatggccc cgatcactgc ttacgcccag   1800
caaaccaggg gccttcttgg gactattgtg accagcttga ctggcaggga taagaatgtg   1860
gtgaccggcg aagtgcaggt gctttctacg gctacccaga ccttcctagg tacaacaata   1920 ggggggggtta tgtggactgt ttaccatggc gcaggctcaa ggacacttgc gggcgctaaa   1980
catcctgcgc tccaaatgta cacaaatgta gatcaggacc tcgttgggtg gccagcccct    2040
ccaggggcta agtctcttga accgtgcacc tgcgggtctg cagacttata cttggttacc    2100
cgcgatgctg acgtcatccc cgctcggcgc agggggggact ccacagcgag cttgctcagc    2160
cctaggcctc tcgcctgtct caagggctcc tctggaggtc ccgttatgtg cccttcgggg    2220
catgtcacgg ggatctttcg ggctgctgtg tgcaccagag gtgtagcaaa gaccctacag    2280
ttcataccag tggaaaccct tagtacacag actaggtccc catccttctc tgacaattca    2340
actcctcccg ccgtcccaca gagctaccaa gtagggtatc ttcatgcccc gaccggtagt    2400
ggcaagagca caaggtccc ggccgcttac gtagcacaag gataccatgt tctcgtgttg      2460
aatccatcag tggcggccac actaggcttc ggctcttaca tgtcgaaagc ctatgggatc    2520
gaccccaacg tccgcactgg gaaccgcact gtcacaactg gtgctaaaact gacctattcc    2580 acctacggta agtttctcgc ggatgggggt tgctctgggg gagcgtatga tgtgattatt    2640
tgtgatgaat gccatgccca agacgctact accatattgg gtattggcac ggtcttagat    2700
caggctgaga cggctggggt gaggctgacg gttctggcga cagcaactcc cccaggcagc    2760
atcactgtgc cacattctaa catcgaggag gtagccctgg gctctgaagg tgagatccct    2820
ttctacggta aggctatacc gatagcccag ctcaagggg ggaggcacct tatcttttgc      2880
cattccaaga aaagtgtga tgagatagca tccaagctca gaggcatggg gctcaacgct    2940
gtagcattct atagggtct tgatgtgtcc atcataccaa cagcaggaga cgtcgtggtt     3000
tgcgccactg acgccctcat gactgggtac accggagact ttgattctgt catagattgc    3060
aacgtgactg ttgaacagta cgttgacttc agcttggacc ccacctttc cattgagact     3120 cacactgctc cccaagacgc ggtttcccgc agccaacgtc gtggccgtac gggccggggt    3180
agactcggca tataccgata tgtcaccccg ggtgaaagac cgtctggaat gtttgactcg    3240
gttgttctct gtgagtgcta tgatgcgggc tgctcgtggt acgatctgca gcccgctgag    3300
actacagtca gactgagagc ttacttgtcc acgccgggtt tacctgtctg tcaagaccat    3360
cttgactttt gggagagcgt ctttactgga ctaactcaca tagatgccca ctttctgtca    3420
cagactaagc agcagggact caacttcccg tacctgactg cctaccaagc cactgtgtgc    3480
gcccgcgcgc aggctcctcc cccaagttgg gacgagacgt ggaaatgtct cgtacggctt    3540
aaaccaacac tacatggacc cacgcccctt ctgtatcggt tggggcctat ccaaaatgaa    3600
acctgcttga cacaccccgt cacaaaatac atcatggcat gcatgtcagc tgatctggaa    3660
gtgaccacca gcgcctgggt gttgcttgga ggggtgctcg cggccctagc ggcttactgc    3720
ttgtcagtcg gctgcgttgt gatcgtgggt catattgagc tggggggcaa gccagcactc    3780
gttccagaca aagaggtgtt gtatcaacaa ttcgatgaga tggaggagtg ctcgcaagct    3840
```

```
gccccatata tcgaacaagc tcaggtaata gcccaccagt tcaaggagaa agtccttgga    3900
ttgctgcagc gagccaccca acaacaagct gtcattgagc ccatagtagc taccaactgg    3960
caaaagcttg aggcgttctg gcacaagcat atgtggaatt ttgtgagtgg gatccagtac    4020
ctagcaggcc tttccacttt gcctggcaac cccgctgtgg cgtctcttat ggcgttcacc    4080
gcttctgtca ccagtcccct gacgaccaac caaactatgt tcttcaacat actcgggggg    4140
tgggttgcta cccatttggc agggcccag agctcttccg cattcgtggt aagcggcttg     4200
gccggcgctg ccataggggg tataggcctg gcagggtct tgattgacat cctggcagga     4260
tacggagctg tgtctcagg cgccttggtg gcttttaaga tcatgggagg agaactcccc     4320
actgctgagg acatggtcaa catgctgcct gccatactat ctccgggcgc cctcgttgtc    4380
ggtgtgatat gtgcagccat actgcgtcga cacgtaggac ctggggaggg ggcggtgcag    4440
tggatgaaca ggctcatcgc attcgcatcc cggggtaacc acgtctcacc gacgcactat    4500
gtccccgaga gcgatgctgc agcgaaggtt actgcattgc tgagttctct aactgtcaca    4560
agtctgctcc ggcgactgca ccagtggatc aatgaagact acccaagtcc ttgctgcggc    4620
gactggctgc gtaccatctg ggactgggtt tgcatggtgt tgtctgactt caagacatgg    4680
ctctccgcta agattatgcc agcgctccct gggctgcctt tcctttcctg tcagaaggga    4740
tacaagggcg tgtggcgggg agacggtgtg atgtcgacac gctgtccttg cggggcgaca    4800 ataccggtc atgtgaagaa tgggtctatg cggcttgcag ggccacgcac atgtgctaac    4860
atgtggcacg gtactttccc catcaatgag taccaccacg acccggcac accttgccca    4920 gcacccaact acactcgcgc attattgcgc gtggctgcca acagctacgt tgaggtgcgc    4980
cgggtggggg acttccacta cattacgggg gctacagaag atgagctcaa gtgtccgtgc    5040
caagtgccgg ccgcagagtt ttttactgag gtggatgggg tgagactcca ccgttacgcc    5100
cctccatgca agcccctgtt gagggatgaa atcactttca tggtagggtt gaactcctac    5160
gcaataggat ctcaactccc ctgtgagccc gaaccagatg tttctgtgct gacctcgatg    5220
ttgagagacc cttcccatat taccgctgag gcagcagcgc gccgccttgc gcgtgggtcc    5280
cctccatcag aggcaagctc atccgccatc caactgtcgg ctccgtcgtt gaaggccact    5340
tgtcagtcgt atgggcctca tctggacgct gagctagtgg atgccaacct gttatggcgg    5400
caggagatgg gcagcactat cacacgggta gagtctgaaa caaggttgt gattcttgat    5460 tcattcgaac tctgagagc cgaaactgat gacgccgagc tctcggtggc tgcagagtgt    5520
ttcaagaagc ctcccaagta tcctccagcc cttcctatct gggctaggcc agactacaac    5580
cctccattgt tagaccgctg gaaagcaccg gattatgttc caccaactgt tcatggatgc    5640
gccttaccac cacggggcgc tccaccggtg cctcccctc ggaggaagag aacaattcag    5700
ctggatggct ccaatgtgtc cgcggcgcta gctgcgctag cagaaagtc attcccgtcc     5760 tcaaagccgc aggaagagaa tagctcatcc tcagggtcg acacacagtc cagcactacc     5820
tctaaggtgc cccccccccc aggaggggaa tccgactcag agtcgtgctc gtccatgcct    5880
cctctcgagg gagagccggg cgatccggat ttgagctgcg actcttggtc cactgtgagt    5940
gacaatgagg agcagaacgt agtctgctgc tccatgtcgt actcttggac cggcgccttg    6000
ataacaccat gtagtgctga ggaggagaaa ctacccatca gcccactcag caactccttg    6060
ttgagacacc ataatctggt ttattcaacg tcgtcaagaa gcgcttctca gcgtcagaag    6120
aaggttacct tcgacaggct gcaggtgctc gacgaccact acaaaactgc tttaaaggag    6180
gtaaaggagc gagcgtctgg ggtgaaggct cgcatgctca ccatcgagga agcgtgcaag    6240
```

```
cttgtccccc cccactctgc ccgttcgaag ttcgggtata gtgcgaagga cgctcgttcc    6300
ttgtccagca gggccgttaa ccagatccgc tccgtctggg aggacttgct ggaagacacc    6360
acaactccaa ttccaacaac catcatggcg aagaacgagg tgttttgtgt ggacccgtt     6420 aagggggcc gcaagcccgc tcgcctcatt gtgtaccctg acctgggggt gcgtgtctgt     6480
gagaaacgcg ccctatatga cgtgatacag aagttgtcaa tcgcgacgat gggtcctgct    6540
tatggattcc agtactcgcc tcagcagcgg gtcgaacgtc tgctgaagat gtggacctca    6600
aagagaaccc ccctggggtt ctcgtatgac acccgctgct ttgactcgac tgtcactgaa    6660
caggatatca gggtggaaga ggagatatat caatgctgta accttgaacc ggaggccagg    6720
aaggtgatct cctccctcac ggagcggctt tactgcgggg gcccatgtt caacagcaag      6780 ggggcccagt gcggttatcg ccgttgccgt gctagtggag ttctaccgac cagctttggc    6840
aacacaatca cttgttacat caaggccaca gcggctgcaa gggccgcggg tctccggaac    6900
ccggactttc ttgtctgcgg agatgatttg gtcgtggtgg ccgagagtga tggcgtcgac    6960
gaggataggg cagccctgag agccttcacg gaggctatga ccaggtactc tgctccaccc    7020
ggagatgctc cacagcctac ctacgacctt gagctcatca catcttgctc ctctaacgtc    7080
tccgtagcac atgacaacaa ggggaggagg tattactacc tcacccgtga tgccactact    7140
cccctggccc gtgcggcttg ggaaacagct cgtcacactc cagttaactc ctggttgggc    7200
aacatcatca tgtacgcgcc taccatctgg gtgcgcatgg tgatgatgac acactttttc    7260
tccatactcc aatcccagga gatacttgat cgcccccttg attttgaaat gtacggggcc    7320
acttactctg tcactccgct ggatttacca gcaatcattg aaagactcca tggtctaagc    7380
gcgttcacac tccacagtta ctctccagta gaactcaata gggtcgcggg gacactcagg    7440
aagcttgggt gccccccct acgagcttgg agacatcggg cacgagcagt gcgcgctaag     7500
cttattgccc agggaggtaa ggccaaaata tgtggccttt atctctttaa ctgggcagta    7560
cgcaccaaga ccaaactcac tccactgcca gccgctagcc agttggactt atccaattgg    7620
ttttcggttg gcgtcggcgg gaacgacatt tatcacagcg tgtcacatgc ccgaacccgc    7680
catttgctgc tttgcctact cctactaact gtaggggtag gcatctttct cctgccagca    7740
cgataagctg gtaggataac actccattcc ttttccttg ttttattt tttttttttt       7800 tttttttt ttttttttt ttctttttt tttttttttt ttttttttg ttttcctct          7860 ttccattctt ttctaacctt aaattttcct ttctttaggt ggctccatct tagccctagt    7920
cacggctagc tgtgaaaggt ccgtgagccg catgactgca gagagtgccg taactggtct    7980
ctctgcagat catgt                                                     7995
```

NUCLEIC ACID CONSTRUCT COMPRISING NUCLEIC ACID DERIVED FROM GENOME OF HEPATITIS C VIRUS OF GENOTYPE 3A

SEQUENCE LISTING

The instant application contains a Sequence Listing which has been submitted electronically in ASCII format and is hereby incorporated by reference in its entirety. Said ASCII copy, created on May 16, 2014, is named HIR-14-1057_SL.txt and is 214,828 bytes in size.

TECHNICAL FIELD

This disclosure relates to a nucleic acid derived from the genome of hepatitis C virus of genotype 3a, a nucleic acid construct comprising the nucleic acid, and a method of screening for an anti-hepatitis C virus substance.

BACKGROUND

In basic research on the hepatitis C virus (hereinafter, also referred to as HCV) and research and development of anti-HCV drugs, an experimental system that enables efficient virus amplification is essential. Specifically, a system for amplifying HCV in cultured cells and a system for evaluating the propagation of HCV in cultured cells are necessary, and it is considered that construction of such systems will allow dramatic progress in the research mentioned above to be realized.

HCV is a virus belonging to the family Flavivirus. It comprises a single-stranded (+) sense RNA as its genome, and it is known to cause hepatitis C. HCV is classified into many types depending on genotype or serotype. According to phylogenetic analysis conducted by Simmonds et al. using nucleotide sequences of HCV strains, HCV is classified into genotypes 1 to 6, and each type is further classified into several subtypes (Simmonds et al., Hepatology, 1994, Vol. 10, pp. 1321-1324). The full length genome nucleotide sequences of a plurality of HCV genotypes have been determined (Choo et al., Science, 1989, Vol. 244, pp. 359-362, Kato et al., Journal of Medical Virology, 1992, Vol. 64, pp. 334-339, Okamoto et al., Journal of General Virology, 1992, Vol. 73, pp. 673-679 and Yoshioka et al., Hepatology, 1992, Vol. 16, pp. 293-299).

HCV infection is spreading all over the world. In Japan, the U.S.A., and Europe, the proportion of patients infected with HCV of genotype 1 is high. In contrast, the proportion of patients infected with HCV of genotype 3 is high in India, Nepal, Pakistan, and Australia (Gravitz, Nature, 2011, Vol. 474, pp. s2-s4 and Rehman et al., Genetic Vaccines and Therapy, 2011, Vol. 9, pp. 2-5).

Until recently, infection of cultured cells with HCV and replication of HCV genomes in cultured cells have been impossible. Accordingly, studies on mechanisms of HCV replication and infection have required in vivo experiments using chimpanzees as experimental animals. However, subgenomic replicon RNAs have been produced from the Con1 strain, the HCV-N strain, the HCV-O strain belonging to HCV genotype 1b, and the H77c strain belonging to HCV genotype 1a. This has enabled studies on the HCV replication mechanism via in vitro experiments using cultured cells (JP 2001-17187 A and Lohmann et al., Science, 1999, Vol. 285, pp. 110-113, Blight et al., Science, 2000, Vol. 290, pp. 1972-1974, Friebe et al., Journal of Virology, 2001, Vol. 75, pp. 12047-12057 and Ikeda et al., Journal of Virology, 2002, Vol. 76, pp. 2997-3006). Herein, the subgenomic replicon RNA of HCV means an RNA which comprises a portion of HCV genome, and can autonomously replicate an RNA derived from the HCV genome when introduced into cultured cells, but does not have an ability to produce infectious HCV particles.

In addition to subgenomic replicon RNAs, full-genomic replicon RNAs producing infectious HCV particles in vitro have been produced from the JFH-1 strain belonging to HCV genotype 2a. This has enabled studies on the HCV infection mechanism via in vitro experiments using cultured cells (Kato et al., Gastroenterology, 2003, Vol. 125, pp. 1808-1817 and Wakita et al., Nature Medicine, 2005, Vol. 11, pp. 791-796). Herein, the full-genomic replicon RNA of HCV means an RNA which comprises the full-length HCV genome; i.e., a 5' untranslated region, structural genes, non-structural genes, and a 3' untranslated region, and can autonomously replicate an RNA derived from the HCV genome when introduced into cultured cells.

At present, RNAs that can produce infectious HCV particles in an in vitro system using cultured cells are limited to those derived from the JFH-1 strain of genotype 2a. RNAs capable of mass-producing HCV particles in an in vitro system for obtaining raw material of an HCV vaccine are limited to HCV of the JFH-1 strain or a full-genomic replicon derived from the JFH-1 strain.

The main therapeutics for hepatitis C are monotherapy using interferon-α or interferon-β and combined therapy using interferon-αα and ribavirin, which is a purine nucleoside derivative. Such therapy, however, is recognized as having a therapeutic effect in only about 60% of all subjects, and it is known that hepatitis C recurs in more than half of even those patients for whom the therapy was effective, in cases in which the therapy was stopped. The therapeutic effect of interferon is associated with HCV genotype, and it is known that the effect on genotype 1b is low and that the effect on genotype 2a or 3a is higher (Mori et al., Biochemical and Biophysical Research Communications, 1992, Vol. 183, pp. 334-342). While the causes of differences in interferon therapeutic effects depending on HCV genotype remain unknown, differences in HCV replication mechanism or replication efficiency are considered to be among the causes.

In recent years, novel therapeutic agents against hepatitis C such as inhibitors against HCV-derived protease or polymerase, have been developed. However, it is reported that TMC435, which is an HCV NS3/4A protease inhibitor, has strong inhibitory effects on genotypes 1 to 6 except for genotype 3a, but weak inhibitory effects on genotype 3a; that is, inhibitory effects against HCV vary depending on genotype (Reesink et al., Gastroenterology, 2010, Vol. 138, pp. 913-921).

The HCV subgenomic replicon RNAs that have been produced are, however, limited to several types derived from HCV strains of genotypes 1a, 1b, and 2a. Full-genomic replicon RNAs capable of producing infectious HCV particles that have been produced are limited to those derived from the genome of the JFH-1 strain of genotype 2a or those derived from a chimeric genome composed of structural genes derived from a strain other than the JFH-1 strain and non-structural genes of the JFH-1 strain. It is therefore difficult to elucidate the correlation between HCV genotype and HCV replication mechanism or replication efficiency. At present, unfortunately, HCV particles that can be artificially prepared as raw materials for HCV vaccines are limited to those of genotype 2a.

In studies using subgenomic replicon RNAs or full-genomic replicon RNAs derived from HCV of the same genotype, HCV replication mechanisms or replication efficiencies cannot be compared between different genotypes. Accordingly, no clues regarding the development of anti-HCV drugs that exert therapeutic effects independently of genotype have been found.

In research and medical fields related to HCV, specifically, obtaining an HCV strain of genotype 3a and production of replicon RNA thereof are strongly demanded in developing genotype-independent anti-HCV drugs and, in particular, anti-HCV drugs against HCV of genotype 3a.

Accordingly, it could be helpful to provide a novel HCV strain of genotype 3a, and, further, replicon RNA having autonomous replication ability derived from a novel HCV strain of genotype 3a.

SUMMARY

We discovered the S310A strain, which is a novel HCV strain of genotype 3a isolated from an acute hepatitis C patient, and succeeded in producing replicon RNA having autonomous replication ability from the S310A strain.

We thus provide:

[1] A nucleic acid comprising, in the following order, a 5' untranslated region comprising the nucleotide sequence of nucleotides 1 to 340 of SEQ ID NO: 1, the nucleotide sequences encoding the amino acid sequence of an NS3 protein of amino acids 1033 to 1663, the nucleotide sequence encoding the amino acid sequence of an NS4A protein of amino acids 1664 to 1717, the nucleotide sequence encoding the amino acid sequence of an NS4B protein of amino acids 1718 to 1978, the nucleotide sequence encoding the amino acid sequence of an NS5A protein of amino acids 1979 to 2430, the nucleotide sequence encoding the amino acid sequence of an NS5B protein of amino acids 2431 to 3021 of SEQ ID NO: 14, and a 3' untranslated region comprising the nucleotide sequence of nucleotides 9407 to 9655 of SEQ ID NO: 1, which are of a genome of a hepatitis C virus of genotype 3a, provided that if the nucleic acid is RNA, thymine (t) in the nucleotide sequence shall be replaced with uracil (u).

[2] The nucleic acid according to [1], wherein
- the nucleotide sequence encoding the amino acid sequence of the NS3 protein comprises the nucleotide sequence of nucleotides 3437 to 5329 of SEQ ID NO: 1,
- the nucleotide sequence encoding the amino acid sequence of the NS4A protein comprises the nucleotide sequence of nucleotides 5330 to 5491 of SEQ ID NO: 1,
- the nucleotide sequence encoding the amino acid sequence of the NS4B protein comprises the nucleotide sequence of nucleotides 5492 to 6274 of SEQ ID NO: 1,
- the nucleotide sequence encoding the amino acid sequence of the NS5A protein comprises the nucleotide sequence of nucleotides 6275 to 7630 of SEQ ID NO: 1, and
- the nucleotide sequence encoding the amino acid sequence of the NS5B protein comprises the nucleotide sequence of nucleotides 7631 to 9406 of SEQ ID NO: 1.

[3] The nucleic acid according to [1] or [2], wherein the 5' untranslated region is a nucleotide sequence comprising deletion, substitution, or addition of one or a plurality of nucleotides in the nucleotide sequence of nucleotides 1 to 340 of SEQ ID NO: 1.

[4] A nucleic acid comprising nucleotide mutation(s) in the nucleotide sequence of the nucleic acid according to any of [1] to [3], wherein the nucleotide mutation(s) include a nucleotide mutation that causes at least one amino acid substitution of the following (a) to (g), as defined on the basis of the amino acid sequence shown in SEQ ID NO: 14:
- (a) a substitution of threonine at position 1286 with isoleucine;
- (b) a substitution of threonine at position 2188 with alanine;
- (c) a substitution of arginine at position 2198 with histidine;
- (d) a substitution of serine at position 2210 with isoleucine;
- (e) a substitution of threonine at position 2496 with isoleucine;
- (f) a substitution of arginine at position 2895 with glycine; or
- (g) a substitution of arginine at position 2895 with lysine.

[5] The nucleic acid according to any of [1] to [4], which further comprises a nucleotide sequence encoding a Core protein, a nucleotide sequence encoding an E1 protein, a nucleotide sequence encoding an E2 protein, a nucleotide sequence encoding a p7 protein, and a nucleotide sequence encoding an NS2 protein of a hepatitis C virus genome.

[6] The nucleic acid according to [5], wherein
- the nucleotide sequence encoding the Core protein encodes the amino acid sequence of Core protein of amino acids 1 to 191 of SEQ ID NO: 14,
- the nucleotide sequence encoding the E1 protein encodes the amino acid sequence of E1 protein of amino acids 192 to 383 of SEQ ID NO: 14,
- the nucleotide sequence encoding the E2 protein encodes the amino acid sequence of E2 protein of amino acids 384 to 752 of SEQ ID NO: 14,
- the nucleotide sequence encoding the p7 protein encodes the amino acid sequence of p7 protein of amino acids 753 to 815 of SEQ ID NO: 14, and
- the nucleotide sequence encoding the NS2 protein encodes the amino acid sequence of NS2 protein of amino acids 816 to 1032 of SEQ ID NO: 14.

[7] The nucleic acid according to [5] comprising the nucleotide sequence shown in any of SEQ ID NOs: 1 and 49 to 51.

[8] The nucleic acid according to [4] comprising the nucleotide sequence shown in any of SEQ ID NOs: 17 to 23 and 54.

The nucleic acid according to any of [1] to [8] may further contain a foreign gene and/or an IRES sequence.

[9] A subgenomic replicon RNA of hepatitis C virus comprising the nucleic acid according to any of [1] to [4] and [8].

[10] A full-genomic replicon RNA of hepatitis C virus comprising the nucleic acid according to any of [5] to [7].

[11] A hepatitis C virus particle containing the nucleic acid according to any of [5] to [7] as a virus genome.

The nucleic acid according to any of [1] to [8] may be DNA. In addition, expression vector containing the nucleic acid according to any of [1] to [8], and, in particular, such DNA is within the scope of the preferred examples.

[12] A cell into which the nucleic acid according to any of [1] to [8] has been introduced.

[13] A hepatitis C virus vaccine comprising the hepatitis C virus particle according to [11] or a part thereof.

[14] An antibody against hepatitis C virus, which recognizes the hepatitis C virus particle according to [11] as an antigen.

[15] A method of screening for an anti-hepatitis C virus agent comprising:
   a step of culturing the cells according to [12] or a mixture of the hepatitis C virus particle according to [11] and hepatitis C virus-sensitive cell in the presence and in the absence of a test substance;
   a step of quantifying the amount of a subgenomic replicon RNA, full-genomic replicon RNA, or hepatitis C virus particle in a culture obtained by the step of culturing; and
   a step of evaluating the result of the step of quantifying, wherein the test substance is determined as a substance having an anti-hepatitis C virus activity if the amount of the subgenomic replicon RNA, full-genomic replicon RNA, or hepatitis C virus particle quantified in the culture prepared by culturing in the presence of the test substance is lower than the amount of the subgenomic replicon RNA, full-genomic replicon RNA, or hepatitis C virus particle quantified in the culture prepared by culturing in the absence of the test substance.

[16] The nucleic acid according to [5], wherein the nucleic acid is a chimeric nucleic acid derived from the genomes of two or more hepatitis C virus strains and comprises, in the following order, from the 5' to 3' direction:
   the nucleotide sequence encoding the Core protein, the nucleotide sequence encoding the E1 protein, the nucleotide sequence encoding the E2 protein, and the nucleotide sequence encoding the p7 protein of a hepatitis C virus genome other than the hepatitis C virus genome shown in SEQ ID NO: 1;
   the nucleotide sequence encoding the NS2 protein of nucleotides 2786 to 3436 of SEQ ID NO: 1, the nucleotide sequence encoding the NS2 protein of a hepatitis C virus genome other than the hepatitis C virus genome shown in SEQ ID NO: 1, or a chimeric NS2 protein consisting of a part of the nucleotide sequence encoding an NS2 protein consisting of nucleotides 2786 to 3436 of SEQ ID NO: 1 linked to a part of the nucleotide sequence encoding an NS2 protein of a hepatitis C virus genome other than the hepatitis C virus genome shown in SEQ ID NO: 1; and
   the nucleotide sequence encoding the NS3 protein consisting of nucleotides 3437 to 5329, the nucleotide sequence encoding the NS4A protein consisting of nucleotides 5330 to 5491, the nucleotide sequence encoding the NS4B protein consisting of nucleotides 5492 to 6274, the nucleotide sequence encoding the NS5A protein consisting of nucleotides 6275 to 7630, and the nucleotide sequence encoding the NS5B protein consisting of nucleotides 7631 to 9406 of SEQ ID NO: 1.

[17] A nucleic acid comprising nucleotide mutation(s) in the nucleotide sequence of the nucleic acid according to [16], wherein the nucleotide mutation(s) include a nucleotide mutation that causes at least one amino acid substitution of the following (a) to (g), as defined on the basis of the amino acid sequence shown in SEQ ID NO: 14:
   (a) a substitution of threonine at position 1286 with isoleucine;
   (b) a substitution of threonine at position 2188 with alanine;
   (c) a substitution of arginine at position 2198 with histidine;
   (d) a substitution of serine at position 2210 with isoleucine;
   (e) a substitution of threonine at position 2496 with isoleucine;
   (f) a substitution of arginine at position 2895 with glycine; and
   (g) a substitution of arginine at position 2895 with lysine.

[18] The nucleic acid according to [16] or [17], which comprises a 5' untranslated region of a hepatitis C virus genome other than the hepatitis C virus genome of SEQ ID NO: 1, instead of the 5' untranslated region comprising the nucleotide sequence of nucleotides 1 to 340 of SEQ ID NO: 1.

[19] A chimeric full-genomic replicon RNA of a hepatitis C virus comprising the nucleic acid according to any one of [16] to [18].

This description includes the disclosure in Japanese Patent Application No. 2011-189695, to which this application claims priority.

We can thus produce a replicon RNA of HCV of genotype 3a having autonomous replication ability in cultured cells.

DETAILED DESCRIPTION

Figure 1:
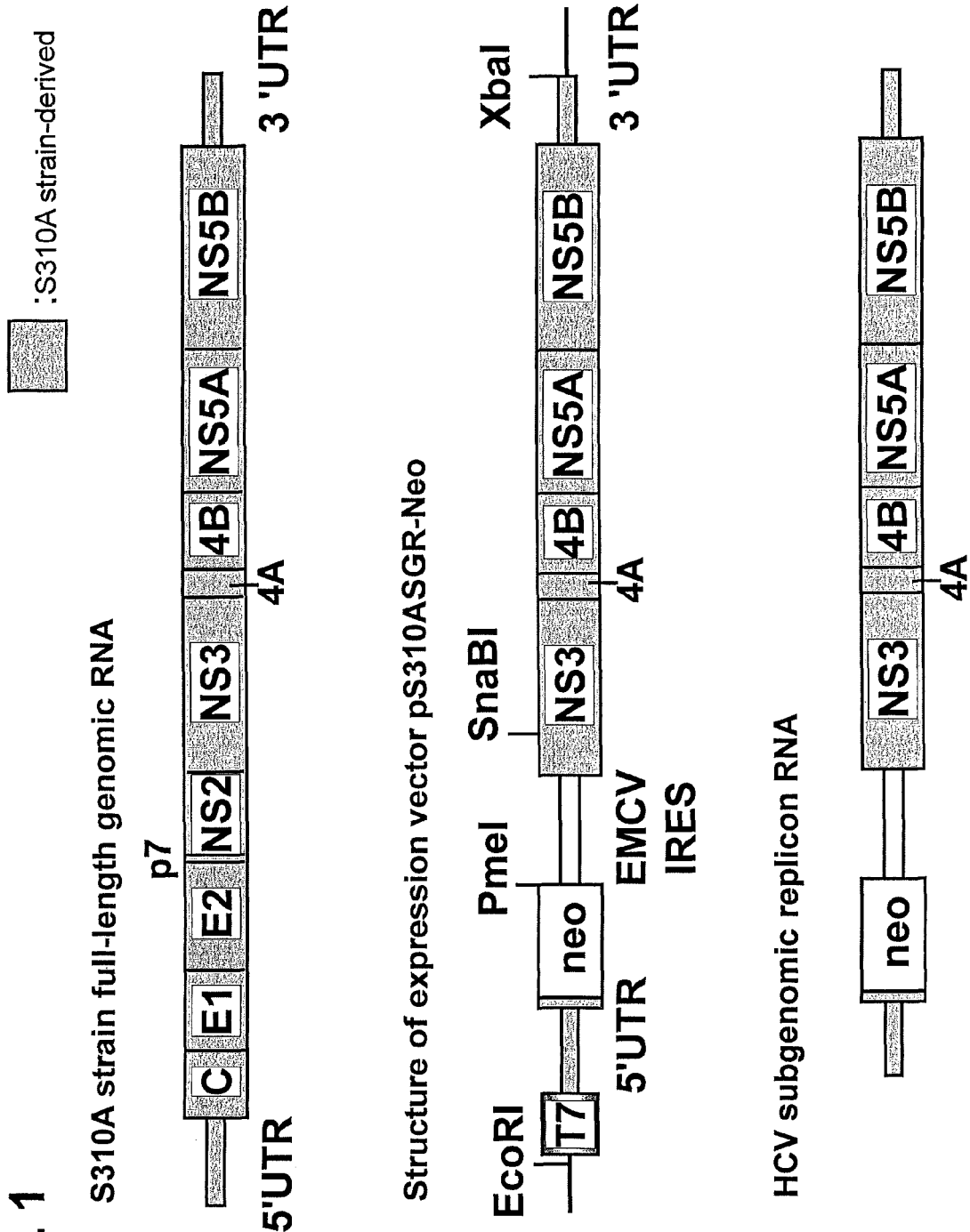
FIG. 1 shows (A) the structure of the full-length genomic RNA of the HCV S310A strain (wild-type), (B) the structure of pS310ASGR-Neo, the S310A strain HCV subgenomic replicon RNA expression vector, and (C) the structure of the S310A strain HCV subgenomic replicon RNA synthesized from pS310ASGR-Neo with T7 polymerase.

The scientific terms, technical terms, and nomenclature used throughout the description are intended to have the same meanings as those generally understood by those skilled in the art unless otherwise specifically defined. The general technology and technical terms in the fields of molecular biology and immunology are based on methods and definitions described in Sambrook et al., Molecular Cloning: A Laboratory Manual (Third Edition, 2001) and Ed Harlow et al., Antibodies: A Laboratory Manual (1988). Furthermore, all documents, patents, and patent applications cited in the description are incorporated by reference herein in their entirety.

Hepatitis C virus (HCV) is a virus with a single-stranded (+) sense RNA as the genome. An HCV genome comprises a 5' untranslated region (5' UTR), a nucleotide sequence encoding a Core protein, an E1 protein, an E2 protein, a p7 protein, an NS2 protein, an NS3 protein, an NS4A protein, an NS4B protein, an NS5A protein, and an NS5B protein (a viral protein coding region); and a 3' untranslated region (3' UTR). The HCV genome (the full-length HCV genome) is an RNA composed of 5' UTR; nucleotide sequences encoding a Core protein, an E1 protein, an E2 protein, a p7 protein, an NS2 protein, an NS3 protein, an NS4A protein, an NS4B protein, an NS5A protein, and an NS5B protein; and 3' UTR, located in this order from the 5' to 3' direction. For the purpose of differentiating the full-length HCV genome from a nucleic acid consisting of a part of the HCV genome, the full-length HCV genome is also referred to as "HCV full-length genome," "full-length HCV genome," "HCV full-length genomic RNA," "full-length HCV genomic RNA," or "full-length genomic RNA."

HCV is actually present as virus particles. The virus particles of HCV (HCV particles) contain HCV genomes inside viral capsids composed of HCV structural proteins.

The Core protein, the E1 protein, the E2 protein, and the p7 protein of HCV are "structural proteins" constituting HCV particles, and nucleic acids encoding such structural proteins are referred to as "structural genes." The HCV genomic sequence comprising such structural genes is also referred to as "structural region." The NS2 protein, the NS3 protein, the NS4A protein, the NS4B protein, the NS5A protein, and the NS5B protein of HCV are "non-structural proteins" that do not constitute HCV particles, and nucleic acids encoding such non-structural proteins are referred to as "non-structural genes." The HCV genomic sequence comprising such non-structural genes are also referred to as "non-structural region." Non-structural proteins have functions involved in, for example, replication of an HCV genome and processing of HCV proteins.

The 5' untranslated region (5' UTR) of HCV provides an internal ribosome entry site (hereafter, referred to as "IRES") for protein translation and an element necessary for replication. The 5' UTR of HCV is a region of about 360 nucleotides from the 5' terminus of the genome.

The 3' untranslated region (3' UTR) of HCV assists replication of HCV. The 3' UTR of HCV contains a variable region, a poly-U region, and an additional region of about 100 nucleotides.

HCV is translated into a single precursor protein (a polyprotein) in which ten viral proteins (i.e., Core protein, E1 protein, E2 protein, p7 protein, NS2 protein, NS3 protein, NS4A protein, NS4B protein, NS5A protein, and NS5B protein) are ligated in this order, and the precursor protein is then cleaved into ten mature viral proteins (Core protein, E1 protein, E2 protein, p7 protein, NS2 protein, NS3 protein, NS4A protein, NS4B protein, NS5A protein, and NS5B protein) with intracellular and viral proteases.

While various HCV genotypes have been known, the HCV genomes of such various genotypes are known to have similar gene structures. The "genotype" of HCV refers to genotypes classified in accordance with the international classification by Simmonds et al.

The nucleic acid consisting of the nucleotide sequence shown in SEQ ID NO: 1 in the Sequence Listing is the genome of the S310A strain, which is a novel HCV strain of genotype 3a isolated from an acute severe hepatitis C patient. While the sequence shown in SEQ ID NO: 1 is a cDNA sequence of full-length genomic RNA of the S310A strain, a nucleotide sequence obtained by replacing the thymine (t) with uracil (u) in the nucleotide sequence is its RNA sequence. A method for isolating the HCV genome from a patient is described in Kato et al., Gastroenterology, 2003, vol. 125, and pp. 1808-1817.

In the full-length HCV genome sequence of the S310A strain (SEQ ID NO: 1), the 5' untranslated region (5' UTR) consists of the sequence of nucleotides 1 to 340 of SEQ ID NO: 1, the Core protein coding sequence consists of nucleotides 341 to 913 of SEQ ID NO: 1, the E1 protein coding sequence consists of nucleotides 914 to 1489 of SEQ ID NO: 1, the E2 protein coding sequence consists of nucleotides 1490 to 2596 of SEQ ID NO: 1, the p7 protein coding sequence consists of nucleotides 2597 to 2785 of SEQ ID NO: 1, the NS2 protein coding sequence consists of nucleotides 2786 to 3436 of SEQ ID NO: 1, the NS3 protein coding sequence consists of nucleotides 3437 to 5329 of SEQ ID NO: 1, the NS4A protein coding sequence consists of nucleotides 5330 to 5491 of SEQ ID NO: 1, the NS4B protein coding sequence consists of nucleotides 5492 to 6274 of SEQ ID NO: 1, the NS5A protein coding sequence consists of nucleotides 6275 to 7630 of SEQ ID NO: 1, the NS5B protein coding sequence consists of nucleotides 7631 to 9406 of SEQ ID NO: 1, and the 3' untranslated region (3' UTR) consists of the sequence of nucleotides 9407 to 9655 of SEQ ID NO: 1. The structure of the full-length HCV genome of the S310A strain is shown in FIG. 1A.

Specifically, the 5' untranslated region (5' UTR) of the full-length HCV genome of the S310A strain (SEQ ID NO: 1) consists of the nucleotide sequence shown in SEQ ID NO: 2, the Core protein coding sequence consists of the nucleotide sequence shown in SEQ ID NO: 3, the E1 protein coding sequence consists of the nucleotide sequence shown in SEQ ID NO: 4, the E2 protein coding sequence consists of the nucleotide sequence shown in SEQ ID NO: 5, the p7 protein coding sequence consists of the nucleotide sequence shown in SEQ ID NO: 6, the NS2 protein coding sequence consists of the nucleotide sequence shown in SEQ ID NO: 7, the NS3 protein coding sequence consists of the nucleotide sequence shown in SEQ ID NO: 8, the NS4A protein coding sequence consists of the nucleotide sequence shown in SEQ ID NO: 9, the NS4B protein coding sequence consists of the nucleotide sequence shown in SEQ ID NO: 10, the NS5A protein coding sequence consists of the nucleotide sequence shown in SEQ ID NO: 11, the NS5B protein coding sequence consists of the nucleotide sequence shown in SEQ ID NO: 12, and the 3' untranslated region (3' UTR) consists of the nucleotide sequence shown in SEQ ID NO: 13.

The amino acid sequence of the precursor protein of the S310A strain is shown in SEQ ID NO: 14. The amino acid sequence of the precursor protein of the S310A strain shown in SEQ ID NO: 14 is encoded by the nucleotide sequence portion consisting of nucleotides 341 to 9406 (including the stop codon) of the cDNA sequence of the full-length genomic RNA of the wild-type S310A strain shown in SEQ ID NO: 1.

We provide the genome of the S310A strain, which is a novel HCV strain of genotype 3a, and a replicon RNA derived from the S310A strain, which has autonomous replication ability is capable of autonomous replication, and nucleic acids encoding them.

The term "nucleic acid" includes RNA and DNA. The term "a protein coding region," "a nucleotide sequence encoding a protein," "a sequence encoding a protein," or "a protein coding sequence" used herein refers to a nucleotide sequence encoding an amino acid sequence of a given protein, which may or may not contain a start codon and a stop codon.

If the nucleic acid is RNA and a nucleotide sequence of or a nucleotide in the RNA is to be identified with reference to a SEQ ID NO: in the Sequence Listing herein, thymine (t) in the nucleotide sequence shown in the SEQ ID NO: shall be replaced with uracil (u).

Preferably, a nucleic acid comprises, in the following order, a 5' untranslated region comprising the nucleotide sequence of nucleotides 1 to 340 of SEQ ID NO: 1; nucleotide sequences encoding the amino acid sequence of NS3 protein of amino acids 1033 to 1663, the amino acid sequence of NS4A protein of amino acids 1664 to 1717, the amino acid sequence of NS4B protein of amino acids 1718 to 1978, the amino acid sequence of NS5A protein of amino acids 1979 to 2430, the amino acid sequence of NS5B protein of amino acids 2431 to 3021 of SEQ ID NO: 14 (a precursor protein encoded by the nucleotide sequence shown in SEQ ID NO: 1); and a 3' untranslated region comprising the nucleotide sequence of nucleotides 9407 to 9655 of SEQ ID NO: 1, which are of a genome of a hepatitis C virus of genotype 3a (the S310A strain or a mutant thereof). Further preferably, the 5' untranslated region of the nucleic acid may comprise deletion, substitution, or addition of one or a plurality of (e.g., 2 to 20, and preferably 2 to 5) nucleotides in the nucleotide sequence of nucleotides 1 to 340 of SEQ ID NO: 1. The 5' untranslated region of the nucleic acid has 95% or more, preferably 97% or more, and more preferably 99% or more, e.g., 99.5% or more nucleotide sequence identity with the nucleotide sequence of nucleotides 1 to 340 of SEQ ID NO: 1.

The nucleic acid may comprise, in the following order, a 5' untranslated region comprising the nucleotide sequence of nucleotides 1 to 340 of SEQ ID NO: 1, the nucleotide sequence encoding the amino acid sequence of NS3 protein of nucleotides 3437 to 5329 of SEQ ID NO: 1, the nucleotide sequence encoding the amino acid sequence of NS4A protein of nucleotides 5330 to 5491 of SEQ ID NO: 1, the nucleotide sequence encoding the amino acid sequence of NS4B protein of nucleotides 5492 to 6274 of SEQ ID NO: 1, the nucleotide sequence encoding the amino acid sequence of NS5A protein of nucleotides 6275 to 7630 of SEQ ID NO: 1, the nucleotide sequence encoding the amino acid sequence of NS5B protein of nucleotides 7631 to 9406 of SEQ ID NO: 1, and a 3' untranslated region of nucleotides 9407 to 9655 of SEQ ID NO: 1. In another preferred example, the 5' untranslated region of the nucleic acid may comprise deletion, substitution, or addition of one or a plurality of (e.g., 2 to 20, and preferably 2 to 5) nucleotides in the nucleotide sequence of nucleotides 1 to 340 of SEQ ID NO: 1. The 5' untranslated region of the nucleic acid has 95% or more, preferably 97% or more, and more preferably 99% or more, e.g., 99.5% or more nucleotide sequence identity with the nucleotide sequence of nucleotides 1 to 340 of SEQ ID NO: 1.

The nucleic acid need not comprise a nucleotide sequence encoding a Core protein, a nucleotide sequence encoding an E1 protein, a nucleotide sequence encoding an E2 protein, a nucleotide sequence encoding a p7 protein, and a nucleotide sequence encoding an NS2 protein of a hepatitis C virus genome. Such nucleic acid may encode an HCV subgenomic replicon RNA.

The nucleic acid may further comprise a nucleotide sequence encoding a Core protein, a nucleotide sequence encoding an E1 protein, a nucleotide sequence encoding an E2 protein, a nucleotide sequence encoding a p7 protein, and a nucleotide sequence encoding an NS2 protein of a hepatitis C virus genome. Such nucleic acid may encode an HCV full-genomic replicon RNA. In such a case, the nucleotide sequence encoding the Core protein, the nucleotide sequence encoding the E1 protein, the nucleotide sequence encoding the E2 protein, the nucleotide sequence encoding the p7 protein, and the nucleotide sequence encoding the NS2 protein may be derived from a genome of a hepatitis C virus of genotype 3a (e.g., the S310A strain or a mutant thereof).

When such nucleotide sequences are derived from the genome of the hepatitis C virus genotype 3a, the nucleotide sequence encoding the Core protein preferably encodes the amino acid sequence of the Core protein of amino acids 1 to 191 of SEQ ID NO: 14. The nucleotide sequence encoding the E1 protein preferably encodes the amino acid sequence of the E1 protein of amino acids 192 to 383 of SEQ ID NO: 14. The nucleotide sequence encoding the E2 protein preferably encodes the amino acid sequence of the E2 protein of amino acids 384 to 752 of SEQ ID NO: 14. The nucleotide sequence encoding the p7 protein preferably encodes the amino acid sequence of the p7 protein of amino acids 753 to 815 of SEQ ID NO: 14. The nucleotide sequence encoding the NS2 protein preferably encodes the amino acid sequence of the NS2 protein of amino acids 816 to 1032 of SEQ ID NO: 14.

The nucleotide sequence encoding the Core protein, the nucleotide sequence encoding the E1 protein, the nucleotide sequence encoding the E2 protein, the nucleotide sequence encoding the p7 protein, and the nucleotide sequence encoding the NS2 protein may be derived from a genome of HCV (e.g., an existing HCV strain) of genotypes other than 3a (e.g., 1a, 1b, 2a, 2b, 2c, 3b, 4, 5a, or 6a). In such a case, the nucleic acid is a chimeric form (chimeric nucleic acid).

The nucleic acid may comprise one or a plurality of (preferably 2 to 50, such as 2 to 10) nucleotide mutations in the nucleotide sequence of the above-mentioned nucleic acid. The nucleotide mutation is, but not limited to, preferably deletion, substitution, or addition of a nucleotide. The nucleotide mutation may be synonymous mutation that does not cause amino acid substitution, or it may be non-synonymous mutation that causes amino acid substitution, provided that the autonomous replication ability is retained. As long as the autonomous replication ability is retained, amino acid substitution may be conservative or non-conservative.

The nucleic acid may comprise a 5' untranslated region derived from a genome of HCV (e.g., an existing HCV strain) of genotype other than 3a (e.g., 1a, 1b, 2a, 2b, 2c, 3b, 4, 5a, or 6a) instead of the 5' untranslated region comprising the nucleotide sequence of nucleotides 1 to 340 of SEQ ID NO: 1.

The nucleic acid may further contain a foreign gene (e.g., a drug resistance gene or a reporter gene) and an IRES sequence.

The nucleic acid may be HCV replicon RNA such as HCV subgenomic replicon RNA or HCV full-genomic replicon RNA, or a nucleic acid encoding the same. The nucleic acid may be, for example, an expression cassette comprising a nucleotide sequence encoding the HCV replicon RNA. The nucleic acid may be DNA, RNA, or a DNA/RNA chimera, and it may contain a modified nucleotide or the like.

The term "replicon RNA" used herein refers to an RNA that can autonomously replicate in cultured cells (typically HCV-sensitive cells). The replicon RNA introduced into cells autonomously replicates, and the RNA copies are distributed to daughter cells, following cell division. Thus, nucleic acids can be stably introduced into cells via the replicon RNA.

The term "replicon RNA of HCV" or "HCV replicon RNA" refers to an autonomously replicable RNA comprising a part or full-length of an HCV genomic RNA. An autonomously replicable RNA comprising a part of an HCV genomic RNA is referred to as "HCV subgenomic replicon RNA," and an autonomously replicable RNA comprising a full-length of an HCV genomic RNA is referred to as "HCV full-genomic replicon RNA." The term "HCV replicon RNA" refers to both HCV subgenomic replicon RNA and HCV full-genomic replicon RNA.

It is preferred that the HCV subgenomic replicon RNA comprise the 5' untranslated region (5' UTR); the nucleotide sequences encoding the NS3 protein, the NS4A protein, the NS4B protein, the NS5A protein and the NS5B protein, and the 3' untranslated region (3' UTR) of HCV in this order from the 5' to 3' direction. It is also preferred that the HCV subgenomic replicon RNA further comprise a foreign gene (e.g., a drug resistance gene or a reporter gene) and an IRES sequence for detection of the HCV subgenomic replicon RNA. In such a case, it is preferred to insert the foreign gene (the drug resistance gene or the reporter gene) and the IRES sequence on the 5' side of the NS3 protein coding sequence of the HCV subgenomic replicon RNA.

The "HCV subgenomic replicon RNA" preferably includes the nucleic acid. The "HCV subgenomic replicon RNA" is preferably expressed from the nucleic acid. A preferred example of "HCV subgenomic replicon RNA" is an RNA comprising the 5' untranslated region (5' UTR), a sequence of 57 nucleotides from the 5' terminus of the nucleotide sequence encoding the Core protein, a foreign gene (a drug resistance gene or a reporter gene), an IRES sequence, the nucleotide sequence encoding the NS3 protein, the NS4A protein, the NS4B protein, the NS5A protein and the NS5B protein, and the 3' untranslated region (3' UTR) of HCV in this order from the 5' to 3' direction.

It is preferred that the HCV full-genomic replicon RNA comprise the 5' untranslated region (5' UTR), the nucleotide sequences encoding the Core protein, the E1 protein, the E2 protein, the p7 protein, the NS2 protein, the NS3 protein, the NS4A protein, the NS4B protein, the NS5A protein and the NS5B protein, and the 3' untranslated region (3' UTR) of HCV located in this order from the 5' to 3' direction. The HCV full-genomic replicon RNA may further comprise a foreign gene (a drug resistance gene or a reporter gene) and an IRES sequence. In such a case, the foreign gene (the drug resistance gene or the reporter gene) and the IRES sequence are preferably located on the 5' side of the nucleotide sequence encoding the Core protein of the HCV full-genomic replicon RNA.

When the full-length HCV genomic nucleic acid has autonomous replication ability, such genome is replicon RNA. Replicon RNA containing the full-length HCV genomic nucleic acid is referred to as HCV full-genomic replicon RNA. An RNA consisting of the HCV full-length genomic sequence (i.e., HCV full-length genomic RNA) and having autonomous replication ability is HCV full-genomic replicon RNA.

Examples of the drug resistance gene that can be contained in the HCV replicon RNA (HCV full-genomic replicon RNA and HCV subgenomic replicon RNA) and the nucleic acid include neomycin resistance genes, hygromycin resistance genes, thymidine kinase genes, kanamycin resistance genes, pyrithiamine resistance genes, adenylyltransferase genes, zeocin resistance genes, puromycin resistance genes, and blasticidin S resistance genes, with the neomycin resistance genes and the hygromycin resistance genes being preferred, and the neomycin resistance genes being more preferred.

Examples of the reporter genes that can be contained in the HCV replicon RNA and the nucleic acid include structural genes of enzymes that catalyze the luminous reaction or color reaction. Preferred examples of the reporter gene include chloramphenicol acetyl transferase genes derived from transposon Tn9, β-glucuronidase or β-galactosidase genes derived from *E. coli*, luciferase genes, green fluorescent protein genes, aequorin genes derived from jellyfish, and secretory placental alkaline phosphatase (SEAP) genes.

The HCV replicon RNA or the nucleic acid may contain either or both the drug resistance gene and the reporter gene. One, or two or more of drug resistance genes or the reporter genes may be contained in the HCV replicon RNA or the nucleic acid. When two or more drug resistance genes or reporter genes are contained, each gene may be ligated to a virus-derived 2A peptide gene in the proper reading frame (i.e., in-frame). Examples of 2A peptides include *Thosea asigna* virus-derived 2A peptides (T2A), Foot-and-mouth disease virus-derived 2A peptides (F2A), *Equin rhinitis* A virus-derived 2A peptides (E2A), and *Porcine tescho* virus 1-derived 2A peptides (P2A) (Kim et al., PLos One., 2011, Vol. 6 (4), e18556).

The "IRES sequence" that can be contained in HCV replicon RNA and the nucleic acid is as described above. For example, the term "IRES sequence" refers to an internal ribosome entry site that can allow a ribosome to bind an internal region of RNA and start translation. Preferred examples of the IRES sequence include EMCV IRES (the internal ribosome entry site of the encephalomyocarditis virus), FMDV IRES, and HCV IRES, with EMCV IRES and HCV IRES being more preferred, and EMCV IRES being the most preferred.

In the HCV replicon RNA and the nucleic acid, the drug resistance gene and/or the reporter gene is ligated to be translated in a proper reading frame (in-frame) from the HCV replicon RNA. The proteins encoded by the HCV replicon RNA or the nucleic acid are preferably ligated to one another through, for example, a protease cleavage site therebetween so that the proteins are translated and expressed as a stretch of polypeptides, cleaved into each protein with a protease, and then released.

The HCV-sensitive cell refers to a cell that allows infection with HCV particles or replication of the HCV replicon RNA in a cell culture system, and examples thereof include Huh7 cells, HepG2 cells, IMY-N9 cells, HeLa cells, 293 cells, and derivative strains of the Huh7 cells such as Huh7.5 cells and Huh7.5.1 cells. Other examples include Huh7 cells, HepG2 cells, IMY-N9 cells, HeLa cells, and 293 cells engineered to express a CD81 gene and/or a Claudin1 gene (Lindenbach et al., Science, 2005, vol. 309, pp. 623-626; Evans et al., Nature, 2007, vol. 446, pp. 801-805; Akazawa et al., J. Virol., 2007, vol. 81, pp. 5036-5045). Huh7 cells and derivative strains thereof are particularly preferred. The term "derivative strain" refers to a strain derived from the cell.

It has been demonstrated that efficient replication of an HCV genome often requires a mutation to occur in the nucleotide sequence of the genome (Lohmann et al., Journal of Virology, 2001, vol. 75, pp. 1437-1449). Mutation for enhancing the replication ability is called adaptive mutation.

The nucleic acid and HCV replicon RNA may comprise an adaptive mutation. Examples of adaptive mutations that enhance the replication ability of the S310A strain HCV subgenomic replicon RNA include T1286I (a mutation of threonine (T) at position 1286 to isoleucine (I)), T2188A (a mutation of threonine (T) at position 2188 to alanine (A)), R2198H (a mutation of arginine (R) at position 2198 to histidine (H)), S2210I (a mutation of serine (S) at position 2210 to isoleucine (I)), T2496I (a mutation of threonine (T) at position 2496 to isoleucine (I)), R2895G (a mutation of arginine (R) at position 2895 to glycine (G)), and R2895K (a mutation of arginine (R) at position 2895 to lysine (K)), as defined on the basis of the amino acid sequence shown in SEQ ID NO: 14 (the full-length amino acid sequence of the precursor protein of the S310A strain). HCV subgenomic replicon RNA or HCV full-genomic replicon RNA having enhanced replication ability or a nucleic acid encoding the same can be obtained by introducing these adaptive mutations alone or in combination into the nucleic acid or HCV replicon RNA such as the HCV genome of the S310A strain. A nucleotide mutation in the nucleic acid or HCV replicon RNA preferably one causing mutation T1286I, R2198H, S2210I, or R2895K in the amino acid sequence, and more preferably one causing mutation R2198H, S2210I, or R2895K in the amino acid sequence. Alternatively, an adaptive mutation described in a publication may be introduced alone or in combination with the mutation described above. Any mutation that enhances the replication ability of the HCV replicon RNA derived from the S310A strain may be introduced. The mutation T1286I occurs in the NS3 protein, the mutations T2188A, R2198H, and S2210I occur in the NS5A protein, and the mutations T2496I, R2985G, and R2985K occur in the NS5B protein.

A mutation can be introduced into the nucleic acid and HCV replicon RNA such as the genome of the isolated wild-type HCV strain of genotype 3a, by PCR or using a commercially available mutagenesis kit (e.g., KOD-Plus-Mutagenesis Kit, manufactured by Toyobo Co., Ltd.). For example, a sequence portion of interest can be amplified by performing PCR with the use of a vector comprising cloned cDNA of the wild-type HCV genomic RNA of genotype 3a as a template and forward and reverse primers designed based on the cDNA sequence and comprising mutations to be introduced. Specifically, the nucleic acid of interest can be amplified by synthesizing a plurality of different PCR products having sequences overlapping each other, mixing the PCR products, and performing PCR using the resulting mixture of the PCR products as a template, a forward primer containing the 5' terminus of the nucleic acid of interest, and a reverse primer containing the 5' terminus of the complementary strand of the nucleic acid. Each terminus of the synthesized nucleic acid is cleaved with a restriction enzyme and then ligated to a vector comprising cloned cDNA of the wild-type HCV genomic RNA cleaved with the same enzyme. Basic techniques of such procedure are also described in, for example, International Publication Nos. WO 04/104198 and WO 06/022422, Wakita et al., 2005, Nature Medicine, No. 11, pp. 791-796, and Lindenbach et al., 2005, Science, No. 309, pp. 623-626.

The nucleic acid or HCV subgenomic replicon RNA can be a nucleic acid comprising, in the following order from the 5' to 3' direction, the 5' untranslated region (5' UTR) (SEQ ID NO: 2), the NS3 protein coding sequence (SEQ ID NO: 8), the NS4A protein coding sequence (SEQ ID NO: 9), the NS4B protein coding sequence (SEQ ID NO: 10), the NS5A protein coding sequence (SEQ ID NO: 11), the NS5B protein coding sequence (SEQ ID NO: 12), and the 3' untranslated region (3' UTR) (SEQ ID NO: 13) of the full-length HCV genome of the S310A strain (SEQ ID NO: 1).

The nucleic acid or HCV subgenomic replicon RNA can be a nucleic acid comprising at least one mutation selected from the group consisting of T1286I, T2188A, R2198H, S2210I, T2496I, R2895G, and R2895K in a nucleotide sequence comprising, in the following order from the 5' to 3' direction, the 5' untranslated region (5' UTR) (SEQ ID NO: 2), the NS3 protein coding sequence (SEQ ID NO: 8), the NS4A protein coding sequence (SEQ ID NO: 9), the NS4B protein coding sequence (SEQ ID NO: 10), the NS5A protein coding sequence (SEQ ID NO: 11), the NS5B protein coding sequence (SEQ ID NO: 12), and the 3' untranslated region (3' UTR) (SEQ ID NO: 13) of the full-length HCV genome of the S310A strain (SEQ ID NO: 1). Preferably, the nucleic acid or HCV subgenomic replicon RNA can be a nucleic acid comprising, in the following order from the 5' to 3' direction, the 5' untranslated region (5' UTR), the NS3 protein coding sequence, the NS4A protein coding sequence, the NS4B protein coding sequence, the NS5A protein coding sequence, the NS5B protein coding sequence, and the 3' untranslated region (3' UTR) of the full-length HCV genome of the S310A strain and comprising the mutation T1286I, R2198H, or R2895K. More preferably, the nucleic acid or HCV subgenomic replicon RNA can be a nucleic acid comprising, in the following order from the 5' to 3' direction, the 5' untranslated region (5' UTR), the NS3 protein coding sequence, the NS4A protein coding sequence, the NS4B protein coding sequence, the NS5A protein coding sequence, the NS5B protein coding sequence, and the 3' untranslated region (3' UTR) of the full-length HCV genome of the S310A strain and comprising the mutation R2198H or R2895K.

The HCV subgenomic replicon RNA may further contain a drug resistance gene and/or a reporter gene and an IRES sequence. In such a case, it is preferred that the drug resistance gene and/or the reporter gene be inserted into downstream of the 5' UTR and the IRES sequence be inserted into a site further downstream thereof.

More preferably, the HCV subgenomic replicon RNA is a nucleic acid consisting of the nucleotide sequence shown in SEQ ID NO: 16 (the HCV subgenomic replicon RNA of the wild-type S310A strain, FIG. 1C). Also preferably, HCV subgenomic replicon RNA is an RNA comprising a mutation selected from the group consisting of T1286I, T2188A, R2198H, S2210I, T2496I, R2895G, and R2895K introduced, more preferably mutation T1286I, R2198H, or R2895K, in the nucleotide sequence shown in SEQ ID NO: 16. Examples thereof include nucleic acids comprising the nucleotide sequences shown in SEQ ID NO: 17 (the sequence comprising the mutation T1286I in an HCV subgenomic replicon RNA of the wild-type S310A strain), SEQ ID NO: 18 (the sequence comprising the mutation R2198H in an HCV subgenomic replicon RNA of the wild-type S310A strain), and SEQ ID NO: 19 (the sequence comprising the mutation R2895K in an HCV subgenomic replicon RNA of the wild-type S310A strain).

The nucleic acid constituting the HCV subgenomic replicon RNA may be a nucleic acid that further comprises another mutation of a nucleotide other than the nucleotide corresponding to the above-mentioned mutation, but has the replication ability equivalent to that of the nucleic acid containing the mutation mentioned above. Examples of such other mutation include substitution of one or more nucleotides, and preferably the nucleic acid having such other mutation comprises a nucleotide sequence having 90% or more, preferably 95% or more, and further preferably 97% or more identity with the nucleotide sequence of the original nucleic acid. In addition, examples of such other mutation include deletion and addition of one or more nucleotides. In that case, preferably the nucleic acid having such other mutation comprises a nucleotide sequence having 90% or more, preferably 95% or more, and further preferably 97% or more identity with the nucleotide sequence of the original nucleic acid. When a mutation is a deletion or addition occurring within a protein-coding sequence, preferably, a reading frame to be translated into an amino acid sequence of a protein is not shifted. Further examples of such other mutation include deletion, substitution, and addition of one or a plurality of nucleotides within the 5' untranslated region or 3' untranslated region of the HCV genome. Preferably, the nucleic acid having such other mutation comprises a nucleotide sequence having 90% or more, preferably 95% or more, and further preferably 97% or more identity with the nucleotide sequence of the original nucleic acid. Furthermore, examples of such other mutation include deletion, substitution, and addition of one or a plurality of nucleotides within the nucleotide sequences encoding the HCV proteins in the HCV genome (viral protein coding region). Preferably, the nucleic acids having such other mutation have 90% or more, preferably 95% or more, and further preferably 97% or more identity to the nucleotide sequence of the original nucleic acid. When a mutation is a deletion or addition, preferably, a reading frame to be translated into an amino acid sequence of the HCV protein is not shifted.

In the description, an amino acid or an amino acid residue is shown using a single character code or a three character code that is generally used in the biology field (Sambrook et al., Molecular Cloning: A Laboratory Manual, Second Edition, 1989), and an amino acid after post-translational modification such as hydration, glycosylation, and sulfation is also included therein.

In the description, an amino acid at a particular position of an amino acid sequence shown in a SEQ ID NO: may be identified by the following expression: "(amino acid) at position 'Y' as defined on the basis of the amino acid sequence shown in SEQ ID NO: 'X'." For example, the phrase "(amino acid) at position 'Y' as defined on the basis of the amino acid sequence of the precursor protein of the S310A strain shown in SEQ ID NO: 14" means that the amino acid of is positioned at the "Y"th position in the amino acid sequence of the precursor protein of the HCV S310A strain shown in SEQ ID NO: 14 when the first amino acid (methionine) at its N-terminus is defined as the first position. When the expression "(amino acid) at position 'Y' as defined on the basis of the amino acid sequence shown in SEQ ID NO: 'X'" is used, the amino acid identified by the expression may or may not be the position "Y" in a mutant (e.g., a truncated sequence) of the sequence shown in SEQ ID NO: "X" as long as it is aligned with the corresponding amino acid at position "Y" of SEQ ID NO: "X." Specifically, for example, the expression "a precursor protein consisting of the amino acid sequence of the NS3 protein, the NS4A protein, the NS4B protein, the NS5A protein, and the NS5B protein of the S310A strain and having substitution of threonine at position 2496 with isoleucine as defined on the basis of the amino acid sequence of the precursor protein of the S310A strain shown in SEQ ID NO: 14," means that threonine, which is located at position 2496 in SEQ ID NO: 14 but is not located at position 2496 in a truncated sequence as counted from the N terminus because of truncation of the N-terminus from the amino acid sequence shown in SEQ ID NO: 14, is substituted with isoleucine in the truncated protein.

In the description, an expression such as R2895K indicates substitution of an amino acid at a particular position. However, such expression may indicate a nucleotide mutation causing such amino acid substitution depending on the context. When a nucleotide mutation is occurred in a nucleic acid and thereby arginine (R) at position 2895 in an amino acid sequence encoded by the original nucleic acid is substituted with lysine (K), for example, such nucleotide mutation is may be also referred to as substitution (or mutation) R2895K. A nucleic acid encoding an amino acid sequence comprising such mutation may be referred to as a nucleic acid comprising substitution (or mutation) R2895K or a nucleic acid into which substitution (or mutation) R2895K had been introduced. Alternatively, such mutation may be referred to as nucleotide mutation causing the substitution (or mutation) R2895K in the amino acid sequence or mutation causing substitution (or mutation) R2895K in the amino acid sequence. For example, HCV replicon RNA into which substitution (or mutation) R2895K had been introduced may be referred to as R2895K mutant HCV replicon RNA. When a plurality of mutations such as amino acid substitutions of T2496I and R2895K, are present simultaneously, such condition may be expressed as "comprising substitutions (or mutations) T2496I/R2895K." The term "amino acid substitution" may be expressed as "amino acid mutation."

A nucleotide mutation causing a particular amino acid substitution can be determined based on the list of genetic codes well known in the art. For example, a mutation causing substitution R2895K is a mutation of the codon encoding arginine; i.e., "CGU," "CGC," "CGA," "CGG," "AGA," or "AGG" to the codon encoding lysine; i.e., "AAA" or "AAG." A nucleotide mutation causing the substitution R2895K in the full-length genomic sequence of the S310A strain (SEQ ID NO: 1) is a mutation of the codon "AGA" (corresponding to position 9023 to 9025 in SEQ ID NO: 1) to the codon "AAG" or "AAA." This is a mutation of a nucleotide sequence of nucleotides 9024 to 9025 in SEQ ID NO: 1,5'-GA-3', to 5'-AG-3' or a change of nucleotide 9024 (G) into adenine (A).

Similarly, amino acid substitution of arginine at position 2198 as defined on the basis of the amino acid sequence of the precursor protein of the S310A strain shown in SEQ ID NO: 14 with histidine is expressed as R2198H. A nucleotide mutation causing the substitution R2198H in the full-length genomic sequence of the S310A strain (SEQ ID NO: 1) is a mutation of the codon encoding arginine "CGU" (positions 6932 to 6934 in SEQ ID NO: 1) to the codon encoding histidine "CAU" or "CAC."

Similarly, amino acid substitution of threonine at position 1286 as defined on the basis of the amino acid sequence of the precursor protein of the S310A strain shown in SEQ ID NO: 14 with isoleucine is expressed as T1286I. A nucleotide mutation causing the substitution T1286I in the full-length genomic sequence of the S310A strain (SEQ ID NO: 1) is a mutation of the codon encoding threonine "ACU" (positions 4196 to 4198 in SEQ ID NO: 1) to the codon encoding isoleucine "AUU," "AUC," or "AUA."

In the description, the nucleotide position of a nucleotide sequence shown in a SEQ ID NO: is based on the nucleotide number when the nucleotide at the first position of the 5' terminus in a nucleotide sequence shown by the SEQ ID NO is defined as the first nucleotide.

The HCV subgenomic replicon RNA can be obtained by transcription (or expression) from an expression vector. Basic techniques relating to construction of an HCV subgenomic replicon RNA expression vector are described in Lohmann et al., Science, 1999, vol. 285, pp. 110-113 and Kato et al., Gastroenterology, 2003, vol. 125, pp. 1808-1817. Specifically, for example, an HCV subgenomic replicon RNA expression vector can be constructed by inserting cDNA composed of the 5' untranslated region (5' UTR), 57 nucleotides of the region encoding the Core protein, a foreign gene (a drug resistance gene or a reporter gene), an EMCV IRES sequence, the nucleotide sequences encoding the NS3 protein, the NS4A protein, the NS4B protein, the NS5A protein and the NS5B protein, and the 3' untranslated region (3' UTR) ligated in this order from the 5' to 3' direction, into downstream of the T7 promoter. When nucleotide sequences are to be ligated to each other, an additional sequence such as a restriction enzyme site, may be inserted into the site of ligation.

The HCV subgenomic replicon RNA can be synthesized from the constructed expression vector for an HCV subgenomic replicon RNA using a polymerase. For example, a nucleic acid prepared via cloning of HCV cDNA under the control of a T7 promoter is used as a template to prepare RNA in vitro by synthesis using the MEGAscript T7 kit (Ambion, Inc.). The HCV subgenomic replicon RNA transcribed from this vector autonomously replicates in the cells transfected with the RNA. This disclosure encompasses the cells transfected with the HCV subgenomic replicon RNA.

In addition to the T7 promoter, any promoter such as an SP6 promoter, a T3 promoter, or a T5 promoter, can be used, with the T7 promoter being preferred.

Examples of vectors that can be used include pUC19 (Takara Bio Inc.), pBR322 (Takara Bio Inc.), pGEM-T, pGEM-T Easy, and pGEM-3Z (Promega Corp.), pSP72 (Promega Corp.), pCR11 (Invitrogen Corp.), and pT7Blue (Novagen, Inc.).

The cells that are transfected with the HCV subgenomic replicon RNA may be any cells that allow replication of the HCV subgenomic replicon RNA such as the HCV-sensitive cells. Huh7 cells and derivative strains thereof are particularly preferred.

HCV subgenomic replicon RNA can be introduced into cells in accordance with any known techniques. Examples of such techniques include calcium phosphate coprecipitation, a DEAE-dextran method, lipofection, microinjection, and electroporation. Lipofection and electroporation are preferred, and electroporation is more preferred.

The replication ability of the introduced HCV subgenomic replicon RNA can be evaluated by measuring functions of a foreign gene ligated to HCV subgenomic replicon RNA; that is, the functions developed along with expression of such gene. When a foreign gene is a drug resistance gene, the number of cells or colonies of cells propagating in a selection medium containing a drug may be counted to evaluate the replication ability of the HCV subgenomic replicon RNA. In such a case, a larger number of cells or colonies of cells indicates higher replication ability. When a foreign gene is an enzyme gene, the enzyme activity thereof may be assayed to evaluate the replication ability of HCV subgenomic replicon RNA. In such a case, higher enzyme activity indicates higher replication ability. Alternatively, the replication ability of HCV subgenomic RNA can be directly evaluated by quantifying the amount of RNA replicated by quantitative PCR.

The HCV full-genomic replicon RNA encompasses HCV full-length genomic RNA, and it can be prepared in the same manner as in the case of the HCV subgenomic replicon RNA described above. The HCV full-genomic replicon RNA may be prepared by introducing an adaptive mutation that enhances the replication ability of the HCV subgenomic replicon RNA into HCV full-length genomic RNA of, for example, the wild-type S310A strain of genotype 3a, as in the case of the HCV subgenomic replicon RNA described above. The HCV genome comprising the adaptive mutation introduced into the HCV full-length genomic RNA of the wild-type S310A strain is referred to as an S310A mutant or a mutated S310A strain.

A mutation may be introduced into the HCV full-length genome of the wild-type S310A strain by the above-mentioned method, or it may be introduced by ligating a structural gene portion of the wild-type HCV genome to a subgenomic replicon mutant.

The HCV full-genomic replicon RNA may be a full-length genomic RNA of the S310A strain (SEQ ID NO: 1), or a replicon RNA comprising the 5' untranslated region (5' UTR) (SEQ ID NO: 2), the Core protein coding sequence (SEQ ID NO: 3), the E1 protein coding sequence (SEQ ID NO: 4), the E2 protein coding sequence (SEQ ID NO: 5), the p7 protein coding sequence (SEQ ID NO: 6), the NS2 protein coding sequence (SEQ ID NO: 7), the NS3 protein coding sequence (SEQ ID NO: 8), the NS4A protein coding sequence (SEQ ID NO: 9), the NS4B protein coding sequence (SEQ ID NO: 10), the NS5A protein coding sequence (SEQ ID NO: 11), the NS5B protein coding sequence (SEQ ID NO: 12), and the 3' untranslated region (3' UTR) (SEQ ID NO: 13) in this order from the 5' to 3' direction.

The HCV full-genomic replicon RNA may be a nucleic acid comprising the adaptive mutation introduced into full-length genomic RNA of the 5310 strain. Preferably, such HCV full-genomic replicon RNA comprises the mutation T1286I, T2188A, R2198H, S2210I, T2496I, R2895G, or R2895K in full-length genomic RNA of the S310A strain (SEQ ID NO: 1), that is, in a nucleotide sequence comprising the 5' untranslated region (5' UTR) (SEQ ID NO: 2), the Core protein coding sequence (SEQ ID NO: 3), the E1 protein coding sequence (SEQ ID NO: 4), the E2 protein coding sequence (SEQ ID NO: 5), the p7 protein coding sequence (SEQ ID NO: 6), the NS2 protein coding sequence (SEQ ID NO: 7), the NS3 protein coding sequence (SEQ ID NO: 8), the NS4A protein coding sequence (SEQ ID NO: 9), the NS4B protein coding sequence (SEQ ID NO: 10), the NS5A protein coding sequence (SEQ ID NO: 11), the NS5B protein coding sequence (SEQ ID NO: 12), and the 3' untranslated region (3' UTR) (SEQ ID NO: 13), in this order from the 5' to 3' direction. Preferably, the nucleic acid comprises the mutation R2198H, S2210I, or R2895K in full-length genomic RNA of the S310A strain (SEQ ID NO: 1), that is, a nucleotide sequence comprising the 5' untranslated region (5' UTR), the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, the NS5A protein coding sequence, the NS5B protein coding sequence, and the 3' untranslated region (3' UTR) in this order from the 5' to 3' direction.

The HCV full-genomic replicon RNA may further contain a drug resistance gene and/or a reporter gene and an IRES sequence. In such a case, it is preferred that the drug resistance gene and/or the reporter gene be inserted into downstream of the 5' untranslated region (5' UTR) and the IRES sequence be inserted into further downstream thereof.

More preferably, the HCV full-genomic replicon RNA mentioned above comprises a nucleotide sequence shown in SEQ ID NO: 49 (a full-genomic nucleotide sequence containing the mutation S2210I), SEQ ID NO: 50 (a full-genomic nucleotide sequence containing the mutation R2198H), or SEQ ID NO: 51 (a full-genomic nucleotide sequence containing the mutation R2895K). Specifically, such RNA is a nucleic acid consisting of the nucleotide sequence shown in SEQ ID NO: 49 having a mutation causing substitution of serine at position 2210 with isoleucine, a nucleic acid consisting of the nucleotide sequence shown in SEQ ID NO: 50 having a mutation causing substitution of arginine at position 2198 with histidine, or a nucleic acid consisting of the nucleotide sequence shown in SEQ ID NO: 51 having a mutation causing substitution of arginine at position 2895 with lysine.

The nucleic acid constituting the HCV full-genomic replicon RNA may be a nucleic acid that further comprises another nucleotide mutation of a nucleotide other than the nucleotide corresponding to the above-mentioned mutation, but has the replication ability equivalent to that of the nucleic acid containing the mutation mentioned above. Such other mutation may be deletion, substitution, or addition of one or more nucleotides, and preferably the nucleic acid having such other mutation comprises a nucleotide sequence having 90% or more, preferably 95% or more, and further preferably 97% or more identity with the nucleotide sequence of the original nucleic acid. In addition, such other mutation may be deletion, substitution, or addition of one or a plurality of nucleotides in the 5' untranslated region or the 3' untranslated region of the HCV genome. Preferably, the nucleic acid having such other mutation comprises a nucleotide sequence having 90% or more, preferably 95% or more, and further preferably 97% or more identity with the nucleotide sequence of the original nucleic acid. Further, such other mutation may be deletion, substitution, or addition of one or a plurality of nucleotides in the nucleotide sequence encoding the HCV protein of the HCV genome (i.e., a viral protein coding region). Preferably, the nucleic acid having such other mutation comprises a nucleotide sequence having 90% or more, preferably 95% or more, and further preferably 97% or more identity with the nucleotide sequence of the original nucleic acid. When a mutation is deletion or addition, preferably, a reading frame to be translated into the amino acid sequence of the HCV protein is not shifted.

The expression vector used in production of the HCV full-genomic replicon RNA can be produced by the technique described in International Publication No. WO 05/080575. Specifically, a DNA clone is produced by reconstructing cDNA corresponding to HCV full-length genomic RNA and inserting the same into downstream of a promoter by a conventional technique. The promoter is preferably contained in a plasmid clone. Examples of promoters that can be used include T7 promoters, SP6 promoters, T3 promoters, and T5 promoters, with T7 promoters being preferred. Examples of vectors that can be used include pUC19 (Takara Bio Inc.), pBR322 (Takara Bio Inc.), pGEM-T, pGEM-T Easy, and pGEM-3Z (Promega Corp.), pSP72 (Promega Corp.), pCR11 (Invitrogen Corp.), and pT7Blue (Novagen, Inc.).

The HCV full-genomic replicon RNA can be synthesized from an expression vector with a polymerase using the produced DNA clone as a template. When producing RNA in vitro with the use of a nucleic acid comprising cloned HCV cDNA under the control of a T7 promoter as a template, RNA can be synthesized using, for example, the MEGAscript T7 kit (Ambion, Inc.). RNA synthesis can be initiated at 5' UTR by a conventional technique. When the DNA clone is a plasmid clone, RNA can also be synthesized using a DNA fragment cleaved from the plasmid clone with a restriction enzyme as a template. It is preferred that the 3' terminus of the synthesized RNA coincide with the terminus of the 3' UTR of the HCV genomic RNA and that any other sequence be not added or deleted.

The HCV full-genomic replicon RNA or the nucleic acid thereof autonomously replicates upon introduction thereof into cultured cells (typically HCV-sensitive cells), and HCV particles (hepatitis C virus) are produced. When the cultured cells (typically HCV-sensitive cells) are infected with the HCV particles containing the HCV full-genomic replicon RNA or the nucleic acid encoding it as the viral genome, HCV particles are produced. That is, cultured cells transfected with the HCV full-genomic replicon RNA or the nucleic acid encoding it or cultured cells infected with the HCV particles containing the HCV full-genomic replicon RNA or the nucleic acid encoding it as the viral genome can be applied to mass production of HCV particles.

More specifically, the HCV particles produced from the cultured cells (typically HCV-sensitive cells) transfected with the HCV full-genomic replicon RNA or the nucleic acid thereof or the HCV particles produced from the cultured cells (typically HCV-sensitive cells) infected with the HCV particles containing the HCV full-genomic replicon RNA or the nucleic acid thereof as the virus genome further infect different cultured cells (typically HCV-sensitive cells), and HCV genomic RNA is replicated therein and packaged. This enables repeated production of HCV particles. Cultured cells can be infected with HCV particles by, for example, adding a culture supernatant of the cells transfected with HCV full-genomic replicon RNA or the nucleic acid encoding it to HCV-sensitive cells (e.g., Huh7 cells).

The cells to be transfected with the HCV full-genomic replicon RNA or the nucleic acid thereof or the cells to be infected with the hepatitis C virus (HCV) particles are preferably cultured cells, which allow replication of the HCV replicon RNA or formation of HCV particles. Examples of such cells include the HCV-sensitive cells described above, and the use of Huh7 cells and derivative strains thereof is particularly preferred.

HCV full-genomic replicon RNA can be introduced into cells by any known methods. Examples thereof include calcium phosphate coprecipitation, a DEAE-dextran method, lipofection, microinjection, and electroporation, with lipofection and electroporation being preferred, and electroporation being more preferred.

The replication ability of the introduced HCV full-genomic replicon RNA can be evaluated by measuring functions of a foreign gene ligated to HCV full-genomic replicon RNA; that is, the functions developed along with expression of such gene. When a foreign gene is a drug resistance gene, the number of cells or colonies of cells propagating in a selection medium containing a drug may be counted to evaluate the replication ability of the HCV full-genomic replicon RNA. In such a case, a larger number of cells or colonies of cells indicates higher replication ability. When a foreign gene is an enzyme gene, the enzyme activity thereof may be assayed to evaluate the replication ability of HCV full-genomic replicon RNA. In such a case, higher enzyme activity indicates higher replication ability. Alternatively, the replication ability of HCV full-genomic RNA can be directly evaluated by quantifying the amount of RNA replicated by quantitative PCR.

This disclosure encompasses the virus genome comprising the nucleic acid as described above and hepatitis C virus (hepatitis C virus) particles containing the nucleic acid described above as the virus genome.

The HCV full-genomic replicon RNA or the nucleic acid thereof has HCV particle-production ability in cultured cells. Whether or not HCV full-genomic replicon RNA or the nucleic acid thereof has HCV particle-production ability can be evaluated by introducing the RNA into cells and assaying the presence of HCV particles in the culture supernatant of the cells.

The HCV particle-production ability of cells can be detected by using an antibody against a protein constituting the HCV particles released into the culture supernatant, e.g., the Core protein, the E1 protein, or the E2 protein. The presence of HCV particles can also be indirectly detected by amplifying the HCV full-genomic replicon RNA contained in HCV particles in the culture supernatant through RT-PCR using a specific primer.

Whether or not the produced HCV particles have infectious ability can be evaluated by treating HCV-sensitive cells (e.g., Huh7 cells) with the culture supernatant of cells transfected with HCV full-genomic replicon RNA or the nucleic acid thereof, immunostaining the cells with an anti-Core antibody, for example, 48 hours later, and counting the number of infected cells. Alternatively, an extract of cells may be subjected to SDS-polyacrylamide gel electrophoresis, and the Core protein may be detected via Western blotting.

We also provide a chimeric nucleic acid derived from the genomes of two or more hepatitis C virus strains, including an HCV strain of genotype 3a (e.g., the S310A strain). Specifically, we provide, for example, a chimeric form of HCV genome (chimeric HCV genome), chimeric form of HCV subgenomic replicon RNA (chimeric HCV subgenomic replicon RNA), chimeric form of HCV full-genomic replicon RNA (chimeric HCV full-genomic replicon RNA), and chimeric form of HCV particles (chimeric HCV particles), comprising the genomic sequence derived from the S310A strain of genotype 3a and an HCV genome other than the HCV genome of the S310A strain (SEQ ID NO: 1) such as a genomic sequence of an existing HCV strain of a various genotype (e.g., 1a, 1b, 2a, 2b, 3a, or 3b) or of an HCV of a genotype other than 3a. The terms "chimeric HCV genome" and "chimeric HCV full-genomic replicon RNA" refer to the HCV genome and the HCV full-genomic replicon RNA comprising HCV genomic sequences of two or more different strains, respectively, and HCV particles produced from the chimeric HCV genome or chimeric HCV full-genomic replicon RNA are referred to as "chimeric HCV particles." Such chimeric HCV genome is within the scope of our nucleic acid.

The chimeric HCV genome may comprise non-structural genes of the S310A strain or an S310A mutant (adaptive mutation-introduced S310A strain) and structural genes of a different HCV strain (i.e., a strain other than the S310A strain or S310A mutant). The chimeric HCV genome may comprise a mutation such as an adaptive mutation or it may be prepared with the use of an S310A mutant. Specifically, an S310A mutant used for production of such chimeric HCV genome comprises the mutation T1286I, T2188A, R2198H, S2210I, T2496I, R2895G, or R2895K introduced, preferably the mutation R2198H, S2210I, or R2895K, into the S310A strain. More specifically, an S310A mutant may be a nucleic acid comprising the nucleotide sequence shown in SEQ ID NO: 49 (a full-genomic nucleotide sequence comprising the mutation S2210I), SEQ ID NO: 50 (a full-genomic nucleotide sequence comprising the mutation R2198H), or SEQ ID NO: 51 (a full-genomic nucleotide sequence comprising the mutation R2895K).

For example, the chimeric HCV genome may comprise, in addition to the nucleotide sequence encoding the Core protein, the nucleotide sequence encoding the E1 protein, the nucleotide sequence encoding the E2 protein, and the nucleotide sequence encoding the p7 protein of an HCV strain; the nucleotide sequence encoding the NS3 protein consisting of nucleotides 3437 to 5329, the nucleotide sequence encoding the NS4A protein consisting of nucleotides 5330 to 5491, the nucleotide sequence encoding the NS4B protein consisting of nucleotides 5492 to 6274, the nucleotide sequence encoding the NS5A protein consisting of nucleotides 6275 to 7630, and the nucleotide sequence encoding the NS5B protein consisting of nucleotides 7631 to 9406 of SEQ ID NO: 1 shown in the Sequence Listing in this order from the 5' to 3' direction.

The chimeric HCV genome may be a nucleic acid comprising:
the nucleotide sequence encoding the Core protein, the nucleotide sequence encoding the E1 protein, the nucleotide sequence encoding the E2 protein, and the nucleotide sequence encoding the p7 protein of the genome of the HCV strain other than the S310A strain (e.g., the genome of an existing HCV strain or that of HCV of a genotype other than 3a);
the nucleotide sequence encoding the NS2 protein consisting of nucleotides 2786 to 3436 of SEQ ID NO: 1 shown in the Sequence Listing, the nucleotide sequence encoding the NS2 protein of a genome of an HCV strain other than the S310A strain (e.g., the genome of an existing HCV strain or that of HCV of a genotype other than 3a), or a nucleotide sequence encoding the chimeric NS2 protein comprising a part of the nucleotide sequence encoding the NS2 protein consisting of nucleotides 2786 to 3436 of SEQ ID NO: 1 shown in the Sequence Listing ligated to a part of the nucleotide sequence encoding the NS2 protein of a genome of an HCV strain other than the S310A strain (e.g., the genome of an existing HCV strain or that of HCV of a genotype other than 3a); and the nucleotide sequence encoding the NS3 protein consisting of nucleotides 3437 to 5329, the nucleotide sequence encoding the NS4A protein consisting of nucleotides 5330 to 5491, the nucleotide sequence encoding the NS4B protein consisting of nucleotides 5492 to 6274, the nucleotide sequence encoding the NS5A protein consisting of nucleotides 6275 to 7630, and the nucleotide sequence encoding the NS5B protein consisting of nucleotides 7631 to 9406 of SEQ ID NO: 1 shown in the Sequence Listing, wherein the nucleic acid comprises the nucleotide sequences encoding the Core protein, the E1 protein, the E2 protein, the p7 protein, the NS2 protein, the NS3 protein, the NS4A protein, the NS4B protein, the NS5A protein and the NS5B protein in this order from the 5' to 3' direction.

The chimeric HCV genome may comprise, at its 5' terminus, a 5' untranslated region of the HCV genome of genotype 3a, for example, a 5' untranslated region comprising the nucleotide sequence of nucleotides 1 to 340 of SEQ ID NO: 1. Alternatively, the chimeric HCV genome may comprise, at its 5' terminus, a 5' untranslated region of a HCV genome other than the HCV genome of the S310A strain (SEQ ID NO: 1) such as the genome of an existing HCV strain of a various genotype or an HCV genome of a genotype other than 3a.

Figure 16:
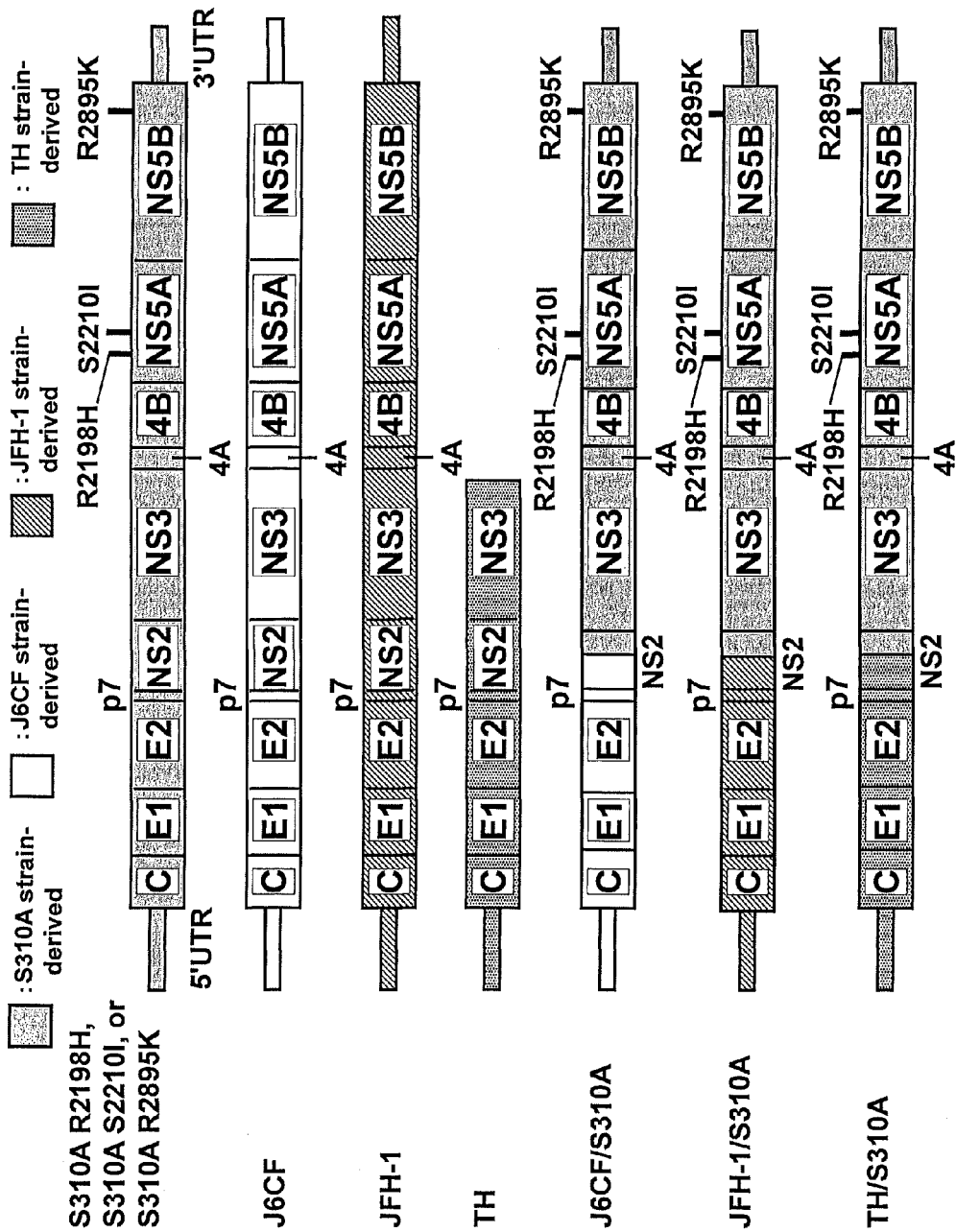
FIG. 16 shows the structures of the HCV genomes of the mutated S310A strain (adaptive mutation-introduced S310A strain), the J6CF strain, the JFH-1 strain, and the TH strain; and the structures of the chimeric HCV genomes comprising non-structural genes of a mutated S310A strain and structural genes derived from the J6CF strain, the JFH-1 strain, or the TH strain. The HCV full-genomic replicon RNAs of the mutated S310A strains (full-length genomic RNA mutants): S310A R2198H, S310A S2210I, and S310A R2895K, comprise mutations R2198H, S2210I, and R2895, respectively. The positions of these mutations are collectively shown on the HCV genome structure indicated on the top, but each RNA comprises a single mutation.

An example of such chimeric HCV genome is shown in FIG. 16. For example, a chimeric HCV genome comprises a 5' untranslated region, structural genes (Core to p7) and an N-terminal fragment of the NS2 gene (e.g., a sequence encoding an amino acid sequence of amino acids 1 to 16 from the N-terminus of the NS2 protein) of the J6CF strain, the JFH-1 strain, or the TH strain; a C-terminal sequence following the fragment of the NS2 gene (e.g., a sequence encoding an amino acid sequence of amino acids 17 to 217 from the N-terminus of the NS2 protein), non-structural genes other than the NS2 gene (NS3 to NS5B), and a 3' untranslated region of the S310A strain. These chimeric HCV genomes may comprise the mutation T1286I, T2188A, R2198H, S2210I, T2496I, R2895G, or R2895K.

We also provide chimeric full-genomic replicon RNA comprising such chimeric HCV genome.

The chimeric HCV genome can be produced by, for example, recombining structural genes in the genome of a mutated S310A strain, i.e., the nucleotide sequences encoding the Core protein, the E1 protein, the E2 protein and the p7 protein, with the structural genes of another HCV strain. Basic techniques therefor are described in, for example, Wakita et al., Nature Medicine, 2005, vol. 11, pp. 791-796, Lindenbach et al., Science, 2005, vol. 309, pp. 623-626, and Pietschmann et al., Proc. Natl. Acad. Sci. U.S.A., 2007, vol. 103, pp. 7408-7413.

According to the phylogenetic analysis using nucleotide sequences of HCV strains, HCV is classified into six types of genotypes 1 to 6, each of which is further classified into several subtypes. Specific examples of known HCV strains are as follows: the H77 strain (GenBank Accession No. AF011751) for an HCV strain of genotype 1a; the J1 strain (GenBank Accession No. D89815), the Con1 strain (GenBank Accession No. AJ238799, also referred to as Con-1 strain or con1 strain), the TH strain (Wakita et al., J. Biol. Chem., 1994, vol. 269, pp. 14205-14210; JP Patent Publication (Kokai) No. 2004-179 A), the HCV-N strain (GenBank Accession No. AF139594), and the HCV-O strain (GenBank Accession No. AB191333) for an HCV strain of genotype 1b; the JFH-1 strain (GenBank Accession No. AB047639, also referred to as the JFH1 strain), the J6CF strain (GenBank Accession No. AF177036), the JCH-1 strain (GenBank Accession No. AB047640), the JCH-2 (GenBank Accession No. AB047641), the JCH-3 strain (GenBank Accession No. AB047642), the JCH-4 (GenBank Accession No. AB047643), and the JCH-5 strain (GenBank Accession No. AB047644), and the JCH-6 strain (GenBank Accession No. AB047645) for an HCV strain of genotype 2a; the HC-J8 strain (GenBank Accession No. D01221) for an HCV strain of genotype 2b; the NZL1 strain (GenBank Accession No. D17763), the K3a/650 strain (GenBank Accession No. D28917), and the S52 strain (GenBank Accession No. GU814263) for HCV strains of genotype 3a; the Tr-Kj strain (GenBank Accession No. D49374) for an HCV strain of genotype 3b; and the ED43 strain (GenBank Accession No. Y11604) for an HCV strain of genotype 4a. A list of GenBank Accession numbers of other strains has also been reported (Tokita et al., Journal of General Virology, 1998, vol. 79, pp. 1847-1857; Cristina, J. & Colina, R., Virology Journal, 2006, vol. 3, pp. 1-8).

The above-mentioned chimeric HCV genome may be a nucleic acid comprising an HCV-derived chimeric gene comprising the nucleotide sequence encoding the Core protein, the nucleotide sequence encoding the E1 protein, the nucleotide sequence encoding the E2 protein, and the nucleotide sequence encoding the p7 protein derived from an HCV strain other than an S310A mutant, the nucleotide sequence encoding the NS2 protein derived from an S310A mutant or an HCV strain other than the S310A mutant, and the nucleotide sequence encoding the NS3 protein, the nucleotide sequence encoding the NS4A protein, the nucleotide sequence encoding the NS4B protein, the nucleotide sequence encoding the NS5A protein, and the nucleotide sequence encoding the NS5B protein derived from the S310A mutant, in this order from the 5' to 3' direction. The NS2 protein may be a chimeric form NS2 protein (chimeric NS2 protein) of the NS2 protein of the S310A mutant and the NS2 protein derived from an HCV strain other than the S310A strain and a mutant thereof. Preferably, an HCV strain other than the HCV S310A strain and a mutant thereof is the existing HCV strain described above.

The term "chimeric NS2 protein" used herein refers to a NS2 protein comprising a part of the amino acid sequence of the NS2 protein of an S310A mutant ligated to a part of the amino acid sequence of the NS2 protein derived from an HCV strain other than the S310A strain and a mutant thereof, and, as a whole, consisting of the full-length amino acid sequence of NS2 protein. In the nucleic acid of the chimeric HCV genome, the NS2 protein may be derived from an S310A mutant, or a chimeric NS2 protein consisting of a part of the NS2 protein derived from an HCV strain other than the S310A mutant and the remaining portion of the NS2 protein derived from the S310A mutant. In that case, the chimeric NS2 protein has functions equivalent to those of a non-chimeric NS2 protein. For example, when the part of the NS2 protein derived from the HCV strain other than the S310A mutant consists of a nucleotide sequence encoding the N-terminal amino acid to the amino acid at position 16 of the NS2 protein, a remaining portion of the NS2 protein derived from the S310A strain or the mutant thereof consists of a nucleotide sequence encoding from the amino acid at position 17 counted from the N terminus to the C terminus.

It is preferred that the nucleic acid of the chimeric HCV genome further comprise 5' UTR on the 5' side of the nucleotide sequence encoding the Core protein and 3' UTR on the 3' side of the region encoding the NS5B protein. 5' UTR and/or 3' UTR may be sequence(s) derived from any HCV strain, and preferably, 5' UTR derived from an HCV strain other than the S310A mutant and 3' UTR derived from an S310A mutant.

In the chimeric HCV genome, an HCV strain other than the S310A mutant, i.e., a known HCV strain, is preferably a strain belonging to genotype 1a, 1b, or 2a. An example of the strain of genotype 1a is the H77 strain. Examples of the strain belonging to genotype 1b include the TH strain, the Con1 strain, the J1 strain, and derivative strains thereof. Examples of the strain belonging to genotype 2a include the JFH-1 strain and the J6CF strain. Preferred strains are the JFH-1 strain, the J6CF strain, and the TH strain. Particularly preferred is the JFH-1 strain. The genomic nucleotide sequence information of HCV strains other than the S310A strain or a mutant thereof is available from the documents mentioned above or from the GenBank.

The nucleic acid of the chimeric HCV genome is, for example, a chimeric nucleic acid derived from the J6CF strain and the S310A strain, which comprises at least one mutation selected from the group consisting of T1286I, S2210I, R2198H, and R2895K. The nucleic acid of the chimeric HCV genome is, for example, a chimeric nucleic acid derived from the JFH-1 strain and the S310A strain, which comprises at least one mutation selected from the group consisting of T1286I, S2210I, R2198H, and R2895K. The nucleic acid of the chimeric HCV genome is, for example, a chimeric nucleic acid derived from the TH strain and the S310A strain, which comprises at least one mutation selected from the group consisting of T1286I, S2210I, R2198H, and R2895K.

FIG. 16 shows the structures of the HCV genomes of the S310A mutant (the S310A strain into which the adaptive mutation of R2198H, S2210I, or R2895K has been introduced), the J6CF strain, the JFH-1 strain, and the TH strain; and the structures of the chimeric HCV genomes comprising the non-structural genes of the S310A mutant (the S310A strain into which the adaptive mutation of R2198H, S2210I, or R2895K has been introduced), and the structural genes of the J6CF strain, the JFH-1 strain, or the TH strain, which are J6CF/S310A, JFH-1/S310A, and TH/S310A respectively, as the examples of chimeric nucleic acids. In the chimeric nucleic acids shown in FIG. 16 (i.e., J6CF/S310A, JFH-1/S310A, and TH/S310A), the 5' untranslated region is derived from the same HCV strain (i.e., the J6CF strain, the JFH-1 strain, or the TH strain) as the strain of the structural region, the 3' untranslated region is derived from the same S310A strain as the strain of the non-structural region, and the NS2 coding sequence is a chimeric sequence of an NS2 sequence derived from the same HCV strain (i.e., the J6CF strain, the JFH-1 strain, or the TH strain) as the strain of the structural region and an NS2 sequence derived from the S310A strain. Such chimeric nucleic acids comprise the adaptive mutation R2198H, S2210I, or R2895K.

We provide an HCV viral genome containing the above-mentioned nucleic acid of the chimeric HCV genome, a hepatitis C virus containing the above-mentioned nucleic acid of the chimeric HCV genome as the viral genome, an HCV full-genomic replicon RNA, an expression vector, or chimeric HCV particles. The characteristics of the chimeric HCV particles are that the chimeric HCV particles can be produced in a cell culture system with high efficiency and that they have high infectivity.

The chimeric HCV gene can be produced by performing PCR to amplify the target regions of HCV genes using vectors comprising cloned cDNAs of the respective HCV genomic RNAs as templates and synthetic DNAs as primers and ligating the amplified regions to each other.

Furthermore, an expression vector for synthesizing an HCV genomic RNA can be produced by ligating cDNA of the chimeric HCV gene to an appropriate restriction enzyme site located downstream of a promoter such as a T7 promoter. Upon introduction of RNA transcribed from this expression vector into HCV-sensitive cells (e.g., Huh7 cells), virus replication and packaging take place, and infectious HCV particles can then be produced.

The replication ability in cells and the HCV particle-production ability of the HCV full-genomic replicon RNA containing the chimeric HCV gene and the infectivity of the produced HCV particles can be verified by the methods described above.

We also provide a method of screening for an anti-hepatitis C virus substance using the HCV subgenomic replicon RNA, HCV full-genomic replicon RNA, or hepatitis C virus particles.

The cultured cells transfected with the HCV subgenomic replicon RNA can be used in screening for a compound that inhibits replication of the HCV subgenomic replicon RNA. That is, it is possible to screen for an anti-HCV agent by culturing the cultured cells transfected with the HCV subgenomic replicon RNA in the presence of a test substance and detecting replicon RNA in the resulting culture. The "culture" contains a culture supernatant and a cell lysate. When the replicon RNA is not present in the culture or the amount thereof is less than that in the absence of the test substance, the test substance can be determined to be capable of inhibiting the replication of the HCV subgenomic replicon RNA.

For example, HCV subgenomic replicon RNA comprising the 5' untranslated region (5' UTR) (SEQ ID NO: 2), 57 nucleotides of the Core protein coding sequence (SEQ ID NO: 3), a luciferase gene, an EMCV IRES sequence, the NS3 protein coding sequence (SEQ ID NO: 8), the NS4A protein coding sequence (SEQ ID NO: 9), the NS4B protein coding sequence (SEQ ID NO: 10), the NS5A protein coding sequence (SEQ ID NO: 11), the NS5B protein coding sequence (SEQ ID NO: 12), and the 3' untranslated region (3' UTR) (SEQ ID NO: 13) of the S310A strain or a mutant thereof ligated in this order from the 5' to 3' direction is introduced into Huh7 cells, and then a test substance is added thereto, and luciferase activity is assayed 48 to 72 hours thereafter. A test substance that can inhibit the luciferase activity more effectively relative to the case of no addition of the test substance can be determined to have an effect to inhibit replication of the HCV subgenomic replicon RNA.

HCV particles (including chimeric HCV particles) obtained by, for example, introducing the HCV full-genomic replicon RNA or the nucleic acid encoding it into cultured cells (typically HCV-sensitive cells) can be used in screening for a neutralizing antibody or a compound that inhibits HCV infection and screening for a compound that inhibits HCV replication. In addition, such HCV particles can be preferably used as vaccines or antigens for anti-HCV antibody production.

The HCV particles can be used in screening for an agent that inhibits HCV infection or replication by, in the presence or the absence of a test substance, culturing the cells producing the HCV particles or culturing the HCV particles with HCV-sensitive cells, i.e., culturing a mixture of the HCV particles and HCV-sensitive cells, or culturing the cells infected with the HCV particles, and detecting the HCV replicon RNA or HCV particles in the resulting culture. The term "detection" used herein refers to quantification of the amount of the HCV replicon RNA or the HCV particles in the culture. When the HCV replicon RNA or the HCV particles are not present in the culture or the amount thereof is less than that in the absence of the test substance, the test substance can be evaluated as being capable of inhibiting HCV infection or replication.

Specifically, it is possible to screen for an anti-HCV agent by culturing HCV-sensitive cells together with the HCV particles in the presence or the absence of a test substance, detecting HCV replicon RNA or HCV particles in the resulting culture, and determining whether or not the test substance inhibits the replication of the HCV replicon RNA or the formation of the HCV particles, for example.

The HCV replicon RNA in the culture can be detected by, for example, measuring the function of a foreign gene ligated to the HCV replicon RNA, i.e., the function developed upon expression of the gene of interest. When the foreign gene is an enzyme gene, for example, the HCV replicon RNA can be detected by measuring the enzyme activity. Alternatively, HCV replicon RNA can be detected by quantifying the amount of RNA replicated by quantitative RT-PCR.

The HCV particles present in the culture can be detected by using an antibody against a protein (e.g., the Core protein, the E1 protein, or the E2 protein) constituting the HCV particles released in the culture supernatant, the presence of the non-structural protein in the infected cells can be detected by immunostaining with an antibody against the non-structural protein, or the HCV genomic RNA contained in the HCV particles in the culture supernatant can be amplified by RT-PCR using specific primers. Thus, the presence of HCV particles can be indirectly detected.

A specific example of HCV full-genomic replicon RNA containing a foreign gene used in the screening is an HCV full-genomic replicon RNA comprising the 5' UTR, 57 nucleotides of the Core protein coding sequence, a luciferase gene, an EMCV IRES sequence, the Core protein coding sequence, the E1 protein coding sequence, the E2 protein coding sequence, the p7 protein coding sequence, the NS2 protein coding sequence, the NS3 protein coding sequence, the NS4A protein coding sequence, the NS4B protein coding sequence, the NS5A protein coding sequence, the NS5B protein coding sequence, and a 3' UTR of the HCV S310A mutant ligated in this order from the 5' to 3' direction. When nucleotide sequences are to be ligated to each other, an additional sequence such as a restriction enzyme site, may be inserted into the site of ligation. The HCV full-genomic replicon RNA is introduced into Huh7 cells, HCV particles are produced, HCV-sensitive cells are infected with the HCV particles, a test substance is added simultaneously, and luciferase simultaneously is assayed 48 to 72 hours thereafter. An agent that inhibits the luciferase activity relative to the case of no-addition of the test substance can be determined to have activity of inhibiting HCV infection. In the method described above, an anti-HCV agent is selected as an agent that can inhibit virus infection or replication.

In the method described above, also, a viral genome containing the HCV full-genomic replicon RNA or the nucleic acid encoding it, and a hepatitis C virus containing the HCV full-genomic replicon RNA or the nucleic acid encoding it as a viral genome can also be used.

Further, we provide a hepatitis C virus (HCV) vaccine comprising the hepatitis C virus (HCV) particles.

In the vaccine use, specifically, the HCV particles or a part thereof may be used as a vaccine without any treatment; however, it is preferred that the HCV particles or a part thereof be attenuated or inactivated by a known method. The virus can be inactivated by adding an inactivating agent such as formalin, β-propiolactone, or glutardialdehyde to, for example, a virus suspension and mixing them, to allow the agent to react with the virus (Appaiahgari, M. B. & Vrati, S., Vaccine, 2004, vol. 22, pp. 3669-3675).

The HCV vaccine can be prepared as an administrable solution or suspension, or it can be prepared in the form of a solid (e.g., a lyophilized preparation) suitable for dissolution or suspension in a liquid to be reconstituted immediately before use. Such solid or preparation may be emulsified or encapsulated in liposomes.

The active immunogenic ingredient such as HCV particles can be often mixed with a pharmaceutically acceptable excipient that is compatible with the active ingredient. Examples of suitable excipient include water, saline, dextrose, glycerol, ethanol, and mixtures thereof.

Furthermore, the HCV vaccine can, if desired, contain a small amount of an auxiliary agent (e.g., a humidifier or emulsifier), a pH adjuster, and/or an adjuvant for enhancing vaccine efficacy.

The adjuvant is a non-specific stimulant to the immune system. These substances enhance the immune response of a host against the HCV vaccine. Accordingly, the HCV vaccine contains an adjuvant. Adjuvant efficacy can be determined by measuring the amount of antibodies resulting from administration of a vaccine made of HCV particles.

Examples of the effective adjuvant include, but are not limited to, the followings: aluminum hydroxide, N-acetylmuramyl-L-threonyl-D-isoglutamine (thr-MDP), N-acetyl-nor-muramyl-L-alanyl-D-isoglutamine (referred to as CGP11637 or nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (referred to as CGP19835A or MTP-PE), and RIBI. RIBI contains three components extracted from bacteria, i.e., monophosphoryl lipid A, trehalose dimycolate, and the cell wall skeleton (HPL+TDM+CWS), in 2% squalene/Tween® 80 emulsion.

One or more compounds having adjuvant activity can be added to the HCV vaccine, according to need. Specific examples of known adjuvants include Freund's complete adjuvants, Freund's incomplete adjuvants, vitamin E, nonionic block polymers, muramyl dipeptide, saponin, mineral oil, vegetable oil, and Carbopol. Examples of adjuvants that are particularly suitable for mucosal application include *Escherichia coli* (*E. coli*) thermolabile toxin (LT) and Cholera toxin (CT). Examples of other suitable adjuvants include aluminum hydroxide, aluminum phosphate, aluminum oxide, oil emulsion (e.g., Bayol® or Marcol 52®), saponin, and vitamin E solubilizates.

The HCV vaccine is generally administered parenterally by injection such as subcutaneous injection or intramuscular injection. Examples of other formulations suitable for other dosage forms include suppositories and, optionally, oral preparations.

In injections for subcutaneous, intracutaneous, intramuscular, or intravenous administration, specific examples of the pharmaceutically acceptable carrier or diluent for the HCV vaccine include stabilizers, carbohydrates (e.g., sorbitol, mannitol, starch, sucrose, glucose, and dextran), proteins such as albumin and casein, protein-containing substances such as bovine serum and skimmed milk, and buffers (e.g., phosphate buffer).

Examples of conventional binders and carriers used for suppositories include polyalkylene glycol and triglyceride. Such suppositories can be made of a mixture containing an active ingredient in a range of 0.5% to 50%, and preferably in a range of 1% to 20%. The oral preparations contain common excipients. Examples of excipients include pharmaceutical-grade mannitol, lactose, starch, magnesium stearate, saccharine sodium, cellulose, and magnesium carbonate.

The HCV vaccine is in the form of a solution, suspension, tablet, pill, capsule, sustained-release formulation, or powder, and it contains an active ingredient (HCV particles or a part thereof) in an amount of 10% to 95%, and preferably 25% to 70%. The HCV vaccine is administered by a method suitable for the dosage form in an amount that allows preventive and/or therapeutic effects to be exerted. The amount of an antigen to be administered is usually in a range of 0.01 µg to 100,000 µg per administration, and it depends on the patient to whom the vaccine is administered, the antibody-synthesizing ability in the immune system of the patient, and the degree of protection intended. The amount also depends on the administration route such as oral, subcutaneous, intracutaneous, intramuscular, or intravenous administration.

The HCV vaccine may be administered according to a single-administration schedule or a multiple-administration schedule, with the multiple-administration schedule being preferred. In the case of the multiple-administration schedule, one to ten separate administrations are performed at the time of initiation of inoculation, and another administration can be subsequently performed with the time interval that is necessary for maintaining and/or enhancing the immune response. For example, the second administration can be performed one to four months later. Administration may be subsequently performed several months later, if necessary. The administration regimens are, at least partially, determined depending on the necessity of an individual, and the regimens depend on the judgment made by a doctor. The HCV vaccine may be administered to a healthy individual to induce an immune response to HCV in the healthy individual for preventing new HCV infection. Furthermore, the vaccine may be administered to a patient infected with HCV to induce a potent immune response to HCV in vivo, and thus the vaccine may be used as a therapeutic vaccine which eliminates HCV.

The HCV particles are also useful as an antigen for producing an anti-HCV antibody. The antibody can be produced by administering the HCV particles to a mammal or a bird. Examples of mammals include mice, rats, rabbits, goats, sheep, horses, cattle, guinea pigs, dromedaries, Bactrian camel, and lama. Dromedaries, Bactrian camel, and lama are suitable for producing an antibody consisting of the H chain. Examples of birds include chickens, geese, and ostriches. Serum is collected from the animal to which the HCV particles have been administered, and the antibody of interest can be obtained in accordance with a conventional technique.

We provide the anti-HCV antibody described above, and such antibody is preferably used as a neutralizing antibody capable of inactivating HCV.

Animal cells immunized with the HCV particles can be used to produce hybridomas that produce monoclonal antibody-producing cells. The hybridomas can be produced by a well-known method such as the method described in Antibodies: A Laboratory Manual (Cold Spring Harbor Laboratory, 1988).

The monoclonal antibody-producing cells may be produced through cell fusion or other techniques such as introduction of oncogenic DNA or immortalization of B lymphocytes via Epstein-Barr virus infection.

A monoclonal or polyclonal antibody obtained by the technique as described above is useful for diagnosis, treatment, and prevention of HCV.

The antibody produced by using the HCV particles as an antigen can be administered as a drug together with, for example, a pharmaceutically acceptable solubilizer, additive, stabilizer, or buffer. Any route of administration may be employed, with subcutaneous, intracutaneous, or intramuscular administration being preferred, and intravenous administration being more preferred.

We also provide a method of treatment or prevention of HCV comprising administering the vaccine or antibody to a subject who is in need of treatment.

We also provide a pharmaceutical composition comprising the vaccine or antibody. Such pharmaceutical composition may comprise a pharmaceutically acceptable carrier such as a solubilizer, additive, stabilizer, or buffer.

EXAMPLES

Our constructs and methods are described in greater detail with reference to the following examples. It should be noted that these examples are provided for illustrative purposes and the technical scope of this disclosure is not limited to these examples.

Example 1

Construction of Wild-Type S310A Strain HCV Subgenomic Replicon RNA Expression Vector The HCV virus strain was isolated from a 71-year-old acute hepatitis C patient, who had been infected with HCV of genotype 3a, and the isolated strain was designated as the S310A strain. This patient was diagnosed as having been infected with HCV of genotype 3a at the age of 59. Because of cirrhosis of the liver, this patient underwent liver transplantation 4 years thereafter. Specifically, RNA was extracted from patient's serum and purified with Isogen-LS (Nippon Gene Co., Ltd.), and cDNA was synthesized using a random hexamer primer. PCR primers were designed based on the conserved sequences of 4 known types of HCV genomes of genotype 3a (i.e., GenBank Accession Nos. AF046866, D28917, X76918, and D17763). cDNA fragments were amplified in nine divided fragments using PCR primers that were designed based on the conserved sequences of four known HCV genomes of genotype 3a (GenBank Accession Nos. AF046866, D28917, X76918, and D17763) and synthesized cDNA. The amplification product of the sequence at the 5' terminus, which is difficult to obtain, was obtained by a 5' RACE method. Each fragment was cloned into a cloning vector, pGEM-T EASY (Promega Corp.), for sequencing. The nucleotide sequences of these clones were analyzed by a conventional method to determine the full-length genomic RNA sequence of the S310A strain. A cDNA fragment corresponding to the full-length genomic RNA was synthesized by a conventional technique. The cDNA sequence corresponding to the full-length genomic RNA sequence of the S310A strain is shown in SEQ ID NO: 1.

With the use of a non-structural region of cDNA corresponding to full-length genomic RNA of the S310A strain (full-length genomic cDNA; SEQ ID NO: 1), which is the novel HCV strain of genotype 3a isolated from the patient with acute hepatitis C obtained as described above, the plasmid pS310ASGR-Neo, which is an HCV subgenomic replicon RNA expression vector, was constructed as described below. FIG. 1 shows the structures of the full-length genomic RNA of the S310A strain, the HCV subgenomic replicon RNA expression vector pS310ASGR-Neo, and an HCV subgenomic replicon RNA expressed from such expression vector. To differentiate from mutants comprising amino acid mutations, the S310A strain without amino acid mutations is referred to as the "wild-type S310A strain" herein.

SEQ ID NO: 1 shows the full-length genomic nucleotide sequence of the wild-type S310A strain. SEQ ID NO: 2 shows the nucleotide sequence of 5' UTR of the S310A strain, SEQ ID NO: 3 shows the Core protein coding sequence of the S310A strain, SEQ ID NO: 4 shows the E1 protein coding sequence of the S310A strain, SEQ ID NO: 5 shows the E2 protein coding sequence of the S310A strain, SEQ ID NO: 6 shows the p7 protein coding sequence of the S310A strain, SEQ ID NO: 7 shows the NS2 protein coding sequence of the S310A strain, SEQ ID NO: 8 shows the NS3 protein coding sequence of the S310A strain, SEQ ID NO: 9 shows the NS4A protein coding sequence of the S310A strain, SEQ ID NO: 10 shows the NS4B protein coding sequence of the S310A strain, SEQ ID NO: 11 shows the NS5A protein coding sequence of the S310A strain, SEQ ID NO: 12 shows the NS5B protein coding sequence of the S310A strain, and SEQ ID NO: 13 shows the nucleotide sequence of 3' UTR of the S310A strain. SEQ ID NOs: 1 to 13 show DNA sequences, but when an RNA sequence is indicated by each SEQ ID NO:, thymine (T) in its nucleotide sequence shown in the SEQ ID NO: shall be replaced with uracil (U).

The amino acid sequence of the HCV precursor protein (polyprotein) encoded by the nucleotide sequence shown in SEQ ID NO: 1 (the full-length genomic sequence of the wild-type S310A strain) is shown in SEQ ID NO: 14. The amino acid sequence shown in SEQ ID NO: 14 is encoded by from nucleotides 341 to 9406 (including a stop codon) of the nucleotide sequence shown in SEQ ID NO: 1. The amino acid sequence of the region from the NS3 protein to the NS5B protein in the precursor protein of the S310A strain is shown in SEQ ID NO: 15. This amino acid sequence (from the NS3 region to the NS5B region) of SEQ ID NO: 15 corresponds to a region of amino acids 1033 to 3021 of the amino acid sequence shown in SEQ ID NO: 14.

The HCV subgenomic replicon RNA expression vector pS310ASGR-Neo was constructed in accordance with the procedure described in the document of Kato et al. (Gastroenterology, 2003, vol. 125, pp. 1808-1817) and International Publication No. WO 04/104198.

Specifically, cDNA of full-length genomic RNA of the wild-type S310A strain (FIG. 1A) was first inserted into a plasmid vector, pUC19, under the control of the T7 promoter to produce a recombinant plasmid, pS310A. Subsequently, the structural region (encoding the Core protein, the E1 protein, the E2 protein, or the p7 protein) and a part of the non-structural region of the recombinant plasmid, pS310A, were substituted with a neomycin resistance gene (neo: also referred to as the "neomycin phosphotransferase gene") and EMCV IRES (the internal ribosome entry site of the encephalomyocarditis virus) to construct the plasmid, pS310ASGR-Neo. This was designated as the HCV subgenomic replicon RNA expression vector, pS310ASGR-Neo.

FIG. 1B shows the structure of the HCV subgenomic replicon RNA expression vector, pS310ASGR-Neo. In the expression vector, pS310ASGR-Neo, 5' UTR, the 57 nucleotides from the N terminus of the Core protein coding sequence (HCV-IRES), the NS3 to NS5B protein coding sequences, and 3' UTR are derived from the S310A strain. In the figure, "T7" denotes the T7 promoter. The T7 promoter is a sequence element necessary for transcribing the HCV subgenomic replicon RNAs from the respective expression vectors using the T7 RNA polymerase. "neo" denotes a neomycin resistance gene, "EMCV IRES" denotes the internal ribosome entry site of the encephalomyocarditis virus, "C" denotes the Core protein coding sequence, "E1" denotes the E1 protein coding sequence, "E2" denotes the E2 protein coding sequence, "p7" denotes the p7 protein coding sequence, "NS2" denotes the NS2 protein coding sequence, "NS3" denotes the NS3 protein coding sequence, "4A" denotes the NS4A protein coding sequence, "4B" denotes the NS4B protein coding sequence, "NS5A" denotes the NS5A protein coding sequence, and "NS5B" denotes the NS5B protein coding sequence. HCV subgenomic replicon RNA produced from the expression vector pS310ASGR-Neo (HCV subgenomic replicon RNA of the S310A strain) is an RNA produced by transcription of the region downstream of the T7 promoter, shown in FIG. 1C. In the figure, "EcoRI," "PmeI," "SnaBI," and "XbaI" indicate restriction enzyme sites. The same applies to FIGS. 9, 10, 12, 14, and 16.

cDNA of S310A subgenomic replicon RNA is ligated to downstream of the T7 promoter of the expression vector, pS310ASGR-Neo. The cDNA nucleotide sequence of HCV subgenomic replicon RNA of the S310A strain is shown in SEQ ID NO: 16.

Example 2

Production of HCV Subgenomic Replicon RNA of Wild-Type S310A Strain

The expression vector, pS310ASGR-Neo, constructed in Example 1 was cleaved with the XbaI restriction enzyme. Subsequently, 20 U of Mung Bean Nuclease was added to 10 to 20 µg of the XbaI-cleaved fragment (the total volume of the reaction solution: 50 µl), followed by incubation at 30° C. for 30 minutes. Mung Bean Nuclease is an enzyme that catalyzes blunting reaction through selective decomposition of the single-stranded portion in a double-stranded DNA. When RNA transcription by an RNA polymerase is carried out with the use of the XbaI-cleaved fragment as a template DNA in that state, in general, replicon RNA having an extra four nucleotides CUAG, which is a part of the XbaI recognition sequence, added to the 3' terminus is synthesized. In Example 2, accordingly, the XbaI-cleaved fragment was treated with Mung Bean Nuclease to remove the four nucleotides CTAG therefrom.

Subsequently, proteins were removed from the solution containing the XbaI-cleaved fragment after Mung Bean Nuclease treatment by conventional techniques to purify an XbaI-cleaved fragment from which four nucleotides CTAG had been removed, and the resultant was used as a template DNA in the subsequent reaction. RNA was synthesized in vitro from the template DNA with the use of MEGAscript® (Ambion, Inc.) through transcription using the T7 promoter. Specifically, 20 μl of a reaction solution containing 0.5 to 1.0 μg of the template DNA was prepared in accordance with the manufacturer's instructions, and the reaction was allowed to proceed at 37° C. for 3 to 16 hours.

After completion of RNA synthesis, DNase I (2 U) was added to the reaction solution for 15 minutes at 37° C. to remove the template DNA, and RNA was extracted with acidic phenol to prepare the HCV subgenomic replicon RNA of the wild-type S310A strain (FIG. 1C) (SEQ ID NO: 16) transcribed from the pS310ASGR-Neo.

Example 3

Establishment of S310A Strain HCV Subgenomic Replicon-Replicating Cell Clone

The HCV subgenomic replicon RNA of the wild-type S310A strain produced in Example 2 (1 μg, 3 μg, 10 μg, or 30 μg) was introduced into Huh7 cells by electroporation. The electroporated Huh7 cells ($3 \times 10^6$ cells) were seeded in a culture dish and cultured for 16 to 24 hours, and G418 (neomycin) was then added to the culture dish. Thereafter, culture was continued while changing the culture solution twice a week.

Figure 2:
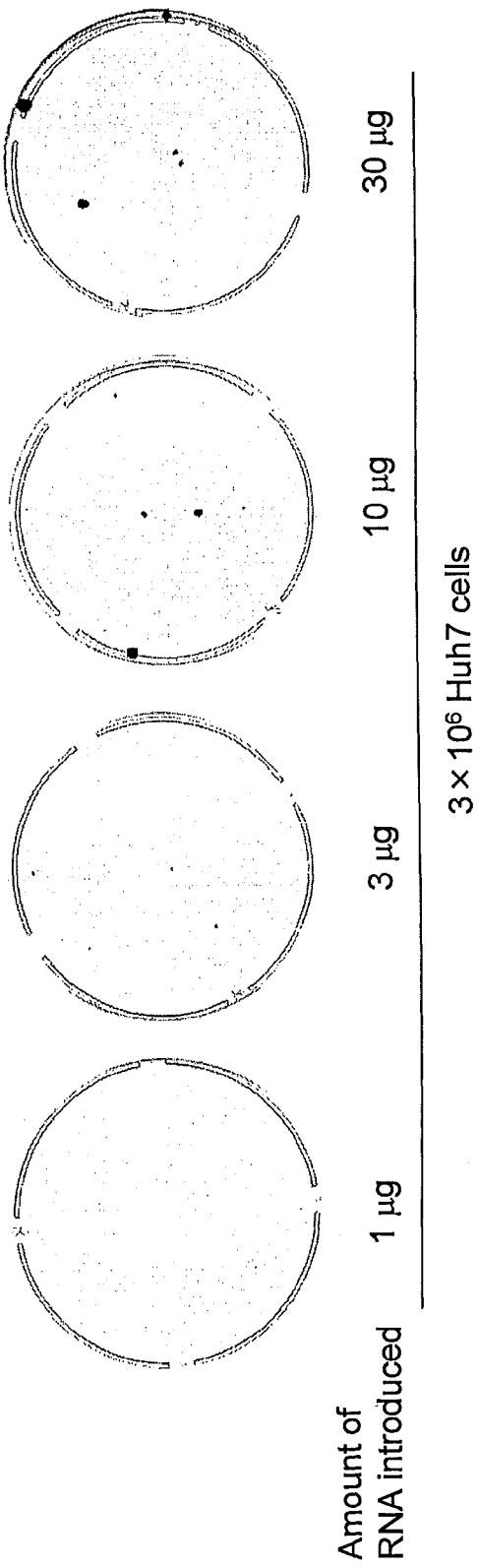
FIG. 2 shows the results of colony formation of Huh7 cells transfected with the HCV subgenomic replicon RNA of the wild-type S310A strain.

After the culture was continued for 21 days after seeding, viable cells were stained with crystal violet. As a result, colony formation of the cells transfected with 10 μg and 30 μg of the HCV subgenomic replicon RNAs of the S310A strains was observed (FIG. 2). Colony formation indicates that the HCV subgenomic replicon RNA was replicated in the cells. These results demonstrate that HCV subgenomic replicon RNA produced with the use of the non-structural genomic region of the wild-type S310A strain has the autonomous replication ability in cultured cells.

Regarding the cells into which HCV subgenomic replicon RNA had been introduced and colony formation was observed, colonies of viable cells were further cloned from the culture dish after 21 days of culture described above, and culture thereof was further continued. As a result of cloning of colonies, 10 cell clones were established. These cell clones were designated as S310A subgenomic replicon-replicating cells and numbered (Clone Nos. 1 to 10). In the thus-established cell clones, HCV subgenomic replicon RNA of the S310A strain that had been introduced autonomously replicates.

Example 4

Quantification of the Copy Number of HCV Subgenomic Replicon RNA in S310A Subgenomic Replicon-Replicating Cells With the use of the S310A subgenomic replicon-replicating cells of the established 10 clones (Clone Nos. 1 to 10), the copy number of intracellular HCV subgenomic replicon RNA was quantified. The quantification of copy number of HCV subgenomic replicon RNA was carried out in accordance with the technique described in Takeuchi et al. (Gastroenterology, 1999, Vol. 116, pp. 636-642) and Kato et al. (Gastroenterology, 2003, Vol. 125, pp. 1808-1817).

This technique is a detection system using TaqMan probe method (PerkinElmer Inc., Applied Biosystems Inc.). Specifically, total RNA was first extracted from the S310A subgenomic replicon-replicating cells in accordance with a conventional technique. Subsequently, cDNA was synthesized from total RNA using rTth DNA polymerase, and the synthesized cDNA template was amplified via PCR using the primers: 5'-CGGGAGAGCCATAGTGG-3' (SEQ ID NO: 24) and 5'-AGTACCACAAGGCCTTTCG-3' (SEQ ID NO: 25). At this time, a probe having the nucleotide sequence 5'-CTGCGGAACCGGTGAGTACAC-3' (SEQ ID NO: 26) to which a fluorescent dye, 6'-carboxy-fluorescein (FAM), had been bound at the 5' terminus and a quencher, 6'-carboxytetramethyl-rhodamine (TAMRA), had been bound at the 3' terminus was added. In the presence of such probe, the probe that had hybridized to the template cDNA is degraded because of 5' exonuclease activity of the Taq polymerase during the process of amplification, the fluorescent dye is released from the probe, suppression by the quencher is released, thereby emitting fluorescence. Thus, such fluorescence was detected with ABI Prism 7700 (ParkinElmer Inc., Applied Biosystems Inc.) to quantify the copy number of HCV subgenomic replicon RNA.

As a control for comparison, the cells into which HCV subgenomic replicon RNA of the JFH-1 strain of genotype 2a had been introduced (the JFH-1 subgenomic replicon-replicating cells) were used. The JFH-1 strain HCV subgenomic replicon RNA expression vector (comprising the 5' untranslated region (5' UTR), the sequence of 57 nucleotides at the 5' terminus of the Core protein coding region, the neomycin resistance gene, the EMCV IRES sequence, the nucleotide sequences encoding the NS3 protein, the NS4A protein, the NS4B protein, the NS5A protein and the NS5B protein, and the 3' untranslated region (3' UTR) of the HCV JFH-1 strain in this order from the 5' to 3' direction) was constructed and HCV subgenomic replicon RNA was produced in accordance with the techniques described in Kato et al. (Gastroenterology, 2003, Vol. 125, pp. 1808-1817) and International Publication No. WO 04/104198. Introduction thereof into the Huh cells and quantification of the copy number were carried out in the manner as described above.

Figure 3:
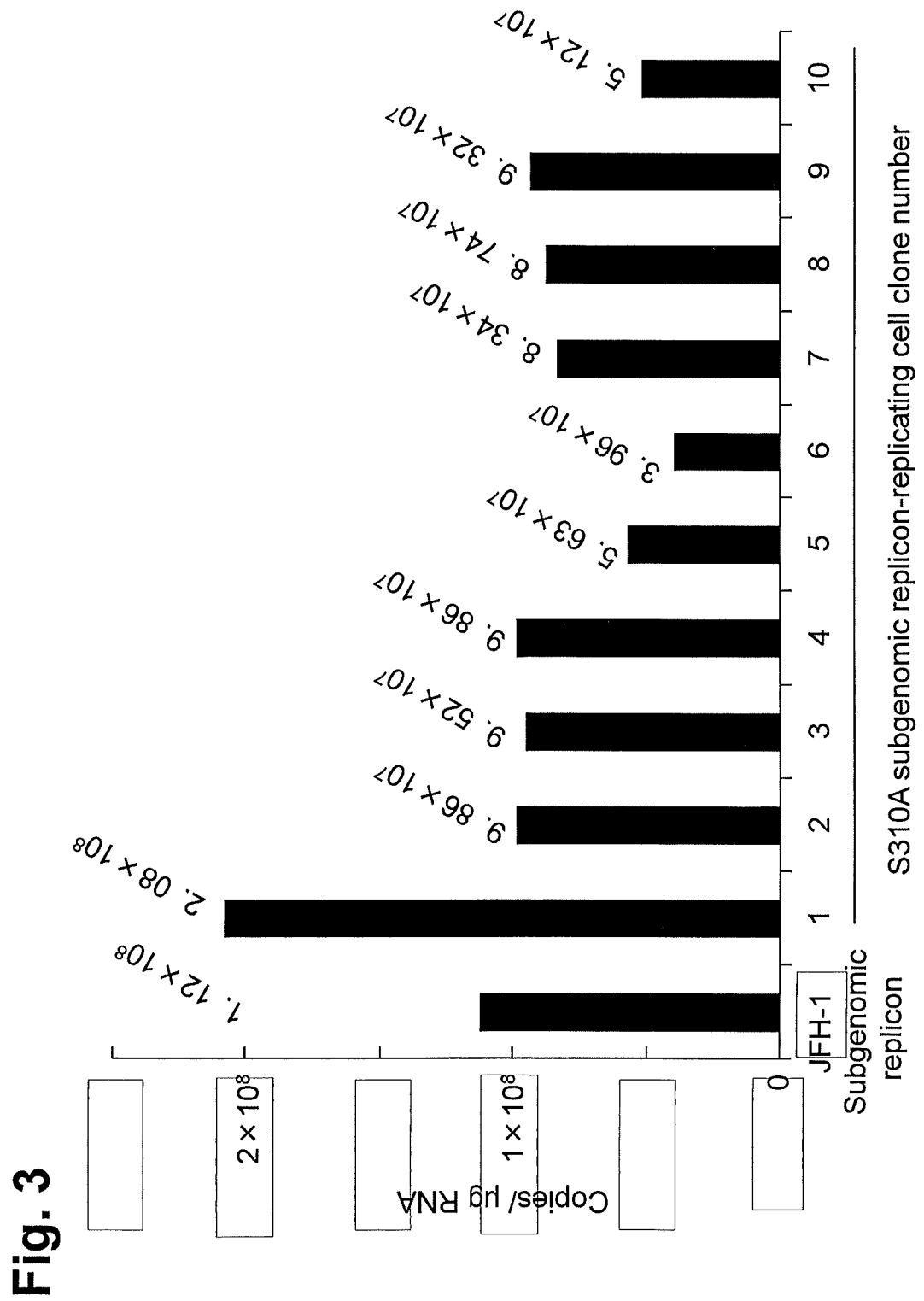
FIG. 3 shows the results of quantification of copy number of HCV subgenomic replicon RNA in the S310A subgenomic replicon-replicating cells (clones).

FIG. 3 shows the results of quantification. Numbers on the horizontal axis of the figure represent the clone numbers of the clones of the S310A subgenomic replicon-replicating cells. The vertical axis represents the copy number of HCV subgenomic replicon RNA copies in the cells per 1 μg of total RNA in the cells. Numbers shown on the top of the bar represent copy numbers of HCV subgenomic replicon RNA in the cells.

As a result, the RNA copy numbers in the S310A subgenomic replicon-replicating cells of the established 10 clones were found to be equivalent to or more than that in the JFH-1 subgenomic replicon-replicating cells. Thus, the replication ability of the HCV subgenomic replicon RNA derived from the S310A strain was found to be substantially equivalent to or more than that of the HCV subgenomic replicon RNA derived from the JFH-1 strain.

Example 5

Effects of Antiviral Agent on Replicon RNA Replication in S310A Subgenomic Replicon-Replicating Cells The effects of antiviral agents on replicon RNA replication in the established S310A subgenomic replicon-replicating cells (clones) were examined.

The S310A subgenomic replicon-replicating cells (clones) and the JFH-1 subgenomic replicon-replicating cells were seeded on 24-well plates at a density of $5 \times 10^4$ cells/well, interferon-α (IFN-α), NS3 protease inhibitors (VX-950 (telaprevir) (Lin et al, Journal of Biological Chemistry, 2004, Vol. 279, pp. 17508-17514) and BILN-2061 (Daniel et al, Nature, 2003, Vol. 426, pp. 186-189)), and NS5B polymerase inhibitors JTK-109 (Hirashima et al, Journal of Medicinal Chemistry, 2006, Vol. 49, pp. 4721-4736) and PSI-6130 (Clark et al, Journal of Medicinal Chemistry, 2005, Vol. 48, pp. 5504-5508) were added to the wells on the following day, and the reaction was allowed to proceed for 3 days. Thereafter, the cells were recovered, total RNAs were extracted therefrom, and the copy number of HCV subgenomic replicon RNA in the cells was quantified in the same manner as in Example 4.

The results are shown in FIGS. 4 to 8. In each figure, the horizontal axis represents the concentration of an inhibitor added. The vertical axis represents change ratio of HCV RNA levels, which is the percentage (%) of the amount of subgenomic replicon RNA per μg of total RNA from cells when an inhibitor was added, relative to the amount of subgenomic replicon RNA per μg of total RNA from cells when no inhibitor was added (0 IU or 0 M) (defined as 100%). In the Figures, the leftmost bar (white) represents the results for the JFH-1 subgenomic replicon-replicating cells, the second bar from the left (light gray) represents the results for the S310A subgenomic replicon-replicating cell clone 6, the third bar from the left (black) represents the results for the S310A subgenomic replicon-replicating cell clone 9, and the rightmost bar (dark gray) represents the results for the S310A subgenomic replicon-replicating cell clone 10 at each inhibitor concentration.

Figure 4:
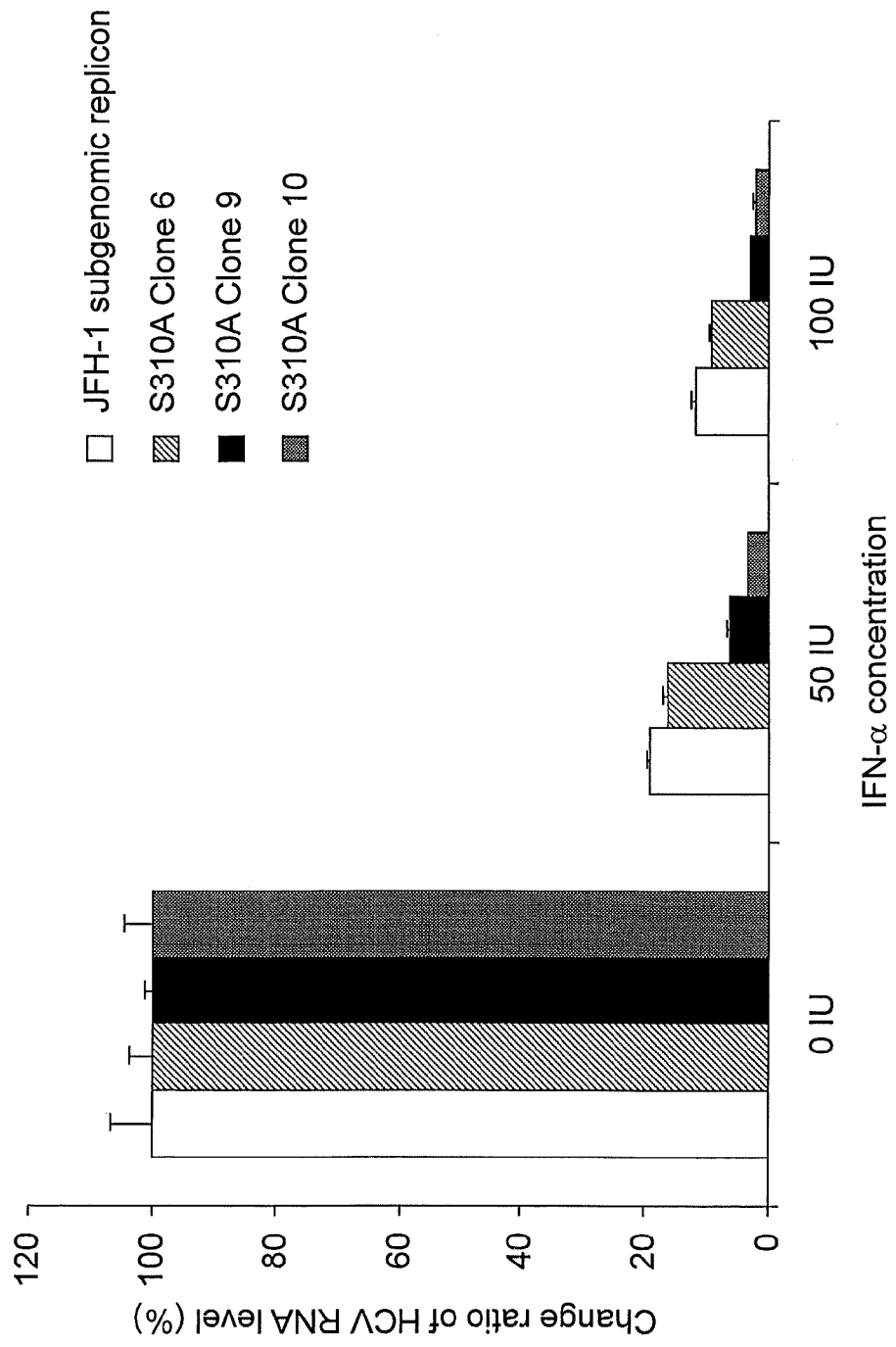
FIG. 4 shows sensitivity of the replication of replicon RNA to interferon in the S310A subgenomic replicon-replicating cells (clones).

As a result of the addition of IFN-α, intracellular RNA replication of the JFH-1 and S310A subgenomic replicon RNAs was found to be markedly inhibited by IFN-α (FIG. 4).

Figure 5:
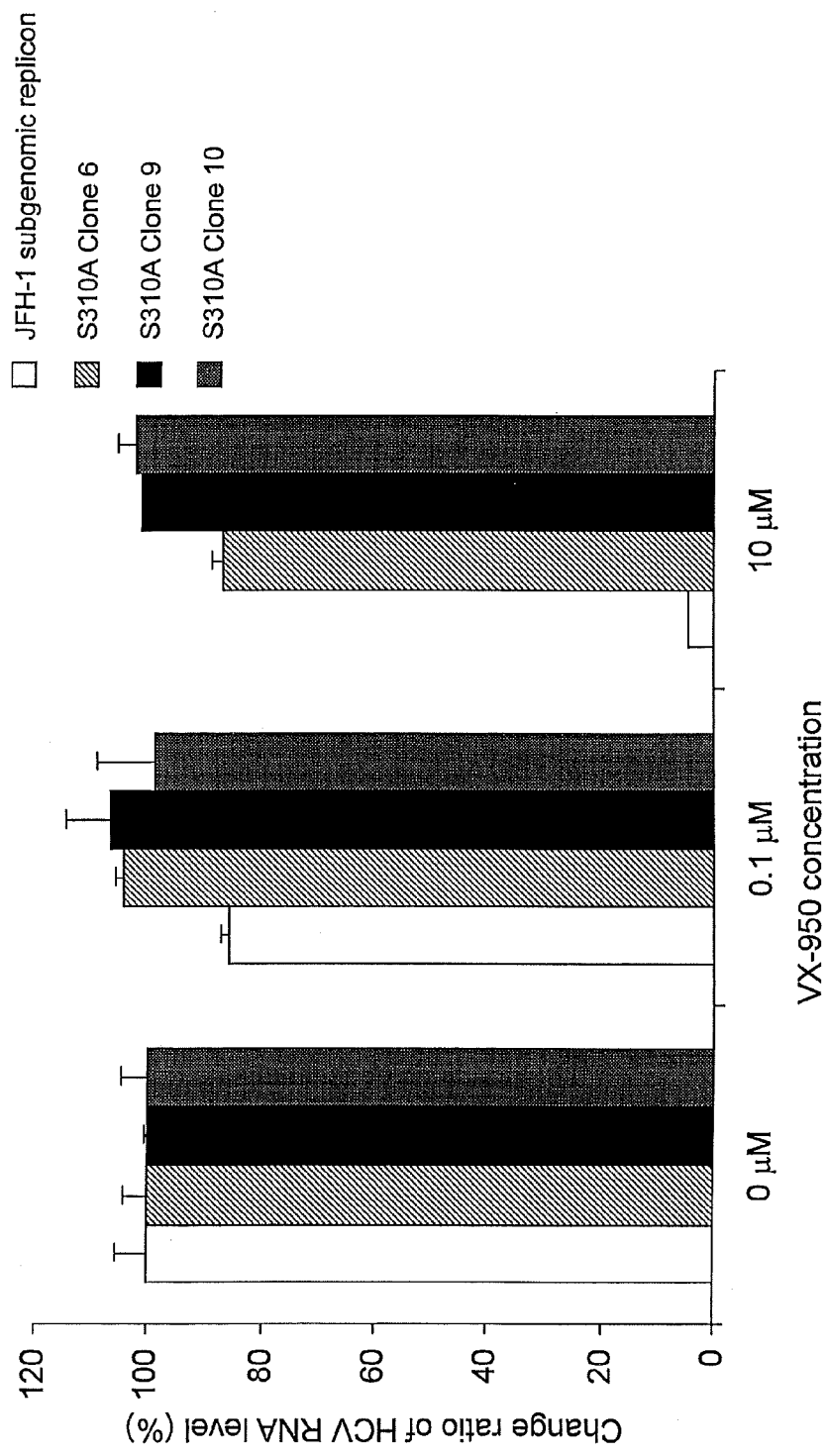
FIG. 5 shows sensitivity of the replication of replicon RNA to an NS3 protease inhibitor, VX-950, in the S310A subgenomic replicon-replicating cells (clones).
Figure 6:
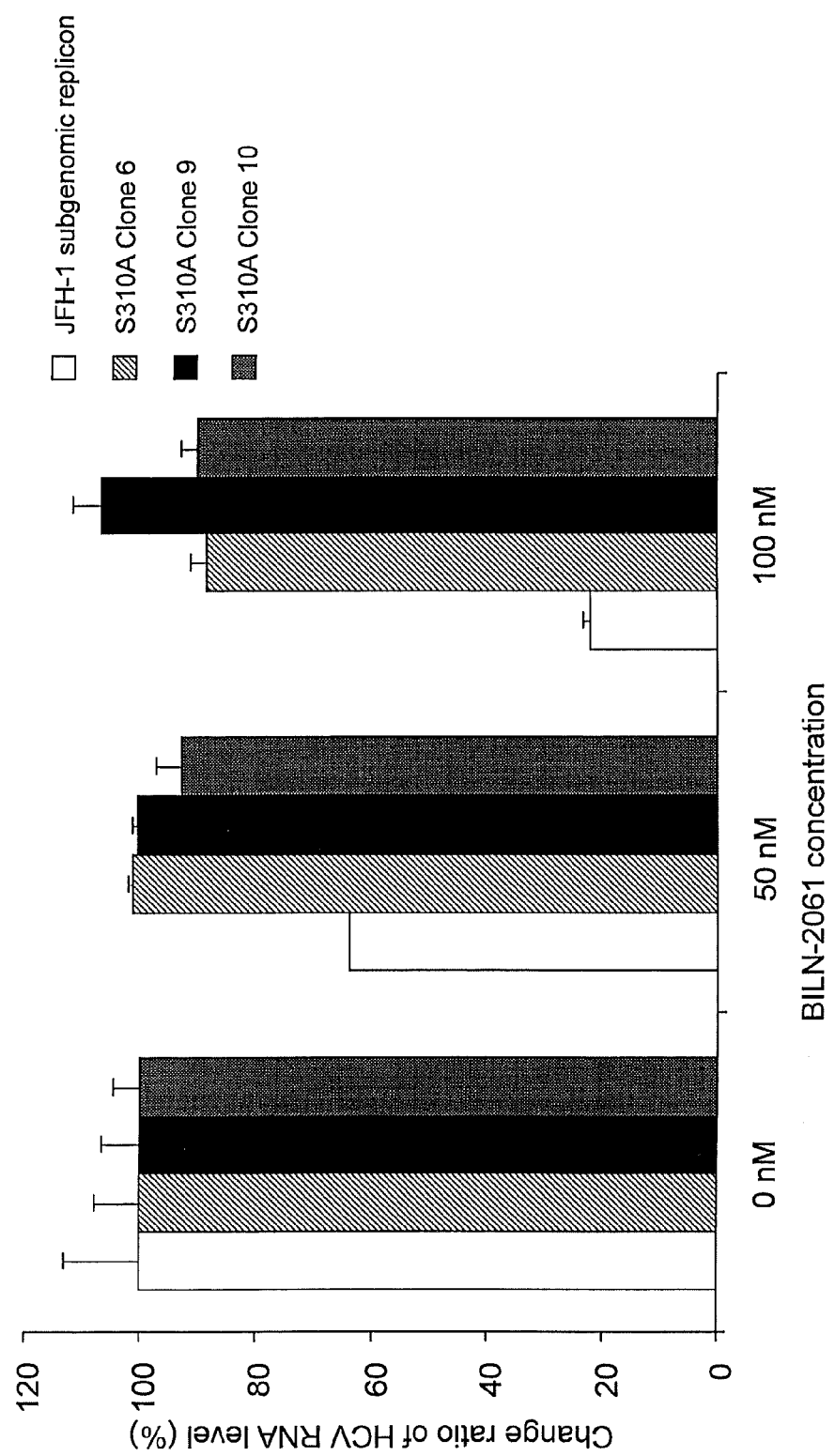
FIG. 6 shows sensitivity of the replication of replicon RNA to an NS3 protease inhibitor, BILN-2061, in the S310A subgenomic replicon-replicating cells (clones).

While NS3 protease inhibitors, VX-950 and BILN-2061, were observed to exert inhibitory activity on replication of the JFH-1 subgenomic replicon, these NS3 protease inhibitors did not inhibit replication of the S310A subgenomic replicons (FIGS. 5 and 6). This indicates that the NS3 protease of genotype 3a would not be inhibited by a conventional NS3 protease inhibitor, unlike the NS3 protease of genotype 2a.

Figure 7:
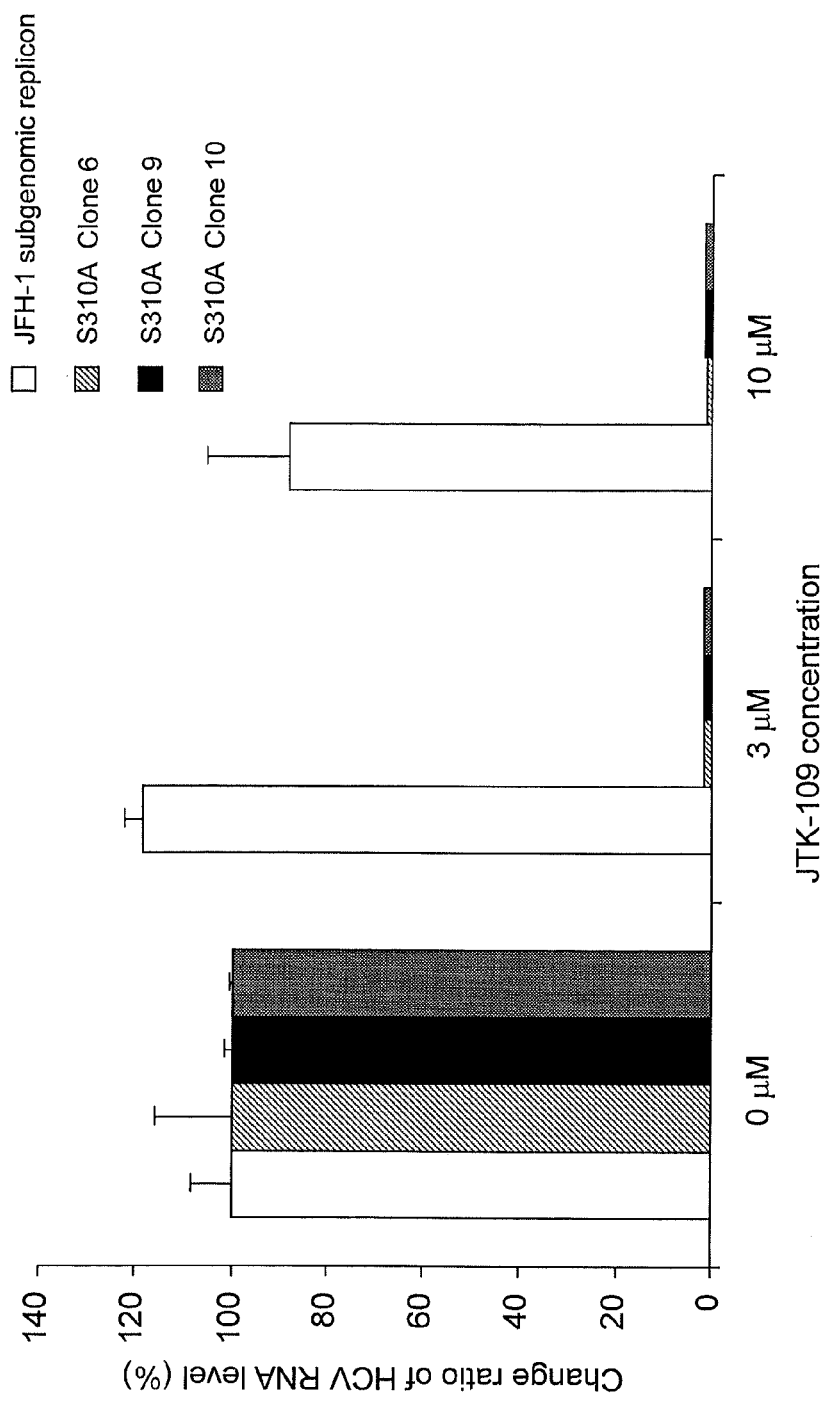
FIG. 7 shows sensitivity of the replication of replicon RNA to an NS5B polymerase inhibitor, JTK-109, in the S310A subgenomic replicon-replicating cells (clones).
Figure 8:
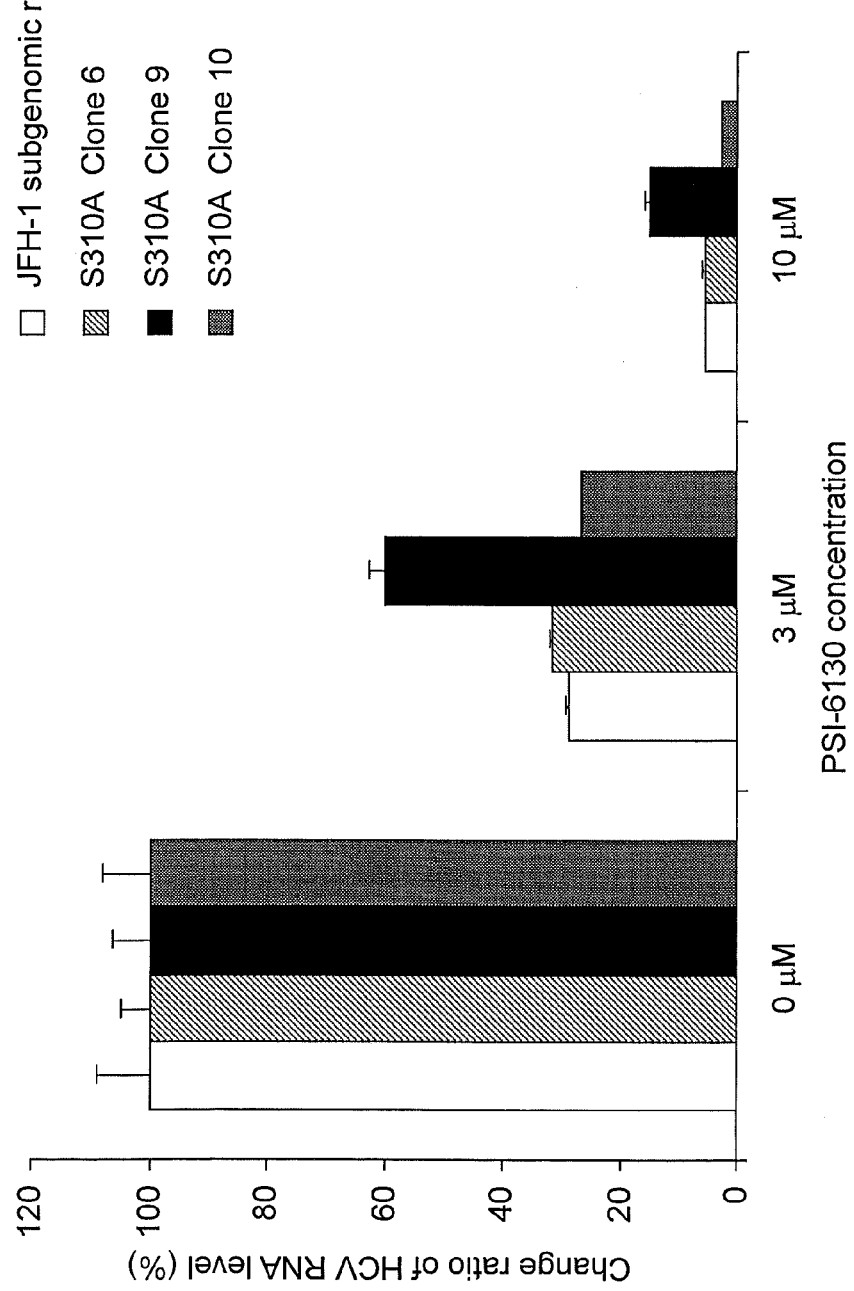
FIG. 8 shows sensitivity of the replication of replicon RNA to an NS5B polymerase inhibitor, PSI-6130, in the S310A subgenomic replicon-replicating cells (clones).

As a result of the addition of the NS5B polymerase inhibitors, JTK-109 and PSI-6130, replication of the JFH-1 subgenomic replicon RNA was observed not to be inhibited by JTK-109; however, replication of the S310A subgenomic replicon RNAs was observed to be markedly inhibited by JTK-109 (FIG. 7). In contrast, PSI-6130 inhibited replication of both the JFH-1 subgenomic replicon RNA and the S310A subgenomic replicon RNAs in a concentration-dependent manner (FIG. 8).

Accordingly, the subgenomic replicon of genotype 3a was found to serve as a preferred tool for evaluating a drug that would inhibit replication of HCV genotype 3a.

In addition, the replication ability of a subgenomic replicon derived from the HCV strain of genotype 3a was found to be influenced by a factor different from that for the replication ability of a subgenomic replicon derived from the HCV strain of genotype 2a. It is considered that the structures of polymerases encoded by the HCV genome are different between genotype 3a and genotype 2a, which leads to the different effects of drug compounds thereon, without intending to be interpreted in a limited extent by that theory.

Example 6

Sequence Analysis of HCV Subgenomic Replicon RNA in S310A Subgenomic Replicon-Replicating Cells HCV subgenomic replicon RNA present in the S310A subgenomic replicon-replicating cells (clones) established in Example 3 was subjected to sequence analysis.

First, total RNAs were extracted from the S310A subgenomic replicon-replicating cells of the established 10 clones and an additional clone (11 clones in total), and HCV subgenomic replicon RNAs contained therein were amplified by RT-PCR. PCR amplification was carried out using cDNA synthesized from HCV subgenomic replicon RNA via reverse transcription as a template and 5'-TAATAC-GACTCACTATAG-3' (SEQ ID NO: 27) and 5'-GCGGCT-CACGGACCTTTCAC-3' (SEQ ID NO: 28) as primers. The PCR amplification product was cloned into a cloning vector for sequencing and it was subjected to sequence analysis by a conventional technique.

As a result of the sequence analysis, adaptive mutations were identified in the HCV subgenomic replicon RNA in the S310A subgenomic replicon-replicating cells and shown in Table 1.

TABLE 1

| Clone Number | Amino acid mutation | Mutation site |
| --- | --- | --- |
| 1 | R2198H | NS5A |
| 2 | R2895G | NS5B |
| 3 | T1286I | NS3 |
| 4 | T1286I | NS3 |
| 5 | T1286I | NS3 |
| 6 | T1286I | NS3 |
| 7 | T1286I | NS3 |
| 8 | T1286I | NS3 |
| 9 | T2496I | NS5B |
|   | R2895K | NS5B |
| 10 | T2188A | NS5A |
| 11 | S2210I | NS5A |

Figure 9:
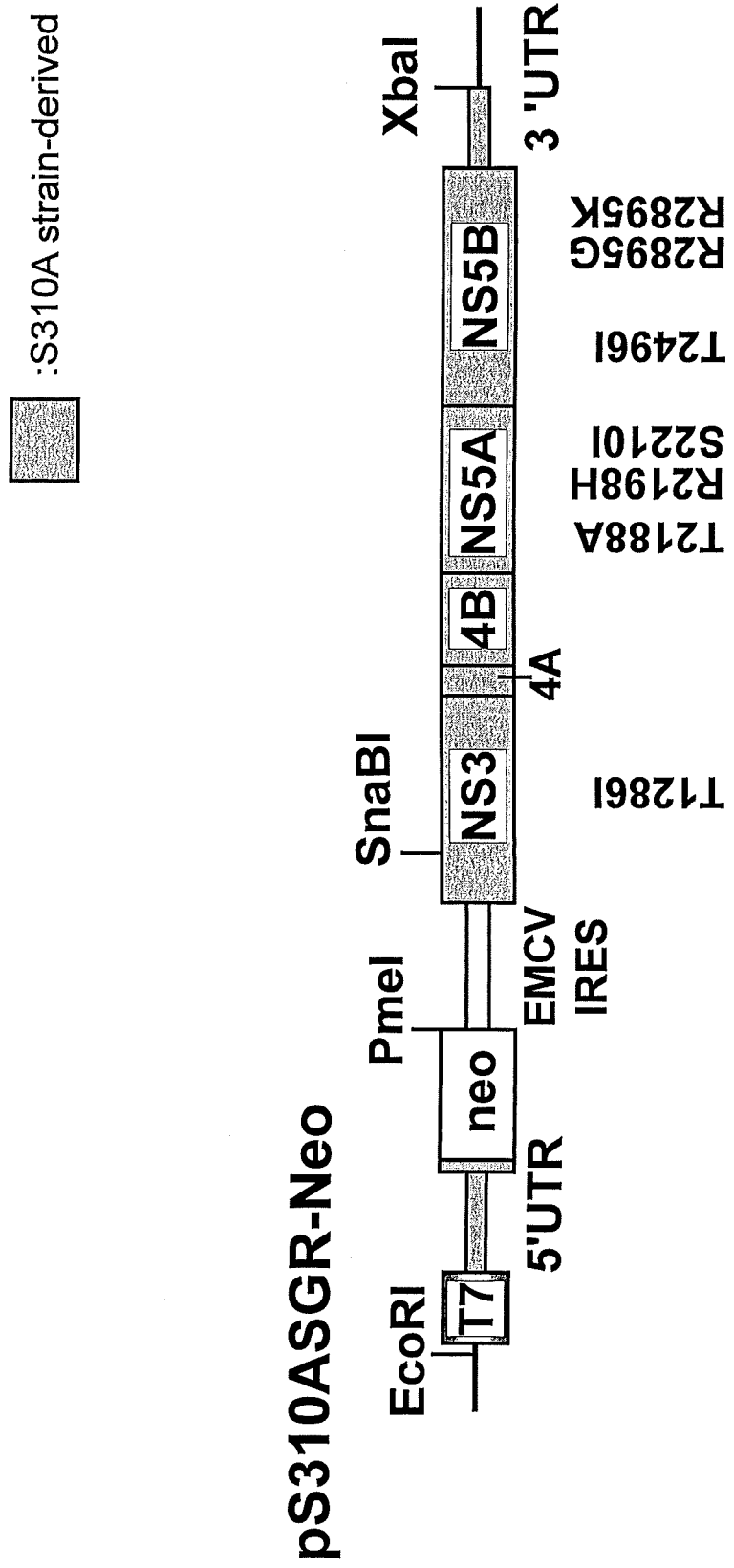
FIG. 9 schematically shows the positions of amino acid substitutions (mutations) identified in the S310A subgenomic replicon-replicating cells (clones) on the structure of pS310ASGR-Neo.

As shown in Table 1, the following nucleotide substitutions causing amino acid substitutions were found in the non-structural region of the HCV subgenomic replicon RNA obtained from the S310A subgenomic replicon-replicating cells: one mutation in the NS3 protein region (T1286I: a mutation of threonine (T) at position 1286 to isoleucine (I)); three mutations in the NS5A protein region (T2188A: a mutation of threonine (T) at position 2188 to alanine (A); R2198H: a mutation of arginine (R) at position 2198 to histidine (H); and S2210I: a mutation of serine (S) at position 2210 to isoleucine (I)); and three mutations in the NS5B protein region (T2496I: a mutation of threonine (T) at position 2496 to isoleucine (I); R2895G: a mutation of arginine (R) at position 2895 to glycine (G); and R2895K: a mutation of arginine (R) at position 2895 to lysine (K)). In Clone 9, the mutations T2496I and R2895K were detected in the NS5B protein at once. FIG. 9 schematically shows the positions of such amino acid substitutions on the expression vector, pS310ASGR-Neo. The positions of such amino acid substitutions are based on the full-length amino acid sequence of the precursor protein of the S310A strain (SEQ ID NO: 14).

Example 7

Mutagenesis into HCV Subgenomic Replicon RNA of Wild-Type S310A Strain and Analysis of Influence Thereof on Replicon Replication Ability Whether or not the nucleotide substitutions that cause amino acid substitutions identified in Example 6; i.e., nucleotide mutations, would affect replication of the HCV subgenomic replicon RNA of the wild-type S310A strain in the cells was examined in the manner described below.

Nucleotide substitutions causing the amino acid substitution T1286I in the NS3 protein region, the amino acid substitutions T2188A, R2198H, and S2210I in the NS5A protein region, and the amino acid substitutions T2496I, R2895G, and R2895K in the NS5B protein region were each introduced alone into the HCV subgenomic replicon RNA expression vector, pS310ASGR-Neo, prepared in Example 1. Also, nucleotide substitutions causing the amino acid substitutions T2496I and R2895K in the NS5B protein region were introduced in combination into the expression vector, pS310ASGR-Neo.

Figure 10:
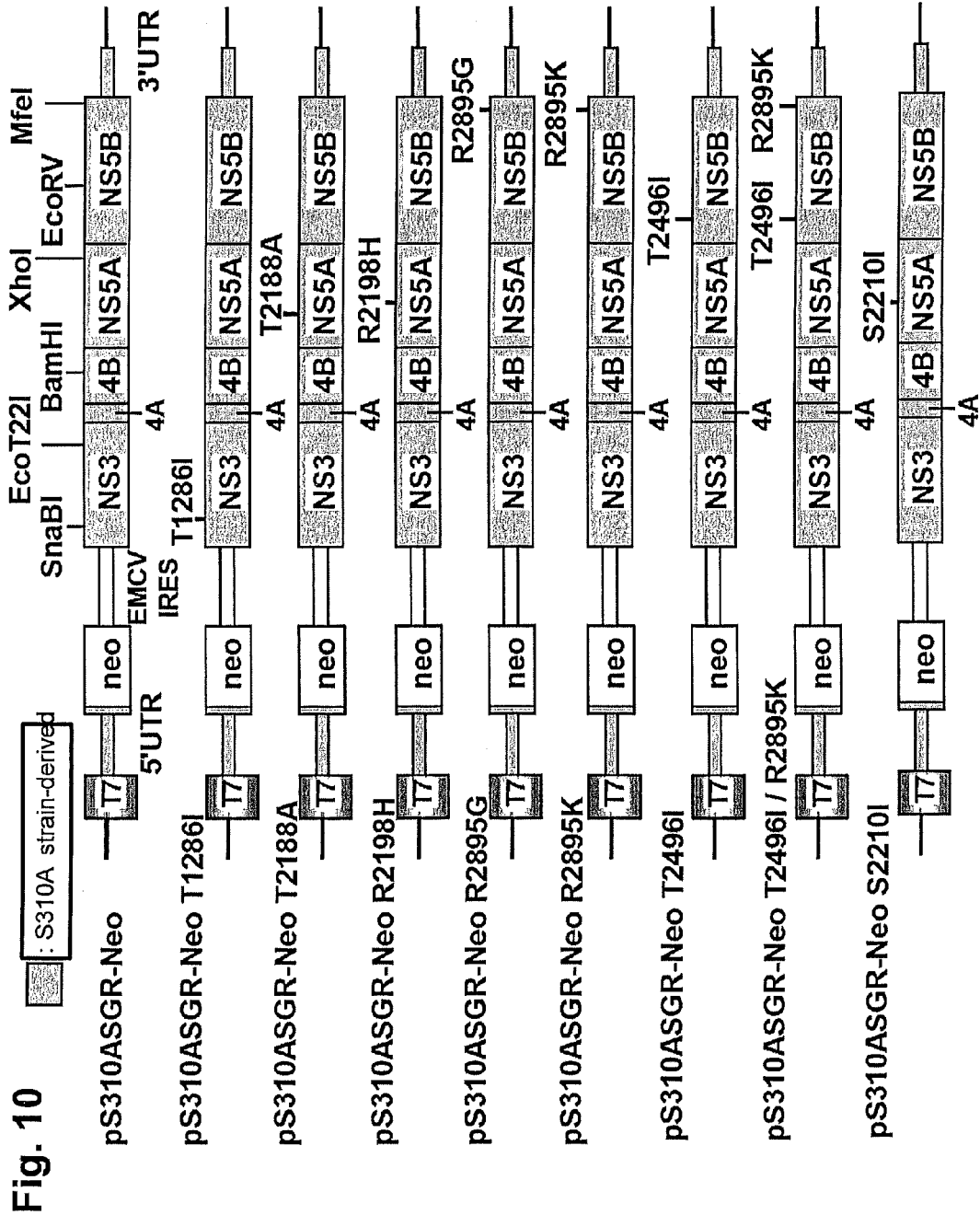
FIG. 10 shows the structure of an HCV subgenomic replicon RNA expression vector of a mutated S310A strain (adaptive mutation-introduced S310A strain).

FIG. 10 shows the structures of the HCV subgenomic replicon RNA expression vectors into which such amino acid substitutions had been introduced. An expression vector resulting from introduction of the substitution T1286I alone into the expression vector, pS310ASGR-Neo, was designated as "pS310ASGR-Neo T1286I." Expression vectors into which the other amino acid substitutions had been introduced alone were designated in the same manner (see FIG. 10). An expression vector resulting from introduction of the substitutions T2496I and R2895K in combination into the expression vector, pS310ASGR-Neo, was designated as "pS310ASGR-Neo T2496I/R2895K."

Specifically, PCR was repeatedly carried out using pS310ASGR-Neo and the PCR product thereof as template DNAs and primers comprising the nucleotide mutations causing the amino acid substitution to be introduced, thereby introducing nucleotide substitutions into pS310ASGR-Neo.

PCR was carried out under the conditions described below. First, 5 µl of 10× buffer and 4 µl of 2.5 mM dNTPs mixture included in the Pyrobest® DNA Polymerase kit (Takara Bio Inc.) and 100 µM primers (forward and reverse primers; 0.25 µl of each) were added to the template DNA for PCR, and deionized water was added to adjust the total amount of the solution to 49.75 µl. Thereafter, 0.25 µl of Pyrobest® DNA Polymerase (Takara Bio Inc.) was added thereto, and PCR was then carried out. The PCR process comprised thermal denaturation at 98° C. for 2 minutes, 25 cycles of 98° C. for 20 seconds, 55° C. for 30 seconds, and 72° C. for 3 minutes, and the final extension at 72° C. for 10 minutes.

To introduce T1286I, first, PCR was carried out using pS310ASGR-Neo as template DNA and primers Neo-S4 (5'-TCCTCGTGCTTTACGGTATC-3' (SEQ ID NO: 29)) and 1286R (5'-GTTCCCAATGCGGACGTTGG-3' (SEQ ID NO: 30)) under the conditions described above. The resulting PCR product was designated as PCR Product No. 1.

Subsequently, PCR was carried out using pS310ASGR-Neo as template DNA and primers 1286F (5'-CCAACGTCCGCATTGGGAAC-3' (SEQ ID NO: 31)) and 5546R (5'-TCCTTGAACTGGTGGGCTATT-3' (SEQ ID NO: 32)) under the conditions described above. The resulting PCR product was designated as PCR Product No. 2.

The PCR products were purified and dissolved in 15 µl of H$_2$O. DNAs of purified PCR Product No. 1 and purified PCR Product No. 2 (1 µl of each) were mixed together. Using the mixture as a template DNA, PCR was carried out using primers Neo-S4 (5'-TCCTCGTGCTTTACGGTATC-3' (SEQ ID NO: 29)) and 5546R (5'-TCCTTGAACTGGTGGGCTATT-3' (SEQ ID NO: 32)) under the conditions described above. The resulting PCR product was designated as PCR Product No. 3. The PCR product was purified and dissolved in 30 µl of H$_2$O.

pS310ASGR-Neo and the purified PCR Product No. 3 were each digested with restriction enzymes SnaBI and EcoT22I, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitution T1286I) was designated as "pS310SGR-Neo T1286I." The sequence of HCV subgenomic replicon RNA synthesized from pS310ASGR-Neo T1286I is shown in SEQ ID NO: 17.

To introduce T2188A, first, PCR was carried out using pS310ASGR-Neo as template DNA and primers 5240F (5'-TGGGGCCTGTCCAAAATGAA-3' (SEQ ID NO: 33)) and 2188R (5'-GCCTCAGCGGCAATATGGGAA-3' (SEQ ID NO: 34)) under the conditions described above. The resulting PCR product was designated as PCR Product No. 4.

Subsequently, PCR was carried out using pS310ASGR-Neo as template DNA and primers 2188F (5'-TTCCCATATTGCCGCTGAGGC-3' (SEQ ID NO: 35)) and 7601R (5'-ACTAACGGTGGACCAAGAGT-3' (SEQ ID NO: 36)) under the conditions described above. The resulting PCR product was designated as PCR Product No. 5.

The PCR products were each purified and dissolved in 15 µl of H$_2$O. DNAs of PCR Product No. 4 and PCR Product No. 5 (1 µl of each) were mixed together. Using the mixture as a template DNA, PCR was carried out using primers 5240F (5'-TGGGGCCTGTCCAAAATGAA-3' (SEQ ID NO: 33)) and 7601R (5'-ACTAACGGTGGACCAAGAGT-3' (SEQ ID NO: 36)) under the conditions described above. The resulting PCR product was designated as PCR Product No. 6. The PCR product was purified and dissolved in 30 µl of H$_2$O.

pS310ASGR-Neo and the purified PCR Product No. 6 were digested with restriction enzymes XhoI and BamHI, and the HCV cDNA fragments were each fractionated via agarose gel electrophoresis, followed by purification. These two DNA fragments were ligated to each other via combining the DNA fragments and the DNA Ligation Kit (Takara Bio Inc.). The resulting recombinant expression vector (comprising a nucleotide substitution causing the amino acid substitution T2188A) was designated as "pS310ASGR-Neo T2188A." The sequence of HCV subgenomic replicon RNA synthesized from pS310ASGR-Neo T2188A is shown in SEQ ID NO: 21.

To introduce R2198H, first, PCR was carried out using pS310ASGR-Neo as template DNA and primers 5240F (5'-TGGGGCCTGTCCAAAATGAA-3' (SEQ ID NO: 33)) and 2198R (5'-GAGGGGACCCATGCGCAAGGC-3' (SEQ ID NO: 37)) under the conditions described above. The resulting PCR product was designated as PCR Product No. 7.

Subsequently, PCR was carried out using pS310ASGR-Neo as template DNA and primers 2198F (5'-GCCTTGCGCATGGGTCCCCTC-3' (SEQ ID NO: 38)) and 7601R (5'-ACTAACGGTGGACCAAGAGT-3' (SEQ ID NO: 36))

under the conditions described above. The resulting PCR product was designated as PCR Product No. 8.

The PCR products were each purified and dissolved in 15 µl of H₂O. DNAs of PCR Product No. 7 and PCR Product No. 8 (1 µl of each) were mixed together. Using the mixture as a template DNA, PCR was carried out using primers 5240F (5'-TGGGGCCTGTCCAAAATGAA-3' (SEQ ID NO: 33)) and 7601R (5'-ACTAACGGTGGACCAAGAGT-3' (SEQ ID NO: 36)) under the conditions described above. The resulting PCR product was designated as PCR Product No. 9. The PCR product was purified and dissolved in 30 µl of H₂O.

pS310ASGR-Neo and the purified PCR Product No. 9 were digested with restriction enzymes XhoI and BamHI, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitution R2198H) was designated as "pS310ASGR-Neo R2198H." The sequence of HCV subgenomic replicon RNA synthesized from pS310ASGR-Neo R2198H is shown in SEQ ID NO: 18.

To introduce T2496I, first, PCR was carried out using pS310ASGR-Neo as template DNA and primers 7276F (5'-GTACCACCAACTGTCCATGGA-3' (SEQ ID NO: 39)) and 2496R (5'-TTAAAGCAATTTTGTAGTGGT-3' (SEQ ID NO: 40)) under the conditions described above. The resulting PCR product was designated as PCR Product No. 10.

Subsequently, PCR was carried out using pS310ASGR-Neo as template DNA and primers 2496F (5'-ACCACTA-CAAAATTGCTTTAA-3' (SEQ ID NO: 41)) and 8579R (5'-CCGCAGACAAGAAAGTCCGGGT-3' (SEQ ID NO: 42)) under the conditions described above. The resulting PCR product was designated as PCR Product No. 11.

The PCR products were each purified and dissolved in 15 µl of H₂O. DNAs of PCR Product No. 10 and PCR Product No. 11 (1 µl of each) were mixed together. Using the mixture as a template DNA, PCR was carried out using primers 7276F (5'-GTACCACCAACTGTCCATGGA-3' (SEQ ID NO: 39)) and 8579R (5'-CCGCAGACAAGAAAGTC-CGGGT-3' (SEQ ID NO: 42)) under the conditions described above. The resulting PCR product was designated as PCR Product No. 12. The PCR product was purified and dissolved in 30 µl of H₂O.

pS310ASGR-Neo and the purified PCR Product No. 12 were digested with restriction enzymes XhoI and EcoRV, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitution T2496I) was designated as "pS310SGR-Neo T2496I." The sequence of HCV subgenomic replicon RNA synthesized from pS310ASGR-Neo T2496I is shown in SEQ ID NO: 22.

To introduce R2895G, first, PCR was carried out using pS310ASGR-Neo as template DNA and primers 7988F (5'-GCTCCGTCTGGGAGGACTTGC-3' (SEQ ID NO: 43)) and R2895G-R (5'-ATGGAGTCCTTCAATGATTGC-3' (SEQ ID NO: 44)) under the conditions described above. The resulting PCR product was designated as PCR Product No. 13.

Subsequently, PCR was carried out using pS310ASGR-Neo as template DNA and primers R2895G-F (5'-GCAAT-CATTGAAGGACTCCAT-3' (SEQ ID NO: 45)) and 3X-54R-2a (5'-GCGGCTCACGGACCTTTCAC-3' (SEQ ID NO: 46)) under the conditions described above. The resulting PCR product was designated as PCR Product No. 14.

The PCR products were each purified and dissolved in 15 µl of H₂O. DNAs of PCR Product No. 13 and PCR Product No. 14 (1 µl of each) were mixed together. Using the mixture as a template DNA, PCR was carried out using primers 7988F (5'-GCTCCGTCTGGGAGGACTTGC-3' (SEQ ID NO: 43)) and 3X-54R-2a (5'-GCGGCTCACGGAC-CTTTCAC-3' (SEQ ID NO: 46)) under the conditions described above. The resulting PCR product was designated as PCR Product No. 15. The PCR product was purified and dissolved in 30 µl of H₂O.

pS310ASGR-Neo and the purified PCR Product No. 15 were digested with restriction enzymes EcoRV and MfeI, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitution R2895G) was designated as "pS310SGR-Neo R2895G." The sequence of HCV subgenomic replicon RNA synthesized from pS310ASGR-Neo R2895G is shown in SEQ ID NO: 23.

To introduce R2895K, first, PCR was carried out using pS310ASGR-Neo as template DNA and primers 7988F (5'-GCTCCGTCTGGGAGGACTTGC-3' (SEQ ID NO: 43)) and R2895K-R (5'-ATGGAGTTTTTCAATGATTGC-3' (SEQ ID NO: 47)) under the conditions described above. The resulting PCR product was designated as PCR Product No. 16.

Subsequently, PCR was carried out using pS310ASGR-Neo as template DNA and primers R2895K-F (5'-GCAAT-CATTGAAAAACTCCAT-3' (SEQ ID NO: 48)) and 3X-54R-2a (5'-GCGGCTCACGGACCTTTCAC-3' (SEQ ID NO: 46)) under the conditions described above. The resulting PCR product was designated as PCR Product No. 17.

The PCR products were each purified and dissolved in 15 µl of H₂O. DNAs of PCR Product No. 16 and PCR Product No. 17 (1 µl of each) were mixed together. Using the mixture as a template DNA, PCR was carried out using primers 7988F (5'-GCTCCGTCTGGGAGGACTTGC-3' (SEQ ID NO: 43)) and 3X-54R-2a (5'-GCGGCTCACGGAC-CTTTCAC-3' (SEQ ID NO: 46)) under the conditions described above. The resulting PCR product was designated as PCR Product No. 18. The PCR product was purified and dissolved in 30 µl of H₂O.

pS310ASGR-Neo and the purified PCR Product No. 18 were digested with restriction enzymes EcoRV and MfeI, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitution R2895K) was designated as "pS310SGR-Neo R2895K." The sequence of HCV subgenomic replicon RNA synthesized from pS310ASGR-Neo R2895K is shown in SEQ ID NO: 19.

Separately, two amino acid substitutions (T2496I and R2895K) were introduced into the NS5B protein region.

Specifically, the above-mentioned pS310ASGR-Neo T2496I and the purified PCR Product No. 18 were digested with restriction enzymes EcoRV and MfeI, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitutions T2496I and R2895K) was designated as "pS310ASGR-Neo T2496I/R2895K." The sequence of an HCV subgenomic replicon RNA synthesized from pS310ASGR-Neo T2496I/R2895K is shown in SEQ ID NO: 20.

To introduce S2210I, PCR was carried out using pS310ASGR-Neo as template DNA and primers 5240F (5'-TGGGGCCTGTCCAAAATGAA-3' (SEQ ID NO: 33)) and 2210R (5'-CGACAGTTGGATGGCGGATGA-3' (SEQ ID NO: 52)) under the conditions described above. The resulting PCR product was designated as PCR Product No. 19.

Subsequently, PCR was carried out using pS310ASGR-Neo as template DNA and primers 2210F (5'-TCATCCGCCATCCAACTGTCG-3' (SEQ ID NO: 53)) and 7601R (5'-ACTAACGGTGGACCAAGAGT-3' (SEQ ID NO: 36)) under the conditions described above. The resulting PCR product was designated as PCR Product No. 20.

The PCR products were each purified and dissolved in 15 μl of H$_2$O. DNAs of PCR Product No. 19 and PCR Product No. 20 (1 μl of each) were mixed together. Using the mixture as a template DNA, PCR was carried out using primers 5240F (5'-TGGGGCCTGTCCAAAATGAA-3' (SEQ ID NO: 33)) and 7601R (5'-ACTAACGGTGGACCAAGAGT-3' (SEQ ID NO: 36)) under the conditions described above. The resulting PCR product was designated as PCR Product No. 21. The PCR product was purified and dissolved in 30 μl of H$_2$O.

pS310ASGR-Neo and the purified PCR Product No. 21 were digested with restriction enzymes XhoI and BamHI, and the HCV cDNA fragments were each fractionated via agarose gel electrophoresis, followed by purification. These two DNA fragments were ligated to each other via combining the DNA fragments and the DNA Ligation Kit (Takara Bio Inc.) The resulting recombinant expression vector (comprising a nucleotide substitution causing the amino acid substitution S2210I) was designated as "pS310SGR-Neo S2210I." The sequence of HCV subgenomic replicon RNA synthesized from pS310ASGR-Neo S2210I is shown in SEQ ID NO: 54.

Subsequently, HCV subgenomic replicon RNAs were synthesized from the expression vectors: pS310ASGR-Neo, pS310ASGR-Neo T1286I, pS310ASGR-Neo T2188A, pS310ASGR-Neo R2198H, pS310ASGR-Neo S2210I, pS310ASGR-Neo T2496I, pS310ASGR-Neo R2895G, pS310ASGR-Neo R2895K, and pS310ASGR-Neo T2496I/R2895K, using MEGAscript® (Ambion) in the same manner as in Example 2. 0.3 μg of each of the resulting HCV subgenomic replicon RNAs was introduced into Huh7 cells via electroporation. Nevertheless, the HCV subgenomic replicon RNA of the wild-type S310A strain (expressed from pS310ASGR-Neo) and T2496I mutant HCV subgenomic replicon RNA (expressed from pS310ASGR-Neo T2496I) were introduced in amounts of 10 μg. The electroporated Huh7 cells were seeded in a culture dish and cultured for 16 to 24 hours, and G418 (neomycin) was then added to the culture dish. Thereafter, culture was continued while changing the culture solution twice a week. After the cells were cultured for 21 days after seeding, viable cells were stained with crystal violet.

Figure 11:
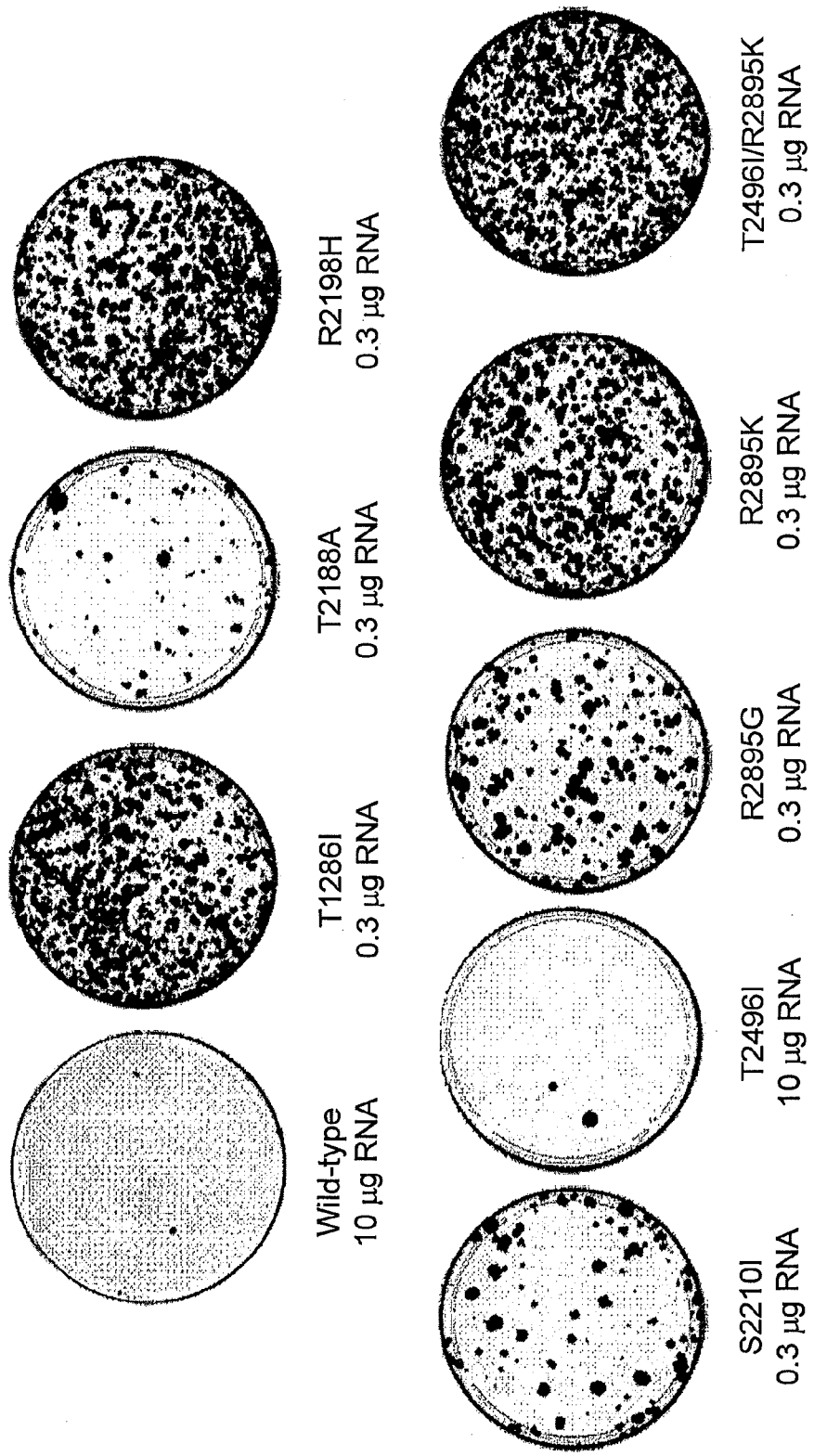
FIG. 11 shows the results of colony formation of cells transfected with the HCV subgenomic replicon RNA of the wild-type S310A strain or the mutant HCV subgenomic replicon RNA thereof.

The results are shown in FIG. 11. In the figure, "wild-type," "T1286I," "T2188A," "R2198H," "S2210I," "T2496I," "R2895G," "R2895K," and "T2496I/R2895K" show the results of staining the cells transfected with HCV subgenomic replicon RNAs produced from pS310ASGR-Neo, pS310ASGR-Neo T1286I, pS310ASGR-Neo T2188A, pS310ASGR-Neo R2198H, pS310ASGR-Neo S2210I, pS310ASGR-Neo T2496I, pS310ASGR-Neo R2895G, pS310ASGR-Neo R2895K, and pS310ASGR-Neo T2496I/R2895K, respectively.

As a result, colony formation was confirmed in all cells transfected with any of the subgenomic replicon RNAs. However, the colony-forming ability of "T2496I" was low, and introduction of 10 μg of RNA is required for colony formation as with the case of "wild-type." Among the clones verified to have colony-forming ability, particularly high-level colony-forming abilities were detected in the clones of "T1286I," "R2198H," "R2895K," and "T2496I/R2895K." The colony-forming ability of "T2496I" was equivalent to that of "wild-type," and no difference was observed between "R2895K" and "T2496I/R2895K." Accordingly, we believe that the amino acid substitution T2496I does not affect to the subgenomic replicon RNA replication ability (FIG. 11).

We therefore demonstrated that the autonomous replication ability is maintained or enhanced when the above-mentioned amino acid mutation is introduced into the HCV subgenomic replicon RNA of the wild-type S310A strain. In particular, we demonstrated that the autonomous replication ability of the HCV subgenomic replicon RNA of the wild-type S310A strain is notably enhanced by introducing the amino acid mutation T1286I, R2198H, or R2895K.

Example 8

Figure 12:
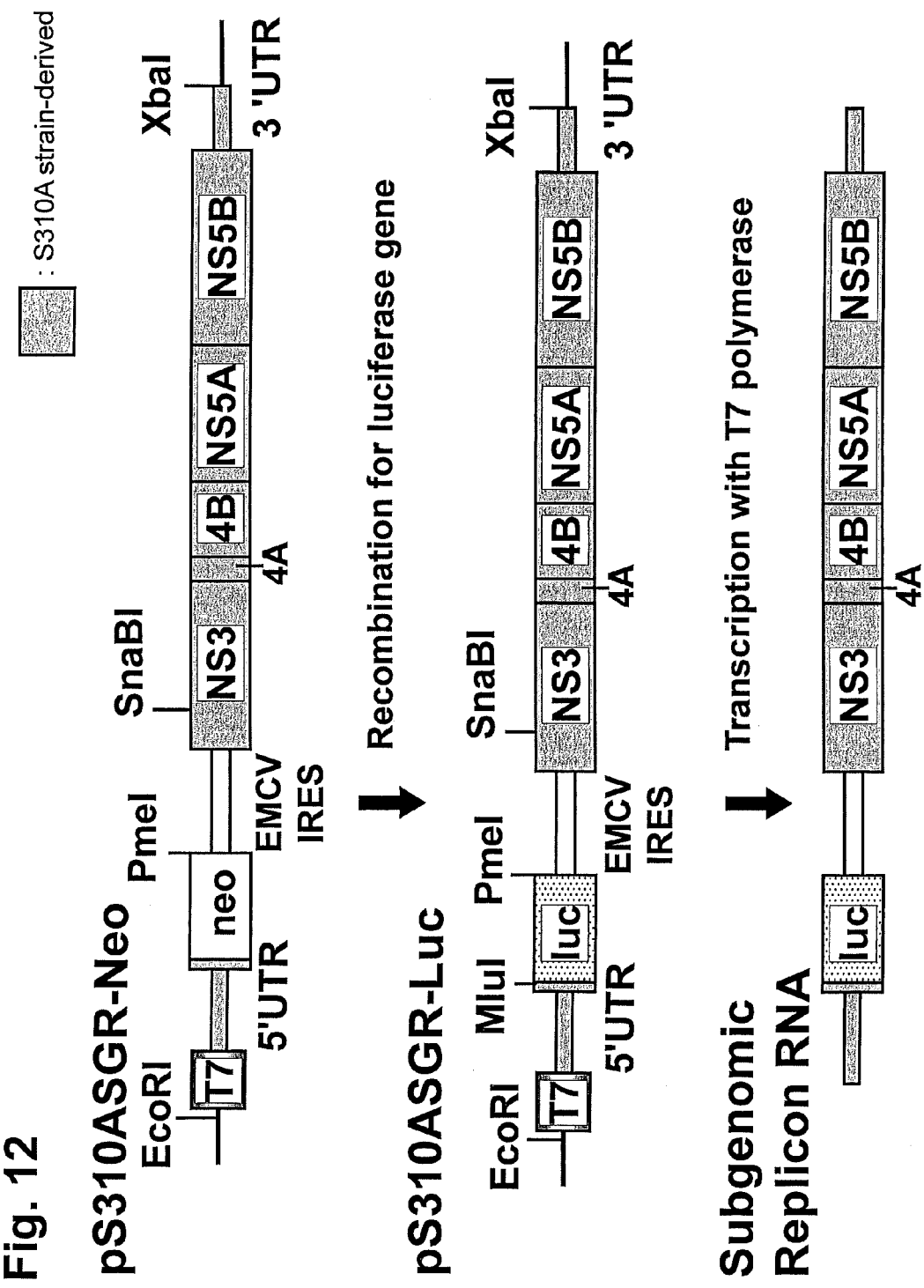
FIG. 12 shows the structures of HCV subgenomic replicon RNA of the S310A strain into which the luciferase gene (Luc) had been inserted instead of the Neo gene and its expression vector, pS310ASGR-Luc, and the processes for preparing them.

Evaluation of Replication Efficiency of S310A Strain Mutant HCV Subgenomic Replicon RNA Using Luciferase Gene In the detection of replicon-replicating cells shown in Example 7 and FIG. 11, replicon-replicating cells can be detected if they have replicon-replicating ability enough to confer minimal neomycin resistance that allows cell survival. Accordingly, the method employed in Example 7 is not suitable for analysis of the replicon replication levels. To perform more quantitative evaluation of replication efficiency of the S310A strain mutant HCV subgenomic replicon RNA, the HCV subgenomic replicon RNA expression vector, pS310ASGR-Luc, was produced by recombination of the neomycin resistance gene in pS310ASGR-Neo with a luciferase gene. FIG. 12 shows the structure of the HCV subgenomic replicon RNA expression vector, pS310ASGR-Luc, and that of HCV subgenomic replicon RNA synthesized from pS310ASGR-Luc.

The expression vector, pS310ASGR-Luc, was constructed in accordance with the procedure described in Kato et al. (Journal of Clinical Microbiology, 2005, Vol. 43, pp. 5679-5684). Specifically, the neomycin resistance gene (neo) in the HCV subgenomic replicon expression vector, pS310ASGR-Neo, was substituted with a firefly luciferase gene (Luc) to construct the expression vector, p310ASGR-Luc (FIG. 12).

Also, the neomycin resistance gene (neo) in the S310A strain HCV subgenomic replicon expression vectors comprising the above-mentioned amino acid mutations was substituted with the firefly luciferase gene (Luc) to construct p310ASGR-Luc mutants. p310ASGR-Luc mutants were designated as follows: "p310ASGR-Luc T1286I" for the T1286I mutant; "p310ASGR-Luc T2188A" for the T2188A mutant; "p310ASGR-Luc R2198H" for the R2198H mutant; "pS310ASGR-Luc S2210I" for the S2210I mutant; "p310ASGR-Luc T2496I" for the T2496I mutant; "p310ASGR-Luc R2895G" for the R2895G mutant; "p310ASGR-Luc R2895K" for the R2895K mutant; and "p310ASGR-Luc T2496I/R2895K for the T2496I/R2895K mutant."

HCV subgenomic replicon RNAs were prepared from the wild-type p310ASGR-Luc and the p310ASGR-Luc mutants in the same manner as in Example 2, 5 μg of each of the resulting RNAs was introduced into 2×10⁶ Huh7 cells via electroporation, and the resultant was seeded on a 12-well plate. The seeded cells were recovered 24 hours and 72 hours later, and the luciferase activity thereof was assayed using the Luciferase assay system (Promega).

Figure 13:
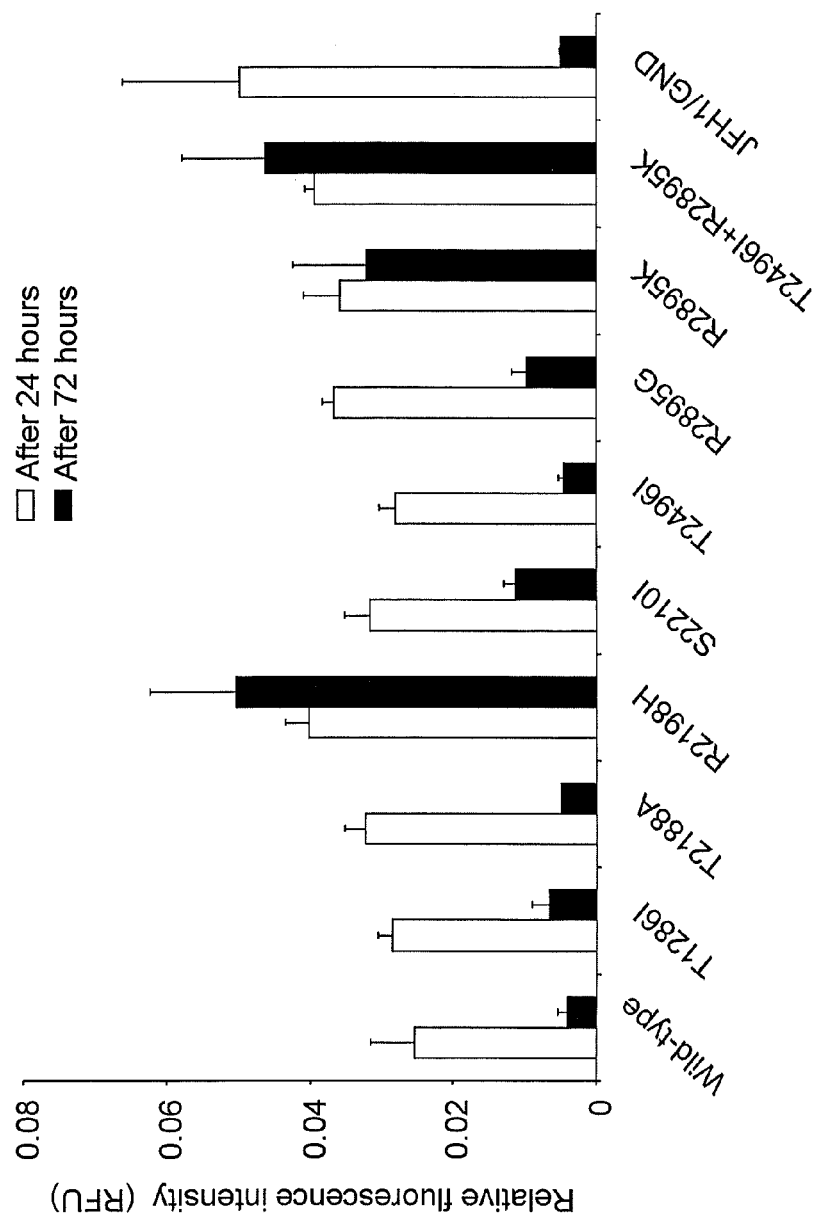
FIG. 13 shows the replication ability (luminescence intensity) of the HCV subgenomic replicon RNA of a mutated S310A strain containing the luciferase gene.

The results are shown in FIG. 13. In the figure, "wild-type," "T1286I," "T2188A," "R2198H," "S2210I," "T2496I," "R2895G," "R2895K," and "T2496I/R2895K" show the results of the cells transfected with HCV subgenomic replicon RNAs produced from pS310ASGR-Luc, pS310ASGR-Luc T1286I, pS310ASGR-Luc T2188A, pS310ASGR-Luc R2198H, pS310ASGR-Luc S2210I, pS310ASGR-Luc T2496I, pS310ASGR-Luc R2895G, pS310ASGR-Luc R2895K, and pS310ASGR-Luc T2496I/R2895K, respectively.

As a negative control, the subgenomic replicon RNA (JFH1/GND) in which the amino acid residue aspartic acid (D) at position 2760 in the NS5B polymerase of the JFH-1 strain had been substituted with asparagine (N) was used (Kato et al., J. Clin. Microbiol., 2005, Vol. 43, pp. 5679-5684). This subgenomic replicon RNA (JFH1/GND) does not have the replication ability 72 hours after transfection due to the mutation of the NS5B polymerase. The vertical axis in the figure represents relative luminescence intensity of luciferase, and a higher luminescence intensity level indicates higher replication ability. When the expression level of the luciferase gene is higher than that of JFH1/GND 72 hours after transfection, it indicates that gene amplification is performed continuously (i.e., the RNA has the autonomous replication ability).

As a result, luciferase gene expression levels for "R2198H," "S2210I," "R2895G," "R2895K," and "T2496I/R2895K" were found to be higher than that of JFH1/GND 72 hours later. This indicates that HCV subgenomic replicon RNAs comprising the amino acid substitution R2198H, S2210I, R2895G, R2895K, or T2496I/R2895K continuously undergo gene amplification.

Example 9

Construction of HCV Full-Genomic Replicon RNA (Full-Length Genomic RNA) Expression Vector of a Mutated S310A Strain To evaluate the HCV particle production ability of the S310A strain HCV full-genomic replicon RNAs comprising the amino acid substitutions identified in Example 6 in cultured cells, the HCV full-genomic replicon RNA expression vectors comprising the full-length HCV genome sequences were constructed.

The expression vector, pS310A, prepared in Example 1 (the recombinant plasmid comprising cDNA of the full-length genomic RNA of the wild-type S310A strain inserted into pUC19 under the control of the T7 promoter) and the various types of pS310ASGR-Neo mutants prepared in Example 7 were used to prepare HCV full-genomic replicon RNA expression vectors.

Specifically, pS310A prepared in Example 1 and pS310SGR-Neo T1286I prepared in Example 7 were digested with SnaBI and BamHI restriction enzymes. The HCV cDNA fragments were each fractionated via agarose gel electrophoresis, followed by purification. The resulting DNA fragment of pS310A and DNA fragment of the pS310ASGR-Neo mutant were ligated to each other via combining such two DNA fragments and the DNA Ligation Kit (Takara Bio Inc.). The resulting HCV full-genomic replicon RNA expression vector comprising the amino acid substitution was designated as "pS310A T1286I."

Similarly, other pS310ASGR-Neo mutants prepared in Example 7 (i.e., pS310ASGR-Neo T2188A, pS310ASGR-Neo R2198H, pS310ASGR-Luc S2210I, pS310ASGR-Neo T2496I, pS310ASGR-Neo R2895G, and pS310ASGR-Neo R2895K) were digested with adequate restriction enzymes (i.e., SnaBI and BamHI for pS310ASGR-Neo T1286I; BamHI and XhoI for pS310ASGR-Neo T2188A and pS310ASGR-Neo R2198H; SacII for pS310ASGR-Neo T2496I; and ScaI for pS310ASGR-Neo R2895G and pS310ASGR-Neo R2895K), and pS310A was digested with the same restriction enzyme as the restriction enzyme that had been used for digestion of the recombination target, each of the pS310ASGR-Neo mutants. The DNA fragment of pS310A and the DNA fragment of the pS310ASGR-Neo mutant, which had been prepared by digestion with the same restriction enzyme, were ligated to each other in the manner described above. The resulting expression vectors for HCV full-genomic replicon RNAs comprising amino acid substitutions were designated as pS310A T2188A, pS310A R2198H, pS310A S2210I, pS310A T2496I, pS310A R2895G, and pS310A R2895K, respectively.

Example 10

Evaluation of HCV Particle-Production Ability in Cells Transfected with HCV Full-Genomic Replicon RNA of S310A Mutant pS310A prepared in Example 1 and the expression vectors prepared in Example 9 were cleaved with the XbaI restriction enzyme, followed by phenol/chloroform extraction and ethanol precipitation. Subsequently, the XbaI fragment was treated with Mung Bean Nuclease to remove the extra four nucleotides, CTAG, at the 3' terminus derived from the XbaI recognition sequence from the XbaI fragment. Next, the Mung Bean Nuclease-treated solution containing the XbaI fragment was subjected to proteinase K treatment, phenol/chloroform extraction, and ethanol precipitation to purify the DNA fragment. RNA was synthesized using this as a template DNA with MEGAscript® T7 kit (Ambion, Inc.).

After the completion of RNA synthesis, the template DNA was removed by adding DNase (2 U) to the reaction solution and reacting them at 37° C. for 15 minutes, and RNA extraction was then performed with acidic phenol. Thus, the HCV full-genomic replicon RNAs of the wild-type S310A strain and the mutated S310A strains were obtained.

Figure 14:
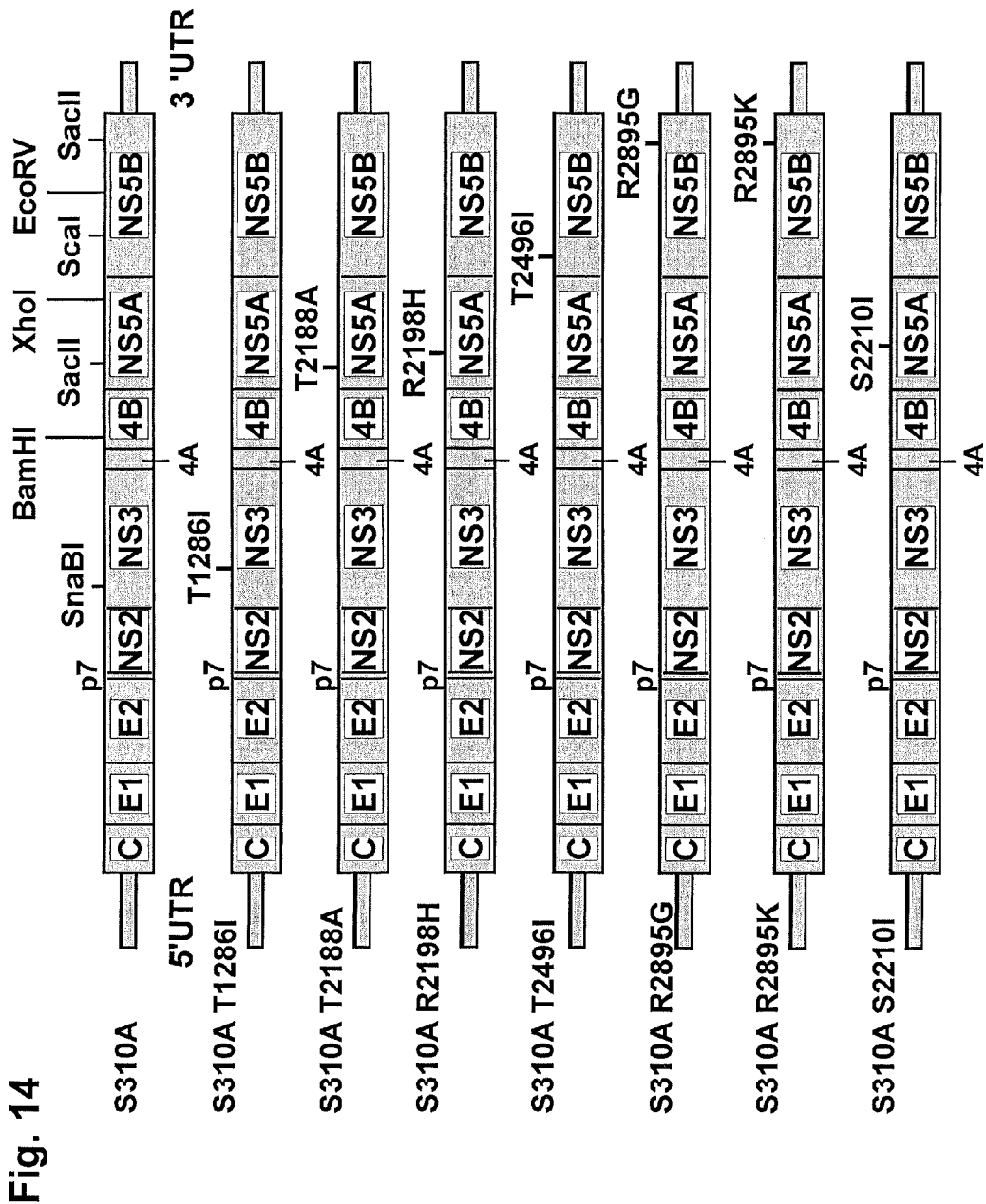
FIG. 14 shows the structure of HCV full-genomic replicon RNA (HCV full-length genome) of a mutated S310A strain (adaptive mutation-introduced S310A strain).

The HCV full-genomic replicon RNAs of the wild-type S310A strain and the mutated S310A strains obtained have the nucleotide sequences identical to those of the full-length genomic RNAs of the wild-type S310A strain and the mutated S310A strains, respectively. In this Example, the HCV full-genomic replicon RNA of the wild-type S310A strain (i.e., full-length genomic RNA of the wild-type S310A strain) is referred to as "S310A," and the S310A strain HCV full-genomic replicon RNAs into which the amino acid substitution (or mutation) T1286I, T2188A, T2198H, S2210I, T2496I, R2895G, or R2895K had been introduced (i.e., mutants of the S310A strain full-length genomic RNA) are referred to as "S310A T1286I," "S310A T2188A," "S310A R2198H," "S310A S2210I," "S310A T2496I," "S310A R2895G," or "S310A R2895K," respectively. FIG. 14 shows the structures of these S310A strain HCV full-genomic replicon RNAs (i.e., HCV full-length genomes).

The resulting HCV full-genomic replicon RNAs (10 μg) of the wild-type and mutated S310A strains were each introduced (transfected) into Huh7 cells by electroporation. The electroporated Huh7 cells were seeded in a culture dish and cultured for 16 to 24 hours, and G418 (neomycin) was then added to the culture dish. Thereafter, culture was continued with subculturing twice a week. The HCV Core protein in the culture supernatant was quantified over time using an HCV antigen ELISA test kit (Ortho-Clinical Diagnostics K.K.) to confirm the production of HCV particles.

Figure 15:
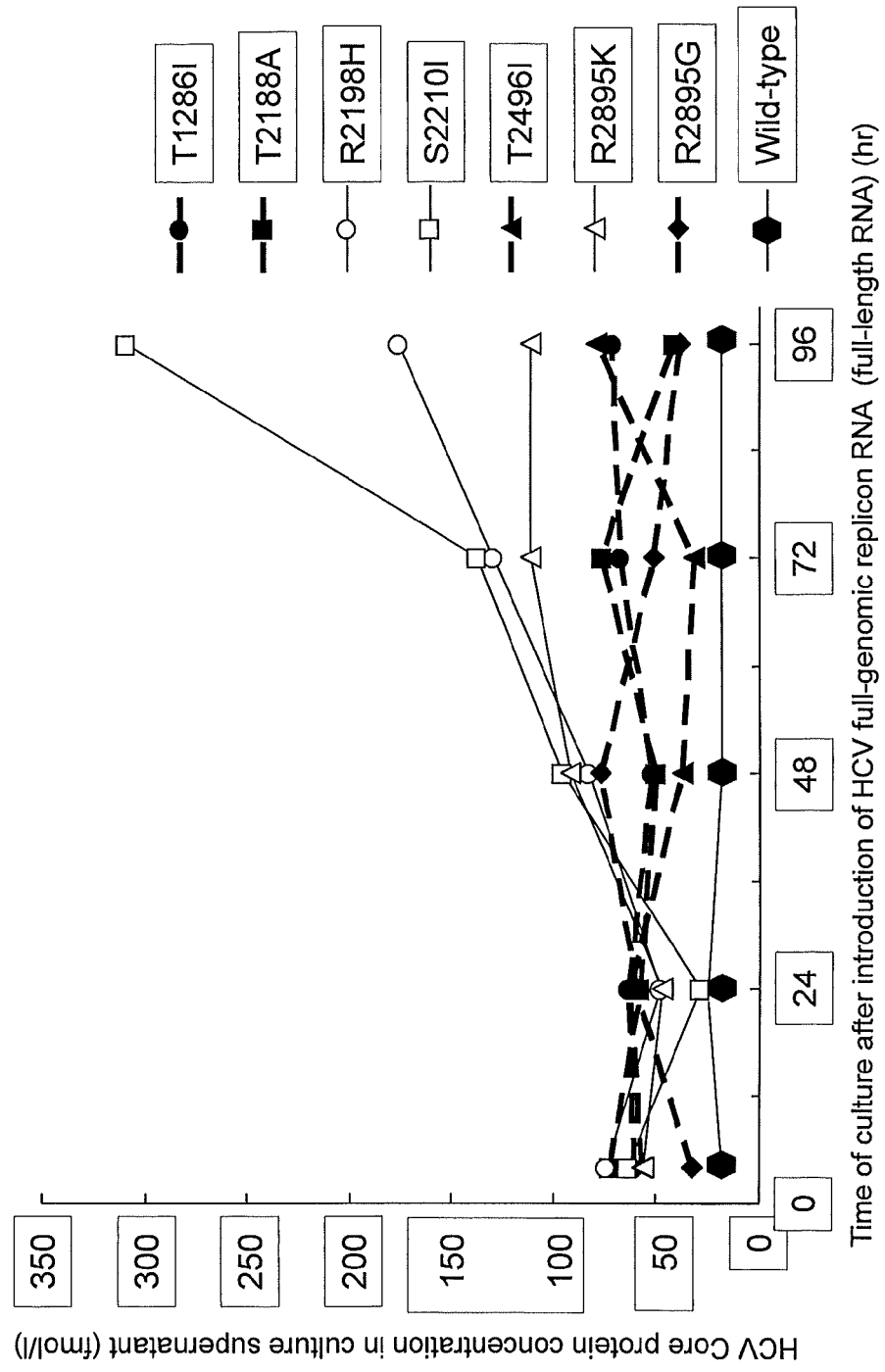
FIG. 15 shows the HCV particle production ability (the amount of Core proteins in the culture supernatant) of HCV full-genomic replicon RNA of a mutated S310A strain (HCV full-length genome).

FIG. 15 shows the results. The horizontal axis of the chart represents cell culture time after introducing HCV full-genomic replicon RNAs (full-length RNAs) of the wild-type S310A strain and the mutated S310A strain into the cells and the vertical axis represents HCV core protein concentration in the cell culture supernatant. "T1286I," "T2188A," "R2198H," "S2210I," "T2496I," "R2895K," and "R2895G" represent cells transfected with HCV full-genomic replicon RNAs (full-length RNAs) of S310A T1286I, S310A T2188A, S310A R2198H, S310A S2210I, S310A T2496I, S310A R2895K, and S310A R2895G, respectively.

In the cells transfected with "S2210I," "R2198H," and "R2895K," elevated HCV core protein concentration was observed in the cell culture supernatant 96 hours after transfection with HCV full-genomic replicon RNA (full-length RNAs). Among HCV full-genomic replicon RNAs of these three mutated S310A strains, the cells transfected with "S2210I" showed the highest HCV core protein concentration in the culture supernatant. This indicates that the mutation S2210I provides the highest HCV particle-production ability. An clear elevation in the HCV core protein concentration in the culture supernatant of the cells transfected with "R2198H" was observed in comparison with other cells. While the HCV core protein concentration in the culture supernatant of the cells transfected with "R2895K" was lower than that in the culture supernatant of the cells transfected with "S2210I" or "R2198H," elevation in the concentration was observed over time.

When the culture supernatants of cells transfected with the HCV full-genomic replicon RNAs of these three mutated S310A strains: "S2210I," "R2198H," and "R2895K," at 96 hours after transfection were added to another Huh7 cell, HCV core proteins were detected for the Huh7 cell. Accordingly, it was confirmed that infectious HCV particles were secreted into the culture supernatants of cells transfected with HCV full-genomic replicon RNA of the mutated S310A strain; i.e., "S2210I," "R2198H," or "R2895K."

The results demonstrate that cells transfected with mutated S310A strain HCV full-genomic replicon RNA (full-length RNA) into which the mutation S2210I (SEQ ID NO: 49), R2198H (SEQ ID NO: 50), or R2895K (SEQ ID NO: 51) had been introduced produce infectious HCV particles.

INDUSTRIAL APPLICABILITY

We can provide HCV subgenomic replicon RNA of genotype 3a and HCV full-genomic replicon RNA capable of producing infectious HCV particles of genotype 3a, which can propagate in cultured cells. They can be used to screen an anti-HCV drug independent of genotype, and in particular, screen an anti-HCV drug against genotype 3a, for which no effective therapeutic agents are available, research concerning the HCV replication mechanism or replication efficiency, and development of HCV vaccines using HCV particles.

All publications, patents, and patent applications cited herein are incorporated herein by reference in their entirety.

Sequence Listing Free Text

SEQ ID NO: 1: cDNA sequence of full-length genomic RNA of the wild-type S310A strain in which a region from positions 1 to 340 is a 5' untranslated region (5' UTR), a region from positions 341 to 913 is the Core protein coding sequence, a region from positions 914 to 1489 is the E1 protein coding sequence, a region from positions 1490 to 2596 is the E2 protein coding sequence, a region from positions 2597 to 2785 is the p7 protein coding sequence, a region from positions 2786 to 3436 is the NS2 protein coding sequence, a region from positions 3437 to 5329 is the NS3 protein coding sequence, a region from positions 5330 to 5491 is the NS4A protein coding sequence, a region from positions 5492 to 6274 is the NS4B protein coding sequence, a region from positions 6275 to 7630 is the NS5A protein coding sequence, a region from positions 7631 to 9406 is the NS5B protein coding sequence, and a region from positions 9407 to 9655 is a 3' untranslated region (3' UTR).

SEQ ID NO: 2: cDNA sequence of the 5' untranslated region (5' UTR) of genomic RNA of the wild-type S310A strain.

SEQ ID NO: 3: cDNA sequence of the Core protein coding sequence of genomic RNA of the wild-type S310A strain.

SEQ ID NO: 4: cDNA sequence of the E1 protein coding sequence of genomic RNA of the wild-type S310A strain.

SEQ ID NO: 5: cDNA sequence of the E2 protein coding sequence of genomic RNA of the wild-type S310A strain.

SEQ ID NO: 6: cDNA sequence of the p7 protein coding sequence of genomic RNA of the wild-type S310A strain.

SEQ ID NO: 7: cDNA sequence of the NS2 protein coding sequence of genomic RNA of the wild-type S310A strain.

SEQ ID NO: 8: cDNA sequence of the NS3 protein coding sequence of genomic RNA of the wild-type S310A strain.

SEQ ID NO: 9: cDNA sequence of the NS4A protein coding sequence of genomic RNA of the wild-type S310A strain.

SEQ ID NO: 10: cDNA sequence of the NS4B protein coding sequence of genomic RNA of the wild-type S310A strain.

SEQ ID NO: 11: cDNA sequence of the NS5A protein coding sequence of genomic RNA of the wild-type S310A strain.

SEQ ID NO: 12: cDNA sequence of the NS5B protein coding sequence of genomic RNA of the wild-type S310A strain.

SEQ ID NO: 13: cDNA sequence of the 3' untranslated region (3' UTR) of genomic RNA of the wild-type S310A strain.

SEQ ID NO: 14: the amino acid sequence of the precursor protein of the wild-type S310A strain in which a region from positions 1 to 191 is the Core protein, a region from positions 192 to 383 is the E1 protein, a region from positions 384 to 752 is the E2 protein, a region from positions 753 to 815 is the p7 protein, a region from positions 816 to 1032 is the NS2 protein, a region from positions 1033 to 1663 is the NS3 protein, a region from positions 1664 to 1717 is the NS4A protein, a region from positions 1718 to 1978 is the NS4B protein and, a region from positions 1979 to 2430 is the NS5A protein, and a region from positions 2431 to 3021 is the NS5B protein.

SEQ ID NO: 15: the amino acid sequence of the region from the NS3 protein to the NS5B protein in the precursor protein of the wild-type S310A strain.

SEQ ID NO: 16: cDNA sequence of HCV subgenomic replicon RNA of the wild-type S310A strain.

SEQ ID NO: 17: cDNA sequence of HCV subgenomic replicon RNA of the S310A T1286I mutant synthesized from pS310ASGR-Neo T1286I.

SEQ ID NO: 18: cDNA sequence of HCV subgenomic replicon RNA of the S310A R2198H mutant synthesized from pS310ASGR-Neo R2198H.

SEQ ID NO: 19: cDNA sequence of HCV subgenomic replicon RNA of the S310A R2895K mutant synthesized from pS310ASGR-Neo R2895K.

SEQ ID NO: 20: cDNA sequence of HCV subgenomic replicon RNA of the S310A T2496I/R2895K mutant synthesized from pS310ASGR-Neo T2496I/R2895K.

SEQ ID NO: 21: cDNA sequence of HCV subgenomic replicon RNA of the S310A T2188A mutant synthesized from pS310ASGR-Neo T2188A.

SEQ ID NO: 22: cDNA sequence of HCV subgenomic replicon RNA of the S310A T2496I mutant synthesized from pS310ASGR-Neo T2496I.

SEQ ID NO: 23: cDNA sequence of HCV subgenomic replicon RNA of the S310A R2895G mutant synthesized from pS310ASGR-Neo R2895G.

SEQ ID NO: 24: primer used for the TaqMan probe method.
SEQ ID NO: 25: primer used for the TaqMan probe method.
SEQ ID NO: 26: probe used for the TaqMan probe method.
SEQ ID NO: 27: primer.
SEQ ID NO: 28: primer.
SEQ ID NO: 29: primer Neo-S4.
SEQ ID NO: 30: primer 1286R.
SEQ ID NO: 31: primer 1286F.
SEQ ID NO: 32: primer 5546R.
SEQ ID NO: 33: primer 5240F.
SEQ ID NO: 34: primer 2188R.
SEQ ID NO: 35: primer 2188F.
SEQ ID NO: 36: primer 7601R.
SEQ ID NO: 37: primer 2198R.
SEQ ID NO: 38: primer 2198F.
SEQ ID NO: 39: primer 7276F.
SEQ ID NO: 40: primer 2496R.
SEQ ID NO: 41: primer 2496F.
SEQ ID NO: 42: primer 8579R.
SEQ ID NO: 43: primer 7988F.
SEQ ID NO: 44: primer R2895G-R.
SEQ ID NO: 45: primer R2895G-F.
SEQ ID NO: 46: primer 3X-54R-2a.
SEQ ID NO: 47: primer R2895K-R.
SEQ ID NO: 48: primer R2895K-F.
SEQ ID NO: 49: cDNA sequence of HCV full-genomic replicon RNA of the S310A S2210I mutant.
SEQ ID NO: 50: cDNA sequence of HCV full-genomic replicon RNA of the S310A R2198H mutant.
SEQ ID NO: 51: cDNA sequence of HCV full-genomic replicon RNA of the S310A R2895K mutant.
SEQ ID NO: 52: primer 2210R.
SEQ ID NO: 53: primer 2210F.
SEQ ID NO: 54: cDNA sequence of HCV subgenomic replicon RNA of the S310A S2210I mutant synthesized from pS310ASGR-Neo S2210I.

The invention claimed is:

1. A nucleic acid comprising, in the following order, a 5' untranslated region comprising a nucleotide sequence of nucleotides 1 to 340 of SEQ ID NO: 1; a nucleotide sequence encoding an amino acid sequence of an NS3 protein of amino acids 1033 to 1663, a nucleotide sequence encoding an amino acid sequence of an NS4A protein of amino acids 1664 to 1717, a nucleotide sequence encoding an amino acid sequence of an NS4B protein of amino acids 1718 to 1978, a nucleotide sequence encoding an amino acid sequence of an NS5A protein of amino acids 1979 to 2430, a nucleotide sequence encoding an amino acid sequence of an NS5B protein of amino acids 2431 to 3021 of SEP ID NO: 14; and a 3' untranslated region comprising a nucleotide sequence of nucleotides 9407 to 9655 of SEQ ID NO: 1, which are of a genome of a hepatitis C virus of genotype 3a, provided that if the nucleic acid is RNA, thymine (t) in the nucleotide sequence is replaced with uracil (u), and comprising nucleotide mutation(s), wherein the nucleotide mutation(s) include a nucleotide mutation that causes at least one amino acid substitution of the following (a) to (g), as defined on the basis of the amino acid sequence shown in SEQ ID NO: 14:

(a) a substitution of threonine at position 1286 with isoleucine;
(b) a substitution of threonine at position 2188 with alanine;
(c) a substitution of arginine at (d) a substitution of serine at position 2210 with isoleucine;
(e) a substitution of threonine at position 2496 with isoleucine;
(f) a substitution of arginine at position 2895 with glycine; or
(g) a substitution of arginine at position 2895 with lysine.

2. The nucleic acid according to claim 1, further comprising a nucleotide sequence encoding a Core protein, a nucleotide sequence encoding an E1 protein, a nucleotide sequence encoding an E2 protein, a nucleotide sequence encoding a p7 protein, and a nucleotide sequence encoding an NS2 protein of a hepatitis C virus genome.

3. The nucleic acid according to claim 2, wherein:
the nucleotide sequence encoding the Core protein encodes the amino acid sequence of Core protein of amino acids 1 to 191 of SEQ ID NO: 14,
the nucleotide sequence encoding the E1 protein encodes the amino acid sequence of E1 protein of amino acids 192 to 383 of SEQ ID NO: 14,
the nucleotide sequence encoding the E2 protein encodes the amino acid sequence of E2 protein of amino acids 384 to 752 of SEQ ID NO: 14,
the nucleotide sequence encoding the p7 protein encodes the amino acid sequence of p7 protein of amino acids 753 to 815 of SEQ ID NO: 14, and
the nucleotide sequence encoding the NS2 protein encodes the amino acid sequence of NS2 protein of amino acids 816 to 1032 of SEQ ID NO: 14.

4. The nucleic acid according to claim 1 comprising the nucleotide sequence shown in any of SEQ ID NOs: 17 to 23 and 54.

5. A full-genomic replicon RNA of hepatitis C virus comprising the nucleic acid according to claim 2.

6. The nucleic acid according to claim 2, wherein said nucleic acid is a chimeric nucleic acid derived from the genomes of two or more hepatitis C virus strains and comprises, in the following order, from the 5' to 3' direction:
the nucleotide sequence encoding the Core protein, the nucleotide sequence encoding the E1 protein, the nucleotide sequence encoding the E2 protein, and the nucleotide sequence encoding the p7 protein of a hepatitis C virus genome other than the hepatitis C virus genome shown in SEQ ID NO: 1;
the nucleotide sequence encoding the NS2 protein of nucleotides 2786 to 3436 of SEQ ID NO: 1, the nucleotide sequence encoding the NS2 protein of a hepatitis C virus genome other than the hepatitis C virus genome shown in SEQ ID NO: 1, or a chimeric NS2 protein consisting of a part of the nucleotide sequence encoding an NS2 protein consisting of nucleotides 2786 to 3436 of SEQ ID NO: 1 linked to a part of the nucleotide sequence encoding an NS2 protein of a hepatitis C virus genome other than the hepatitis C virus genome shown in SEQ ID NO: 1; and
the nucleotide sequence encoding the NS3 protein consisting of nucleotides 3437 to 5329, the nucleotide sequence encoding the NS4A protein consisting of nucleotides 5330 to 5491, the nucleotide sequence encoding the NS4B protein consisting of nucleotides 5492 to 6274, the nucleotide sequence encoding the NS5A protein consisting of nucleotides 6275 to 7630, and the nucleotide sequence encoding the NS5B protein consisting of nucleotides 7631 to 9406 of SEQ ID NO: 1.

7. The nucleic acid according to claim 6, which comprises a 5' untranslated region of a hepatitis C virus genome other than the hepatitis C virus genome of SEQ ID NO: 1, instead of the 5' untranslated region comprising the nucleotide sequence of nucleotides 1 to 340 of SEQ ID NO: 1.

8. A cell into which the nucleic acid according to claim 1 has been introduced.

9. A cell into which the nucleic acid according to claim 2 has been introduced.

10. The nucleic acid according to claim 1, wherein the 5' untranslated region is a nucleotide sequence comprising deletion, substitution, or addition of one or a plurality of nucleotides in the nucleotide sequence of nucleotides 1 to 340 of SEQ ID NO: 1.

11. The nucleic acid according to claim 2, wherein the 5' untranslated region is a nucleotide sequence comprising deletion, substitution, or addition of one or a plurality of nucleotides in the nucleotide sequence of nucleotides 1 to 340 of SEQ ID NO: 1.

12. The nucleic acid according to claim 3 comprising the nucleotide sequence shown in any of SEQ ID NOs: 49 to 51.

* * * * *